US011903755B2

(12) United States Patent
Ken et al.

(10) Patent No.: US 11,903,755 B2
(45) Date of Patent: Feb. 20, 2024

(54) NON-CONTACT ANGLE MEASURING APPARATUS

(71) Applicants: Weng-Dah Ken, Hsinchu (TW); Fang-Chi Kan, Taipei (TW)

(72) Inventors: Weng-Dah Ken, Hsinchu (TW); Fang-Chi Kan, Taipei (TW)

( * ) Notice: Subject to any disclaimer, the term of this patent is extended or adjusted under 35 U.S.C. 154(b) by 774 days.

(21) Appl. No.: 16/910,088

(22) Filed: Jun. 24, 2020

(65) Prior Publication Data
US 2020/0397391 A1 Dec. 24, 2020

Related U.S. Application Data

(62) Division of application No. 15/473,631, filed on Mar. 30, 2017, now abandoned.
(Continued)

(51) Int. Cl.
*A61B 6/00* (2006.01)
*G01N 37/00* (2006.01)
(Continued)

(52) U.S. Cl.
CPC .......... *A61B 6/4258* (2013.01); *A61B 6/4035* (2013.01); *G01B 9/02* (2013.01);
(Continued)

(58) Field of Classification Search
CPC ... A61B 6/4258; A61B 6/4035; A61B 5/0059; G01B 9/02; G01B 15/00; G01B 2290/55;
(Continued)

(56) References Cited

U.S. PATENT DOCUMENTS

2009/0125242 A1  5/2009  Choi
2012/0188538 A1  7/2012  Patil
(Continued)

FOREIGN PATENT DOCUMENTS

CN  1488150 A  4/2004
CN  2757187 Y  2/2006

OTHER PUBLICATIONS

Wang Zhixia, Research on Dynamics of Chaos in Bose-Einstein Condensate, <China Doctoral Dissertations Full-text Database>, 2010 vol. 1, Dec. 16, 2009, China, pp. 13-14.
(Continued)

*Primary Examiner* — Md M Rahman
(74) *Attorney, Agent, or Firm* — Winston Hsu

(57) ABSTRACT

A non-contact angle measuring apparatus includes a matter-wave and energy (MWE) particle source and a detector. The MWE particle source is used for generating boson or fermion particles. The detector is used for detecting a plurality peaks or valleys of an interference pattern generated by 1) the boson or fermion particles corresponding to a slit, a bump, or a hole of a first plane and 2) matter waves' wavefront-split associated with the boson or fermion particles reflected by a second plane, wherein angular locations of the plurality peaks or valleys of the interference pattern, a first distance between a joint region of the first plane and the second plane, and a second distance between the detector and the slit are used for deciding an angle between the first plane and the second plane.

9 Claims, 128 Drawing Sheets
(124 of 128 Drawing Sheet(s) Filed in Color)

Related U.S. Application Data

(60) Provisional application No. 62/316,507, filed on Mar. 31, 2016.

(51) Int. Cl.
| | | |
|---|---|---|
| *G01B 9/02* | (2022.01) | |
| *H01J 37/244* | (2006.01) | |
| *G01N 23/20* | (2018.01) | |
| *H01J 37/26* | (2006.01) | |
| *G01B 15/00* | (2006.01) | |
| *G04F 5/14* | (2006.01) | |
| *H01J 37/04* | (2006.01) | |

(52) U.S. Cl.
CPC .............. *G01B 15/00* (2013.01); *G01N 23/20* (2013.01); *G01N 37/005* (2013.01); *G04F 5/14* (2013.01); *H01J 37/04* (2013.01); *H01J 37/244* (2013.01); *H01J 37/26* (2013.01); *G01B 2290/55* (2013.01); *H01J 2237/06383* (2013.01); *H01J 2237/24557* (2013.01); *H01J 2237/24571* (2013.01); *H01J 2237/24578* (2013.01); *H01J 2237/24585* (2013.01); *H01J 2237/2614* (2013.01)

(58) Field of Classification Search
CPC ........ G01B 11/26; G01B 11/00; G01N 23/20; G01N 37/005; G04F 5/14; H01J 37/04; H01J 37/244; H01J 37/26; H01J 2237/06383; H01J 2237/24557; H01J 2237/24571; H01J 2237/24578; H01J 2237/24585; H01J 2237/2614
USPC .......................................................... 356/138
See application file for complete search history.

(56) References Cited

U.S. PATENT DOCUMENTS

| | | | |
|---|---|---|---|
| 2012/0281813 A1* | 11/2012 | Lidestri | ............... G21K 1/06 378/73 |
| 2014/0368793 A1 | 12/2014 | Friedman | |
| 2016/0282102 A1 | 9/2016 | Olszak | |
| 2016/0282190 A1 | 9/2016 | Olszak | |
| 2018/0138330 A1* | 5/2018 | Choi | ............... G06F 30/23 |

OTHER PUBLICATIONS

Zhao Wenbin, Research on Opto-VLSI-Based Tunable Filter, <Wanfang Degree Database>, Dec. 31, 2012, China, pp. 1-5.

D. R. Herrick et al., Spin-Rotation Effects in the Stern-Gerlach Deflection Spectra of $^3\Sigma-$ Molecules and Their Complexes with Argon, Journal of Molecular Spectroscopy, 1989, pp. 61-81, vol. 133, Academic Press, Inc., XP023948409, 1989.

K Rubin et al., Atom interferometer using two Stern-Gerlach magnets, Laser Physics Letters, 2004, coverpage & pp. 184-193, vol. 1, No. 4, ASTRO Ltd., XP093091593, 2004.

T. Rieger et al., Continuous loading of an electrostatic trap for polar molecules, Aug. 25, 2005, pp. 1-4, arXiv, XP080194611, Aug. 25, 2005.

* cited by examiner

Type-I EPR Pairs
Are with the same
polarization

Type-II EPR Pairs
with H/V-paired or
entangled Polarization

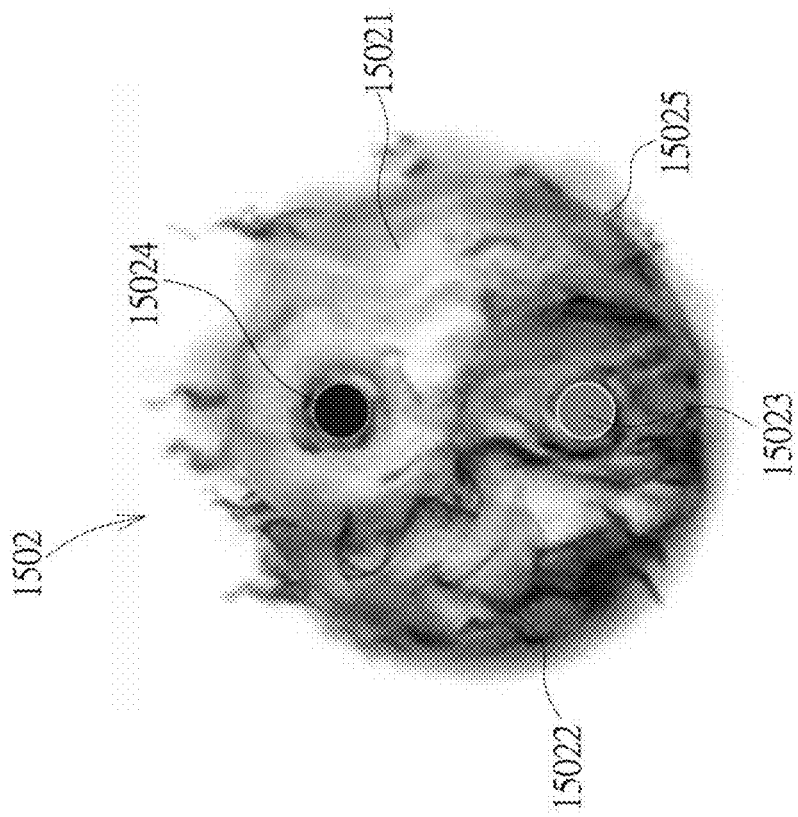
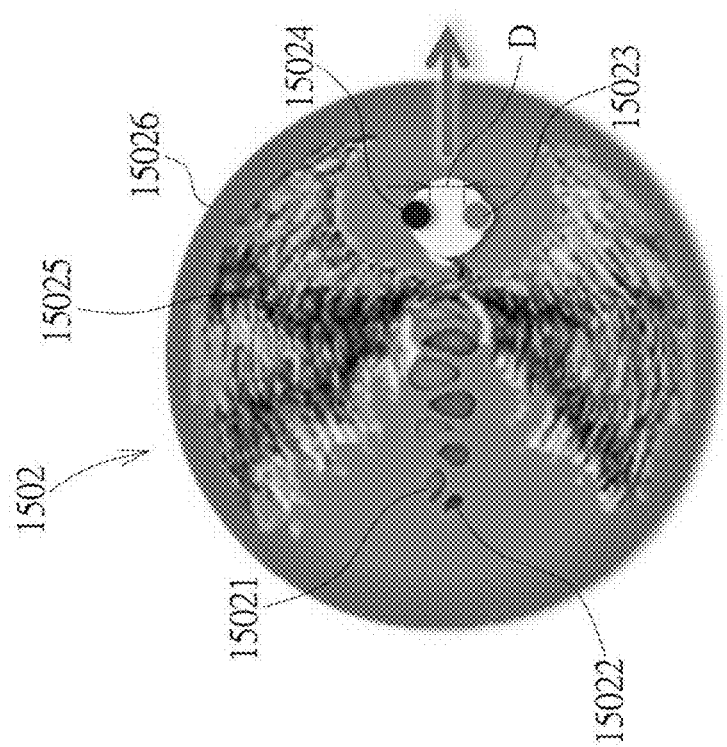
FIG. 15A
FIG. 15B

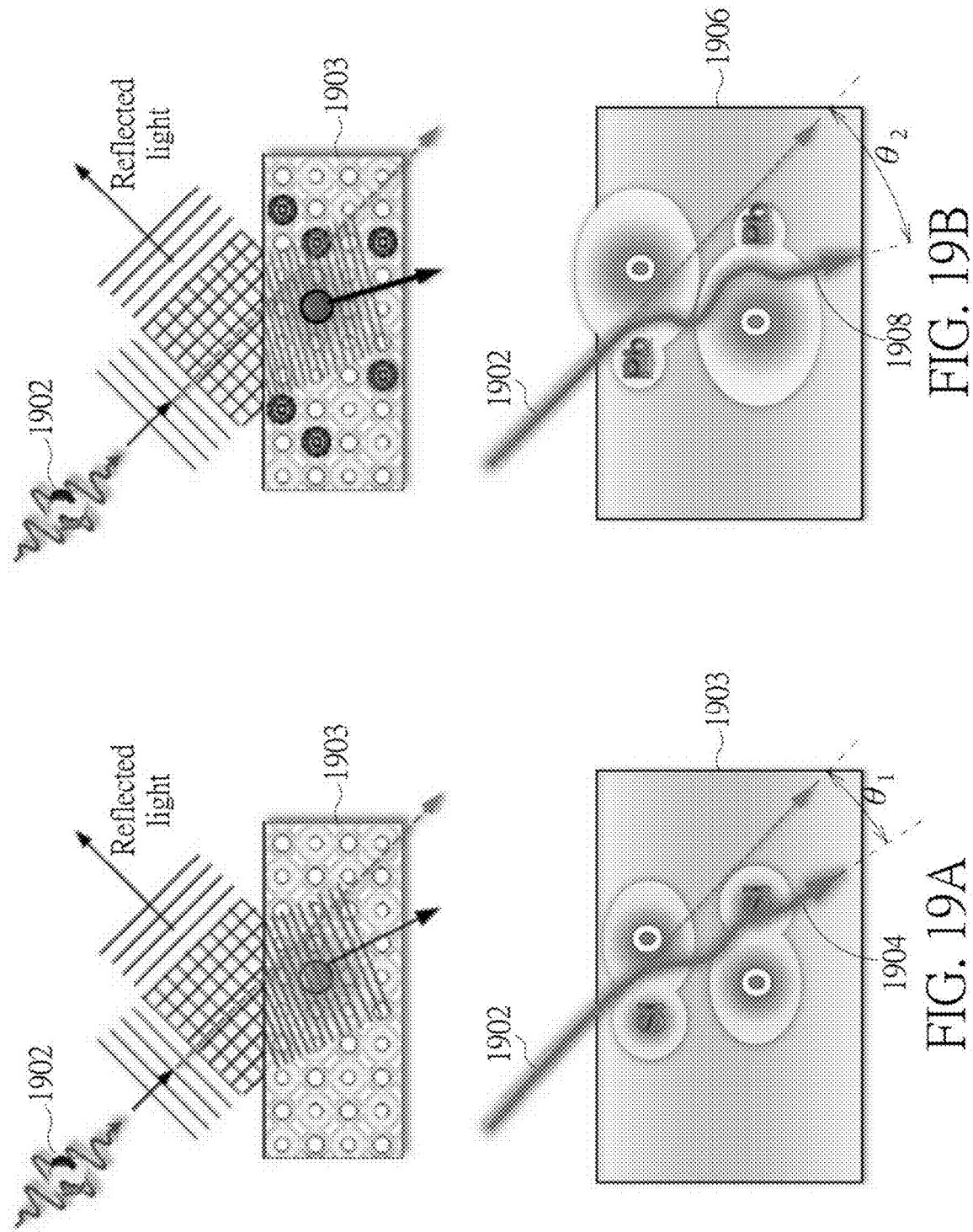

$$F_D = P_e \cdot \nabla(E_z)$$

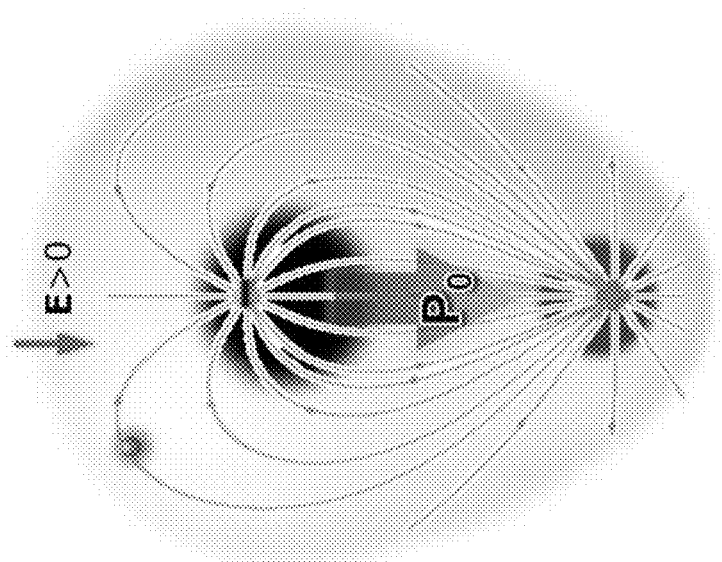
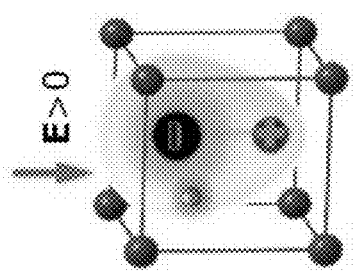
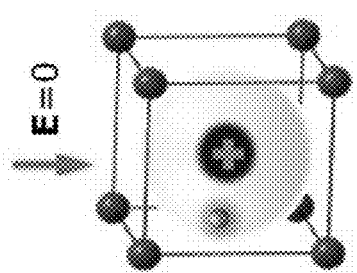
FIG. 41

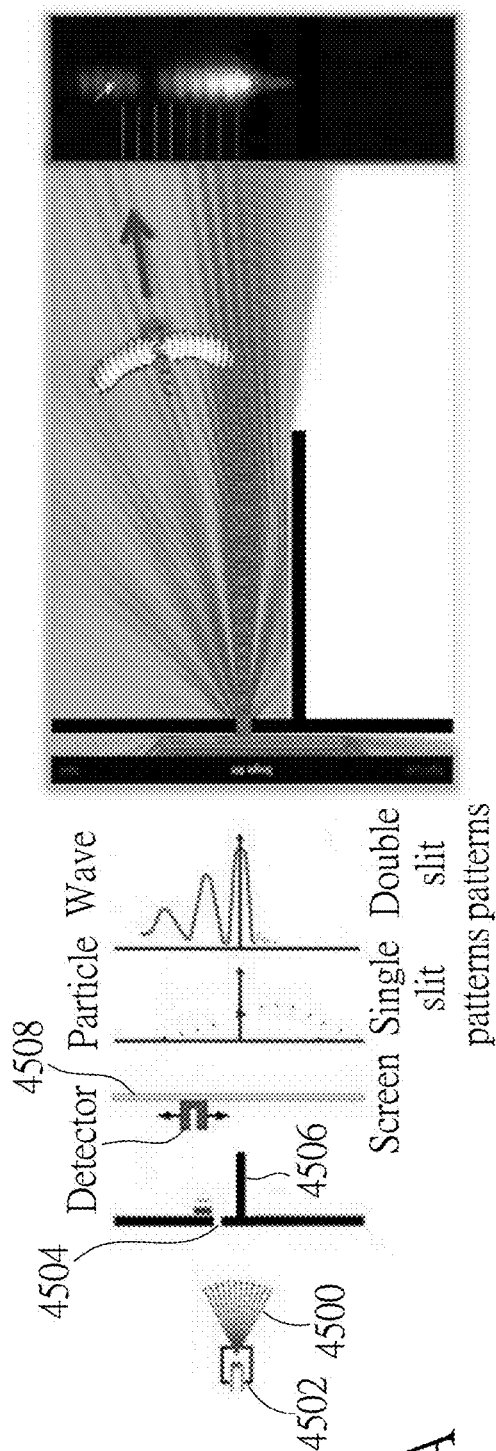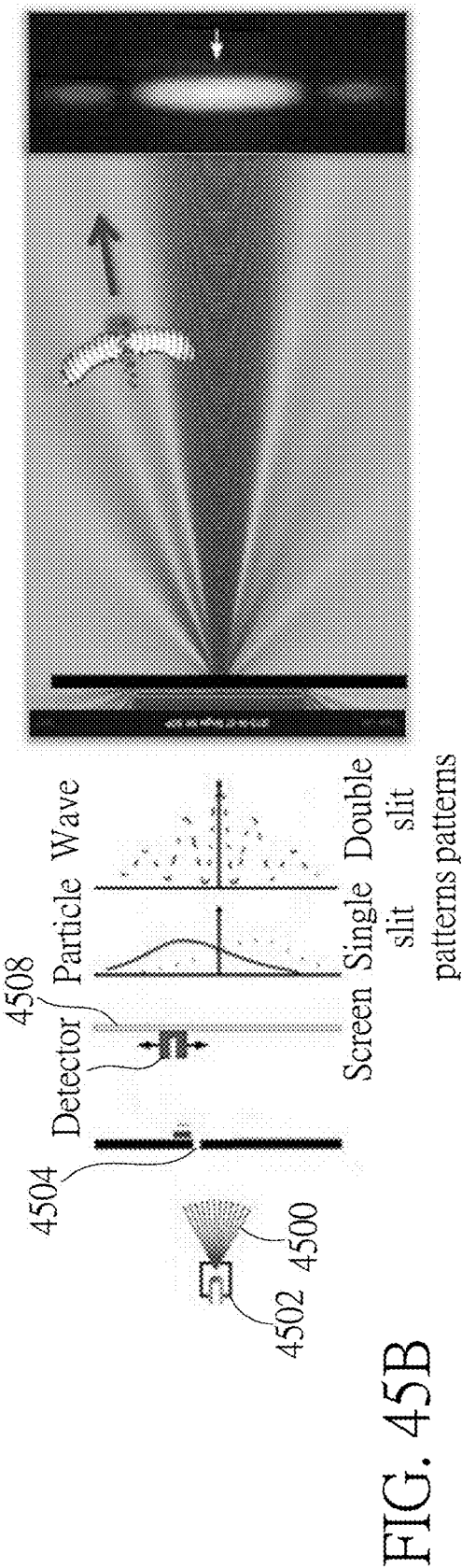
FIG. 45A
FIG. 45B

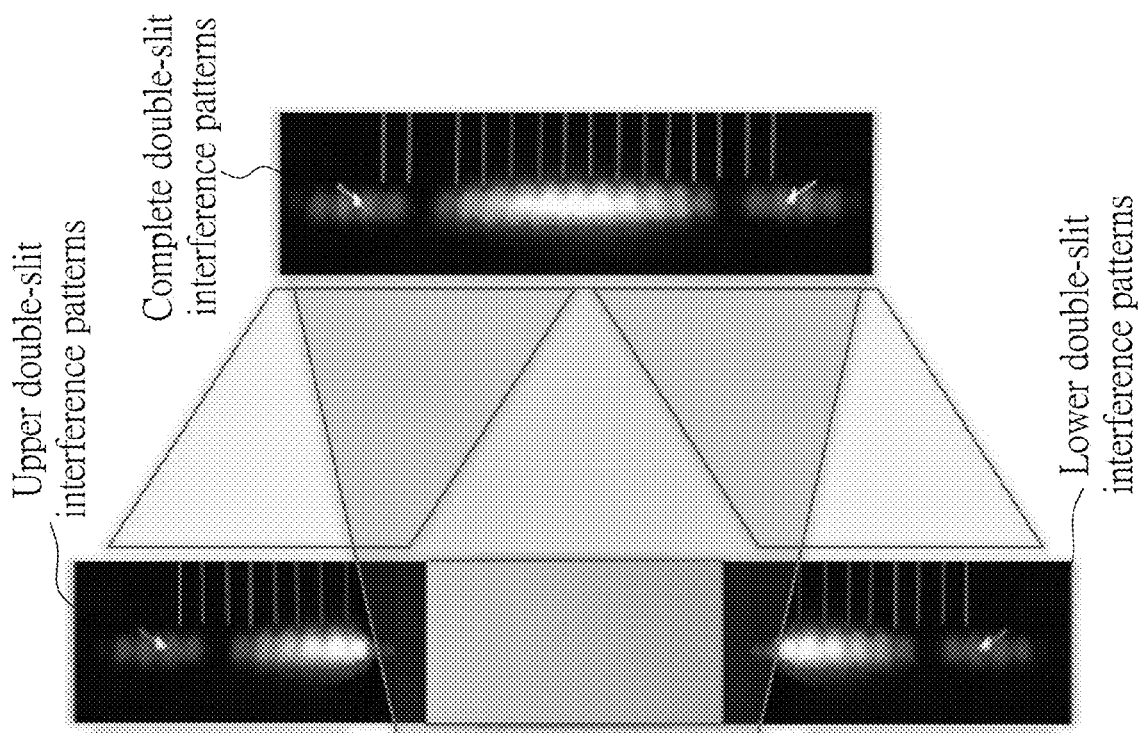
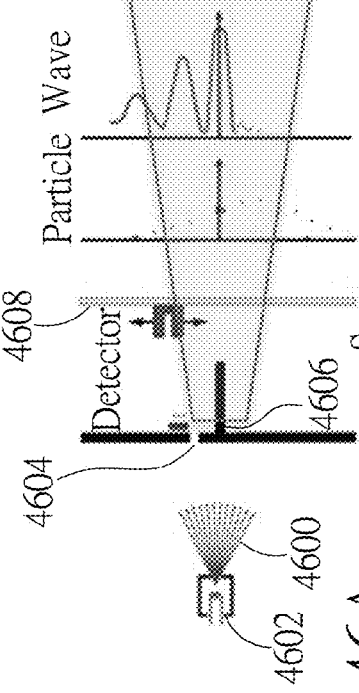
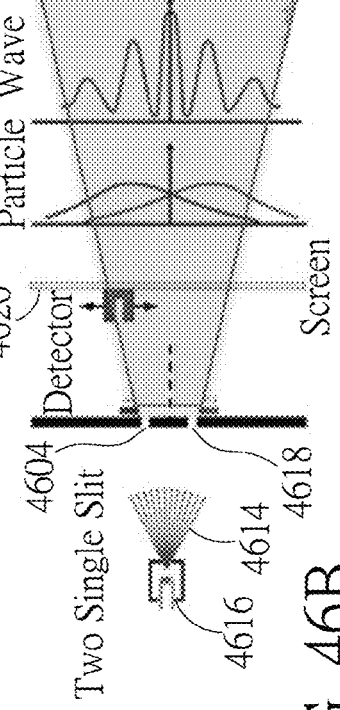
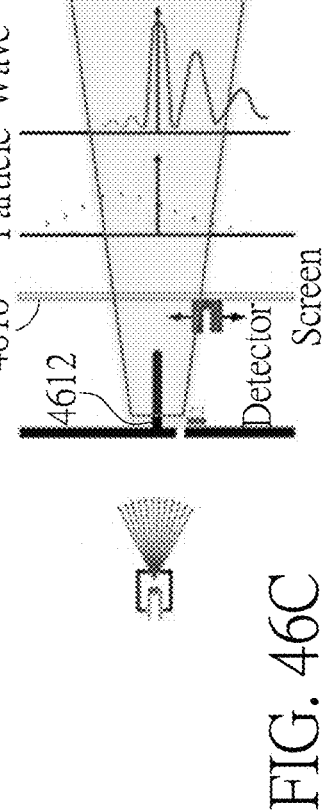
FIG. 46A  FIG. 46B  FIG. 46C

| Angle b/w Polarizers A&B (deg) → | 0.0 | 22.5 | 45.0 | 67.5 | 90.0 | Account |
|---|---|---|---|---|---|---|
| Malus Law's Idea Raw average (hits) → | 93 | 83 | 61 | 39 | 31 | 248 |
| Malus' Adj. Coincidence Rates (hits) → | 70 | 60 | 38 | 16 | 8 | - |
| Aspect's Raw Coincidence Rates (hits) → | 96 | 87 | 63 | 38 | 28 | 248 |
| Aspect's Adj. Coincidence Rates⁻¹ (hits) → | 73 | 64 | 40 | 15 | 6 | - |

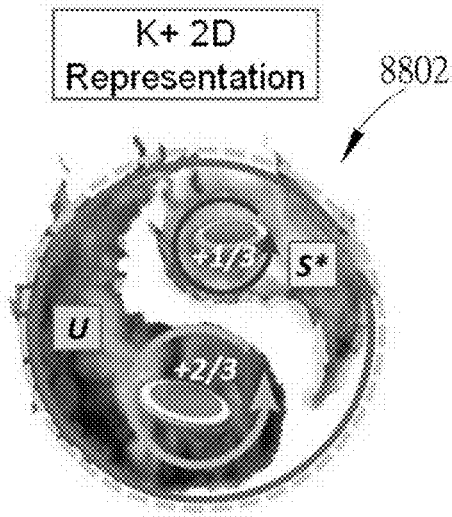 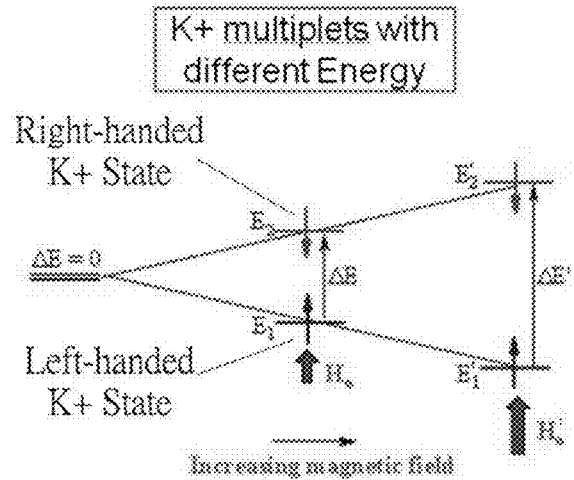
FIG. 88A  FIG. 88B
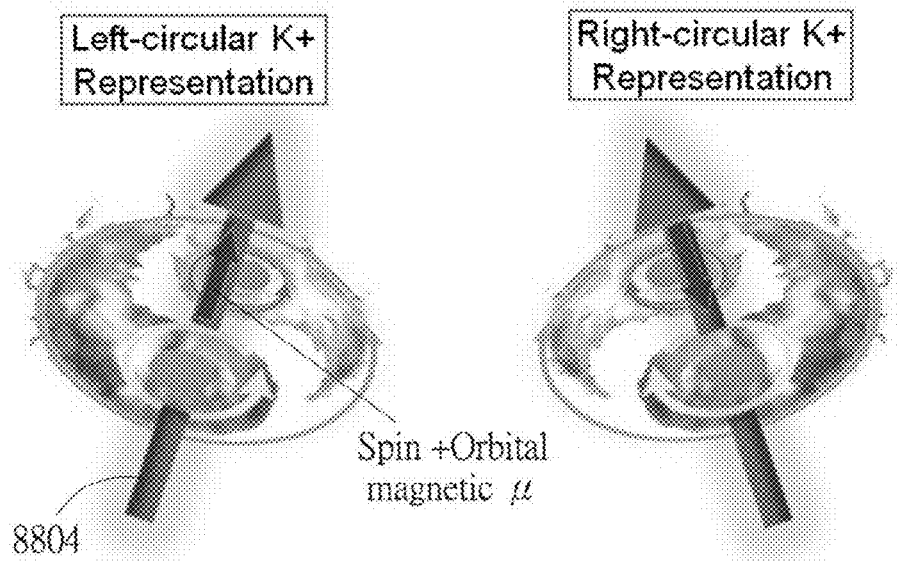
FIG. 88C

| Laser cart 1/2 state | Laser cart 1/2 on/off | Detector 1 Intensity | Detector 2 Intensity | Detector 3 Intensity | Screen Patterns | Screen Intensity |
|---|---|---|---|---|---|---|
| A | on/off | off/off | ~200% | ~0% | ~100% | No Fringe | ~100% |
| B | on/off | on/off | ~200% | ~100% | ~100% | Fringes | ~100% |
| C | on/off | off/on | ~200% | ~0% | ~100% | Fringes | ~100% |
| D | on/off | on/on | ~200% | ~100% | ~100% | No Fringe | ~100% |

FIG. 106

NON-CONTACT ANGLE MEASURING APPARATUS

CROSS REFERENCE TO RELATED APPLICATIONS

This is a division of U.S. patent application Ser. No. 15/473,631, filed on 2017 Mar. 30, which claims the benefit of U.S. provisional application No. 62/316,507, filed on Mar. 31, 2016. The contents of these applications are incorporated herein by reference.

BACKGROUND OF THE INVENTION

1. Field of the Invention

The methods and apparatus relate to the newly discovered embodiments which are associated with matter wave property of the fundamental particles such as bosons (e.g. photon) and/or fermions (e.g. electron, neutron), etc. The present invention includes remote angle measurement tools. However, having answered those unanswered paradoxes in the human history by this invention, it can be recognized the present invention has a much broader ranges of applicability with various science fields and different areas in science and nature.

2. Description of the Prior Art

In 1900, Lord Kelvin said, "There is nothing new to be discovered in physics now. All that remains is more and more precise measurement." Later years, Scientist found Quantum physics is not a complete theory, even though correct, by seeing that one believe a whole description of the physical reality can be provided eventually including wave-particle duality of light (Photon) and the like. While Niels Bohr and Alert Einstein were on good terms personally but carried on a never-ending debate, among the most famous quotes Albert Einstein said "All those 50 years of conscious brooding have brought me no nearer to the question—what are light quanta?" and said "No reasonable definition of reality could be expected to permit quantum mechanics.", and Niels Bohr said "Everything we call real is make of things we cannot call real." Having been known well for so many decades or hundreds of years, matter is structured from the smallest particles, such as bosons or fermions up to the size of the universe. Also, visible and invisible light, as being associated with all types of electromagnetic radiation (EMR or EM radiation) or electromagnetic wave (EMW or EM Wave), are experimentally found to be always moving at the same speed "c (speed of light)" in the vacuum of universe. In classical physics, the term light sometimes refers to electromagnetic radiation of any wavelength, whether visible or not. In this sense, gamma rays, X-rays, microwaves and radio waves are also light. Like all types of light, visible light is emitted and absorbed in tiny "packets" called photons and exhibits properties of both waves and particles. This property is referred to as the wave-particle duality. The study of light, in particular visible light which has been known as optics, is an important research area in modern physics of past hundreds of years. In the present invention, shall refer "Light" and "Photon" substantially as the same matter or object interchangeably.
(Reference: 1) Theories of light, from Descartes to Newton A. I. Sabra CUP Archive, 1981; 2) Dirac, P. A. M. (1930). The Principles of Quantum Mechanics; 3) Feynman, Richard P.; Leighton, Robert B.; Sands, Matthew (1965), and the Feynman and Lectures on Physics. 1-3. Addison-Wesley; 4) Francis A. Jenkins & Harvey E. White Fundamentals of Optics (4-th.ed.) McGraw-Hill 1976) in the prior art, light can be regarded as a form of an electromagnetic wave (EMW) described by Maxwell's equations. Also, as a particle, the light can be detected through its effects, e.g. heat of an object illuminated by the light, Photoelectric effect current converted from the light, particle-like mechanical pressure ("Maxwell force") caused by the light. The energy $E_m$ (or motion mass equivalent energy) corresponding to the light is conveyed through a stream of particles ("photons") with ballistic behavior, e.g. shadow, pressure behavior, photoelectric effect, and so on. In addition, the energy $E_m$ can be also conveyed through EM waves in nature with wave behavior, e.g. reflection, interference, refraction, diffraction, polarization, and so on. Therefore, as shown in FIGS. 1A-1C, when light 102 encounters an object 104, according to a composition of the object 104 and a wavelength of the light 102, the light 102 is either absorbed, transmitted, reflected, refracted (shown in FIG. 1A), scattered (shown in FIG. 1B), or diffracted (shown in FIG. 1C), and so on. Recent years, Quantum field Theory (QFT) also depicted the $M_E$ (energy equivalent mass) by considering the well-known Einstein's general relativity for light quanta (i.e. photons). The QFT "statistically and mathematically" reconciles the two points of view, through the "Wave-Particle Duality" assertions of "Probability" wave-functions associated with a point-like particle (i.e. dimension-less).

(References: 1) Feynman, Richard P.; Robert B. Leighton; Matthew Sands (1965). The Feynman Lectures on Physics, Vol. 3. US: Addison-Wesley. pp. 1.1-1.8; 2, 4, 5) Einstein, A; B Podolsky; N Rosen (1935-05-15). "Can Quantum-Mechanical Description of Physical Reality be Considered Complete?" Physical Review. 47 (10): 777-780; 3) Schrödinger, Erwin (November 1935). "Die gegenwärtige Situationin der Quantenmechanik (The present situation in quantum mechanics)". Naturwissenschaften. 23(48): 807-812; 6) Aharonov, Y; Bohm, D (1959). "Significance of electromagnetic potentials in quantum theory". Physical Review. 115: 485-491) In past hundreds and thousands of years in science history, a bunch of physical paradoxes or puzzles are apparent contradiction in realism physical descriptions of the universe. While many physical paradoxes have acceptable resolutions, there are many others defy resolutions and may indicate flaws that are seemingly contradictory in different aspects of either theory, causality or reality. Among those paradoxes, the most famous ones are:
1) The double-slit experiment? Or, is light a wave or particle?
2) The EPR (entanglement) paradox? Or, the incomplete physics behind QM's (QuantumMechanics') non-locality andnon-realism?
3) The Schrödinger's cat paradox? Or, the Wavefunction collapsed if it has been conscious measured?
4) Einstein: QM reality Cannot be Considered Complete!
5) Einstein: Do you believe, was the moon still there while you did not look at it? Is "Causality" always true and backwards in time is possible (violation of cause and effect)?
6) Why AB & AC scalar/vector potentialeffects under null EM field?
7) What is the reality behind HBT (Hanbury-Brown-Twiss) stellar intensity interferometry experiment?

8) What are the basic building blocks of matter, how if it is from Yin-yang or Taiji?
9) Why does the electron have a spin (magnetic moment)? If Electron a real "point" particle?
10) How did the universe begin? Will the universe end, and if so, how and when with what form?

A. In Regard to Reflection and Refraction
(Reference: Born and Wolf (1959). Principles of Optics. New York, NY: Pergamon Press INC.)

Please refer to FIGS. 2A, 2B. As shown in FIG. 2A, when incident light 202 (with wavelengthX) encounters first material (e.g. SiO2) 204, a portion of the incident light 202 is reflected to form reflected light 206 by interface property discontinuity (e.g. air vs. SiO2 covalence bond 207, etc.) of the first material 204, wherein wavefront 208 of the reflected light 206 follows Huygens principle, and the reflected light 206 has same wavelength λ. In addition, as shown in FIG. 2A, another portion of the incident light 202 is refracted to form refracted light 210 due to electric dipole polarization (e.g. the SiO2 covalence bond 207, etc.) and EM oscillation effects of matters of the first material 204, wherein the refracted light 210 has a slower speed due to electric dipole relaxation effect and follows Snell's Law (wherein index of refraction corresponds to SiO2 is 1.4), and has wavelength λ1 less than the incident wavelength A typically because a refraction index of Sio2 is >1.

Similarly, as shown in FIG. 2B, when the incident light 202 encounters second material (e.g. SiO2+PbO) 212, because the second material 212 reveals higher index of refraction (n is between 1.5-2.0), associating with stronger EM-dipole oscillation radiation or interference, and has larger scattering cross-sections of PbO ionic-bond centers (because PbO ionic-bond 209 produces stronger EM dipole interactions), refracted light 214 shown in FIG. 2B has a more shorter wavelength λ2, wherein the wavelength λ2 is less than the wavelength λ1 and A typically, and refraction angle θ1 shown in FIG. 2A is greater than refraction angle θ2 shown in FIG. 2B.

B. In Regard to Spatial and Temporal Coherence
(Reference: M. Born; E. Wolf (1999). Principles of Optics (7th Ed.). Cambridge University Press; Rolf G. Winter (2008) "Coherence", Access Science, McGraw-Hill)

In view of Electro-Magnetic Wave (EMW), ordinary candle, electric bulb, Sun or black-body emissions are all spatial and temporal incoherent sources typically, but light from much far distance outer space (e.g. start light) is coherent light, wherein spatial incoherent corresponds to size of an EMW source and temporal incoherent corresponds to randomized wavelength or frequency of the EMW sources. Please refer FIG. 3. Although light 302 emitted from electric bulb 304 is spatial and temporal incoherent, the light 302 can become spatial coherent light 306 through pinhole 308 (i.e. spatial filter), and the spatial coherent light 306 can become spatial and temporal coherent light 310 through frequency filter 312 (i.e. wavelength filter). Because each tiny source is coherent and can create its own interference pattern, spatial coherence of incoherent source can be improved by reducing emitting size or area of the incoherent source, or by placing the incoherent source at very far location to let the incoherent source be like a point source, etc.

Refer to FIGS. 4, 5. FIG. 4 is a diagram illustrating Michelson interferometer, and FIG. 5 is a diagram illustrating Yang's Double slits experiment with an electric bulb. As shown in FIG. 4, light 402 from point source 404 (with spatial coherence) can be split into two light beams 406, 408 by beam splitter 410, and the light beams 406, 408 from unequal paths (d1≠d2 causing temporal incoherence effect) do not interfere and cannot typically form an interference pattern on detector 412, wherein distance d1 between the beam splitter 410 and mirror 414 is different from distance d2 between the beam splitter 410 and mirror 416. In addition, light waves with equal paths, but from "different spatial points" (i.e. p1≠P2) on its "source or wavefront" do not interfere typically. As shown in FIG. 5, incoherent light 502 from electric bulb 504 (without spatial coherence) cannot form an interference pattern on detector 506 through two pinholes 508, 510, wherein a distance between the pinhole 508 and the detector 506 is equal to a distance between the pinhole 510 and the detector 506.

C. In Regard to Light Polarization

Both electric and magnetic fields of Electromagnetic Wave (EMW) 602 are oscillating, but in spatial orthogonal directions (shown in FIG. 6), wherein both electric field and magnetic field of the EMW 602 are perpendicular (i.e. light is a transverse wave) to a traveling direction of the EMW 602. In addition, on the other hand, the oscillation of the electric field and the magnetic field of the EMW 602 may be in a single direction (linear polarization) while going through linear polarizer 604, or may rotate at an optical frequency (Circular or Elliptical polarizations) while going through a circular polarizer (shown in FIG. 7).

D. Classical Model—Spatial and Temporal Coherence

In view of prior arts' EMW theory, as shown in FIG. 3, ordinary candle, electric bulb, Sun or black-body light emissions from a local distance are all spatial and temporal incoherent sources typically, wherein spatial incoherent corresponds to size of an EMW source and temporal incoherent corresponds to a wavelength or frequency dispersions of the EMW sources. But, in contrast, Star light or photon coming from much far distance outer space (e.g. start light) is coherent light.

Light wave is a "spherical" tiny wavefront while it has just emitted from sources, it reveals the "plane" wave characteristics at distance far away from the sources. To observe a fine interference pattern, the path difference of "two" light waves or Photon particles originating from the "coherent" source should keep smaller than its "coherent length or Coherence time". As shown in TABLE 1, is a summary of coherence properties of light associated with various light sources.

TABLE 1

| light sources | Spatial | Temporal | Chromatic | Remarks |
| --- | --- | --- | --- | --- |
| Thermal (Black-body) | incoherent | incoherent | Polychromatic (multi-color) | light bulb or Sun, etc. |
| Gas discharge | incoherent | incoherent | ~monochromatic | Na, He, Ne, or Hg Lamp, etc. |
| light-emitting | inco- | inco- | ~mono- | III-V |

TABLE 1-continued

| light sources | Spatial | Temporal | Chromatic | Remarks |
|---|---|---|---|---|
| diode (LED) | herent | herent | chromatic | semiconductor Compound LEDs |
| CW Laser (continuous wave) | coherent (collimated) | coherent | Strictly monochromatic | HeNe, Ar+, etc. |
| Pulse Laser | coherent (collimated) | ~coherent | Qusai-monochromatic | ~ns if Q-switched ~ps to fs if Mode-locked |

Each tiny point of the light "source" is coherent, can create its own interference pattern. For incoherent sources, they can get overlapped without having interference and not showing constant wave-phase relationship. We can improve the spatial coherence by reducing just the size of the source opening. Or, it can be achieved by increasing the distance between source and the diffractive object by reducing its view angle, etc.

E. Linear and Circular Polarization

Prior art said, both electric and magnetic fields of an EMW 602 are oscillating and transverse wave, but in spatial orthogonal directions (shown in FIG. 6), wherein both an electric field and a magnetic field of the EMW 602 are perpendicular to a traveling direction of the EMW 602, and the EMW 602 is non-polarized. In addition, the oscillation of the electric and magnetic fields of the EMW 602 may be in a single direction (Linear polarization) after going through a linear polarizer 604. Or, (as shown in FIG. 7) a liner polarized light may get rotated of its optical polarization direction after going through a quarter wave-plate or optical rotator as to forming the Circular or Elliptical polarizations light.

F. Classical Optic Nonlinearity Requires a Mathematical Fitting Model

1) Kerr Effect:
John Kerr discovered in 1875, external Electric (E) field caused double (birefringence) refraction in glass. Most materials show it, but certain ones display it more strongly than others.
2) OKE (Optical Kerr Effect) or AC Kerr Effect:
Light irradiation on some objects can induce non-linear polarizations in Media, e.g. self-focusing effect.
3) QEO (Quadratic Electro-Optic) or DC Kerr Effect:
The prior art Reveals a special case of slow varying external E field, i.e. voltage, across a material, such as KTN crystal Under E field influence, the material becomes birefringence with showing different indices of refraction for light (Photon) polarized parallel to versus light perpendicular to the applied E field directions. Kerr media reveals higher index of refraction for light polarized parallel to applied E field, and becomes nominal index of refraction for light polarized perpendicular to applied E field. The output light becomes elliptical polarized if input light is 45° polarized to applied E field direction due to different light dispersion (that is, light speed dispersion) in two orthogonal (vertical and horizontal) directions.

G. Single-Slit and Double-Slit Experiments with Classical QM Wave Statistical Models Double-slit (Young's) experiment revealed that light and matter, e.g. electron, neutron, etc., can display the subtle characteristics of wave and particle duality. The Double-slit experiment displays probabilistic nature of QM characteristics. Double-slit experiment belongs to a general class of those QM "double path" experiments, in which a wave is split into two separate waves that later combine into a single wave while it passing through the double slits (Reference: Rae, Alastair I. M. (2004). Quantum Physics: Illusion or Reality? UK: Cambridge University Press.).

Wavefront Split:
As shown in FIG. 8(a), when partition 802 blocks slit 1, laser light generated by laser source 804 passes through slit 2 to form single-slit interference patterns on screen and detector 806 (as shown in FIG. 8(b)). In addition, when the partition 802 does not block the slit 1, the slits 1, 2 make light wavefront of the laser light generated by the laser source 804 split spatially into two separate ones that get combined later on to form double-slit interference patterns on the screen and detector 806 (as shown in FIG. 8(c)). In addition, characteristics of the single-slit interference patterns and the double-slit interference patterns are shown in FIG. 8 (a), wherein shown in FIG. 8 (a), light intensity I1 is a spatial function of x, light intensity I2 is another spatial function of x, I0 is the light intensity of a single slit interference pattern located at x=0, and x=a distance of the detector 806 toward a center line (where x=0) of the slits 1, 2.

Classical wave theory indicated, for an incoherent light source, it will form a Double-slit interference pattern with $2I_0$ intensity at the x=0. But, a coherent light (e.g. Laser) source will form Double-slit interference pattern with $4I_0$ at x=0.

Amplitude/Phase Split:
Michelson, Mach-Zehnder and other interferometers split the light amplitude into two separate and coherent copies of wavefront (i.e. amplitude or phase) of by half-mirrored Beam Splitter

H. Schrödinger's Cat

In another prior art called Schrödinger's Cat which was named after famous QM thought experiment of Schrödinger as cited in References. Finally, Schrödinger's Cat (

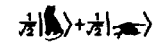

) got disproved by DSS experiments of the present invention. DSS experiments firstly conceived that the Cat can own a "defined-but-unknown state" before opening the Box enclosing the Schrodinger's Cat (Reference: Gribbin, John (2011). In Search of Schrodinger's Cat: Quantum Physics And Reality. Random House Publishing Group.).

I. Copenhagen Interpretation and Orthodox QM Theory

In another prior art of Copenhagen Interpretation and Orthodox QM Theory: In viewing of "Observer-created Universe" and according to such interpretation, one may postulate that "Consciousness Causes the Collapse" of the Wavefunctions of QM "Mathematical Model" founded realism of our world, though Orthodox Quantum Theory does deny the existence of underlying Quantum Universe's Local Realism (Reference: Howard, Don (2004). "Who invented the Copenhagen Interpretation? A study in mythology". Philosophy of Science.).

J. Parallel Universes

In another prior art of Parallel Universe (many-world) theory: A photon confronted w. two slits causes Universe to split into two; with the Photon going through one slit in one universe and the other slit in the other universe (Reference: Vaidman, Lev. "Many-Worlds Interpretation of Quantum Mechanics". The Stanford Encyclopedia of Philosophy.).

K. "Classical" QM Model of Light BS (Beam Splitter) Model—Hidden Variable Required In viewing of the prior art theory, as shown in FIG. 9(a), when incident light 902 (appearing at upper left corner) hits beam splitter (BT) 904, reflected light 906 is generated in 50% probability (shown in FIG. 9(b)) and transmitted light 908 is generated in 50% probability (shown in FIG. 9(c)), wherein the beam splitter 904 has Classical QM Beam-splitter Transfer Matrix BT1, and Ψ is a wave function of incident photon 902 MW (matter wave).

BT1 is a classical QM Beam-splitter Transfer Matrix of 50% transmitted: 50% reflected for BS with 50%-50% splits. The QM's hidden variable is needed to interpret BS or PBS (polarization BS) properties in this regard.

L. Classical QM Model for SPDC—1 Theory and the Phase-Matching Effects

Spontaneous Photon Down Conversion (SPDC) is a secrete property of non-linear crystals: Spontaneous parametric down-conversion is essential in QM optics to create EPR paired Photons (Reference: Walborn, S. P.; Monken, C. H.; Pádua, S.; Souto Ribeiro, P. H. (2010). "Spatial correlations in parametric down-conversion" (PDF). Physics Reports. 495 (4-5).

As shown in FIG. 10, when photon 1002 transmits through non-linear crystal 1004, the photon 1002 will encounter a certain probability % of being split into two lower energy photons 1006 (signal), 1008 (idler), wherein the photons 1002, 1006, 1008 need to follow the Energy and Momentum Conservations (as shown in FIGS. 11A, 11B), i.e. essentially $\omega 1002 = \omega 1006 + \omega 1008$ and K-pump (K1002) =K-signal (K1006)+K-idler (K1008). The excited atom or energy-squeezed vacuum will relax toits ground states in two stages by 1) emitting the photon 1006 at one frequency. Then, after "the lifetime of the intermediate state" of the cascade emission transitions, 2) emitting the photon 1008 at once.

Typically, there is "Entanglement" between the spatial polarization or temporal phase of the ensemble of each photon pairs. Paired Photons are phase-matched or have correlated H/V polarizations. According to prior arts, there is no phase or polarization entanglement among successive paired Photon sets.

M. Classical QM Model for SPDC-2 EPR Photon Phase-Matching Theories (Reference: Shih, Yanhua (2003). "Entangled Biphoton Source—Property and Preparation". Reports on Progress in Physics. 66 (6): 1009-1044)

The fundamentals why some amount of input photons being split is not understood as of now. In some prior arts, it is theorized by random fluctuations of excited atoms or energy-squeezed vacuum, and hence the photon pairs are created at random instance of time.

As shown in FIG. 12, it is postulated by QM, when photon 1202 transmits through non-linear crystal 1204, the photon 1202 will reveal certain probability % of being split into two photons 1206 (signal), 1208 (idler). Output of a Type-I down converter (shown in FIG. 13A) is a one-mode squeezed vacuum that contains only even photon number terms, output of the Type-II down converter (shown in FIG. 13B) is a two-mode (Horizontal-& Vertical-polarization) squeezed vacuum effects.

N. Hidden Variables—a Short History Einstein-Podolsky-Rosen (EPR) Paradox

1) EPR Story began in 1935 or earlier (References: 1) Einstein, Albert, Boris Podolsky, and Nathan Rosen. "Can quantum-mechanical description of physical reality be considered complete?" Physical review 47.10 (1935): 777; 2) Bohr, N. (1935). "Can quantum-mechanical description of physical reality be considered complete?" Physical review, 48(8), 696):

Started with a famous paper by Einstein, Podolsky and Rosen (EPR) in 1935. They claim QM (quantum mechanics) is incomplete as it predicts quantum states that have bizarre properties contrary to any "reasonable" complete physical theory. Einstein in particular believed that, via interaction of hidden variables, quantum mechanics was an approximation to a local, deterministic theory. EPR favors a local, deterministic theory and it is called "local hidden variable" theory. EPR believed, however, such a theory is possible. Entanglement (of Bell states) is possible inside the local and realist space-time of nuclei which is within the coherent time/length of particular particle sets, such as TWO electrons in ONE Hydrogen (H2) molecular.

2) Bell's Theorem Kicked Off Deeper Disputes Since 1964

Quantum mechanics permits states that cannot be described by local hidden variable. The peculiar mixture properties of quantum states permitted in QM called Entangled States. Under incidental data adjustments, it showed ameasurement on one particle of singlet state affects the state of the other, even if they are space-like separated macroscopically. Local hidden variable and Realism theories can be experimentally falsified and our Nature is weird. Many prior arts disclosed we canutilize this weirdness toguarantee perfectly secure communication in future QM communication applications.

O. QM Formalism of 4-Force Models Gravitational, EM, QED and QCD Theories (References: 1) "Standard Model of Particles and Interactions". Jhu. Edu. Johns Hopkins University. Archived from the Original on Mar. 4, 2016. Retrieved Aug. 18, 2016; 2) Meinard Kuhlmann, "Physicists Debate Whether the World is Made of Particles or Fields—or Something Else Entirely", Scientific American, 24 Jul. 2013)

Fundamental Forces in Universe are defined by a few interactions in space-time that are not reducible to more basic ones.

There are four fundamental interactions (gravitational, electromagnetic, strong nuclear, and weak nuclear) are known in classical QM theories, each one of the 4 fundamental interactions had been understood as the subtle dynamics of "Field" properties.

The prior arts disclosed: 1) gravitational force is modeled as a continuous classical field. 2) Electromagnetism and gravity produce significant forces at macroscopic scales where the effects can be seen directly in our daily life. The two nuclear interactions produce strong forces at microscopic level, subatomic distances. 3) The strong nuclear interaction is responsible for the binding force of atomic nuclei. 4) The weak nuclear interaction also acts on the nucleus, mediating radioactive beta-decay process. In addition, the prior arts disclosed, elementary particles corresponding to the 4 fundamental interactions are shown in FIG. 14.

P. What is Electron and Positron? Various Developed in Past Hundreds of Years

Prior Art Theories, in Past Hundreds of Years:

The electron is a subatomic particle (symbol e–), with an elementary and quantized unit negative charge. Electrons belong to the first generation of the lepton particle family, and are generally thought to be elementary particles because they posses no known components or substructure inside. Quantum mechanical properties of the electron include an intrinsic point-like angular momentum (spin) of a half-integer value, expressed in units of the reduced Planck constant (h) and a unit mass of $m_e$. Electron is observed as being a point-like particle associated with the duality properties of displaying its mass (me) and matter wave (MW) properties. Detected through the electron effects, e.g. particle-like mechanics or ballistic objects or ballistic mechanics, can be generating EM waves or light (photon) if accelerated in free space or conductors.

Those "Electron" particles associated with matters disclose its photoelectric behavior, e.g. Solar cell or photovoltaic stimulating effects by receiving or absorbing Light energy (or mass equivalent energy). The electron displays its natures through interaction with matters, e.g. reflection, transmission, interference, refraction, diffraction, or magnetic spin polarizations (e.g. spin up or spin down, etc.). The electron also shows quantized spin angular momentum (half-integer spin, e.g. spin-up with ms=+½ or spin-down with ms=–½) under influence of a magnetic field or matters (e.g. atoms) In addition, Quantum Field Theory (QFT) "statistically and mathematically" reconciles two points of view, through "Wave-Particle Duality" assertions of "Probability" wave-functions associated with a point-like particle (i.e. dimension-less) of electron, positron and all other fermions. Electron (e–) and positron (e+) are perhaps the simplest of the elementary particles in Universe. They appear to be point-like, that is, with no apparent internal structure, and seem to be truly elementary ones.

Q. On the EPR Paradox Quantum Entanglement Vs. Local Realist

The prior arts disputed and indicated, it was controversial through out of past century for two different camps which one was leading by A. Einstein (EPR) theory and the other was leading by B. QM theory, such as Niels Bohr, etc.

EPR Story began in 1935 or earlier: They claim quantum mechanics is incomplete as it predicts states that have bizarre properties contrary to any 'reasonable' complete physical theory. Einstein in particular believed that, via interaction of hidden variables, quantum mechanics was an approximation to a local, deterministic theory. EPR favors a local, deterministic theory and it is called "local hidden variable" theory.

Bell's Theorem kicked off deeper disputes since 1964 by advocating that QM permits states that cannot be described by local hidden variable. The peculiar properties of states permitted in QM called Entangled (singlet) States associated with closed mathematical representations.

Seemingly, Local hidden variable theories and Realism can be experimentally falsified and our Nature is weird, in case of that one neglected the loopholes behind the entanglement test data. We can see, there is another Galilei's championing of Heliocentrism against Geocentrism for long years. The present invention unveils the essence on the QM Quantum Entanglement versus Einstein (EPR) Local Realism theories associated with a few key aspects as shown in TABLE 2 and TABLE 3 in below.

TABLE 2

| QM Orthodox Theory | EPR Local Realism | Remarks |
|---|---|---|
| A. Trait and Wavefunctions of EPR Source ||||
| Photon pairs and its polarizations ||||
| Photon pairs do not have definite polarization while being created. Their polarization collapse to given state if either one being measured | Shared and acquired a property at source side before their emission. Given polarization state existed while being emitted or before measured | EPR Theory: Photons properties were unknown but determined before or while their emission at source end |
| Singlet with Symmetry wavefunction ||||
| $\|\phi_{12}\rangle = (\|HH\rangle +/- \|VV\rangle)/\sqrt{2}$ | $\|\phi_1\rangle$ = Random polarization $\|\phi_2\rangle = e^{i\delta} * \|\phi_1\rangle$ | Following PEP, photons spatial polarization is random, but is temporal orthogonal and matched with $\delta = +/- \pi/2$ for SPDC Type-I, etc. |
| Singlet with Anti-Symmetry wavefunction ||||
| $\|\Psi_{12}\rangle = (\|HV\rangle +/- \|VH\rangle)/\sqrt{2}$ | $\|\Psi_1\rangle = (\cos(\omega t + \alpha), 0)$ or $(0, \sin(\omega t + \alpha))$, $\|\Psi_2\rangle = +/- R_{90} * \|\Psi_1\rangle$ (Jones Vectors) | Following PEP, photons polarization is HV (+/- $R_{90}$) spatial matched, but not entangled for SPDC Type-II, etc. |
| HOM Effect & Model ||||

TABLE 2-continued

| QM Orthodox Theory | EPR Local Realism | Remarks |
|---|---|---|
| Modeled with indistinguishable photon pairs, got bunching at BS output due to unknown Interference or hidden variable effects | Modeled with a New MW QFT. Laser EPR pairs showed bunching effects with orthogonal in temporal for Type-I or in spatial for Type-II SPDCs | BS is a MW generator and it follows PEP, Huygens principle and Fresnel theories, etc. |
| B. Experimental Proofs ||| 
| Theoretical explanation |||
| Spooky-action at distance, i.e. an explanatory theory with FTL actions happening in our space-time. Uknown and new Interaction might exist in Universe that can have subtle force exchange with FTL speed | States are definite and measurable experimentally. Satisfy Locality, Realism and Causality (Free will) by following Relativistic (light speed) limit for all bosons/fermions interactions | Seemingly, just another Galilei's championing of Heliocentrism vs. Geocentrism. It was controversial through out of the past century |
| Bell Inequality Test |||
| Perfect matched and violated Bell theory if data being adjusted or offset (visibility ~100%) | Meeting Bell Inequality Test, classical Malus Law predicted its visibility well | Bell's comment ... Our past pictures of Nature could be experimentally falsified (by entanglement). |

TABLE 3

| QM Orthodox Theory | EPR Local Realism | Remarks |
|---|---|---|
| C. Loopholes & Disproof of QM vs. EPR Theories |||
| Locality Theory |||
| Entanglement = nonlocality. Entanglement is necessary condition for violating of a Bell inequality | There is No or little influence b/w space-like separated events/matters | By meeting Bell's test, it showed realistic and localism predicts different rotation results from QM |
| Realism Theory |||
| Bell inequalities violation provide bounds on local, realistic models | Objects' states are unknown but pre-existed independent of measurement choices of later on | Up until this point all discussion was metaphysics |
| Free will (No-enhancement) |||
| John Bell, What is proved by impossibility proofs is lack of imagination (of scientist) | We can chose what we measured independently of the particle states under measuring | EPR Theory: detection events are independent and local realist one |
| Fair sampling |||
| Incomprehensive and not logical, test data adjustment or offset required | The trait of Photon pairs is a given hidden variable. Following Malus Law, it is really complete, local and Realist | Bell's detection events are seemingly entangled, and need to do accidental event's subtracting or offset adjustment |

TABLE 3-continued

| QM Orthodox Theory | EPR Local Realism | Remarks |
|---|---|---|
| Rotational Invariance | | |
| Predicted null effect if one arm's polarization being rotated 90° in a Faraday rotator before detecting | Predicted 90° shift output, if one arm rotated 90° in polarization with Faraday rotator before detecting | Einstein - Do you believe, was the moon still there while you did not look at it? |
| HOM Reconfirmations | | |
| Predicted null effect if one arm's polarization being rotated 90° in a Faraday rotator before detecting | Photon pairs showed anti-bunching effect if one arm's got rotated 90° either in Temporal or Spatial wise. | BS is a inductive MW generator and it follows PEP, Huygens principle and Fresnel theories, etc. |
| D. Champion of Advocates | | |
| Original ones | | |
| Von Neumann (1932), Bohr (1935), Schrödinger (1935), etc. | Einstein, Podolsky and Rosen (1935), "We believe, however, such a theory (hidden variable) is possible." | There was no computer and no Laser sources in 1935 to prove or disprove EPR or Bell state violation |
| Late comers | | |
| Bohm (1952), Bell (1964), CHSH (1972), Aspect (1981) and hundreds more of recent ones | UK/Caroline Thompson's articles (1993-Feb. 2006) and the present invention (2014 ~), etc. | Entanglement and Bell states violation are possible within a short range inside of localized nuclei |

R. In Regard to Prior Art Patent Application

Among those prior arts inventions, there is a prior art invention is most related and can be differentiate with the discovered invention of the present invention. In the following, it is self-explained the drawbacks of those related prior art patents, tools and methods inventions before the invention of the present invention.

Remote Angle Measurement:

Prior arts for angle measurement tools and methods have some drawbacks, e.g. requiring long base lines or target objects for alignments, requiring contact mode to determine an angle and its directions, requiring complicated optical alignment steps, not fitting into a small space or object which target resided in, accuracy being not good enough and a measurement cycle time is long, and so on.

In a prior art (CN 103913132A) disclosed for Laser based angle measurement tools and methods. The prior art discloses a laser angle measuring gauge which is composed of a gauge body, a first stand bar, a second stand bar, a first laser device and a second laser device connected. The laser angle measuring gauge is simple in structure and convenient to use, and non-contact type measurement of various angles is achieved. On the other hands, that TWO Laser angle measurement tools requires manual alignment for the two different directions of TWO different objects in macroscopic metrics to determine the angle between to point of interests. However, this type of method and tool cannot easily perform the ONE Laser one-pass measurement and/or automatic computing the inner angle in between two microscopic plane surfaces jointed together.

In another prior art (Motamedi et al. (U.S. Pat. No. 7,796,782)) disclosed a method measures the distance between two arbitrary points of interest from the user position by determining the range and angle between the two points with only ONE Laser beam. Please refer to FIGS. 1A, 1B and Col. 4, lines 33-54 of Motamedi. Col. 4, lines 33-54 of Motamedi discloses "When the laser beam 10 strikes the scanning mirror 26, the reflection from the mirror 26 forms a stationary circular beam directed to a target plane 27 . . . . If an AC voltage is applied with a DC bias that places the cantilever beam 24 in position 2 (see FIG. 1B), FIG. 1A and FIG. 1B can be seen as illustration of the movement of the scan beams 16 and 18. In this case, the angle formed between the scan beams 16 and 18 is referred to herein as the "scan angle" $2\alpha$. Note that scan angle $2\alpha$ can also be measured as the two times of angle $\alpha$ between the position 3 and position 4, of the cantilever beam 24", so according to Col. 4, lines 33-54 of Motamedi, Motamedi needs to apply the AC voltage to cantilever beam 24 to control movement of cantilever beam 24, wherein reflected light of laser beam 10 is also moved with the movement of cantilever beam 24. Therefore, a distance corresponding to straight scan line 28 on target plane 27 can be measured by scan angle $2\alpha$ and measurements of a distance from scanner 11 to each of two endpoints 20 and 22 of scan beams 16 and 18. Therefore, because measurement of the distance of straight scan line 28 corresponds to scan angle $2\alpha$ and the distance from scanner 11 to each of two endpoints 20 and 22, measure method of Motamedi is more complicated (that is, Motamedi needs complicated optical alignment steps to measure the distance of straight scan line 28.

In some other angle measurement known methods, it required long base lines or target objects for alignments. It required either in contact mode as to determine the angle, or its directions required complicated optical alignment steps which cannot fit into a small space or object which target DUT (samples or Device-Under-Test) resided in. The accuracy of those methods or tools are not good enough and its measurement cycle time is quite long without having the automation capability.

SUMMARY OF THE INVENTION

All kinds of experimental results of the present invention have evidenced the postulated theory of the present invention as followings:
1) The background of universe comprises hidden "mass-less" charge Quanta (Yang) and anti-charge (Yin) Quanta which are the most elementary ones among known elementary particles, including the known fermions (e.g. quarks, leptons, antiquarks, and antileptons), as well as the bosons (e.g. photons and gauge bosons).
2) EM wave is created by Electromagnetic field polarization and ripple effects of hidden Yin-Yang charge Quanta in a vacuum of our universe. The EM wave is formed and propagated via interactions of polarized latent (i.e. not being born yet) Yin or Yang charge Quanta associated with the Vacuum.
3) There is a "mass-less" MW wavefront, associated with each boson (e.g. photon) and fermion (e.g. electron) elementary particles, sees the solar systems, and perhaps the entire Universe by obeying the Relativistic Theory and Dirac equation either in macroscopic or microscopic aspects.

As a representation of new light Model, the present invention discovers and evidences following properties of light (i.e. photon):

Light is comprised of a pair of Charge Quanta, matter Wave (MW) and mass-equivalent energy $E_m$ (i.e. it is equivalent to relativistic $M_E$; energy-equivalent mass or motion mass) packet which is associated with a finite size and traveling wave solution with stable life-time in Universe.

In Sun, an energy packet of a photon is born to see the Solar system and perhaps the entire Universe, via the wavefront of its mass-less MW (i.e. a matter Wave tensor in space-time) at the light speed.

The "rotating double strands" of energy ($E_m$) twists represents the "+/−energy (i.e. mass) phase polarizations" of Vacuum, get entangled with a pair confined anti-charge and charge Quanta in our space-time, that refers to the fine structure of a Photon. Under the same model or representation, each boson comprises of two rotating partner (double) strands of "energy and anti-energy threads" which are wound together in a twisted form so as to form a boson in the space-time, just like a pair of rotating binary stars.

Light energy $E_m$ (or mass $M_E$) propagating at a speed of "c". Light energy $E_m$ (or mass $M_E$) reveals its particle-like "photon" with ballistic-mass behavior, e.g. shadow, impact or pressure behaviors, photoelectric effects and the like. Also, MW of light, it is associated with the energy core of a photon, conveys the wave behavior of a single Photon, e.g. polarization, interference, refraction, diffraction, "virtual-photon or -particle strong interactions" by following Quantum Wave Mechanics.

A set of "MW" equations associated with photon's mass-equivalent energy $E_m$ (or energy-equivalent mass $M_E$) reconciles the two viewpoints of light duality, through the articulate "MW and Energy (i.e. MWE)" Packet (or MWE Particle) theory.

The present invention discovers the basic theory and model representation for both bosons and fermions. Also, the present invention contributes the methods and apparatus coming from the new light model which has been manifested by MW-and-Energy (MWE) Packet postulated theory. Through MWE Packet theory and related experiments, it has been proved the "Wave-and-Particle" duality properties of light in Nature. The summary shall be described in a few key aspects as follows.

A. Fundamental Science Technology

The present invention set up the No. 1 record in human history of measuring separately the MW, MWE Packet behaviors associated with the light (i.e. Photon). Having beam splitter (BS) act as conjugate non-Hermitian MW* generator by following Pauli Exclusion Principle, the present invention discovers the inventive use of Mach-Zehnder interferometer and non-linear Kerr Cell (non-linear) Deflectors as to manifesting the New light Model and proving the validity of Einstein's Local-Realism Theory.

The present invention creates the new quantum theory of optical coherence for light quanta (i.e. Photon), it discovers ground-breaking experimental methods that enable the human being as to measure and manipulate the individual quantum particle (e.g. single Photon) measuring systems. It devices the fundamental particle-based remote precision angle measurement methods and tools for nano-meter scale geometry or even sub-atomic structures of different objects.

The present invention has developed of new methods and apparatus to cool and trap atoms or ions or fundamental particles by using the spatial-lattice structures via MW property associated with bosons (e.g. laser light/Photon) or fermions (e.g. Electrons), etc.

The present invention has discovered the fundamental work piece in boson's and/or fermion's MW ultra-high resolution optics and imaging systems, and for the design of the first non-invasive high power 3D imaging microscope for observing atomic level structures or living cells in Bioscience areas.

The present invention reinvents and solidifies basic work on Quantum information and Quantum-entanglement communication technologies. Also, it services the development of the new non-invasive holographic 3D imaging methods and tools by utilizing the MW wavefunction and new diffuser materials as to create most fine image resolutions without having the speckle noises. Also, it predicts and new methods of controlling the life-time of neutron diffusion technique to be applicable to the future movable or even portable mini-scale nuclear power plant methods and apparatus.

The present invention discovers a single Photon (MWE packet) interferes with the conjugate MW* of itself. It can be evidenced physically by the interfering patterns in between MWE wavefunction and its replica MW or conjugate MW* wavefunction, either generated by an amplitude split method of beam splitter, or by the Wave-front split method of a double slits. In the broader scopes, all the interferometry or beam splitters have so far been constructed successfully for electrons, neutrons and a number of different atoms and molecules shall be sharing the same New Model for BS and light (i.e. Photon). For the first time in Human history, the present invention disprove the Schrodinger's Cat, Wheeler's delayed decision and Quantum Erase theories of QM, it DOES reveal that BS can generate inductively conjugate MW* for incident light Quanta (MWE) in no time while a Photon's path information being well defined.

B. Exemplary Embodiments and Future Development in Nature

The central fallacy of classical QM, which occurs always in any multi-path information experiment, is due to the insistence on a QM idea that the paths of Photons will not be defined through different paths of an interferometer. It is important to emphasize, the present invention evidences Einstein's principle of Local-Realism Theory, while the respective Photon's interfering pattern's can still been seen by excluding (or deflecting) the Photon (MWE) information of the other path respectively.

In this context, the importance of those embodiments of this invention acting as the most fundamental evidences for us to manifest new duality of all boson and/or fermion becomes quite clear. Also, it discovers the origin of the broken symmetry, predicts the existence of at least the MW and teaches the non-Hermitian properties of beam-splitter and MW* while a BS has been encountering fundamental particles, e.g. bosons and/or fermions in nature.

The present invention penetrates and invalidates the postulations of parity violations (i.e. violation of fundamental symmetry law) in the beta-decay of neutral Co60. It discovers the unified theory of the parity conservation law among interactions of elementary particles, by including the Pauli Exclusion Principle, the non-Hermitian MW* wavefunction and a few basic conservation laws, e.g. energy, momentum and angular momentum conservations.

The present invention has decisive contributions to the larger scopes of future Science technology and Nature research projects, including 1) the way to set up and theorize the new unified theory in between of the strong and gravitational interactions, 2) theoretical and experimental studies of the most fundamental Elementary Quanta in the universe, e.g. Yin-/Yang-charge Quanta, double-strained energy packet associated with point-like positive energy and negative energy states. The present invention serves the fundamental works in quantum electrodynamics (QED), with deep ploughed consequences for the theoretical physics of elementary particles and universe, especially, for the statistical interpretation of the properties for non-Hermitian MW wavefunction and for the laws governing the interactions/forces among multiple bosons or fermions, including the Concise Grand Unification Theory (GUT) and a new set of General Conservation Laws (GCL).

The present invention indicates the road way to theoretically discover a mechanism that contributes to our understanding of the origin of mass, orbital and spin angular momentums of boson/fermion subatomic particles, and it is predicted that it can be further confirmed through the high energy Physics Laboratory apparatus, such as the ATLAS and CMS experiments by using Synchrotron Collider, Large-Hadron Collider (LHC), and the like. Also, the present invention create a new page to renovate General Relativities in physics concerning to the very large scale of Galaxy space in Universe. It is well known, the rotational curves (or orbital speeds) of galaxies and stars do not follow the rules found in other orbital systems such as stars, planets and moons that have most of their mass at the centre, like the Solar system. Stars revolve around their galaxy's centre at equal or increasing linear speed over a large scale of distances toward the edge of a galaxy. In contrast, the orbital velocity of planets in Solar systems and moons orbiting planets decline with distance while it reflecting the mass distributions within such Star system. The mass estimations for galaxies based on the light they emit are far too low to explain well the velocity observations.

In cosmology, the galaxy rotation curve paradox is the discrepancy between 1) observed galaxy rotation curves and 2) the theoretical prediction, by assuming a centrally dominated mass associated with the observed luminous materials. When mass profiles of galaxies are calculated from the distribution of stars in spirals and mass-to-light ratios in the stellar disks, they do not match with the calculated masses derived from the observed rotation curves and the law of gravity. A past prior art solution to this paradox is to hypothesize the existence of dark matter and to assume its distribution from the galaxy's center out to its halo far away to the edge of the galaxy space.

By far, the take-away alternative is to take the advantage of the new Concise GUT (Grand Unification Theory) of this invention, the most notable point of the NEW theory of this invention is that we do not need to appeal for hypothetical New Newtonian Dynamics, which involves modifying the laws of Gravity. Having said that, the present invention offers the most simple, concise and successful theoretical model as to spell out the rotation curves paradox as followings:

1) All kinds of emission foams or halos of massive energetic particles (e.g. fermions, bosons, photons, gaseous, black-holes, gray-holes and the like) have been keeping emitting for millions of years in the background of the galaxy space. The relativistic and scalar/vector potential dependent mass (or energy) of those massive emission particles and the like, including lights, will respect simply the classical-Relativistic Newtonian Gravity Dynamics.

2) The total sum of scalar/vector potential dependent relativistic-energy or -mass possessed by those numerous energetic (mass)particles, either it is a dark or a bright ones, including all latent energies associated with the background temperature, various scalar field or vector field potentials of the Galaxy system in all its forms (e.g. E, B, G, W field potentials of Concise GUT), are conserved and respect the Relativity energy and mass conservation rules. Their total energy-equivalent mass will still obey the classical Newtonian Gravity Dynamics in galaxy space as well.

C. Moreover, the Present Invention can Solve Major Challenges for Future TCAD (Technology Computer Aided Design)/TCAM (Technology Computer Aided Manufacturing) Extendibility Major challenges TCAD/TCAM Extendibility: It Needs to connect multiple measurements/methods at nanoscale to properties in a large area using modeling and simulation. For Example, Simulations of SRAM cell show that each transistor experiences a different stress field—measuring one transistor dose. The future TCAD/TCAM requires being able to do the most precision Modeling, Simulation, and Metrology for Final Stress in SRAM Cell I-V characteristics or behavioral changes (Reference: Investigation of E-beam patterned nanostructures using Mueller Matrix based Scatterometry, G. R. Muthinti, B. Peterson, and A. C. Diebold, Metrology, Inspection, and Process Control for Microlithography XXVI, SPIE Advanced Lithography, San Jose, Feb. 13-16, 2012.).

An embodiment of the present invention provides a non-contact angle measuring apparatus. The non-contact angle measuring apparatus includes a matter-wave and energy (MWE) particle source and a detector. The MWE particle source is used for generating boson or fermion particles. The detector is used for detecting a plurality peaks or valleys of an interference pattern generated by the boson or fermion particles corresponding to a slit, a bump, or a hole of a first plane and matter waves associated with (or coherent) the boson or fermion particles reflected by a second plane, wherein angular locations of the plurality peaks or valleys of the interference pattern, a first distance between a joint region of the first plane and the second plane, and a second distance between the detector and the slit, the bump, or thehole areused for deciding an angle between the first plane and the second plane.

As exemplary major challenges for mission critical TCAD/TCAM extendibility: It needs to connect multiple measurements/methods at nanoscale to properties in a large area using modeling and simulation. For Example, Simulations of SRAM cell show that each transistor experiences a different stress field—measuring one transistor dose. The future TCAD/TCAM requires being able to do the most precision Modeling, Simulation, and Metrology for Final Stress in SRAM Cell I-V characteristics or behavioral changes.

The present invention utilizes matter wave of bosons (e.g. Photon) and/or fermions (e.g. electron, neutron) to apply to non-contact angle measuring apparatus. Because matter wave of bosons and fermions does not include energy, the present invention not only can solve disadvantages corresponding to remote angle measurement shown in description of the prior art, but can also satisfy the above mentioned future development in Nature.

These and other objectives of the present invention will no doubt become obvious to those of ordinary skill in the art after reading the following detailed description of the preferred embodiment that is illustrated in the various figures and drawings.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

FIG. 15A is a diagram illustrating the 3D representation of a light quantum (photon) new model associated with the space-time limit of universe.

FIG. 15B is a diagram illustrating the 2D representation of a light quantum (photon) new model associated with a pair of rotating charge (+) and anti-charge (−) quanta.

FIG. 19A is a diagram illustrating a new light model corresponding to reflection and refraction of the incident light when the incident light encounters the first material associated with smaller refractive index.

FIG. 19B is a diagram illustrating a new light model corresponding to reflection and refraction of the incident light when the incident light encounters the second material associated with greater refractive index.

FIG. 41 is a diagram illustrating KTN's QEO effect by causing asymmetrical electric dipole polarization with changing the crystal MWF and scalar/vector potential distributions of the crystal materials when the external electric field is applied.

FIG. 45A is a diagram illustrating sidewall reflecting MW wavefront-split of the light and forming the upper-half interference patterns of the double-sit experiment when light passes through slit, and FIG. 45B is a diagram illustrating the conventional single-slit interference patterns.

FIGS. 46A, 46C are diagrams illustrating sidewall reflecting MW wavefront-splits of the light to form upper-part and lower-part of double-slit interference patterns on screen when light passes through upper/lower slits respectively, and FIG. 46B is a diagram illustrating complete double-slit interference patterns being formed on screen if the sidewalls are with about negligible thickness.

FIGS. 88A, 88B, 88C are diagrams illustrating a new model for T-θ Puzzle or Kaon (K+) decay paradox.

FIG. 106 is a diagram illustrating self-explained experiment results corresponding to FIG. 105.

FIG. 110 is a diagram illustrating a non-contact angle measuring apparatus according to a first embodiment of the present invention.

FIGS. 111A, 111B are diagrams illustrating another embodiments of non-contact angle measuring apparatus.

FIG. 112A is a diagram illustrating a mission critical inspection apparatus according to a second embodiment of the present invention.

FIG. 112B is a diagram illustrating another embodiment of non-uniform magnetic arrays of the MW filter applied to a mission critical inspection apparatus for fermion particles.

FIG. 113 is a diagram illustrating the mission critical CD and defect inspection apparatus being a part of precision overlay measurement or alignment system to inspect Box-in-Box (BiB) or Box-on-Box (BoB) patterns for precision overlay or alignment purposes.

FIGS. 114, 115 are diagrams illustrating typical semiconductor wafer or mask tooling inspection defects being characterized with spots, satellite, surface/substrate contaminations, bridging, residues, nano-bubbles, miss-happen or missing contacts/via-holes, etc.

FIG. 116 is a diagram illustrating a mission critical transmission-type non-invasive diagnosis and/or treatment apparatus according to a third embodiment of the present invention.

FIG. 117 is a diagram illustrating a transmission-type non-invasive measuring apparatus according to a fourth embodiment of the present invention.

FIG. 118 is a diagram illustrating a fermion source including a plurality or array of Field Emission (FE) tips being coupled with a plurality of bias voltages and electrodes to select desired QM spins.

FIG. 119 is a diagram illustrating transmission-type measuring apparatus FIG. 119(c) of the fourth embodiment of the present invention versus other prior art embodiments FIG. 119(a), 119(b).

FIG. 120A is a diagram illustrating an apparatus for generating a virtual space-time lattice according to a fifth embodiment of the present invention.

FIG. 120B is a diagram illustrating magnification of 3D view of the virtual space-time lattice.

Figure 121A:
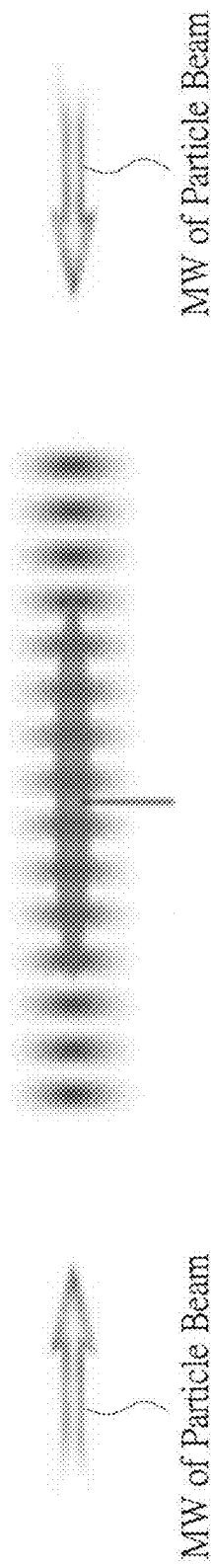
Figure 121B:
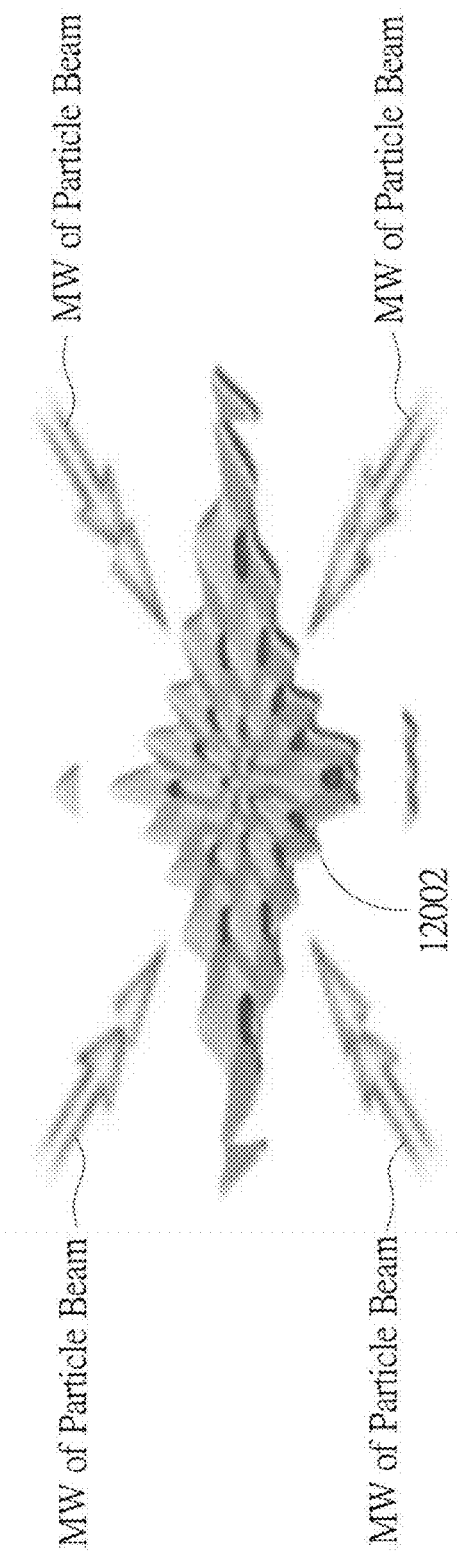

FIGS. 121A, 121B are diagrams illustrating the virtual space-time lattice being one-dimensional or two-dimensional spatial lattices according to another embodiment of the present invention.

Figure 122:
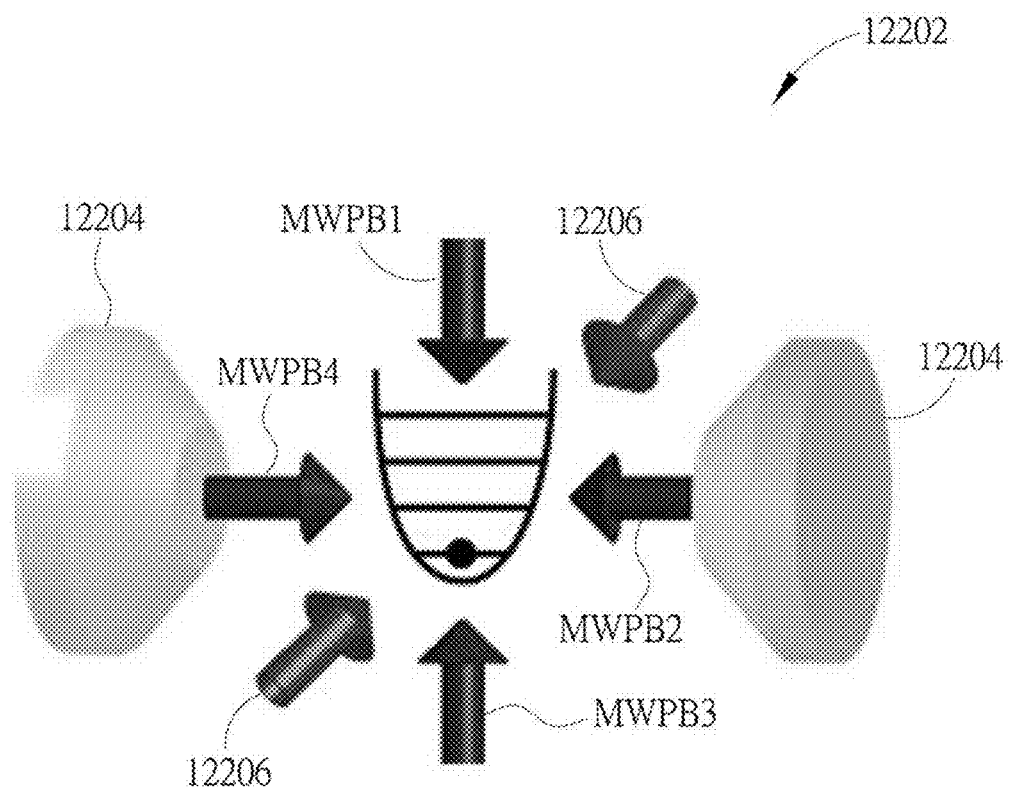

FIG. 122 is a diagram illustrating a Magnetic MW Trap (i.e. MMT) according to a sixth embodiment of the present invention.

Figure 123A:
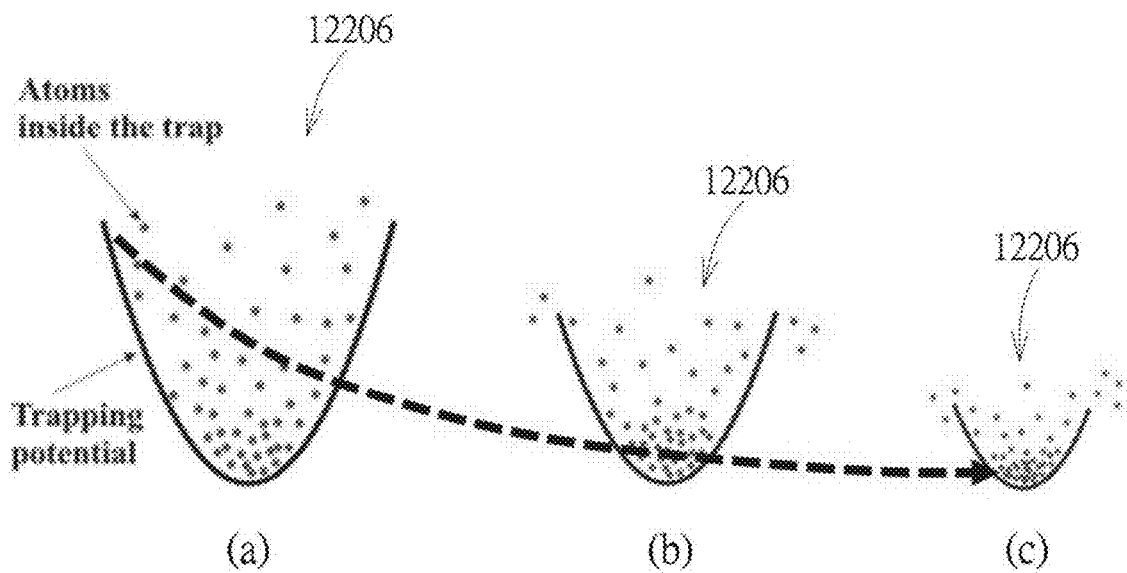
Figure 123B:
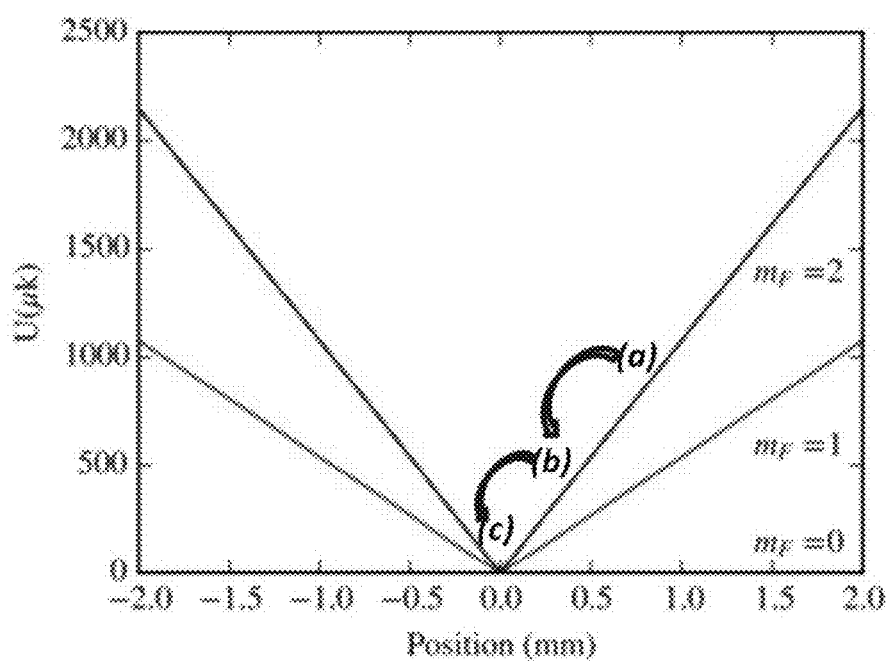

FIGS. 123A, 123B are diagrams illustrating a sequence of steps of cooling down process by state (a)→state (b)→state (c) of the free atom cluster for making fine atomic clock.

Figure 124:
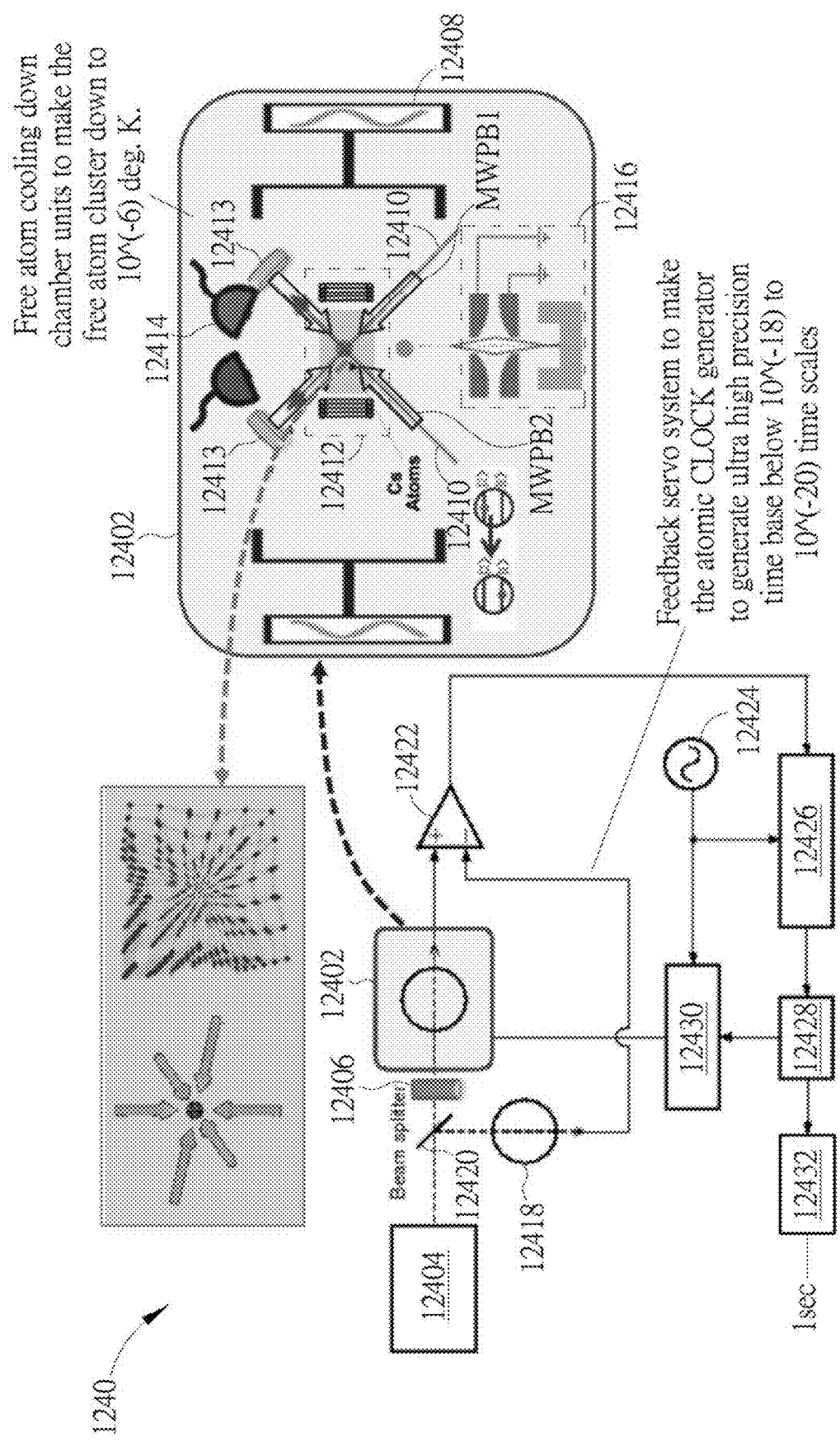

FIG. 124 is a diagram illustrating an ultra-fine atomic clock according to a seventh embodiment of the present invention.

DETAILED DESCRIPTION

Before describing the embodiments of the present invention, matter wave (MW), gravitational wave (GW), matter wave field (MWF), gravitational wave field (GWF), mass equivalent energy ($E_m$), energy equivalent mass ($M_E$), electron mass ($m_e$), light or photon (i.e. GW-and-energy particle, GWE packet, GWE particle, MW-and-energy packet, MWEpacket, MWEparticle, or MW-and-energy packet/particle), electromagnetic field (EMF), electromagnetic wave (EM wave, EMW), fermion pair production (FPP), boson pair production (BPP), charge quanta confinement (CQC), Pauli Exclusion Principle (PEP), and concise grand unification theory (concise GUT) are pre-defined terminologies for our reference only.

1. As shown in FIG. 15A, an MWE Packet, i.e. a packet of energy thread (Yang+) 15021 and an anti-energy thread (Yin−) 15022, is a "traveling" MW tensor solution via mass-less charge quantum 15023 (charge quantum, Yang +) and mass-less anti-charge quantum 15024 (anti-charge quantum, Yin−) interacting with MW (matter wave) 15025 of the photon 1502 in Universe all the time, wherein label 15026 represents a limit of the MW 15025 in the Universe.
2. The photon's equivalent mass ($M_E$) and its mass-equivalent energy ($E_m$) dissolve and convert into other forms of energy, e.g. kinetic energy, potential energy or heat, etc., once it comes to a stop in space-time. Also, it indicates rest mass of the photon 1502 is equal to 0 while its energy vanished.
3. Moving mass-equivalent energy ($E_m$) of the photon 1502 is equal to $\hbar\nu$.
4. Motion mass or energy equivalent mass of the photon 1502 is equal to $E_m/c^2$.
5. Speed c of the photon 1502 is equal to $3\times10^8$ m/sec in vacuum (i.e. MW's group velocity).

A. Duality Properties of Light MWE (Matter Wave and Energy) Packet

Please refer FIGS. 15A-15B. FIG. 15A is a diagram illustrating a three-dimensional (3D) view representation of photon 1502, and FIG. 15B is a diagram illustrating an x-axis section view representation of the photon 1502 discovered by the present invention. As shown in FIGS. 15A-15B, the present invention discovers the photon 1502 can be regarded interchangeably as Gravitational Wave and Energy (GWE) packet or matter wave and energy (MWE) packet, wherein GWE and MWE are essentially the same thing in Physics, and wherein GW and MW are the same thing n Physics as well, and the photon 1502 has commonly known characteristics as follows:

When the photon 1502 (i.e. MWE particle) travels at light speed c, it can still carry a momentum associated with the motion equivalent mass ($M_E$). In addition, $\hbar$ is Planck's constant ($6.6262*10^{(-34)}$ J*sec), $\nu$ is the temporal oscillation frequency of MWE packet (1/sec), $c=\lambda\nu$ "dispersion relation" hold in vacuum only, and $\lambda$ is wavelength (m). Also another representation of a liner polarized Photon, as shown in FIG. 15A, a diameter D corresponding to the rotating motion diameter of anti-charge quantum (Yin−) and charge quantum (Yang+) is much less than λ and the arrow indicates the traveling direction of MWE packet or photon.

Figure 16:
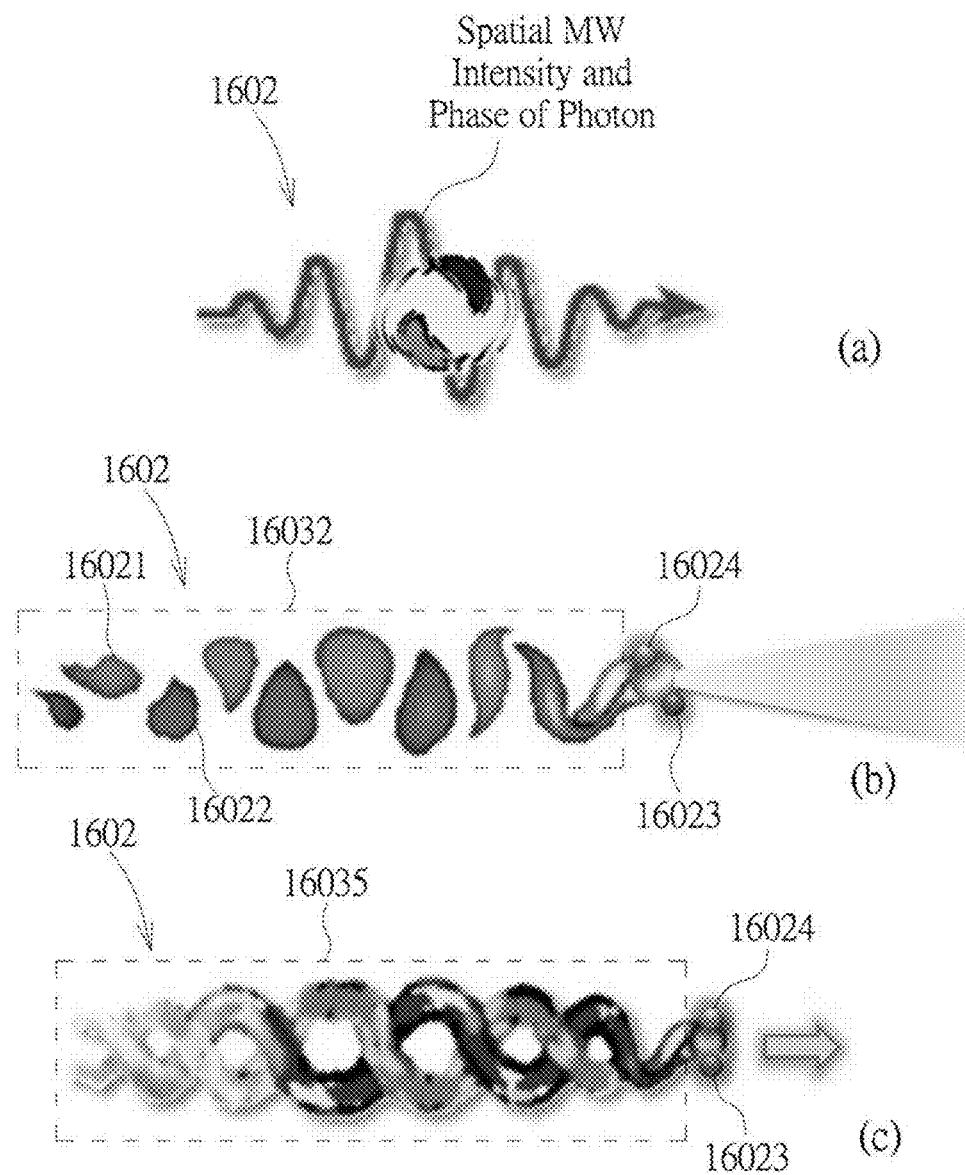
FIG. 16 is a diagram illustrating various two-dimensional (2D) representations of the photon.
Figure 17:
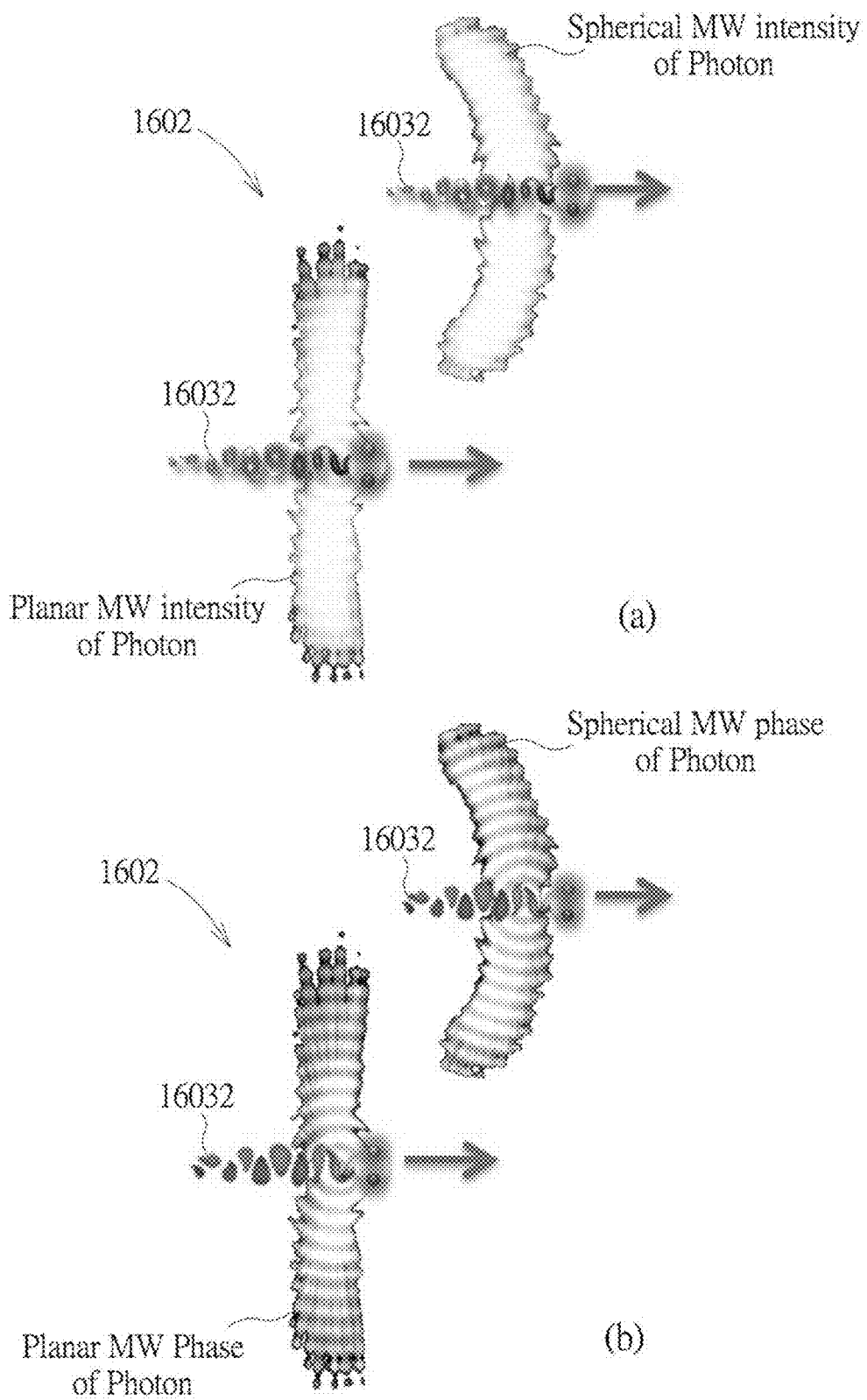
FIG. 17 is a diagram illustrating cross-sectional view representation of the photon.

B. Present Invention Discovers a Few Useful Representations for Describing the Properties of a Light MWE Packet Model in Essence Please refer to FIGS. 16, 17. FIG. 16 is a diagram illustrating various two-dimensional (2D) representation of photon 1602, and FIG. 17 is a diagram illustrating various cross-sectional view representation of the photon 1602. FIG. 16(*a*) shows that the photon 1602 has associated Spatial MW Intensity and Phase, and energy core 16032 of linear polarization photon, FIG. 16(*b*) shows the energy core 16032 of linear polarization photon, anti-charge quanta 16024, charge quantum 16023, energy thread (Yang+) 16021 and anti-energy thread (Yin−) 16022 of the photon 1602, and FIG. 16(*c*) shows the cross-sectional view representation of energy core 16035 of circular polarization of the photon 1602.

FIG. 17(*a*) shows spherical MW intensity and planar MW intensity cross sectional view representations of the photon 1602, and FIG. 17(*b*) shows spherical MW phase and planar MW phase cross sectional view representations of the photon 1602.

C. Light Irradiation Spectrum of MWE Packet for Sunspot

The present invention indicates the EM wave is generated by interaction of Yin(−) or Yang(+) mass-less-charge Quanta with the electric dipole polarization state of Vacuum, i.e. it is not with having the same inner structure of the light or photon. In addition, the present invention models the light by a traveling MWE packet which is associated with the energy $E_m$ (or motion mass $M_E$) of a light Quantum having a finite size and stable life-time. MWE wavefront packet is Relativity and time-varying traveling "tensor" solution of a single Photon which couples to every objects of our Universe in all aspects, such as geometry, composition, kinetic energy, scalar/vector potential or shape of those objects.

Figure 18:
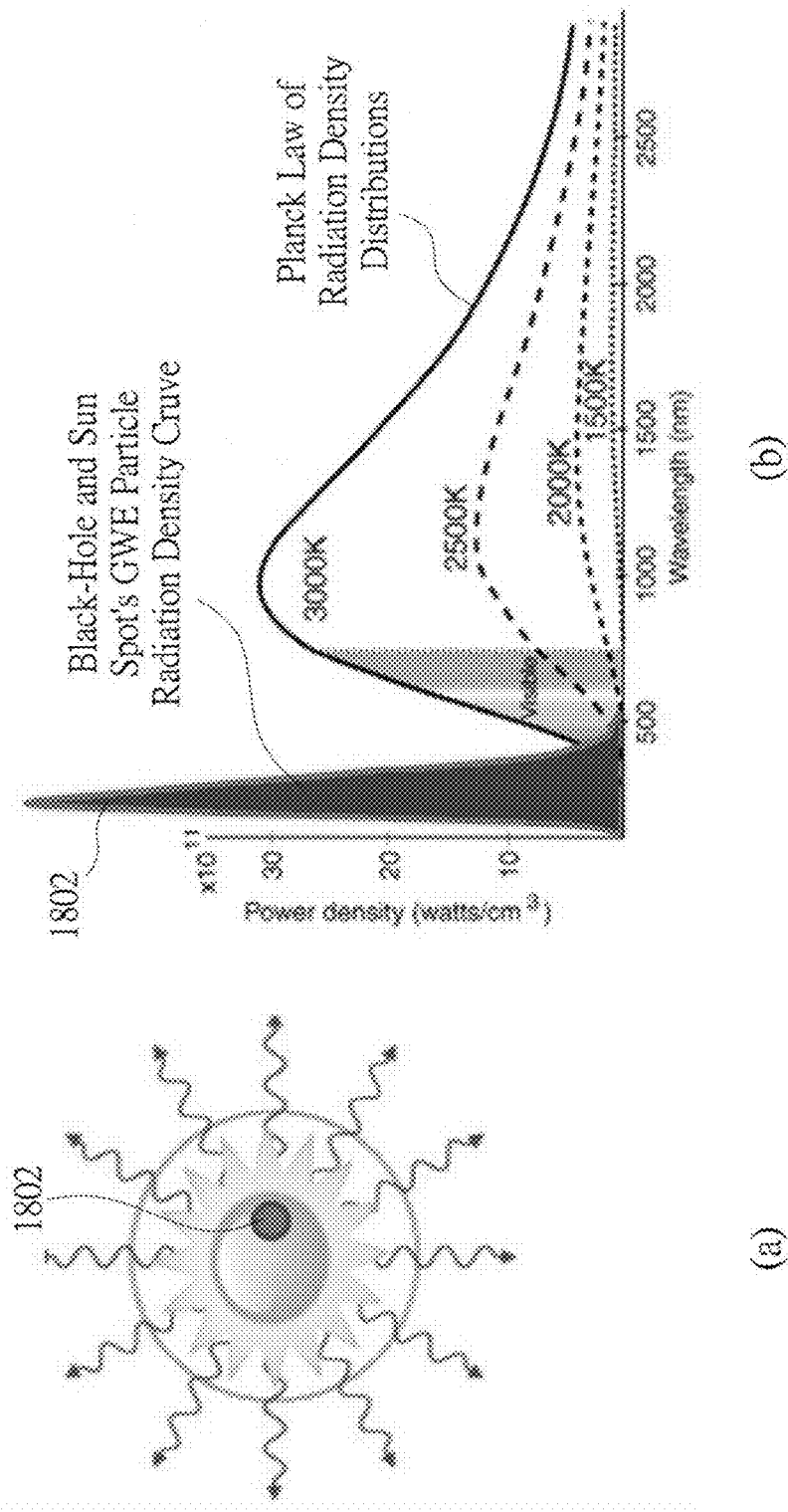
FIG. 18 is a diagram illustrating the light (Photon) MWE particles irradiation of the sun, and the cosmological Blackhole, dark star spot and the dark sunspot followed Planck's and Relativity Theories by forming gigantic scale of high-energy short-wavelength photon radiations.

The present invention also discovers that the light is a MWE packet or particle with mass ($M_E$). Coincidentally, the light (Photon) MWE particles irradiation of the Sun (as shown in FIG. 18(*a*), followed the Planck "Blackbody Radiation Theory". Furthermore, the cosmological Blackhole (or Gray-hole), dark starspot and the dark Sunspot 1802 followed Planck's and Relativity Theories by forming gigantic scale of high-energy short-wavelength photon radiations (as shown in FIG. 18(*b*) with wide ranges of MWE packets (or GWE particles) once in a while, such as Quasar and dark Sunspot radiations, etc. Based on the Concise GUT's prediction of this invention, it is believed that the black holes in deep universe all are comprised of particles or matters primarily with mono-polarity energy (i.e. are deficient or inadequate of the opposite type of energy so as to form regular matters or particles such as proton, neutron, etc.), either positive or negative energy associated with extremely dense MWF around the equator of the rotating (or spinning) black holes. The same theory predicted that dark Sunspot is literally a miniaturized black hole rotating inside the body of the Sun for millions of years, wherein the Sunspots possess extremely dense MWF around the spinning equator of itself by introducing the Gravitational collapse effect in its equator zone. There is no any radiation or light can be escaping from the Sunspot around its equator except those particles with very high energy and extremely short wavelength (such as x-ray or Gamma-ray) can be leaving the Sunspot along its North- or South-pole polarized directions with less or minimal Gravitational collapse effect.

D. New Model for Light Refraction

Figure 1A:
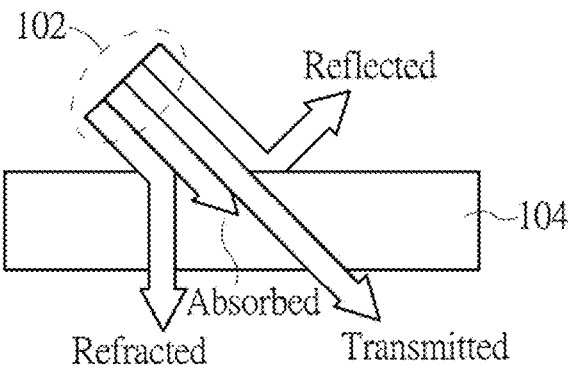
FIGS. 1A-1C are diagrams illustrating the light is either absorbed, transmitted, reflected, refracted, scattered, or diffracted when the light encounters an object.
Figure 1B:
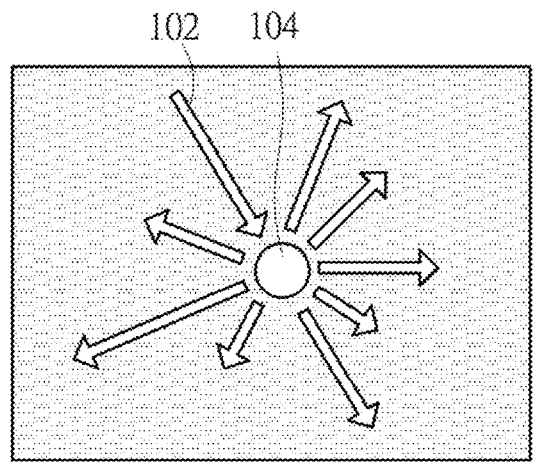
Figure 1C:
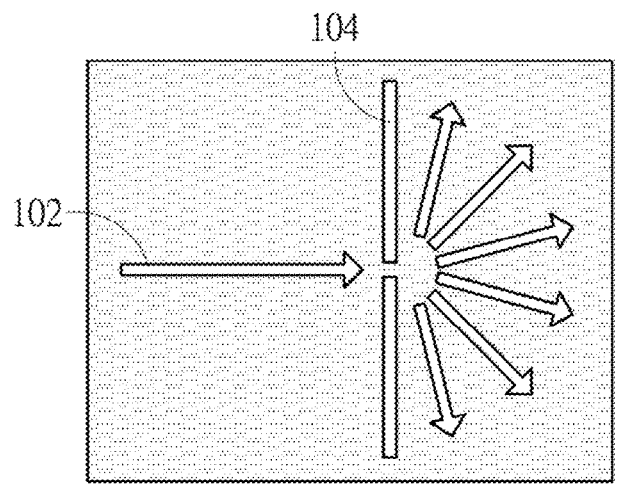
Figures 2A, 2B:
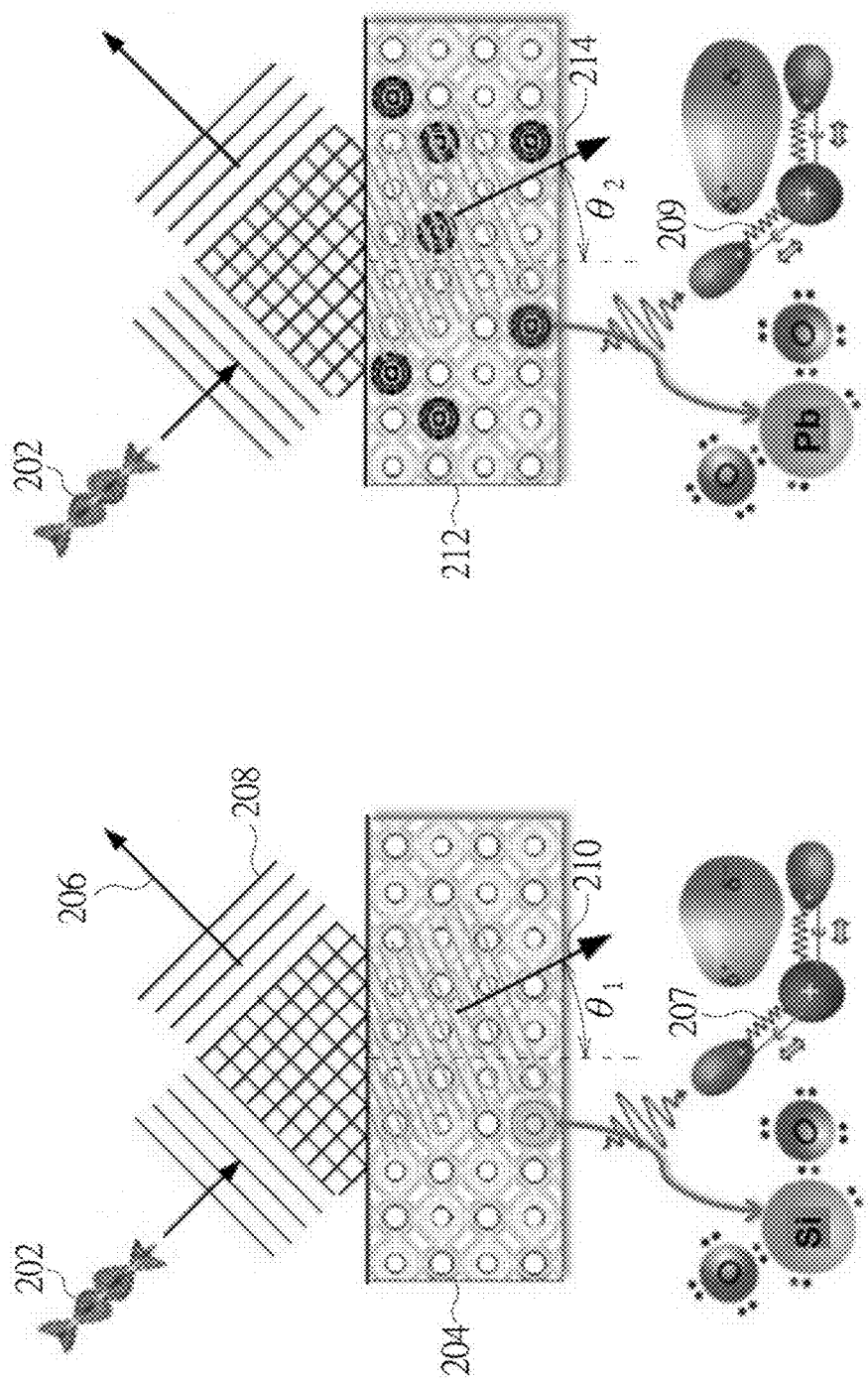
FIG. 2A is a diagram illustrating reflection and refraction of light when light encounters materials associated with smaller refractive index.
FIG. 2B is a diagram illustrating reflection and refraction of light when light encounters materials associated with greater refractive index.
Figure 3:
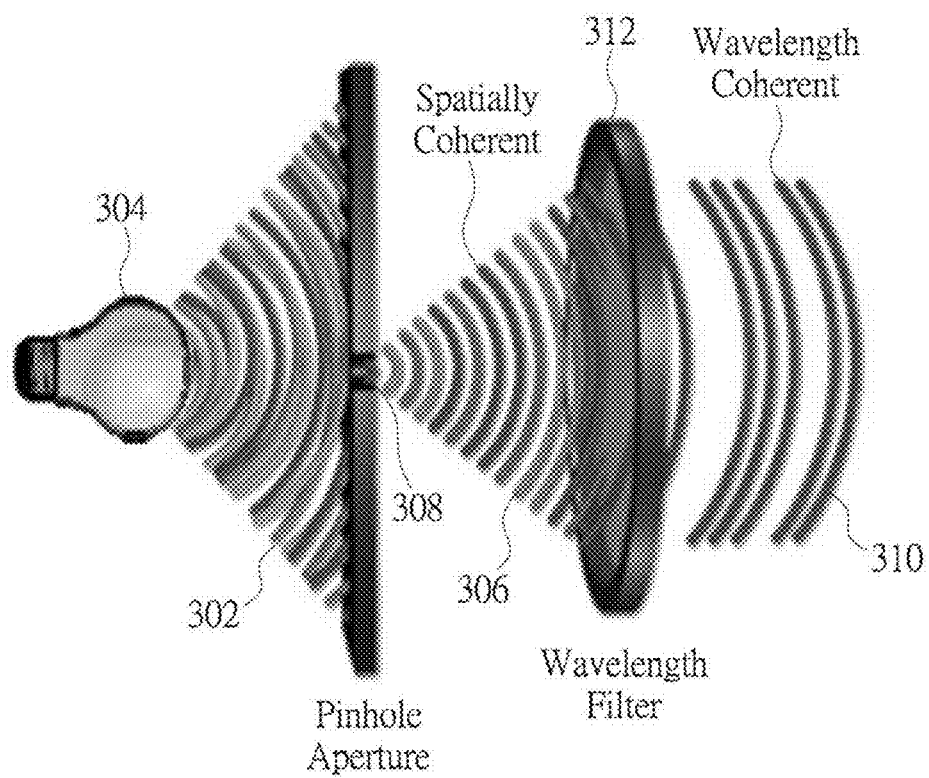
FIG. 3 is a diagram illustrating incoherent light emitted from electric bulb becoming spatial and temporal coherent light by spatial and wavelength filter.
Figure 4:
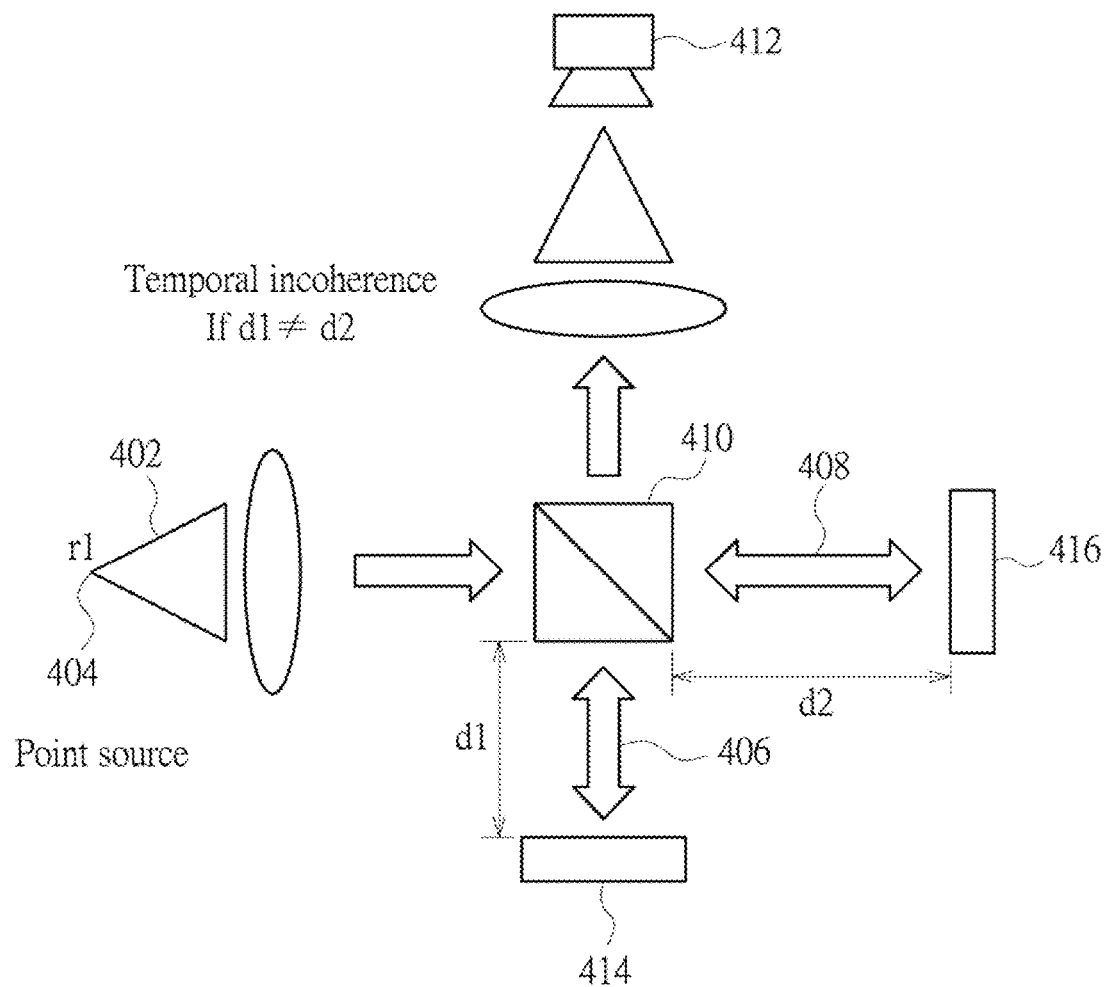
FIG. 4 is a diagram illustrating Michelson interferometer.
Figure 5:
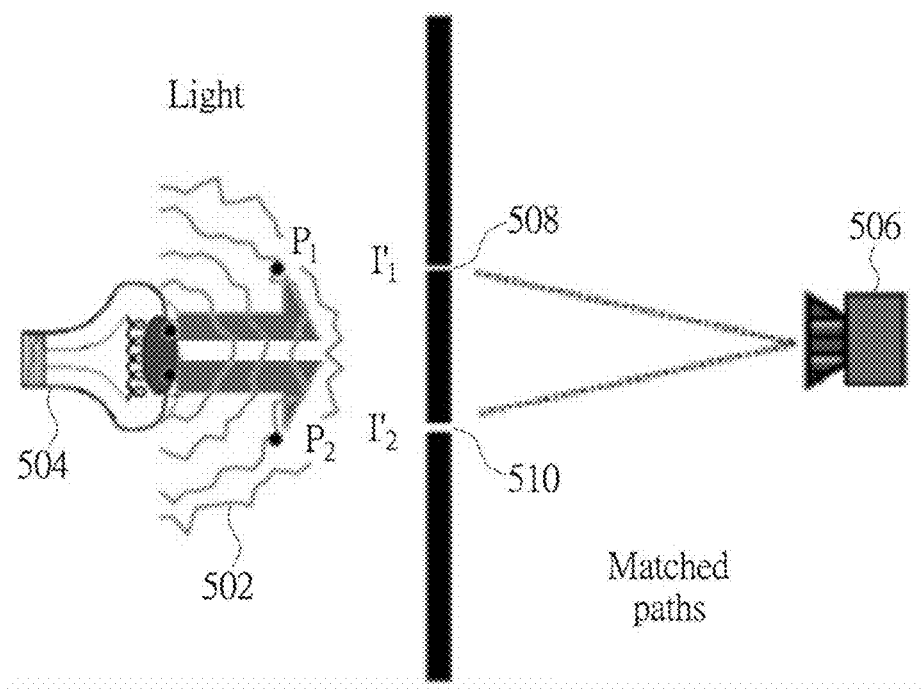
FIG. 5 is a diagram illustrating Yang's Double slits experiment with incoherent light source.
Figure 6:
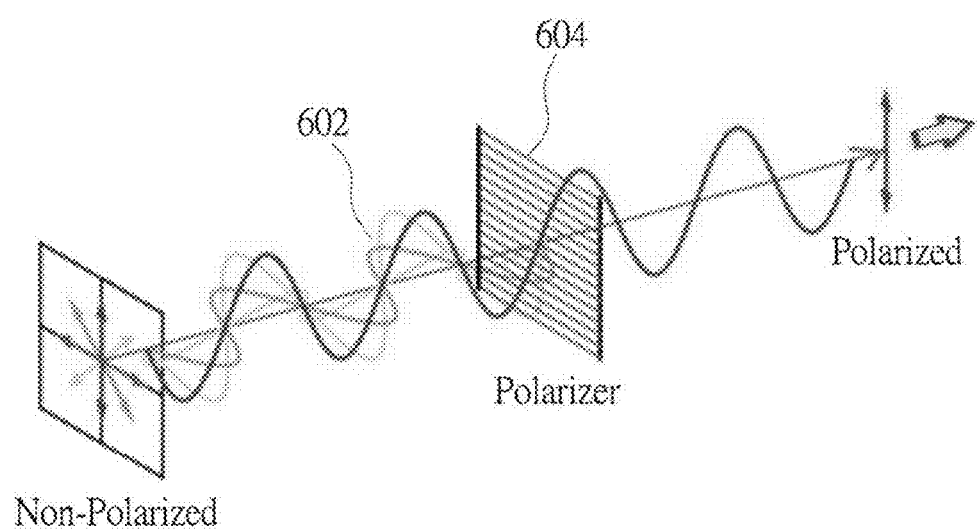
FIG. 6 is a diagram illustrating both electric and magnetic fields of a non-polarized light EMW being oscillating, but in spatial orthogonal directions.
Figure 7:
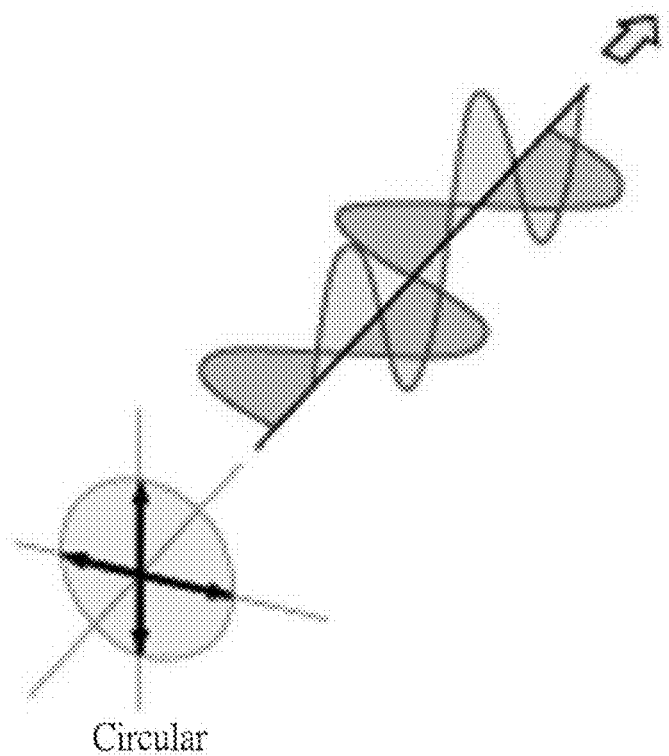
FIG. 7 is a diagram illustrating the circular oscillation of the electric and magnetic fields of the circular polarized light.
Figure 8:
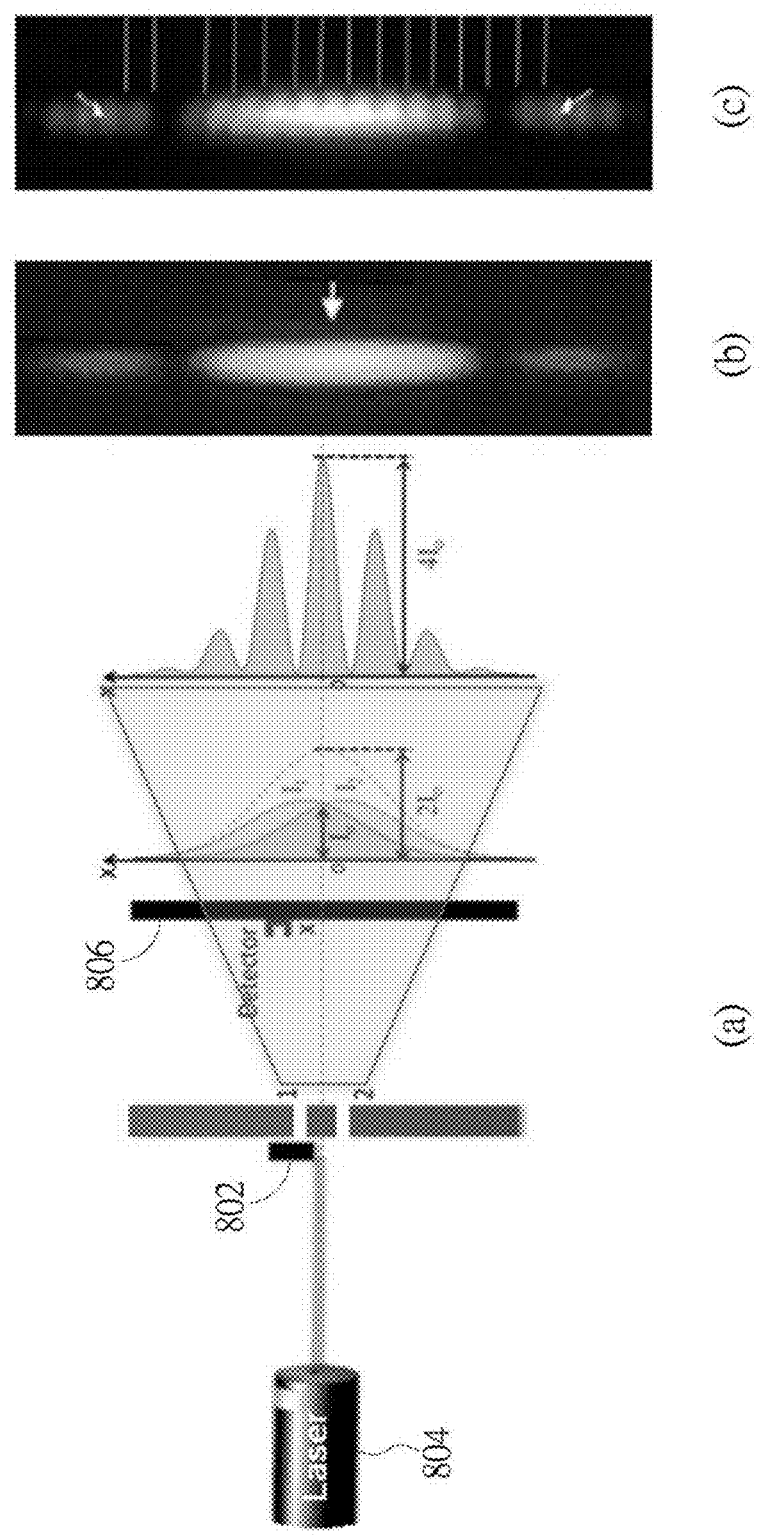
FIG. 8 is a diagram illustrating wavefront split when partition blocks slit 1, laser light passes through slit 2 to form single-slit interference patterns on screen.
Figure 9:
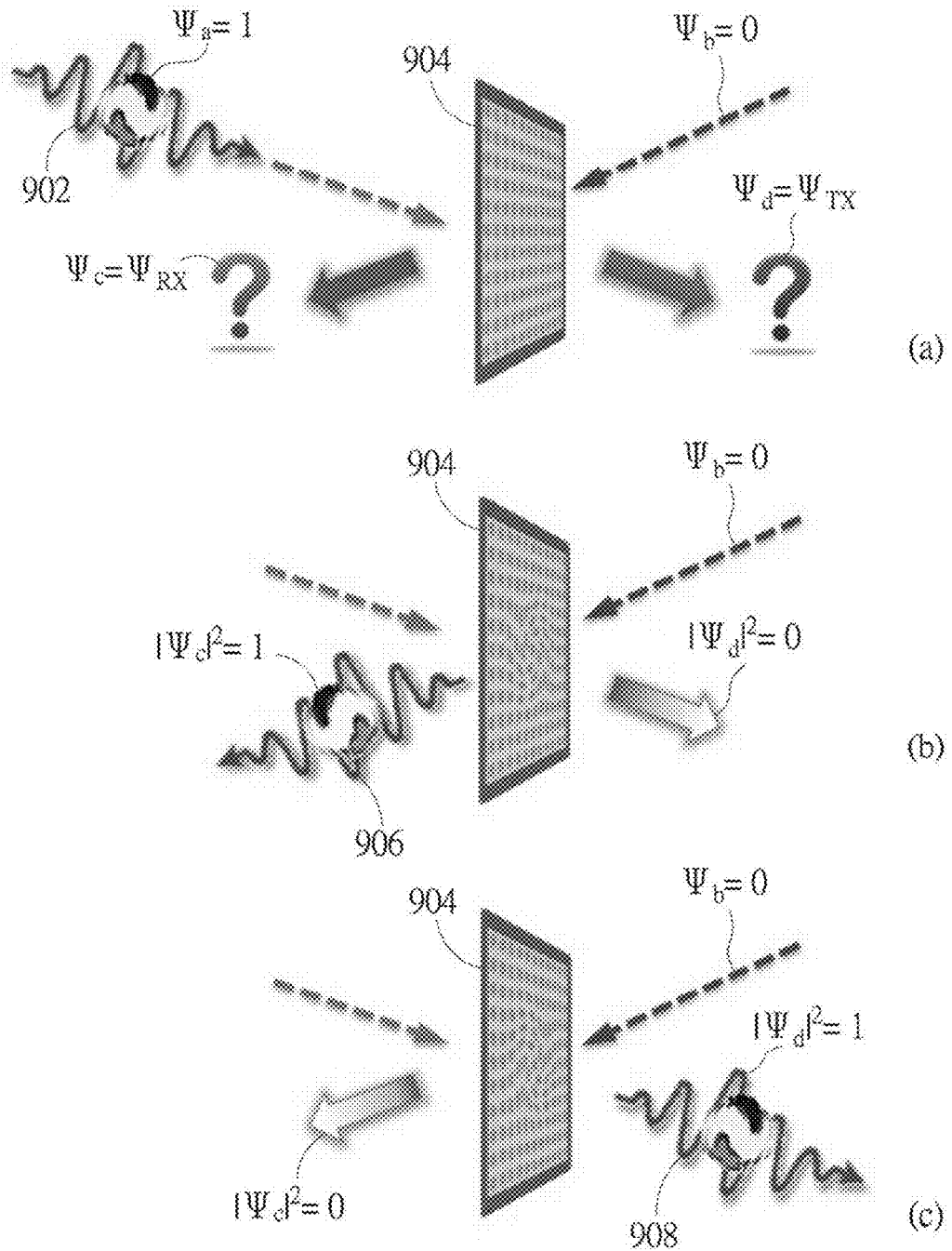
FIG. 9 is a diagram illustrating reflected light being generated in 50% probability and transmitted light is generated in 50% probability when incident light hits beam splitter.
Figure 10:
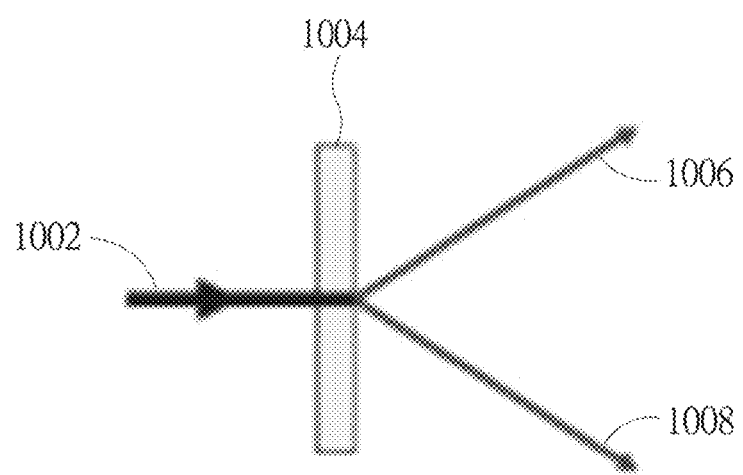
FIG. 10 is a diagram illustrating classical QM model for SPDC-1 theory and the phase-matching effects.
Figure 11A:
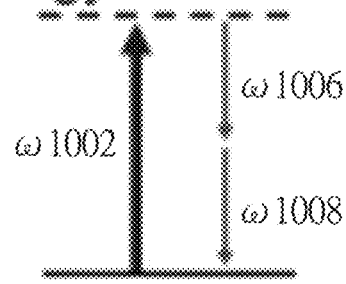
FIGS. 11A, 11B are diagrams illustrating the photons following the Energy and Momentum Conservations.
Figure 11B:
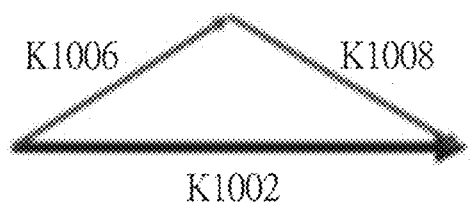
Figure 12:
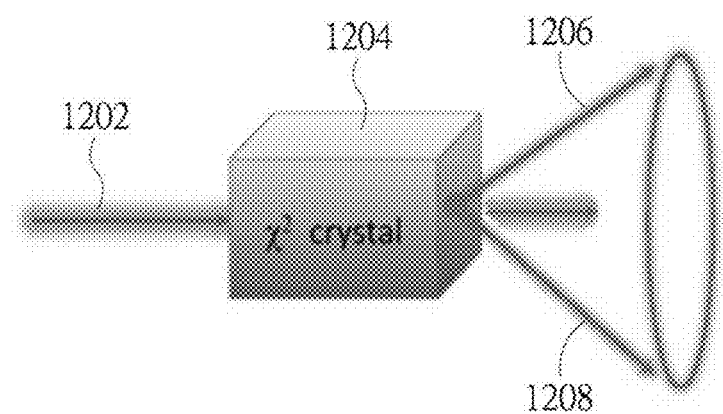
FIG. 12 is a diagram illustrating classical QM model for SPDC-2 EPR photon phase-matching theories.
Figure 13A:
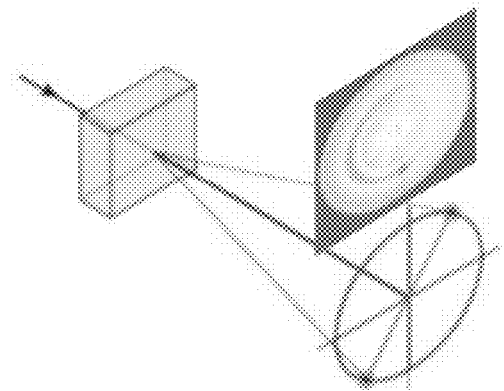
FIG. 13A is a diagram illustrating output of a SPDC Type-I down converter.
Figure 13B:
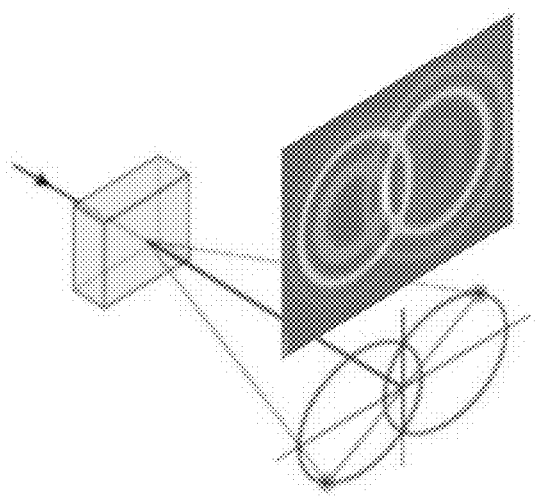
FIG. 13B is a diagram illustrating output of a SPDC Type-II down converter.
Figure 14:
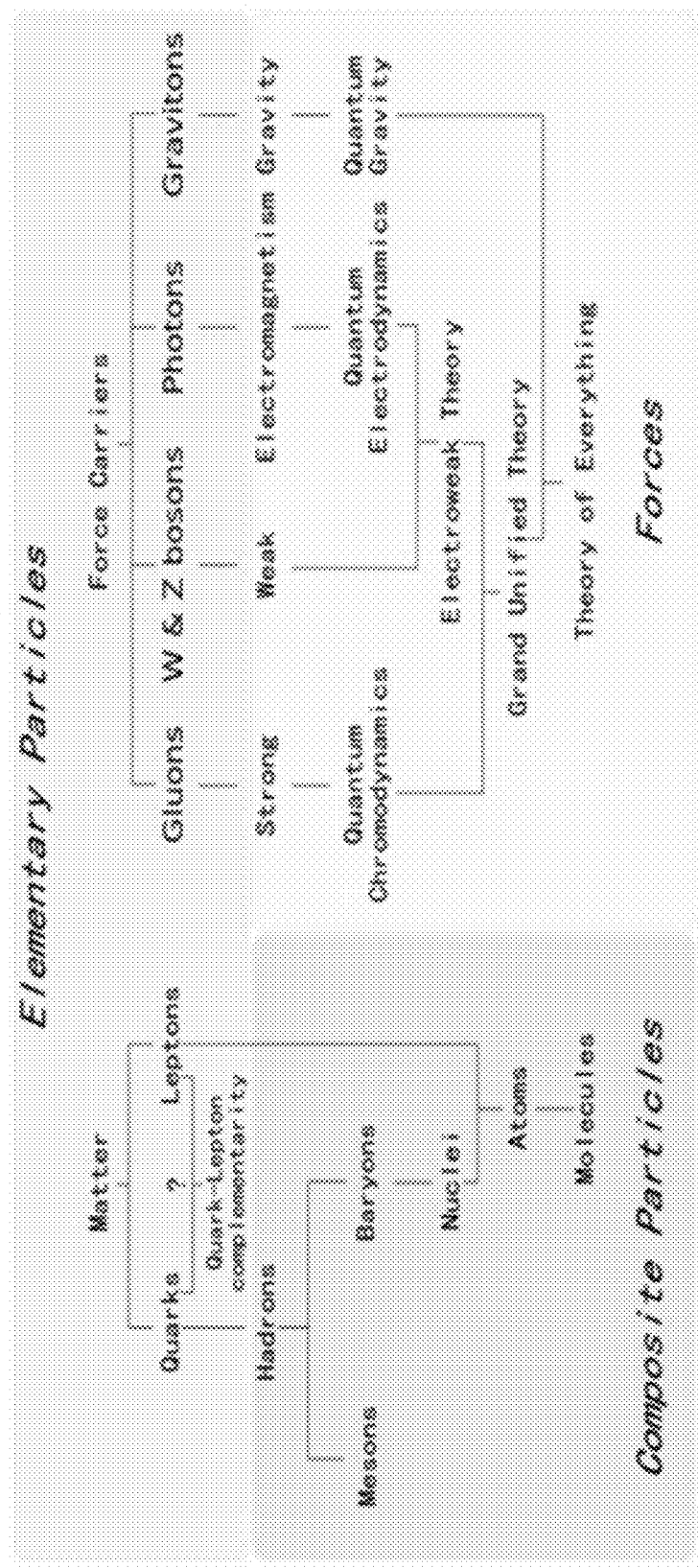
FIG. 14 is a diagram illustrating elementary particles disclosed by the prior art corresponding to the 4 fundamental interactions and forces.

In addition, reflection and refraction shown in FIGS. 2A, 2B can be explained by MWE new theory shown in FIGS. 19A-19B. As shown in FIG. 19A, when incident light 1902 (with wavelength λ) encounters first material (e.g. SiO2) 1903, a portion of the incident light 1902 is refracted to form refracted light 1904 due to SiO matter wave field (MWF) of the first material 1903, wherein wavelength λ1 of the refracted light 1904 is less than the wavelength λ of the incident light 1902. Similarly, as shown in FIG. 19B, when the incident light 1902 encounters second material (e.g. SiO2+PbO) 1906, because PbO MWF is greater than or denser the SiO MWF, when a portion of the incident light 1902 is refracted to form refracted light 1908 due to of the second material (e.g. SiO2+PbO) 1906, the refracted light 1908 has more shorter wavelength λ2, wherein the wavelength λ2 is less than the wavelength λ1 and λ typically, and angle θ1 shown in FIG. 19A is less than angle θ2 shown in FIG. 19B. In addition, relationships between the incident light 1902, the refracted light 1904, and the refracted light 1908 can be referred to the Dirac (Wave) Equation, where in Dirac Wave Equation relates the energy operator (Hamiltonian) with the time derivative of MW function ψ=ψ(x, t) for a particle or photon with coordinates (x, t) in space-time. Not only Dirac's equation has far deeper implications for the structure of matter and introduces new mathematical class of objects/matters that are now essential elements of fundamental physics, but also it manifests the Snell's Law refraction effect in SiO2 vs. SiO2+PbO materials, i.e. denser or greater MW field shall incur the shorter MW wavelength and slower traveling speed associating with the higher energy state in MW field owing to the time dilation and nano-scale MWE gravitational lensing effects manifested by the relativistic Dirac equations (Reference: Dirac, P. A. M. (1928). "The Quantum theory of the electron". Proceedings of the Royal Society A: Mathematical, Physical and Engineering Sciences.

Also, while light MWE packet hitting those energy dispersion centers (e.g. atomic or molecular with polarized MWF, by shortening its wavelength λ' in all directions, the object's MWF and its scalar/vector potential shall modulate a few physical properties in space-time, including 1) the curvature, 2) density of the Space, 3) Relativity phase and 4) the speed of incident light. All those MWF (i.e. optical density dependent) induced scattering wavefront adds up to give a particular refraction wavelength λ' by following Snell's Law and Huygens principle.

E. New Model for Light Dispersion

Figure 20A:
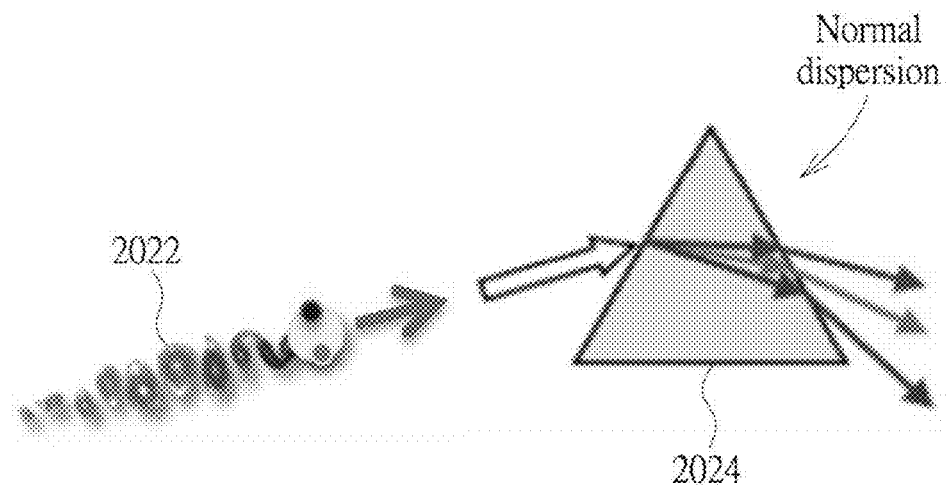
FIG. 20A is a diagram illustrating normal dispersion (refraction) of the incident light when incident light encounters glass prism.

When incident light 2022 encounters glass prism 2024, normal dispersion (refraction) of the incident light 2022 is shown in FIG. 20A. The normal dispersion (refraction) of the incident light 2022 is conveyed by elastic matter wave's refraction and/or diffraction microscopic effects among MWE of the incident light 2022, object's MWF tensors of the glass prism 2024, and its associated scalar/vector potentials in the sub-wavelength atomic space. The present invention discovers that sub-wavelength diffraction effect of MWF explains that light birefringence property which is the optical property of a material having a refractive index that depends on the polarization and propagation direction of light. These optically anisotropic materials are said to be birefraction (or birefringence) objects.

Figure 20B:
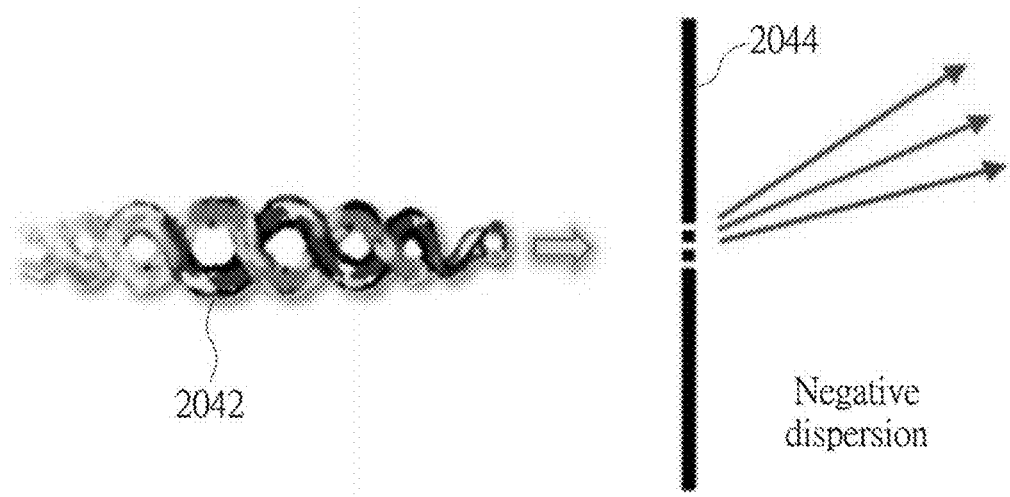
FIG. 20B is a diagram illustrating the negative dispersion being revealed by the MW wavefront-splits' interferences of the light MWE and the multiple slits.

In addition, as shown in FIG. 20B, when polychromatic (or white) light 2042 encounters multiple slits (or a single slit) 2044, the negative dispersion (diffraction and/or birefraction effect) is revealed by the MW wavefront-splits' interferences of the polychromatic light 2042 MWE and object's MWF tensors of the multiple slits 2044 in space-time, which has got evidenced by the most recent experimental proofs of the present invention. Microscopically, the light MWE dispersion effects shall still follow 1) The Huygens Principle, and 2) The Dirac Wave Equation in sub-wavelength atomic space of our Space-time.

F. New Model for Light Transmission, Reflection, and Absorption

Figure 21:
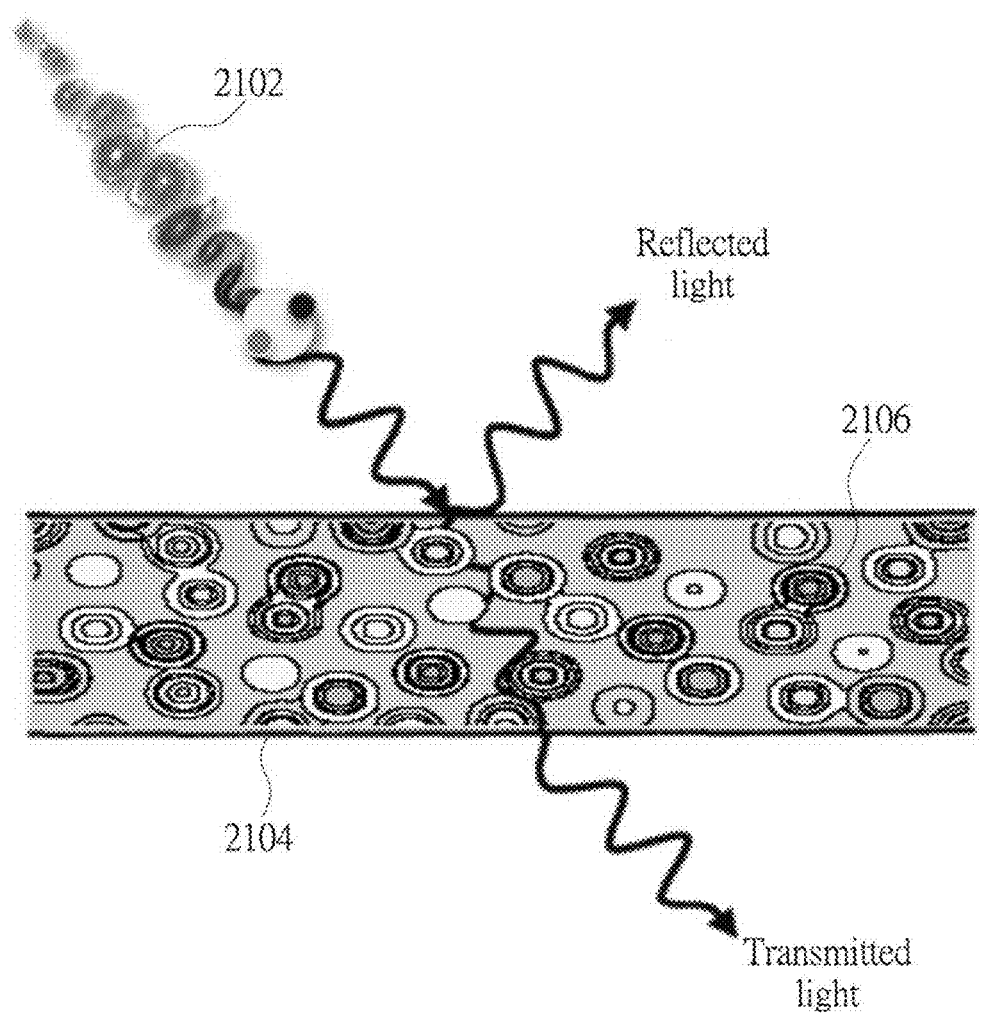
FIG. 21 is a diagram illustrating MWE wavefront of the incident light interacting with MWF of the object and its scalar or vector potential defined by its geometry, shape, kinetic energy, and others.
Figure 22:
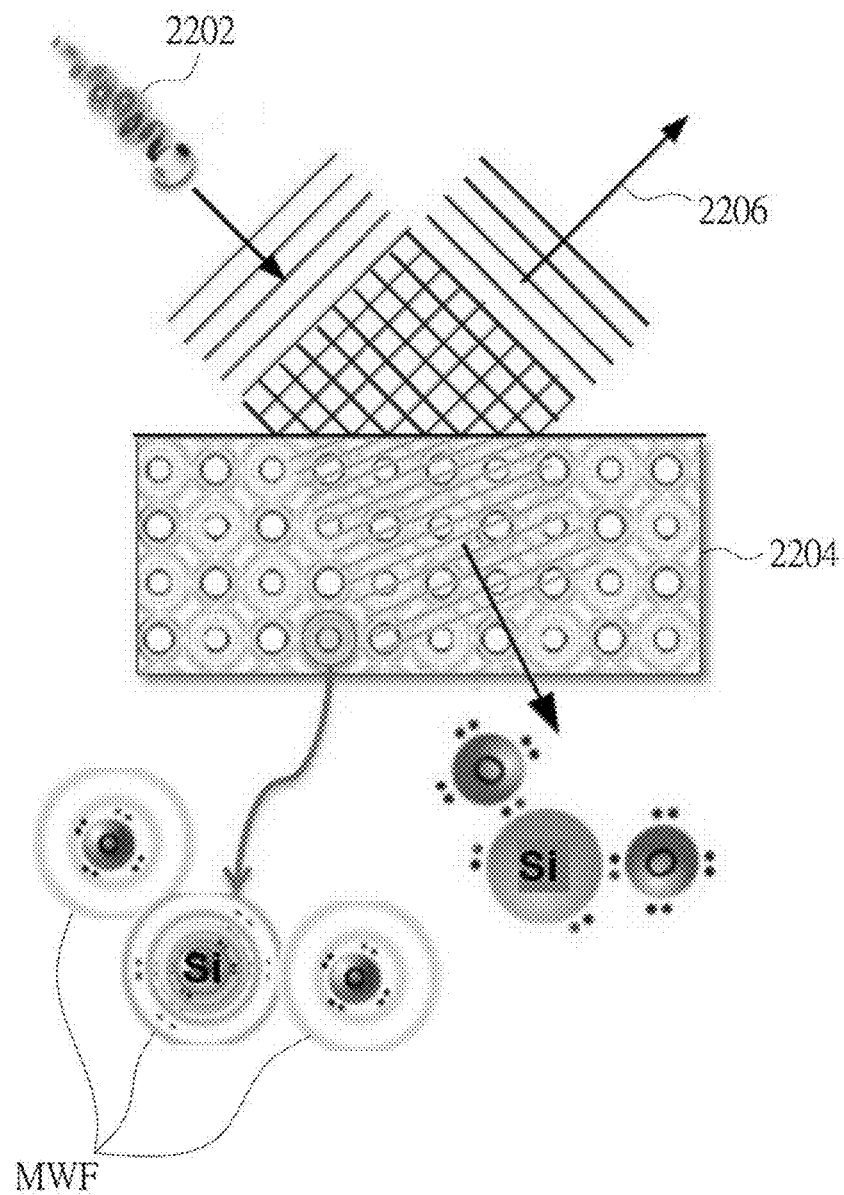
FIG. 22 is a diagram illustrating a portion of the MWE of the incident light getting reflected by the MWF tensor of the object due to the MWF and its scalar or vector potential discontinuity effect at object-air interface.

When incident light 2102 strikes object (medium) 2104, MWE wavefront (i.e. de Broglie's matter Wave shown in FIG. 21) of the incident light 2102 interacts with MWF tensor of the object 2104 and its scalar/vector potential defined by its geometry, shape, kinetic energy, and others of the object 2104. As shown in FIG. 21, aportion (transmitted light) of the incident lights 2102 passes (transmits) through MWF 2106 (i.e. De Broglie matter Wave field) of the object 2104. In addition, the MWF 2106 of the object 2104 and the scalar/vector potential of the object 2104 slow down the MWE speed of the incident light 2102, and meanwhile the MWE of the incident light 2102 reveals refractive index characteristics, wherein the greater gradient (or denser) of average polarization MWF or its scalar/vector potential is, the larger the refractive index will be for the object 2104. The MWE wavefront of the incident light 2102, not passing through the MWF 2106 of the object 2104, is said being blocked, reflected or attenuated (Absorbed) collectively by the MWF 2106 of the object 2104. As shown in FIG. 22, light reflection is conveyed by elastic energy scattering effects between the MWE of incident light 2202 and MWF tensor and its scalar/vector potential of object 2204.

A portion of the MWE of the incident light 2202 (i.e. reflected light 2206) gets reflected by the MWF tensor of the object 2204 due to the MWF and its scalar/vector potential discontinuity effect, i.e. light speed encountered discontinuity effect at object-air interface (Air vs. SiO2 discontinuity, etc.).

G. New Model for Light or Photon Scattering Effects

Figure 23A:
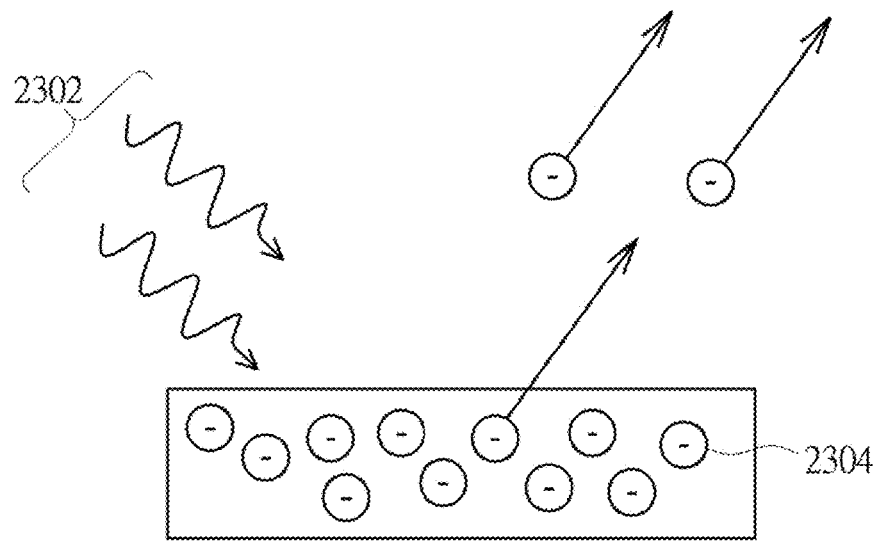
FIG. 23A is a diagram illustrating, the incident light getting reflected or scattered owing to its MWE wavefront interacting with MWF of atom.

As shown in FIG. 23A, when incident light 2302 with MWE's wavelength λ strikes on tiny particle 2304 (e.g. atom or object), and can get scattered. It reveals, MWE wavefront of the incident light 2302 interacts with MWF and its scalar/vector potential of the matter (i.e. the tiny particle 2304). The MWE of the incident light 2302 "Relativity" interacting with the tiny particle's 2304 MWF tensor which is associated with its geometry, composition, electric dipole polarization, kinetic energy and its atomic structure (i.e. shape) of the tiny particles 2304 in space-time, etc.

Figure 23B:
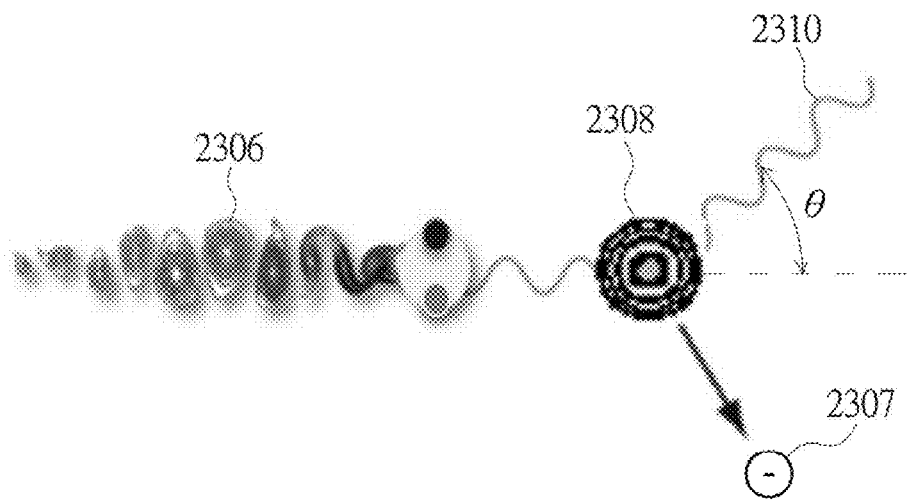
FIG. 23B is a diagram illustrating Compton scattering of Compton Photon colliding with target.

Known interactions (the incident light 2302 vs. the tiny particles 2304) are described as follows:
1) Low-energy scattering phenomena: Photoelectric or photo-voltaic effects.
2) Mid-energy scattering phenomena: Thomson scattering, or Compton scattering. As shown in FIG. 23B, Compton Photon 2306 of wavelength λ comes in from the left, collides with target 2308, and new Photon 2310 of wavelength λ' emerges at angle θ due to MWF of target 2308, wherein energy of the Compton Photon 2306 is much larger than binding energy of atomic electron of the target 2308, so electron 2307 of the target 2308 could be scattered (i.e. ionized) as being a free electron due to the collective interaction effects of wavefunction of electron 2307, MWE of incident light 2302 and the MWF of the target 2308.
3) High-energy phenomena: Quantum Optics of BS (Beam Splitter) or spontaneous parametric down-conversion (SPDC) effects, Pair productions and pair annihilation effects in Particle Physics (Reference: Das, A.; Ferbel, T. (2003-12-23). Introduction to Nuclear and Particle Physics. World Scientific).

H. New Model for Light Attenuation and Absorption

Figure 24A:
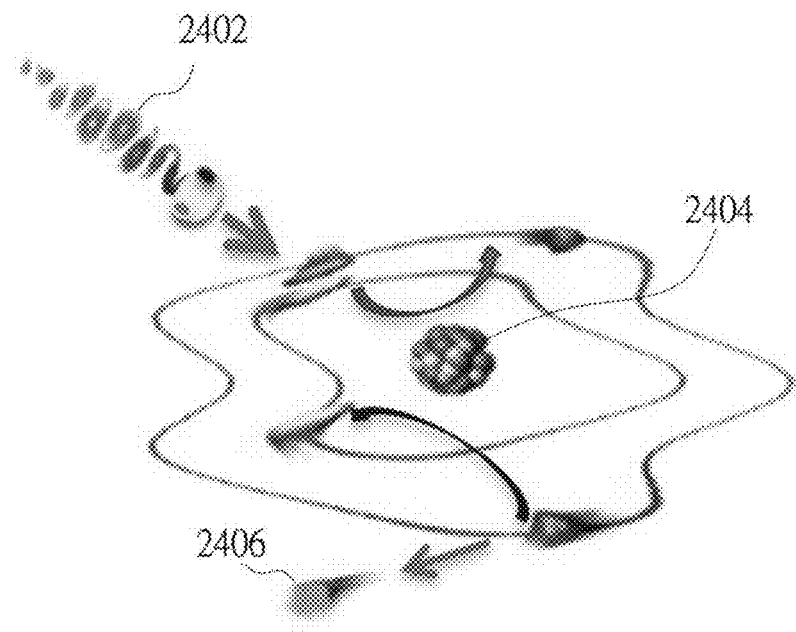
FIG. 24A is a diagram illustrating being absorbed by atom MWF tensor of object, and new photon emerging spontaneously.
Figure 24B:
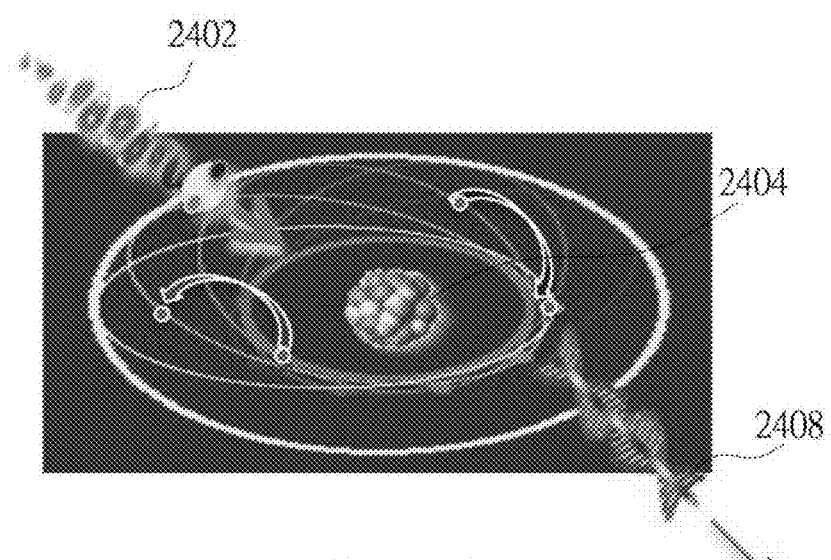
FIG. 24B is a diagram illustrating MWE packet of the incident light changing electron's potential or its orbital momentum.

The present invention discovers, when light MWE packet strikes an object (matter), absorption or attenuation interaction with the object's MWF tensors is revealed. Absorption mechanisms of visible light, say, via Carbon atom or molecule Chemical bond's MWF (or the scalar/vector potential) of the object.
1) Atomic Photon absorption and emission: as shown in FIG. 24A, incident light 2402 with MWE's wavelength λ comes in, absorbed by atom MWF tensor of object 2404, and new photon 2406 of wavelength λ' emerges spontaneously with a time delay after the incident light 2402 being absorbed by the object 2404.
2) Atom or chemical-bond excitations: as shown in FIG. 24B, the incident light 2402 with MWE's wavelength λ comes in, MWE packet of the incident light 2402 can change electron's scalar/vector potential or its orbital momentum associated with the object 2404, split the electron orbital energy levels into precession or multiple ones with raising electron-atomic bond temperatures and changing MWF (or its scalar/vector potentials) of the object 2404, and EM wave 2408 with wavelength λ1 is emitted spontaneously with a time delay after the incident light 2402 being raising the scalar/vector potential of the object 2404.
3) Light to EMW and to Dark energy conversions: an EM wave can be emitted by anti-Charge (or Charge) Quanta associated with the excited Electron (or Positron) in matter. Eventually, EMW energy gets dispersed and immersed into the background (e.g. Dark Energy) state of Universe with raising certain degree of object or Vacuum background potentials or temperatures.

I. Total Internal Reflection (TIR) and Optic Waveguide

Figure 25A:
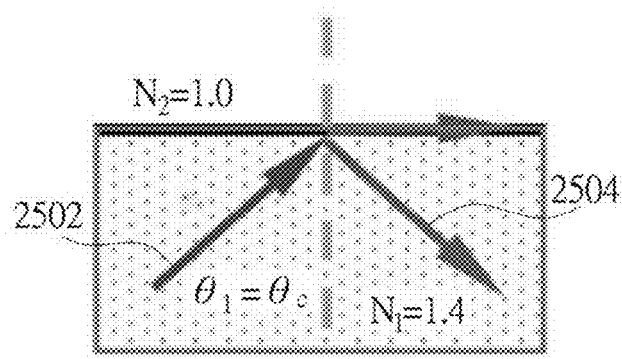
FIGS. 25A, 25B are diagrams illustrating Total Internal Reflection (TIR) being formed when angle of incidence light MWE is equal to or exceeds critical angle.
Figure 25B:
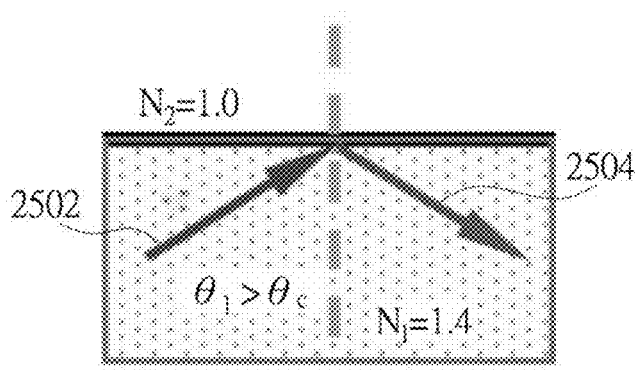

Total Internal Reflection (TIR): when angle θ1 of incidence light MWE 2502 is equal to (shown in FIG. 25A) or exceeds (shown in FIG. 25B) critical angle θc, TIR rays 2504 are forming in where index-matched surface plane, e.g. sin θc=n2/n1, and n1(1.4)>n2(1.0).

Optic Fiber is a cylindrically symmetric light MWE conduction tube. The optic fiber can be applied to "light or Optical integrated semiconductor chips" or "Optical cables," respectively, where light is guided around with few restrictions or absorptions in the optical fiber. The optical fiber can yield fiber glasses with low losses (<0.25 dB/km) for optical telecomm, imaging (e.g. endoscopes) and pressure sensing application systems as well.

Figure 25C:
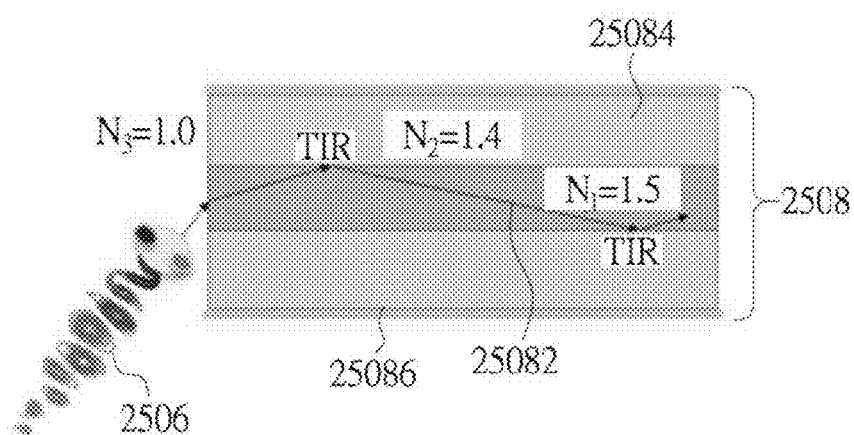
FIG. 25C is a diagram illustrating total internal reflection occurring in the optical fiber.

Typical enclosure materials for fibers are dielectrics. Classical EMW theory predicted server attenuation shall occur if Metal enclosure was used. On the other hand, based on the present invention, the prediction by MWE light model of the present invention may prove that the Photon MWE packet will not get too much dispersed while immerse in Hg Liquid by an experimental setup. That is, as shown in FIG. 25C, when incident light MWE 2506 injects into optical fiber 2508, total internal reflection occurs in the optical fiber 2508, wherein the optical fiber 2508 is composed of first dielectric 25082 (with refractive index N1 (e.g. 1.5)) and second dielectric 25084 (with refractive index N2 (e.g. 1.4)), and the optical fiber 2508 can be enclosed by either a dielectric or a metal enclosure 25086 that may not impact absorptions or total internal reflections of the incident light MWE 2506.

J. New Model of Coherence Associated with Individual MWE Particle of Light

The present invention unveils "Coherence" is the intrinsic property of each "SINGLE" Photon (MWE packet) associated with all light sources. Coherent Photon's MWE wavefunction tensor is able to create interference, so long as it reveals a "Stable (Temporal) and Wide (Spatial)" phase relationships, e.g. with long coherence time or length, along its traveling direction in Space-time.

In order to observe clear Photon interference effect, both spatial and temporal coherence must exist for each individual Photons. Incoherent Photon MWE tensor keeps changing its own phase-frequency relations along with time in its traveling direction which, in turn, makes a stable interference pattern impossible due to lack of either Spatial or Temporal coherence of its own. Also, the present invention discovers that the Photon's polarization direction is substantially independent of its own coherence properties.

Figure 26:
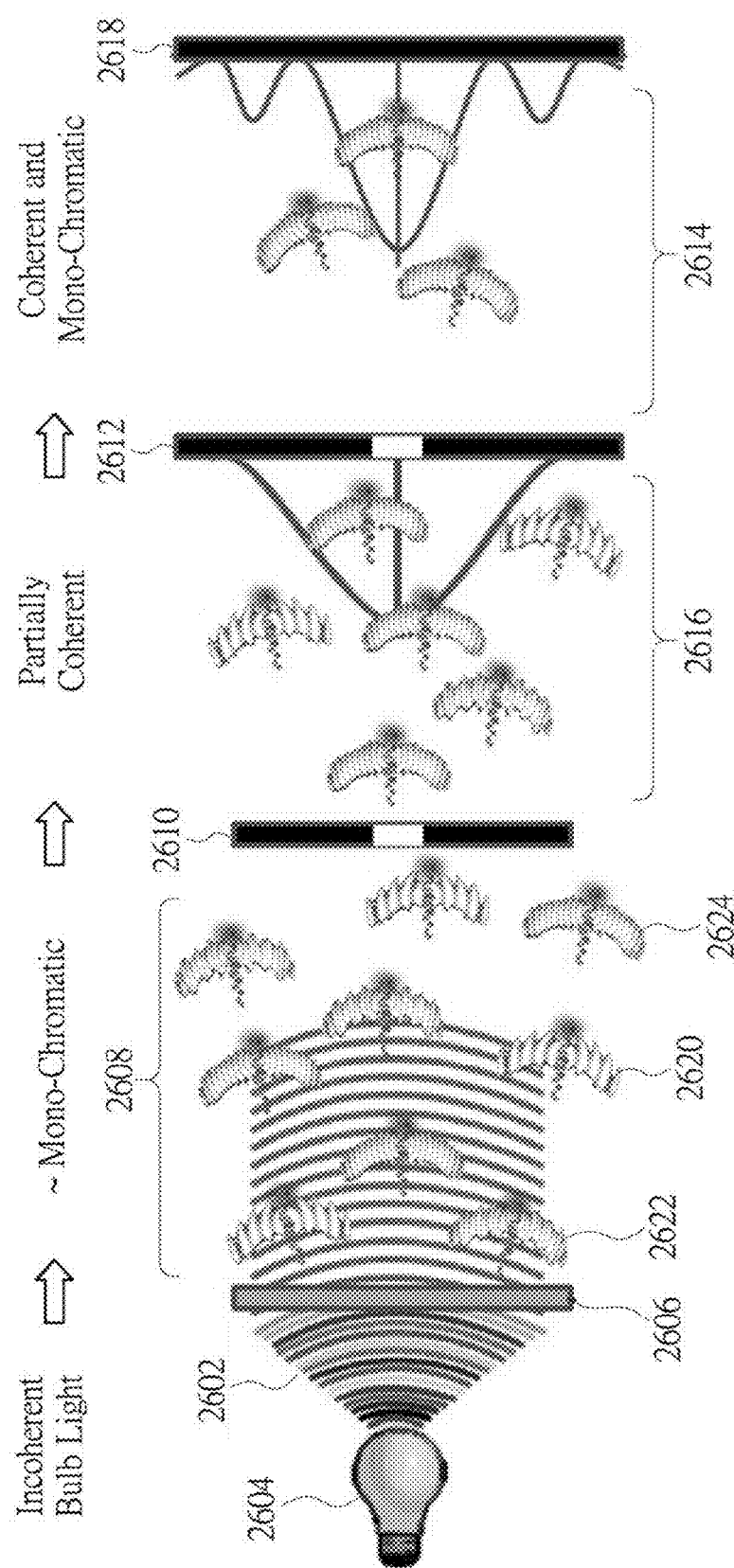
FIG. 26 is a diagram illustrating photons emitted collectively from electric bulb being comprised of properties with all kinds of individual photons characterized with spatial and temporal incoherent photons, partially coherent photons and coherent photons.
Figure 27A:
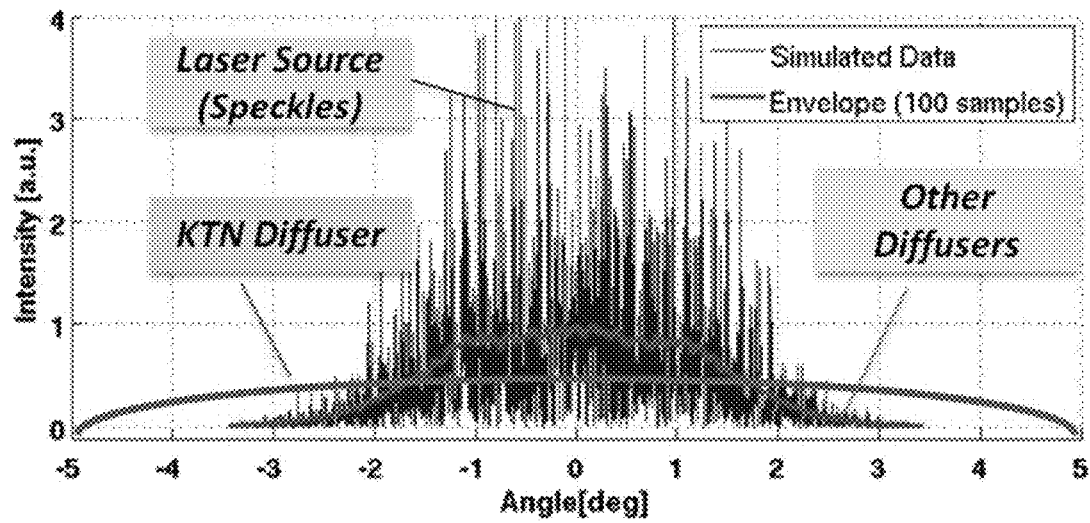
FIG. 27A is a diagram illustrating KTN laser super uniformity diffuser for biotechnology and material synthesis.
Figure 27B:
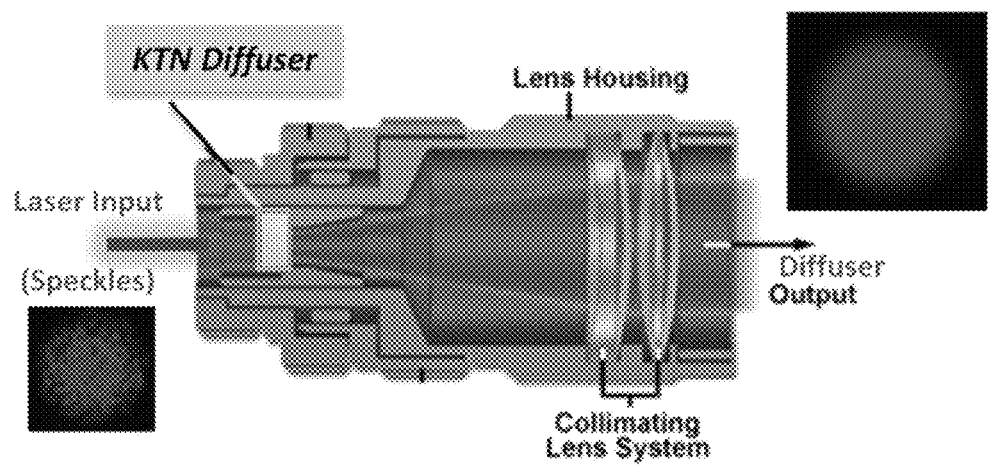
FIG. 27B is a diagram illustrating KTN laser diffuser lens system.
Figure 27C:
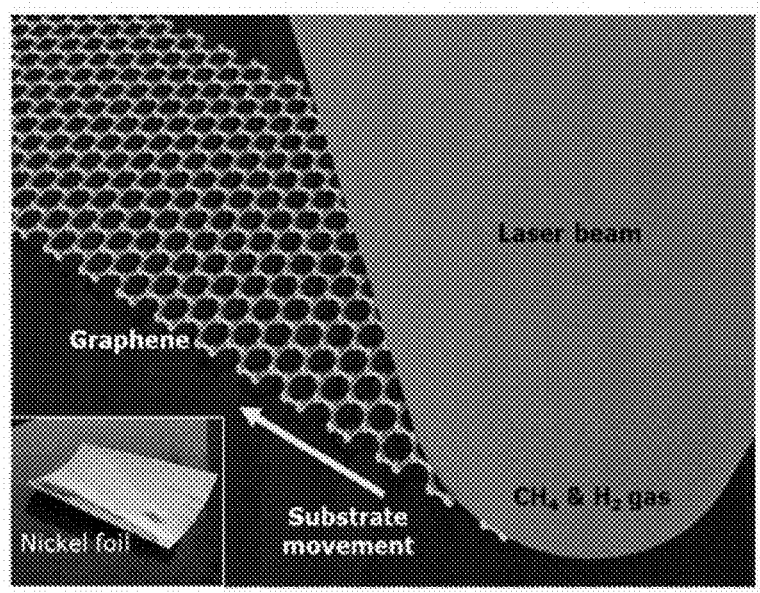
FIG. 27C is a diagram illustrating KTN laser diffuser catalyst effects in biotechnology and material synthesis.
Figure 27D:
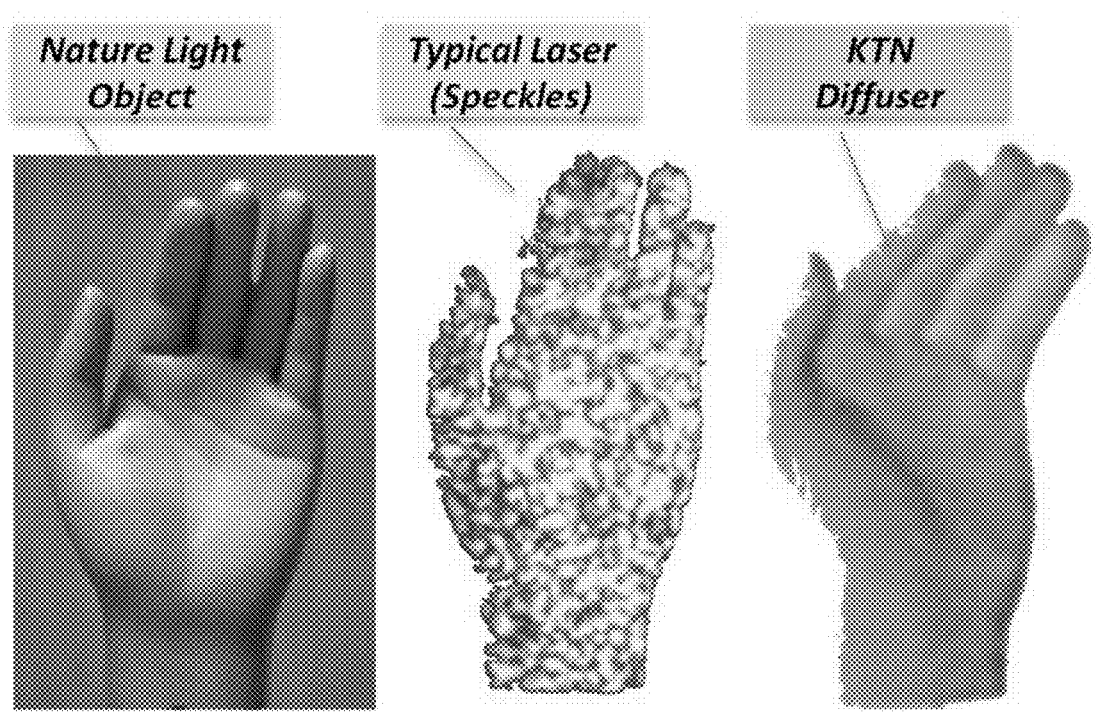
FIG. 27D is a diagram illustrating KTN resolution enhancement for laser 3D holography.

As shown in FIG. 26, photons 2602 emitted collectively from electric bulb 2604 are comprised with all kinds of individual photons characterized with spatial and temporal (temporal means frequency or phase) incoherent photon 2620, partially coherent photon 2622 and coherent photon 2624 properties, e.g. shown in FIG. 26 are the three different coherence representations of Photon 2620, 2622 and 2624. After the Photons 2602 are filtered by Optic wavelength (λ) Filter 2606, mono-chromatic Photons 2608 characterizing collectively with a plurality of coherence properties is generated. When the mono-chromatic Photons 2608 are filtered by Spatial Filter Slit 2610, the mono-chromatic Photons 2608 spread out and travel toward Diffraction Single Slit plane 2612 with showing a blurring bell-shape intensity distribution upon hitting plane 2612. For the majority of those partially coherent 2622 or incoherent photons 2620, they will be diffracted toward and impinge the middle or far edge locations respectively on the bell-shape intensity distribution curve showing on plane 2612. In addition, the coherent component Photons 2614 of partially coherent Photons 2616 pass through diffraction single slit 2612, those coherent Photons 2614 will be created and show up collectively with a famous single-slit interference pattern on the screen 2618.

K. New Model of Coherence Associated with Rotational Charge Quanta

The present invention discovers photon MWE's spatial and temporal coherences are dependent typically for most cases of the real-world environment. It reveals interactions between "Rolling Pairs" of Yin(−) and Yang(+) Charge Quanta with "its own" MWE or MWF of outside "Matter's (e.g. Atom's)". For certain cases, a photon can be with temporal incoherent (frequency-jitter or ω-jitter) but keep about spatial (polarization- or spatial-jitter) coherent, e.g. the pair of idler and signal photons generated from a nonlinear crystal SPDC effect such as in BBO (Beta barium borate) crystal and the like. Or, a photon can be with spatial incoherent but keep most of the temporal coherence properties, e.g. most temporal coherent property of a Photon at the output port of a KTN (Potassium-Tantalate Niobate) crystal has being preserved while a Laser beam of photons passing through the crystal with QEO (Quadratic Electro Optical) effect, and vice versa.

In an embodiment, the present invention demonstrates and explores the second order QEO effect of Potassium-Tantalate Niobate (KTN) crystal as to Develop NEW and WIDE ranges of new applications beyond fast optical scanner, varifocal lens, etc. (Reference: K. Nakamura, "Optical Beam Scanner Using Kerr effect and Spacecharge-controlled Electrical Conduction in KTa1-xNbxO3 crystal," NTT Technical Review, Vol. 5, No. 9, 2007. NTT Japan).

Among those new innovations of the present invention, as shown in FIGS. 27A, 27B, 27C, 27D, by partially removing, smoothing, mixing or averaging the spatial coherence of input Laser light, not only we discover the method and apparatus for creating a super-uniform illumination optics, but also we combine the advantage of KTN super-uniform illumination optics with various other fields, including optical beam diffusers or DOE (Diffraction-Optical Element) such that we are able to seek better utility for whole family of KTN or QEO nonlinear devices.

Figure 28:
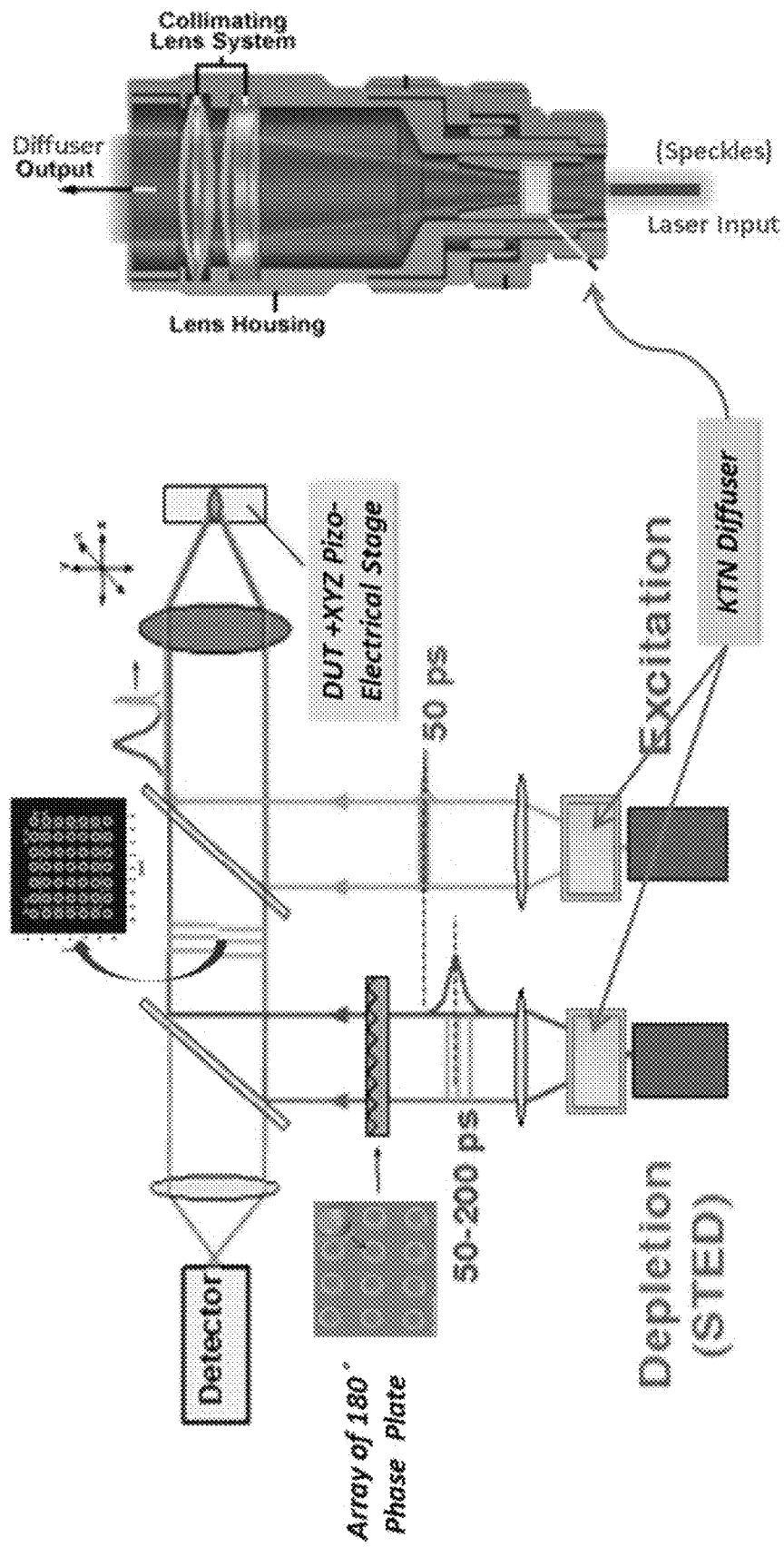
FIG. 28 is a diagram illustrating super-uniform laser illumination solutions on STED biotechnology and life-science.

As shown in FIG. 28, the present invention unveils the "Super Uniform" Laser illumination method and apparatus can attract the keen interest of bio-scientific community in view of their potential to enhance seed germination, seedling growth, physiological, biochemical and yield attributes of plants, cereal crops and vegetables. On the other hand, there are a few major Challenges in Biotechnology or OCT Laser Imaging technologies, including the side effect of Laser/Photo-bleaching or Photo-toxicity effect, i.e. Living or target object permanently is unable to fluoresce, caused by non-specific reactions between fluorophore (fluorescent chemical compound) and molecules owing to "non-uniform illumination or Laser Intensity over dose" effects. In Laboratory observation of fluorescent molecules or living cells, it is most problematic in non-uniform illumination of time-lapse super-resolution microscopy, e.g. Super-resolution methods STED, etc. Long acquisition time or smaller FOV (field of View) of Super-resolution scopes requires small pixels in nm scale, which means more non-uniform illumination time is needed to acquire images from in a given FOV sample.

There are some high-value applications and knowhow of the present invention, including Use KTN QEO device and Laser beam apparatus:

1) To develop catalyst illumination optics or apparatus for Biotechnology and 2D/3D material synthesis.

2) To do pixel resolution enhancement for the finest pixel imaging system for Laser Holography technology by using super-uniform illumination optics of this invention.

3) To do Bio-Science Laser imaging and OCT (Optical Coherence Tomography) medical imaging applications by using super-uniform illumination optics of this invention.

Most of "Frequency or wavelength Filtered" monochromatic natural light sources are still incoherent ones, e.g. Photons coming from Black-body radiations, Sun radiations, electric bulbs, candles, etc. due to randomized atomic-level MWF and MWE interference effects associated with randomized incoherent MWF of light source's at high temperatures.

Figure 29:
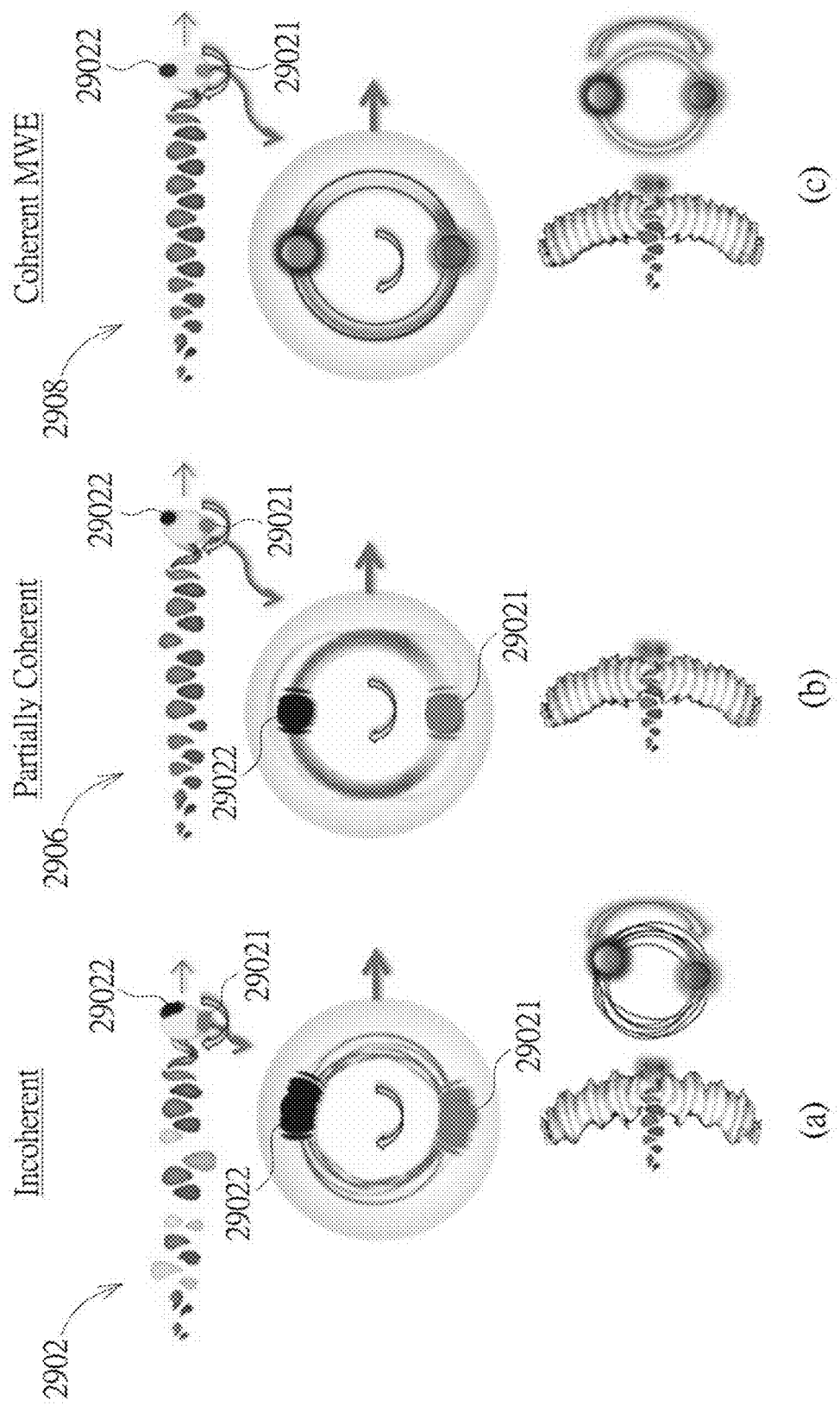
FIG. 29 is a diagram illustrating new representations of incoherent photon, partially coherent photon, and coherent photon.

As shown in FIG. 29(a), photon 2902 is incoherent, Yin-Yang Charge Quanta 29022, 29021 of the photon 2902 have certain amount of spatial-jitter (or polarization-jitter) and ω-jitter (or Frequency-jitter) accordingly. As another representation shown in FIG. 29(b), photon 2906 is partially coherent, wherein Yin-Yang Charge Quanta 29022, 29021 of the photon 2906 have less spatial-jitter and less ω-jitter than the incoherent photon 2902. Also as shown in FIG. 29(c), photon 2908 is a coherent one, wherein Yin-Yang Charge Quanta 29022, 29021 of the photon 2908 is characterized with about zero spatial-jitter and zero ω-jitter.

L. Postulate of Space-Time Coherence in Galaxy Scale

Figure 30:
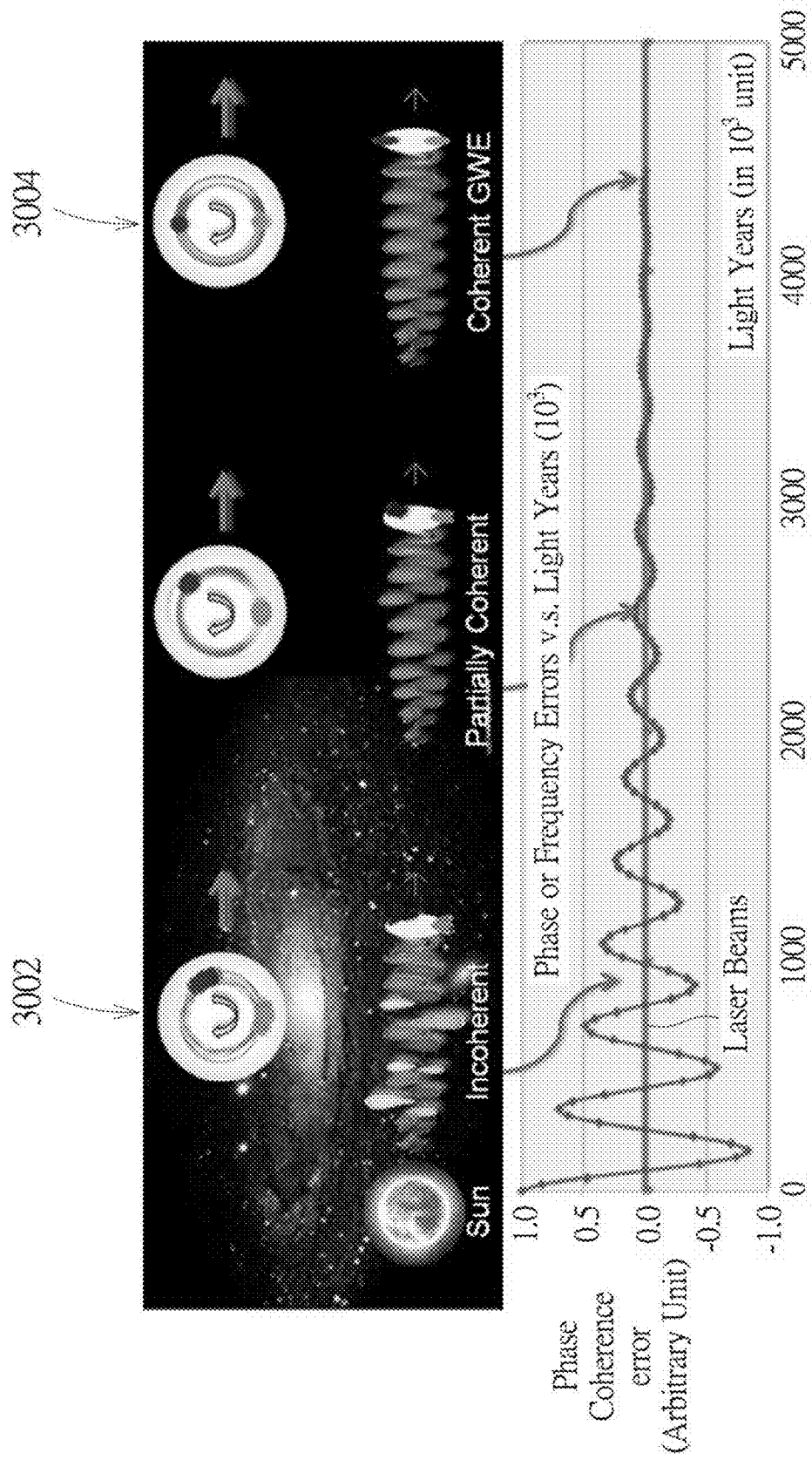
FIG. 30 is a diagram illustrating "Open Space" performing the function of a "Gigantic pin-hole like spatial filter" to make Sun light eventually coherent.

Light MWE (Photon) feels an infinitesimal damping or dispersion factor associated with Universal Constants, e.g. $\mu 0$ (Permeability of Vacuum), $\epsilon 0$ (permittivity of Vacuum), etc. in space-time limit of Universe. As shown in FIG. 30, the "Open Space" performs the function of a "Gigantic pin-hole like spatial filter" to make Sun light (a newly borne Photon) 3002 eventually a coherent (a mature and developed photon) MWE 3004 within the limit of Universe after traveling millions or billions of light years distance away from its emission sources, e.g. the Sun, a star and the like. Eventually, the spatial coherent length of the MWE 3004 will be coming with longer than a few hundreds or even thousands of meters in length, and so will the temporal coherence be longer than what it can be expected in real life. This theory evidences that the present invention discovers the fundamental story behind those giant stellar interferometers on the earth.

M. New Theory on HBT Interferometry Evidences Intensity Interference Theory is Incomplete (Reference: Michelson, Albert Abraham; Pease, Francis G. (1921). "Measurement of the Diameter of Alpha Orionis with the Interferometer". Astrophysical Journal. 53: 249-59.)

Figure 31:
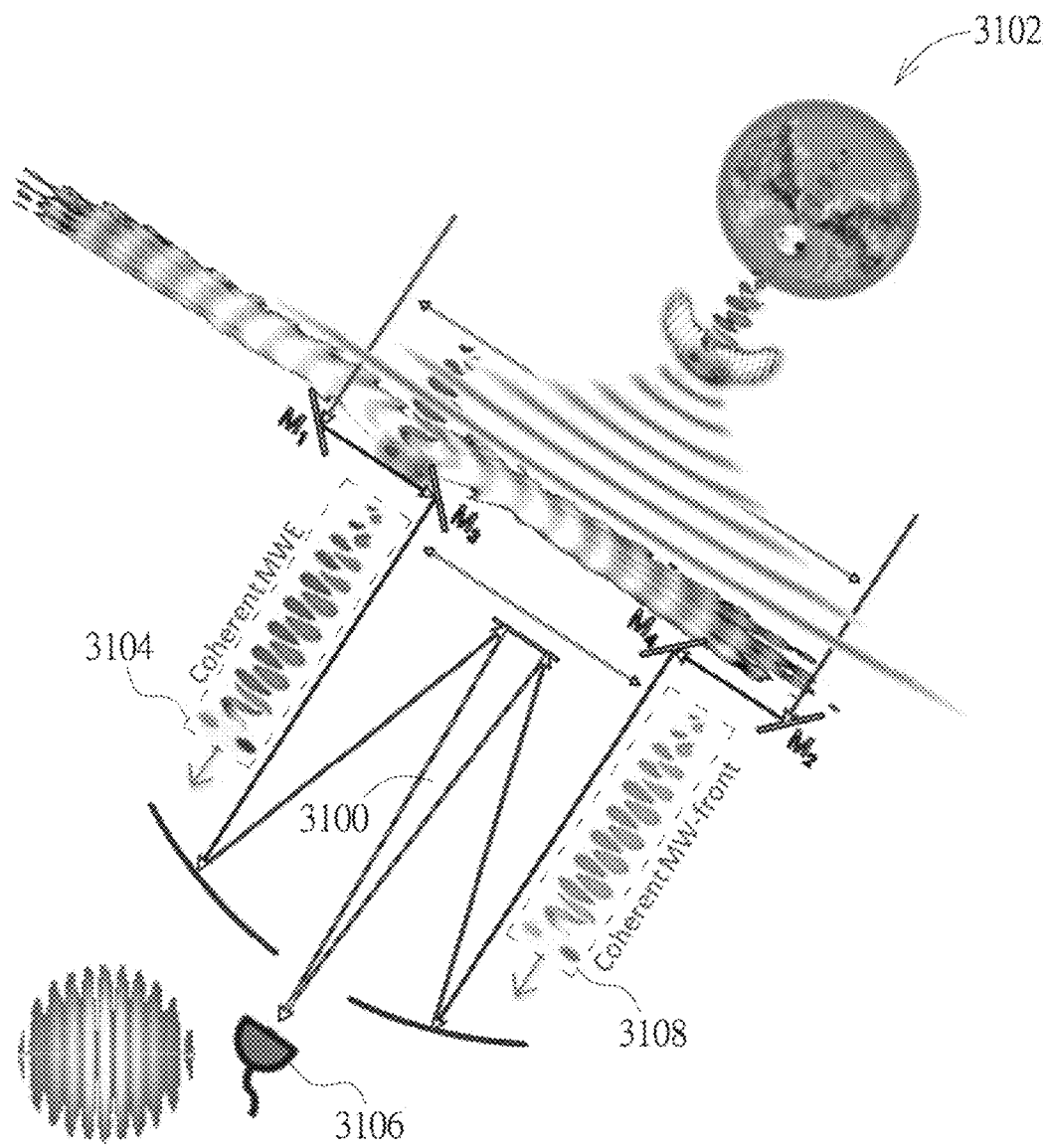
FIG. 31 is a diagram illustrating a stellar photon MWE packet being given birth in outer space millions years ago and carrying the structural aperture DNA of its Mother Stellar.

As shown in FIG. 31, a Stellar Photon MWE packet 3102 had given birth in millions or billions years ago in outer space, it carries and remembers the structural aperture shape of its Mother Stellar (DNA of its Source MWF) by following Huygens Principal.

Finally, each Stellar Photon becomes mature and coherent light 3104 for an observer, while it has been traveling via a long journey to the interferometer and detector 3106 of a distant Earth away from its Mother Stellar. The photon MWE 3104, along its coherent MW wavefront 3108, conveys its Mother Stellar DNA (e.g. structural aperture size, its spatial distribution or geometry, etc.) information to a Michelson Stellar interferometer 3100 via interference effect in between photon MWE 3104 and its coherent matter wavefront 3108. It evidences the same or similar interference process of the classical Two-slit (or Fresnel Bi-prism) interference effect by obeying Huygens principle.

On the other hand, what is the reality or causality story behind another type of stellar interferometer, i.e. HBT (Harry-Brown-Twiss) stellar intensity interferometer? The present invention teaches that a bunch of Laser-like free photon emission groups creates spatial coherent photon speckle patterns as to forming a star background radiation pattern in all directions toward the space with respect to the distant galaxy observers on earth. In turn, the distant observer can see a spatially correlated photointensity interference pattern producing by the mutual interference of a plurality set of random-in-temporal but coherent-in-spatial light (photon) MWE groups. This phenomenon had ever been investigated by scientists since the time of Newton. But Light speckles have come into prominence since the invention of the laser and have now found a variety of applications. Speckle patterns typically occur in diffuse reflections of monochromatic light or star light, such as gas discharge light, black-body light radiations, stellar light, many-particle nuclei decay produced emission groups of boson or fermion particles, gas discharge light and laser light, etc. Such speckle property may occur on the cases such as HBT stellar intensity interferometer, while paper, white paint, rough surfaces, or in media with a large number of scattering centers or particles in space, such as airborne dust or in cloudy liquids.

N. New Model of Polarization (I)— Liner and Circular Polarizations of MWE Particles (Reference: Liu, Ming, et al. "Light-Driven Nanoscale Plasmonic Motors." Nature Nanotechnology 5.8 (2010): 570-573)

Figure 32:
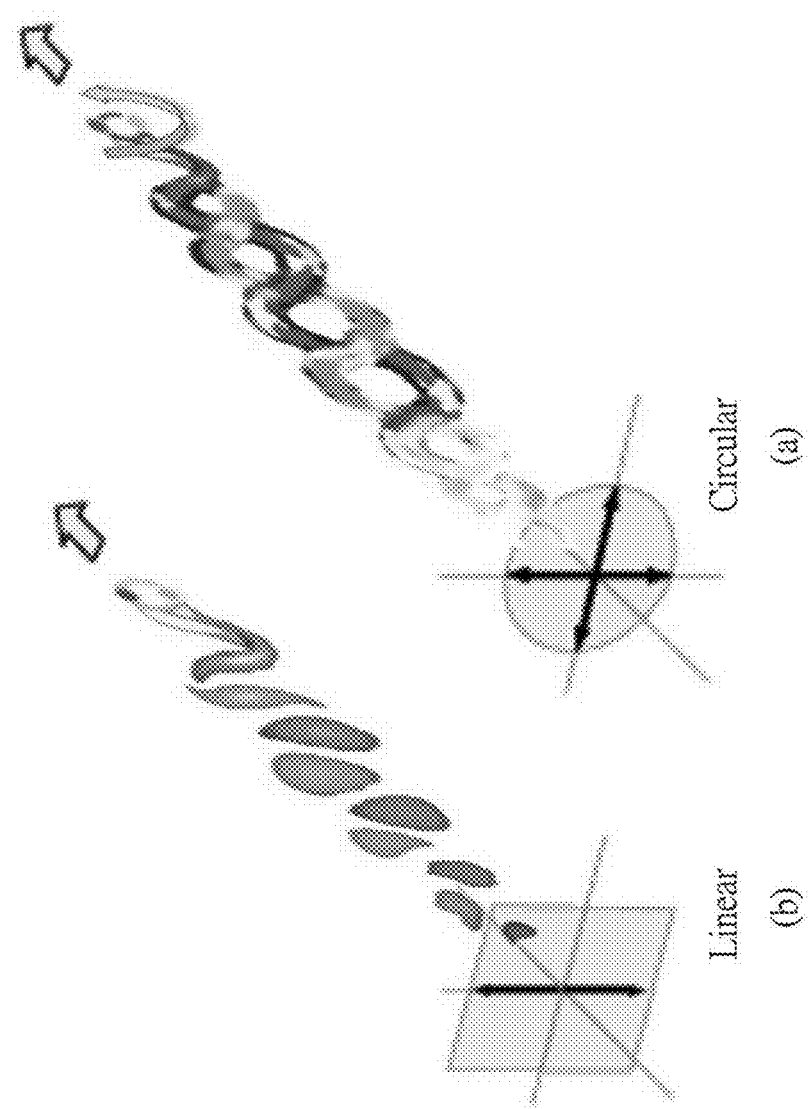
FIG. 32 is a diagram illustrating circular polarization, elliptical or linear polarization photons.

Most of natural light sources irradiate natively with randomly polarized photons, including a mixture of indefinite states of circular (shown in FIG. 32 (a)), elliptical or linear (shown in FIG. 32(b)) polarizations, which reveal the randomized atomic-level source MWF and Light MWE interference effects associated with a randomized incoherent MWF of light source's at high temperatures.

Figure 33:
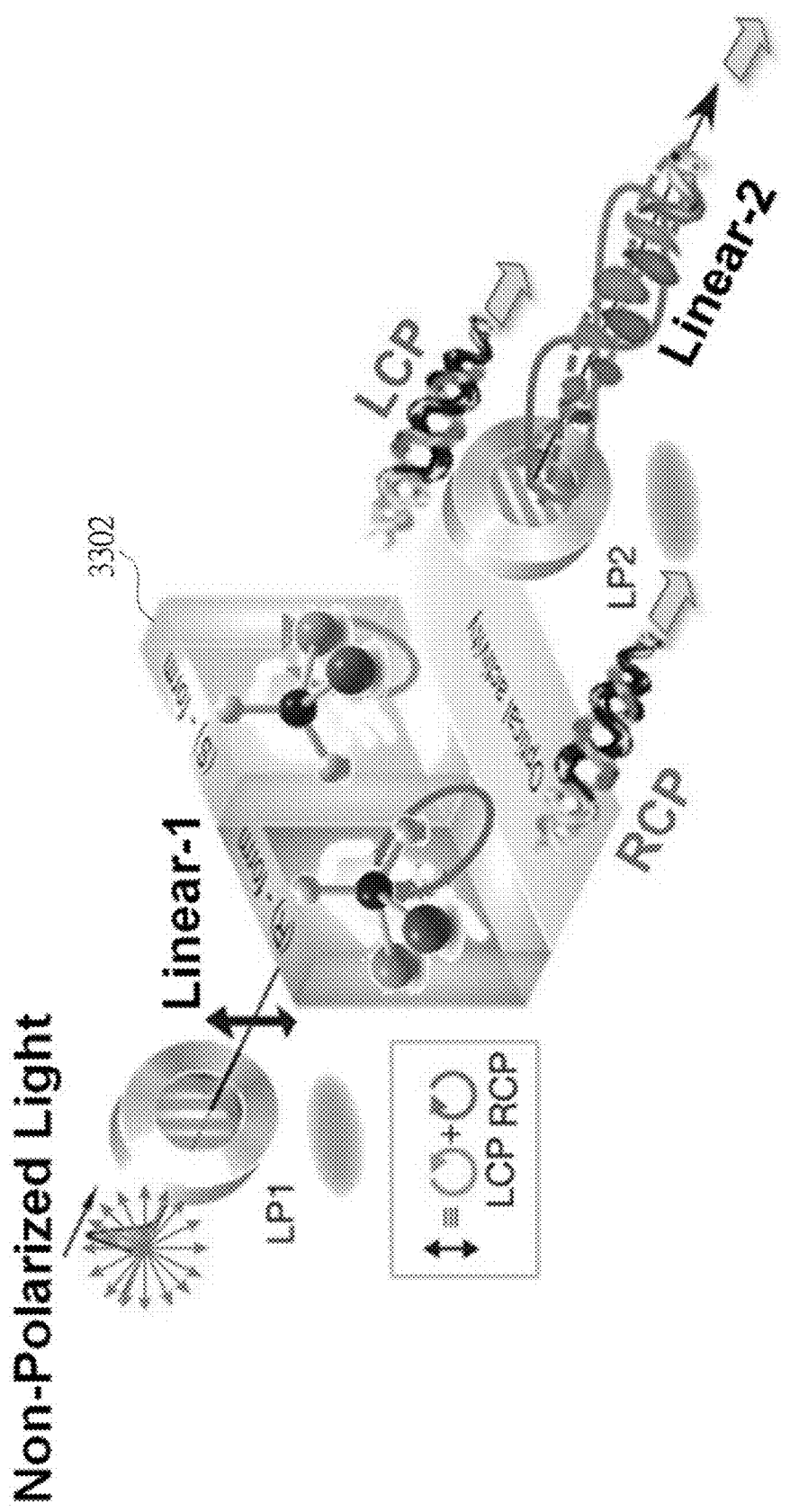
FIG. 33 is a diagram illustrating circular-Dichroic (CD) materials getting interfered with LP photons or generating circularly polarized components of light through the effect of Optical rotatory Dispersion.

As shown in FIG. 33, circular-Dichroic (CD) materials 3302 get interfered with LP photons or generating circularly polarized components of light through the effect of ORD (Optical rotatory Dispersion), i.e. it shows differential absorption of Photons with Left- (LCP) and Right- (RCP) Circular polarizations.

The present invention's MWE packet model of Photon, i.e. a particle associated with certain amount of energy (MEE or mass-equivalent energy) and mass (EEM or mass-equivalent energy), can well explain why Photon with Circular polarizations can make nano-object with ultra high spin speed. Also, photon with Linear polarization can also make nano-motor spinning and converting the Linear momentum of Photon into rotational movement and mechanical motion (Reference: Liu, Ming, et al. "light-driven nanoscale plasmonic motors." Nature nanotechnology 5.8 (2010):570-573) (i.e. angular momentum).

O. New Model of Polarization (II)— Liner and Circular Polarizations of MWE Particles The present invention discovers the "Rolling Pairs" of Yin(-) and Yang(+) Charge Quanta and its MWE packet of a Photon interact with object's MWF so as to modulate outgoing light MWE into either Linear or Circular polarizations according to "object's MWF atomic- or molecular level fine structures". That is why a Photon can have infinite numbers of Spatial polarization (or Spin) Eigen States.

Figure 34:
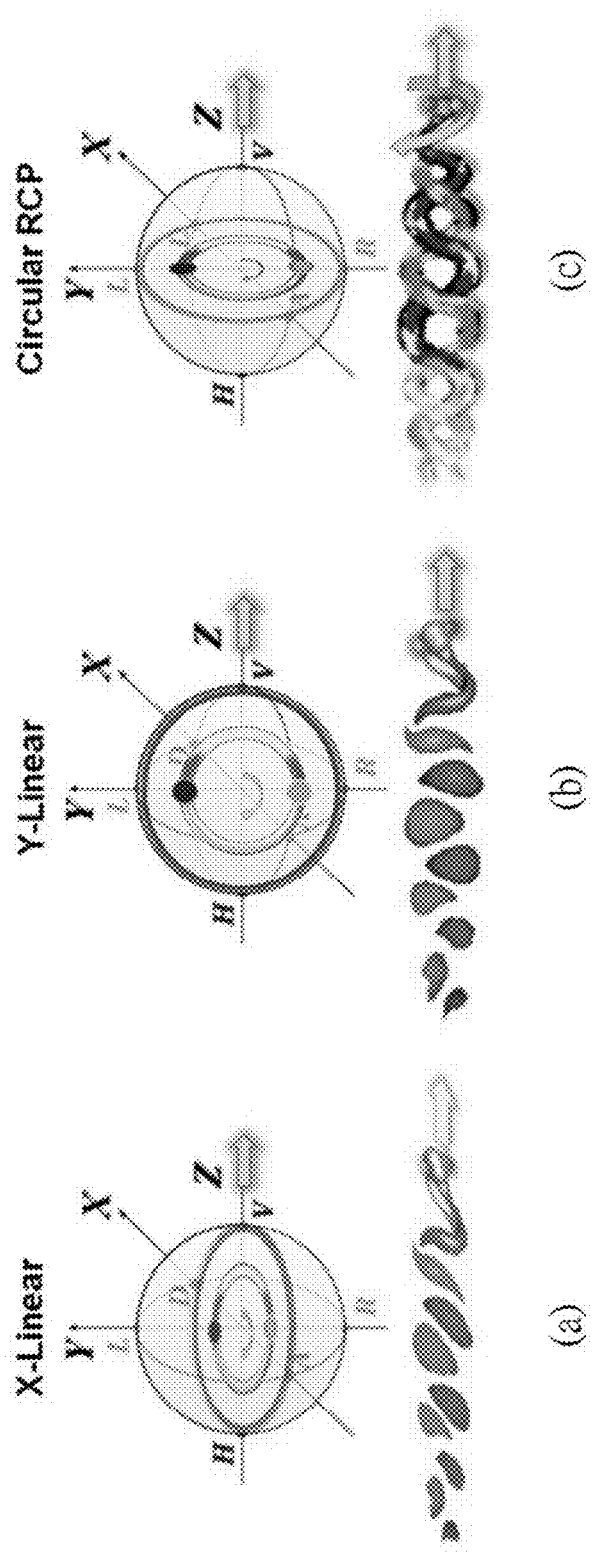
FIG. 34 is a diagram illustrating the new models of (a) X-linear, (b) Y-linear and (c) right circular polarized photons with a light wave traveling along Z-axis.

As shown in FIG. 34, the generalized Photon MWE polarization Spheres with a light wave traveling along Z-axis being:

1) Horizontal polarization: as shown in Red Collar (AHDV plane) shows MWE Linear polarization at X-axis direction (shown in FIG. 34(a)), the present invention indicates it is a degenerate state with TWO hidden states, i.e. LCP and RCP if viewed from Y direction.

2) Vertical polarization: as shown in Blue Collar (RHLV plane) MWE Linear polarization at Y-axis direction (shown in FIG. 34 (b)), the present invention indicates it is a degenerate state with TWO hidden states, i.e. LCP and RCP if viewed from X direction.

3) Circular polarization: as shown in Green Collar (RALD plane) MWE Circular polarization (RCP) plane is in orthogonal at Z-axis (shown in FIG. 34(c)), and the like for LCP. In total, it is associated with TWO different Circular polarization states if viewed from z-axis.

P. QM Spins of Photon MWE Packet with Circular Polarizations

Figure 35:
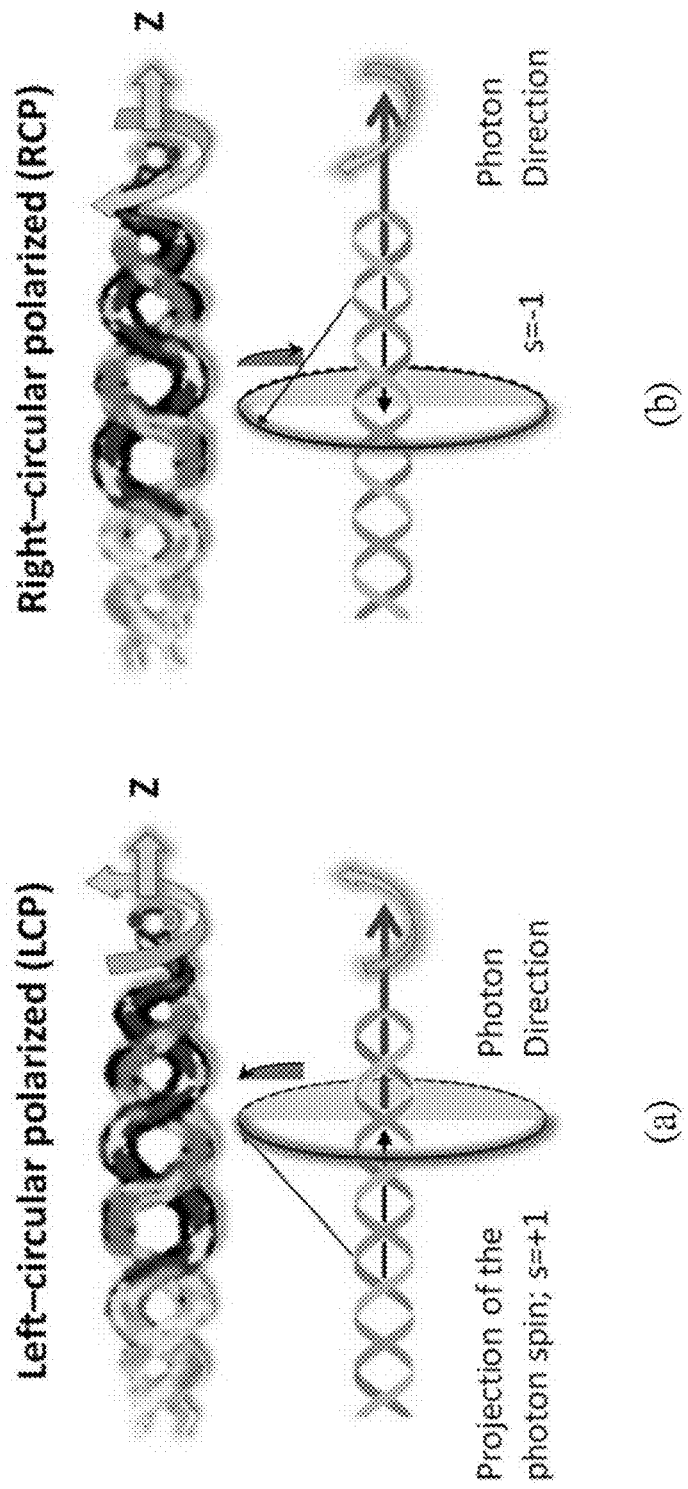
FIG. 35 is a diagram illustrating rotating double strands representation of photon spin of (a) the Left-circular polarized (LCP) photons and (b) right-circular (RCP) photons respectively.

The "rotating double strands" of Photon represents the "positive (+) or negative (−)" Energy (or Mass) polarization states of vacuum. As shown in FIGS. 35(a), 35(b), the Left-circular (LCP) and right-circular (RCP) respectively are the polarized photons that represent two possible "Spin Eigen states (i.e. invariant Eigen-values (1, −1) of its angular momentum)" for a Photon moving in Z-direction if it is observed from the standpoint of the receiver.

Projection of the photon "spin S" on to the direction of photon propagation is equal to $+1\hbar$ (or $-1\hbar$) for the left- (or right-) circular polarized Photon respectively from receiver viewpoint.

Figure 36:
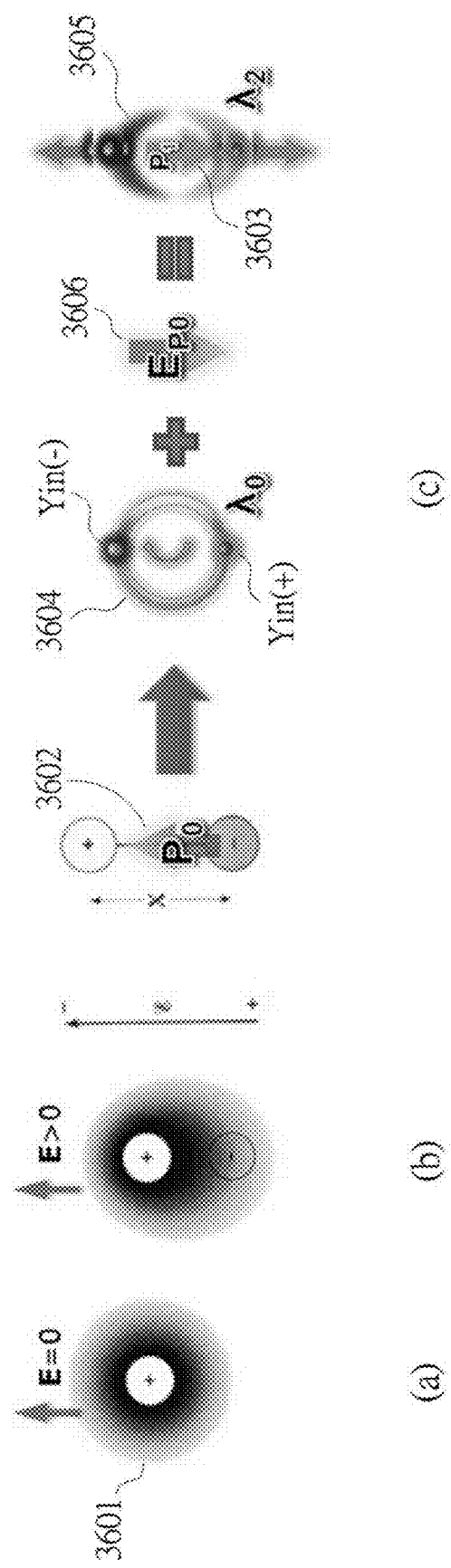
FIGS. 36, 37A, 37B, 38A, 38B are diagrams illustrating atomic MWF and light electric dipole polarization effects.

Q. Physics Inside of Optic Nonlinearity: Atomic MWF and Light Electric Dipole Coupled Effects 1) Atom Structure in Quantum Scale:

Atom 3101 can be representing electrically by positively charged core and surrounding (e.g. s, p, d, f orbital, etc.) electrons. The electron cloud in equilibrium state of external field E=0 (shown in FIG. 36 (a)), in external field E>0 (shown in FIG. 36 (b)), and its electric dipole 3602 representation for the atom 3601 with dipole moment separation of x. Applied external E field distorts the electron cloud and displaces electrons in atomic level space-time (shown in FIG. 36(c)). It gives rise to electric dipole 3602 for atom. The electric dipole 3602 is represented by object's electric dipole polarization or "P0" and it causes the λ2 of interacting photon 3605 is less than (<) the λ0 of incident photon 3604 by following Dirac Equation while MWE of the incident photon 3604 passing through and interacting with the electric dipole 3602 of the atom 3601.

(Dirac Equation can refer to Dirac, P. A. M. (1930). "A Theory of Electrons and Protons". Proceedings of the Royal Society A: Mathematical, Physical and Engineering Sciences. 126 (801): 360.)

2) Origin of Optic nonlinearity:

The present invention discovers the atom 3601 asymmetrical electric dipole 3602 interacting with the incident photon 3604 MWE and generating inductively P1 3603 of light photon 3605. Under applied external field E>0, object "polarization MWF potential" of P0 and inductive field EP0 3606 (=P0/ε0) interact with inductive electric dipole P1 3603 α EP0 3606 (P1//P0) of light (Photon). Object's polarization MWF of the electric dipole 3602 disperses the interacting light λ2 associated with inductive P1 3603 of the interacting Photon to reveal the change of object effective refractive index can be proportional to external field E^2.

R. Physics Behind Optic Nonlinearity (I)— Atomic MWF and Light Electric Dipole Coupled Effect The present invention invents QEO-like (Quadratic Electro-Optic) apparatus, which consists of a plurality of asymmetrical conductive electrodes coating with null, one or more layers of insulator or covalent bond materials. The coating materials have relatively high ionization energies and it is difficult to release its valence orbit electrons. Also, the insulator coating has relatively high electron affinities without introducing many discharges or sparking effects between electrodes having voltage or electric field bias.

Figure 37A:
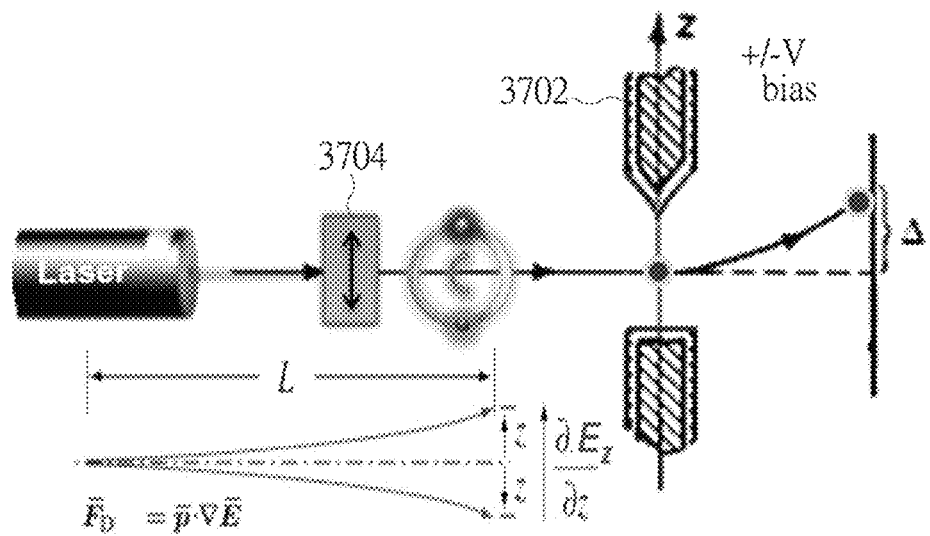
Figure 37B:
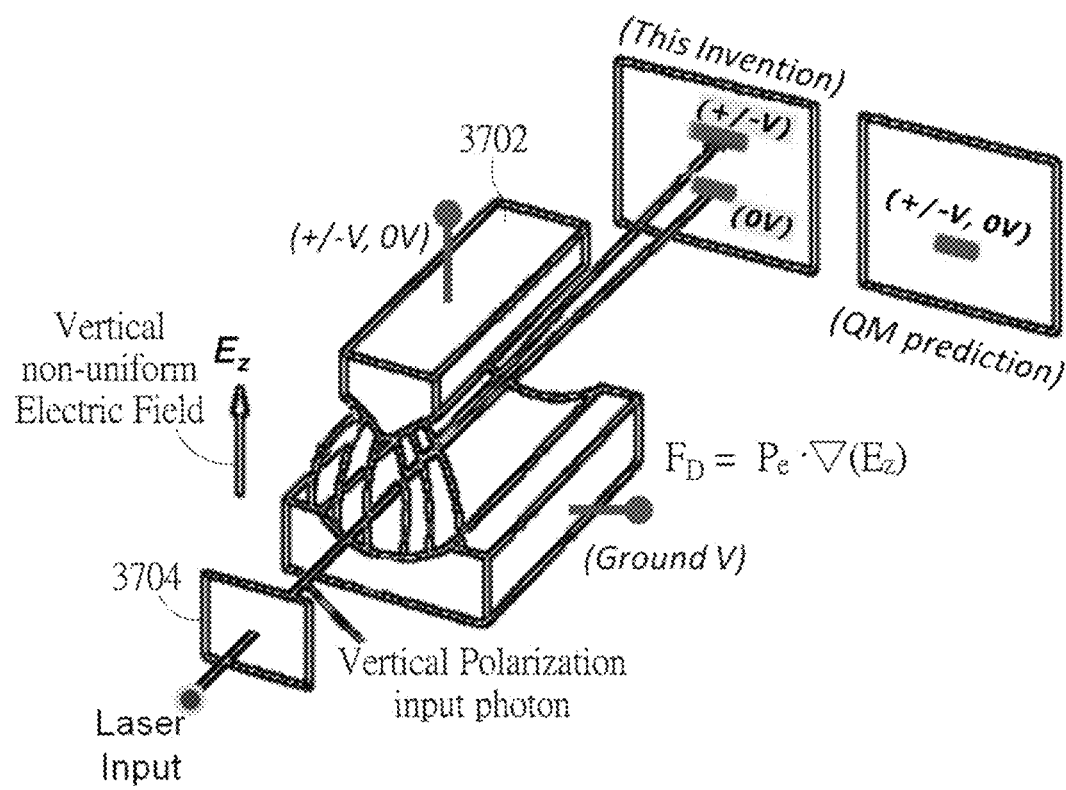

As shown in FIGS. 37A, 37B, one electrode 3702 is included with a sharp angle or tip in one side and having a voltage or electric field bias. The inhomogeneous or non-uniform electric field (E) will bend electric polarized photon's (i.e. its electric dipole being polarized by vertical polarizer 3704) deflection direction trajectory which is proportional to the amount of electric polarization ($P_e$) of incident Photon and the Gradient of Electric field in z-axis, i.e. deflection force of $F_D = P_e \cdot \nabla(E_z)$.

S. Physics Behind Optic Nonlinearity (II)— Atomic MWF and Light Electric Dipole Coupled Effect While sharp electrode 3802 is under +/−V bias versus other electrode 3804, incident V-polarized (i.e. Vertical polarized) coherent photon 3806 will be deflected toward the sharp electrode 3802 direction (that is, upward direction in FIGS. 38A, 38B) by non-uniform electrical field $\vec{E(z)}$, wherein the incident V-polarized coherent photon 3806 can generate a corresponding inductive electric dipole $\vec{Pe}(Ez)$ when the incident V-polarized coherent photon 3806 passes through the non-uniform electrical field $\vec{E(z)}$, and the corresponding inductive electric dipole $\vec{Pe}(Ez)$ interacting with the non-uniform electrical field $\vec{E(z)}$ can generate upward force $\vec{F_D}$. If neglecting photon MWE diffraction effects along the sharp edge of the sharp electrode 3802, incident H-polarized (i.e. Horizontal polarized) photons will keep moving straight without being deflected upward or downward by the non-uniform electrical field $\vec{E(z)}$ owing to that the inductive electric dipole is negligible small for such H-polarized incident photon.

Figure 38A:
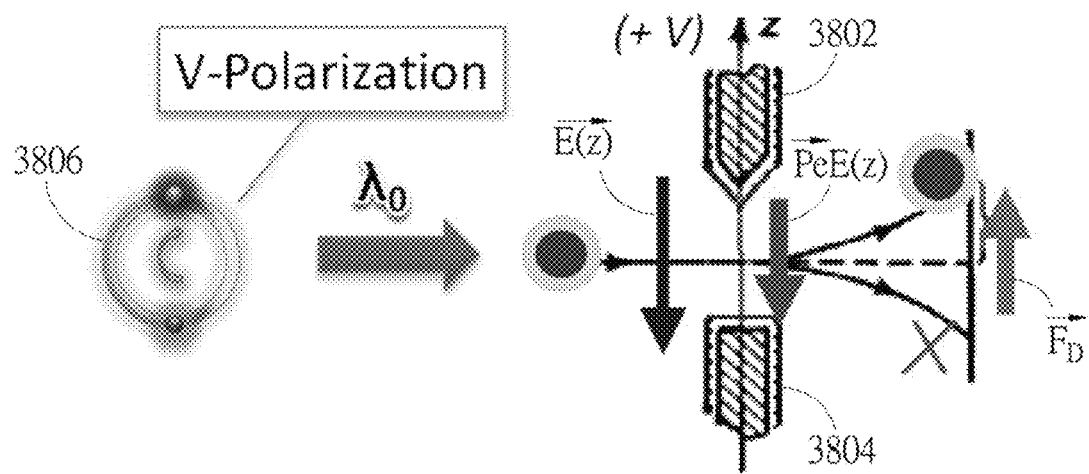
Figure 38B:
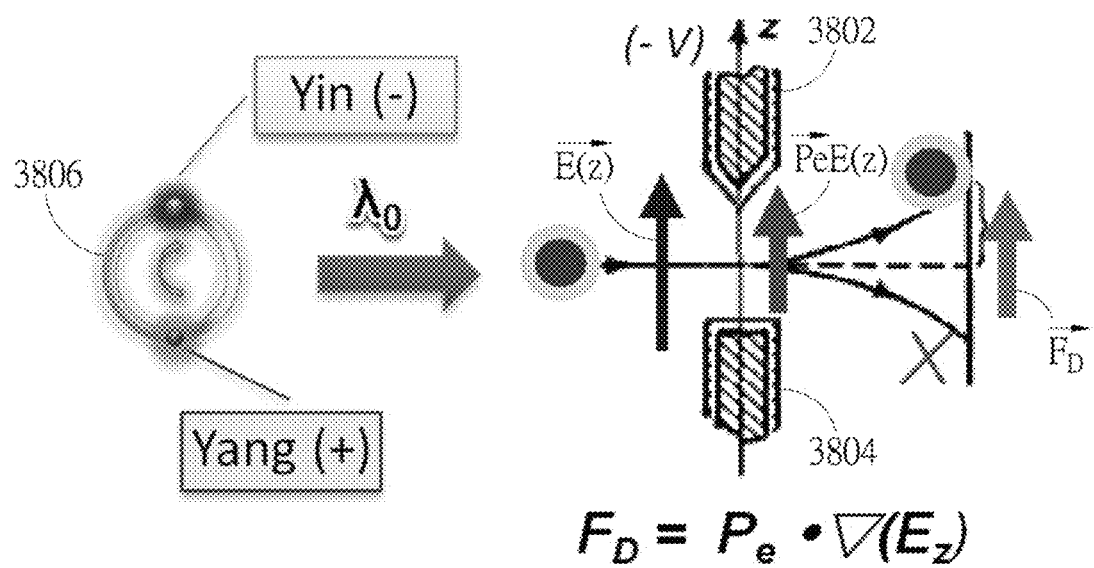

In addition, overall summary corresponding to FIGS. 38A, 38B are shown in TABLE 4 and TABLE 5, respectively.

TABLE 4

| z-axis | V(z) | $\vec{E(z)}$ | Grad (Ez) | $\vec{Pe}$ (Ez) | $\vec{F_D}$ |
|---|---|---|---|---|---|
| 4 | 20 | −8 | −2 | <0 | >0 (upward) |
| 3 | 12 | −6 | −2 | <0 | >0 (upward) |
| 2 | 6 | −4 | −2 | <0 | >0 (upward) |
| 1 | 2 | −2 | −2 | <0 | >0 (upward) |

TABLE 5

| z-axis | V(z) | $\vec{E(z)}$ | Grad (Ez) | $\vec{Pe}$ (Ez) | $\vec{F_D}$ |
|---|---|---|---|---|---|
| 4 | −20 | 8 | 2 | >0 | >0 (upward) |
| 3 | −12 | 6 | 2 | >0 | >0 (upward) |
| 2 | −6 | 4 | 2 | >0 | >0 (upward) |
| 1 | −2 | 2 | 2 | >0 | >0 (upward) |

T. New Model of Optic Nonlinearity QEO Effect

Figure 39:
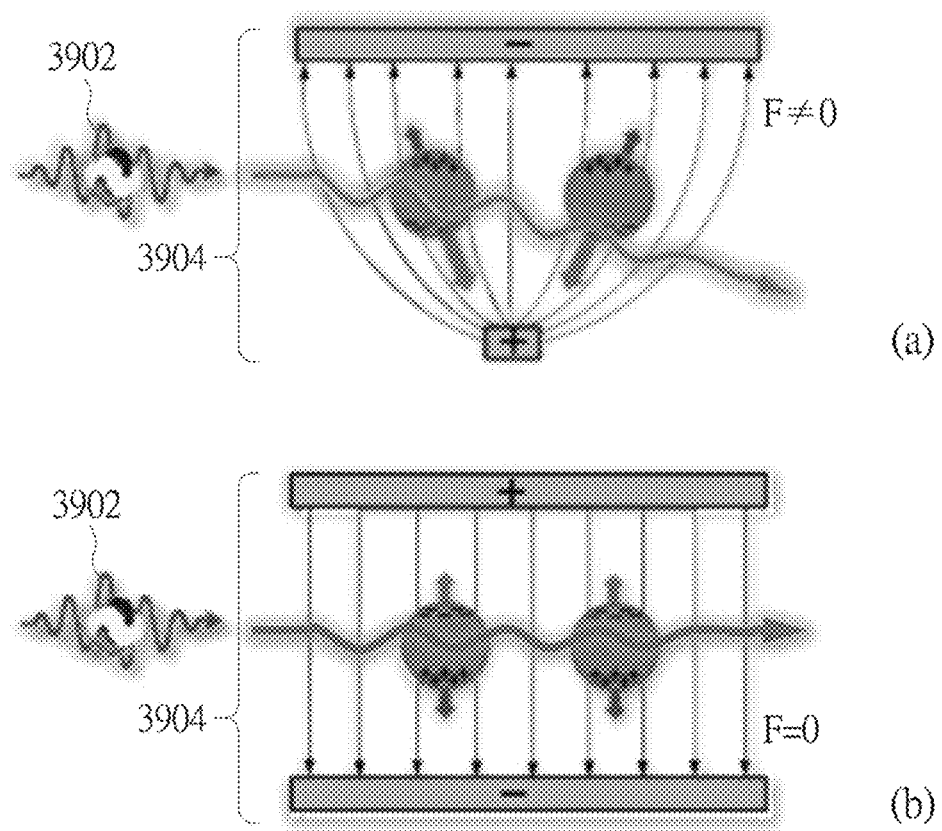
FIG. 39 is diagram illustrating DC Kerr (QEO) effect revealing by the analogous physics of DEP (Dielectrophoresis) effect.
Figure 40:
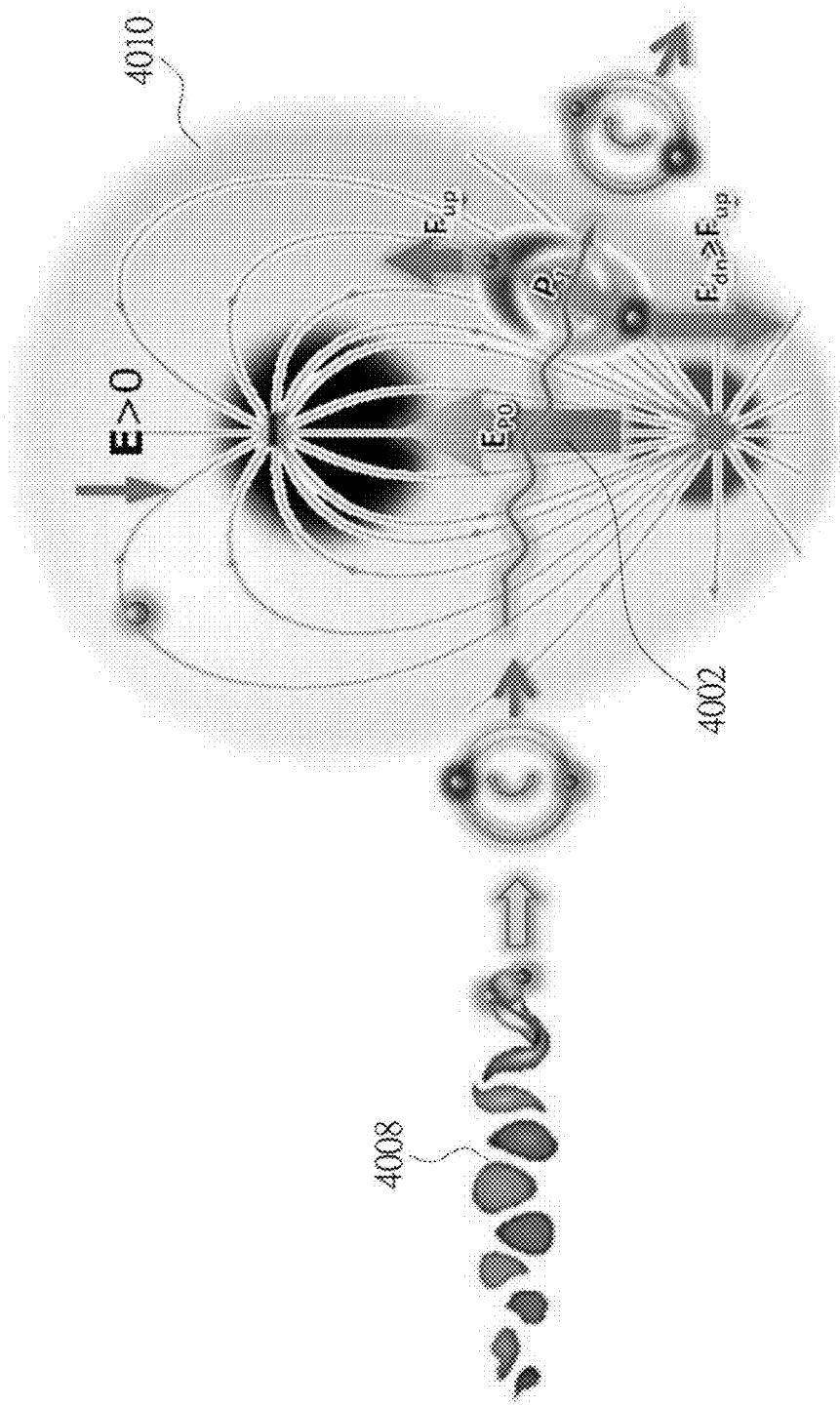
FIG. 40 is diagram illustrating all typical particles or molecules exhibiting DEP effect in presence of non-uniform E fields.

DC Kerr or Quadratic Electric Optical (QEO) effect reveals similar physics of the well-known DEP (Dielectrophoresis) effect, a non-zero inductive force is exerted on incident photon 3902 by media 3904 while immersing in a non-uniform E field (shown in FIG. 39(a)), and no net force is exerted on the incident photon 3902 by the media 3904 while immersing in uniform E field (shown in FIG. 39(b)). All typical particles or molecules may exhibit DEP effect in presence of non-uniform E fields, the DEP force ($F_{DEP}$) depends strongly on both medium and particle's atomic-level fine structures, polarizations and frequency of external E field as well (shown in FIG. 40). The present invention unveils the Photon QEO effect is a dual-analogue phenomena to the well-known Stern-Gerlach effect for deflecting an atom or a fermion into either spin-up or spin-down Quantum spin states. As shown in FIG. 40, the nonlinear QEO effect displays the similar physics of the well-known DEP effect, a non-zero inductive force is exerted on incident photon 4008 with vertical polarization by a media, molecule or object 4010 with electric dipole while immersing in a non-uniform and inductive atomic-level field EP0 4002 under the presence of external field E>0. Via the new theory discovered by the present invention, the incident photon MWE 4008 interacts with MWF of the object 4010 and makes the effective (or appearance) refractive index of object 4010 show second order proportional to external field $E^2$.

U. New Theory of KTN's DC Kerr Effect (Reference: K. Nakamura, "Optical Beam Scanner Using Kerr Effect and Spacecharge-Controlled Electrical Conduction in KTa1-xNbxO3 Crystal," NTT Technical Review, Vol. 5, No. 9, 2007. (NTT Japan))

In an embodiment, the KTN's QEO effect is derived from asymmetric MWF polarizations in entire Space-time under external field E>0. As shown in FIG. 41(a), when external electric field E is equal to 0, KTN's QEO effect does not cause asymmetrical polarization P0 of crystal MWF distribution, and as shown in FIG. 41(b), when the external electric field E is greater than 0, KTN's QEO effect causes asymmetrical (or non-uniform) electric dipole polarization P0 with changing the crystal MWF and scalar/vector potential distributions, while we are about to integrate mathematically its MWF (or electric dipole polarization) over Space-time.

Figure 42A:
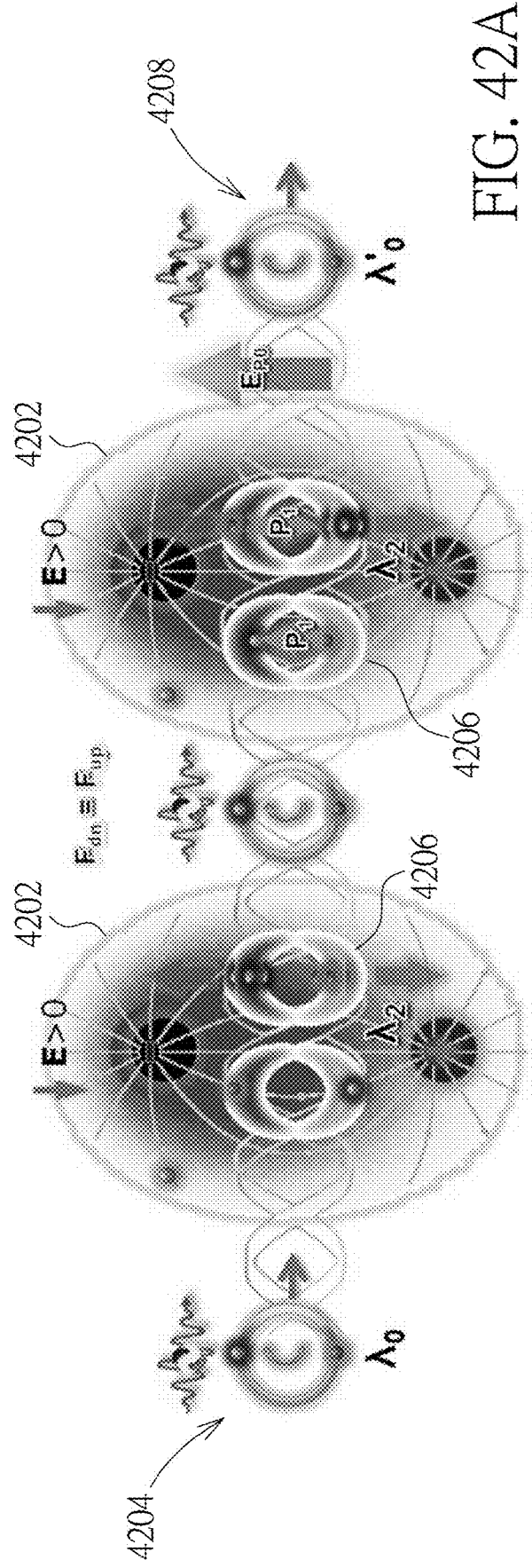
FIG. 42A is a diagram illustrating linear symmetric dispersion object with symmetric electric dipole polarization fine structures under an external electric field.
Figure 42B:
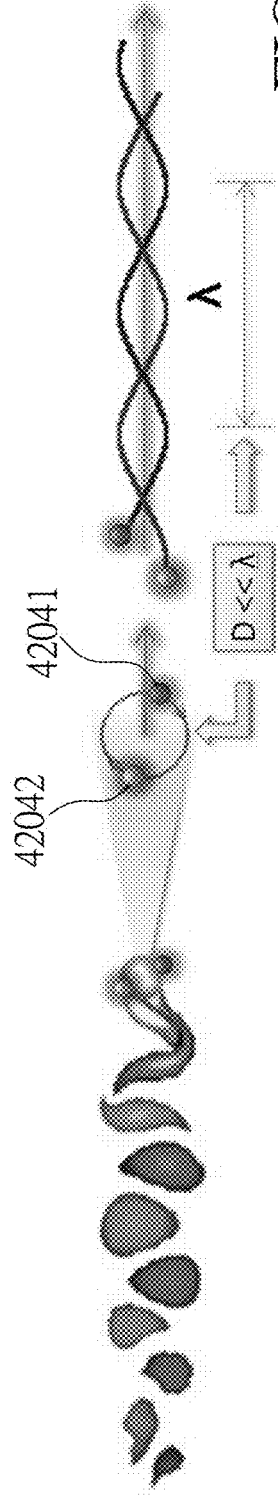
FIG. 42B is a diagram illustrating the new light model representations of rotating pair of charge and anti-charge quanta.

As shown in FIG. 42(a), linear dispersion (refraction) object 4202 is with symmetric electric dipole polarization Fine Structures under an external electric field E>0. Inductive electric dipole P1 of vertical polarized light MWE 4204 sees symmetric Inductive electric dipole moments and the integral net force in all direction is symmetrically averaging of zero (or null) by doing integral over space-time throughout the entire atomic structures. The Object 4202 MWF potential of a symmetric Ep0>0 creates wavelength λ2 of the of interacting light 4206 less than wavelength λ2 of the of incident photon light 4204 and emersion Photon 4208 owing to light electric dipole P1 MWF or scalar/vector potential interaction effect by following Dirac Equation. Also, as shown in FIG. 42(b), diameter D between Yin(−) and Yang(+) Charge Quanta 42042, 42041 of the light 4204 is much less than the wavelength λ0 (or λ2 and λ'0) of the light 4204 (or 4206 and 4208) respectively.

Figure 43:
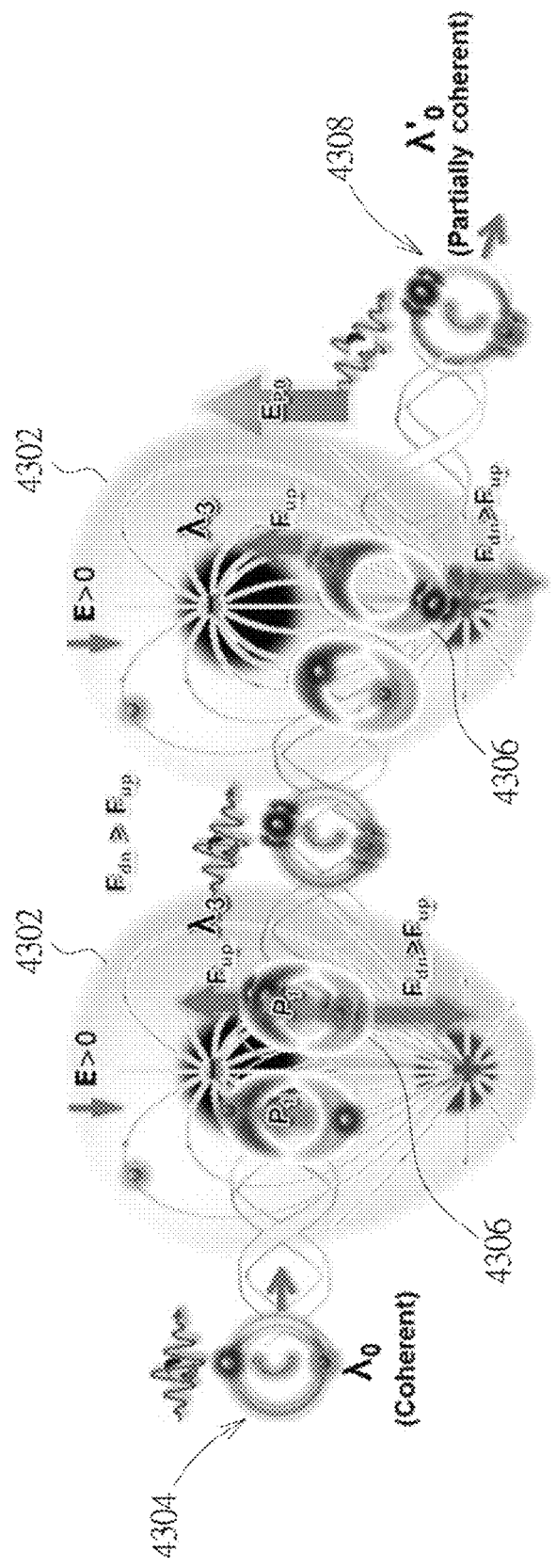
FIG. 43 is a diagram illustrating nonlinear symmetric dispersion object with asymmetric electric dipole polarization fine structures under external electric field.

As shown in FIG. 43, nonlinear dispersion (refraction) object 4302 is with asymmetric electric dipole polarization Fine Structures under external electric field E>0. Inductive electric dipole P1 of vertical polarized photon 4304 sees asymmetric inductive electric dipole moments and integral net force in all direction shows asymmetrically averaging of non-zero inductive force by doing integral over Space-time throughout the entire atomic structures.

The Object 4302 MWF potential of the asymmetric Ep0>0 creates wavelength λ3 of the interacting photon 4306 is less than wavelength λ0 of the of incident photon 4304 and emersion photon 4308 owing to light electric dipole P1 MWF or scalar/vector potential interaction effect by following Dirac Equation. The present invention unveils the immersing photon 4308 revealed itself being partially "Spatial Incoherent" due to inductive field Ep0 was spatially incoherent while interacting with P1 over plurality of atoms in entire Space-time.

V. Nonlinear Interaction of Atomic MWF and Light Electric Dipole

Electric dipole polarization nonlinearity indicates that external E-field induced some changes for refraction (dispersion) index. Also, Object's matter wave field MWF creates refraction (or dispersion) in between photon MWE and atomic MWF (Matter Wave field) tensors, owning to its scalar/vector potentials refraction effect associated with the object in atomic sub-wavelength space.

Figure 44:
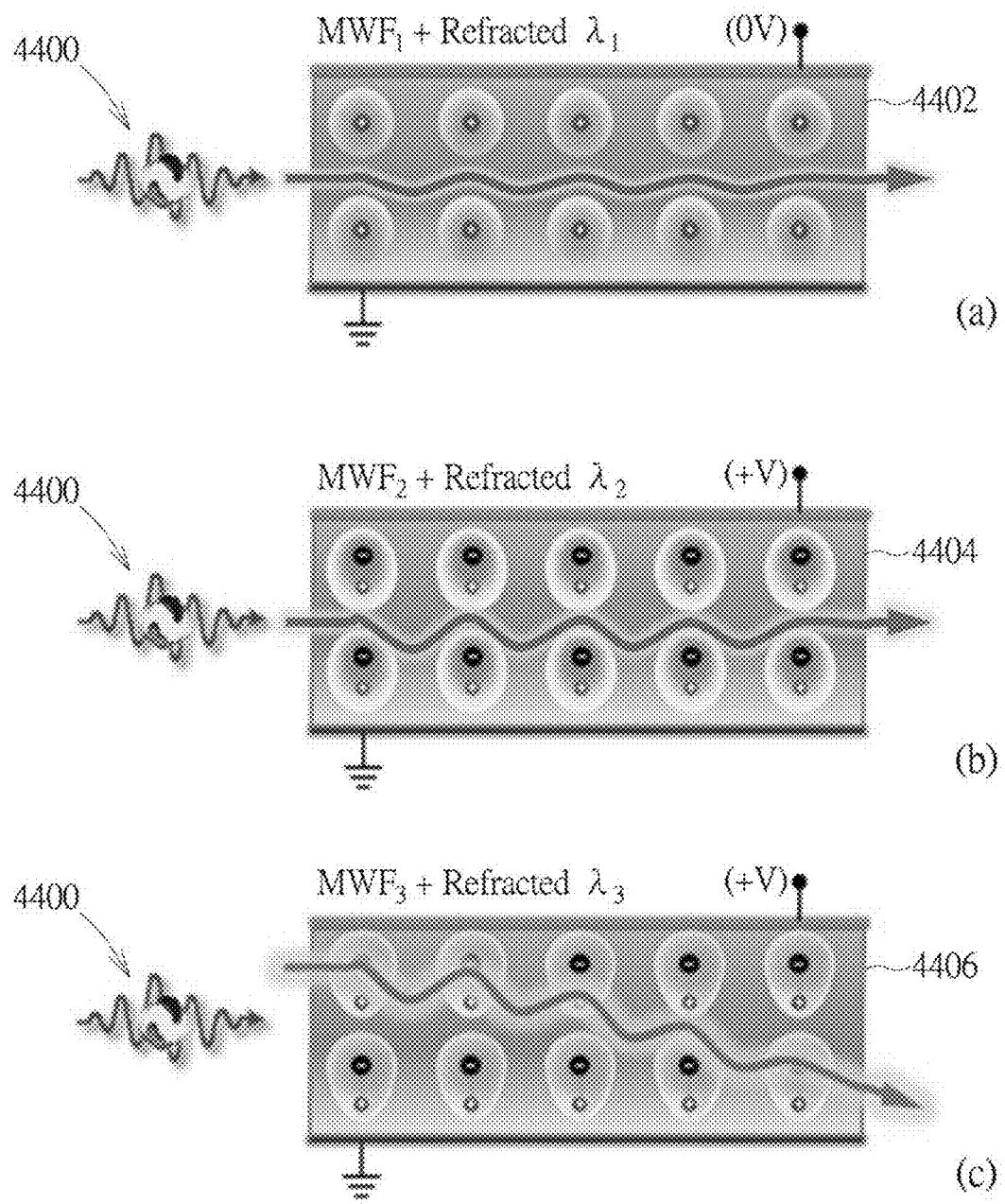
FIG. 44 is a diagram illustrating three representations for different optical matters, (a) most objects having symmetrical electric dipole polarization under no external field, (b) under external E field >0, an object having symmetrical integral polarization and (c) under external E field >0, another object having asymmetrical integral polarization.

As shown in FIG. 44(a), without external E-field and polarization Poling (that is, external E=0), most objects 4402 (MWF1) shows integral symmetrical electric dipole polarization in space-time and incident photon 4400 refraction effect follows Snell's Law, wherein the incident photon 4400 has wavelength λ 0.

As shown in FIG. 44(b), for object 4404 with symmetrical integral (average) polarization (MWF2), the inductive electric dipole polarization changes of refraction index (or dispersion) of the incident photon 4400 follows a liner function of external E-field, owning to MWF2 of the object 4404 and its optical density is about linearly proportional to external field E applied.

As shown in FIG. 44(c), for object 4406 with asymmetrical integral (average) polarization (MWF3), the inductive electric dipole polarization changes of refraction index (or dispersion) of the incident photon 4400 follows "Quadratic or nonlinear" trend along with the external E-field due to electric dipole-dipole Interaction in between MWFs (i.e. MWF1 4402, MWF2 4404 and MWF3 4406) dipoles and inductive electric dipole of the incident photons 4400.

W. DSS (Double-Single-Slit) Experiment Evidences the MWE New Light Model

As shown in FIG. 45(a), the present invention discovers when light 4500 generated by coherent (e.g. Laser) source 4502 passes through slit 4504, sidewall 4506 can reflect matter wave MW of the light 4500, wherein the sidewall 4506 can be a plate comprised of conductor, semiconductor, insulator, dark or transparent materials. Therefore, by following the Huygens principle, reflected wavefront of photon matter wave MW can combine with original matter wavefront of the light 4500 MWE packet so as to form substantially half double-slit interference patterns on screen and detector 4508. In one embodiment, the sidewall 4506 can be a bare plate of glass (e.g. SiO2) and the like material without the mirror coating on it. In another embodiment, the sidewall 4506 covering with dark material can be comprised of materials with reflectance less than 50% or with transmittance less than 50%, i.e. majority of the light gets absorbed while light (MWE packet) striking on the sidewall 4506 at about normal incident angles.

In addition, as shown in FIG. 45(b), when the light 4500 generated by the coherent (e.g. Laser) source 4502 passes through the slit 4504, if the sidewall 4506 does not exist, the original matter wave of the light 4500 MWE packet can form single-slit interference patterns on the screen and detector 4508 by follow the prior art classical theory and Huygens principle.

X. DSS1 (Double-Single-Slit 1) Experiment Reveals the MWE Coherent Wavefront Effect As shown in FIG. 46(a), the present invention discovers when light 4600 generated by coherent source 4602 passes through upper slit 4604, sidewall 4606 can reflect matter wavefront of the light 4600, so reflected wavefront of photon matter wave of the light 4600 can combine with original matter wavefront of the light 4600 MWE packet to form upper part of double-slit interference patterns on screen and detector 4608. Similarly, as shown in FIG. 46(c), lower double-slit interference patterns can be formed on screen and detector 4610.

In addition, as shown in FIG. 46(b), if the sidewall 4606 and sidewall 4612 are close to each other until the sidewall 4606 is get merged with the sidewall 4612 and with having about negligible thickness (e.g. sidewalls with zero thickness but opaque for light), then complete double-slit interference patterns can be formed on screen and detector 4620 while light 4614 generated by coherent source 4616 passes through the upper slit 4604 and lower slit 4618. The present invention discovers, DSS-1 Experiment reveals the light MWE packet convey the wave-particle duality while it can be obeying "Causality" and "Local Realism" theories which were supported by Albert Einstein a hundred years ago.

Figure 47:
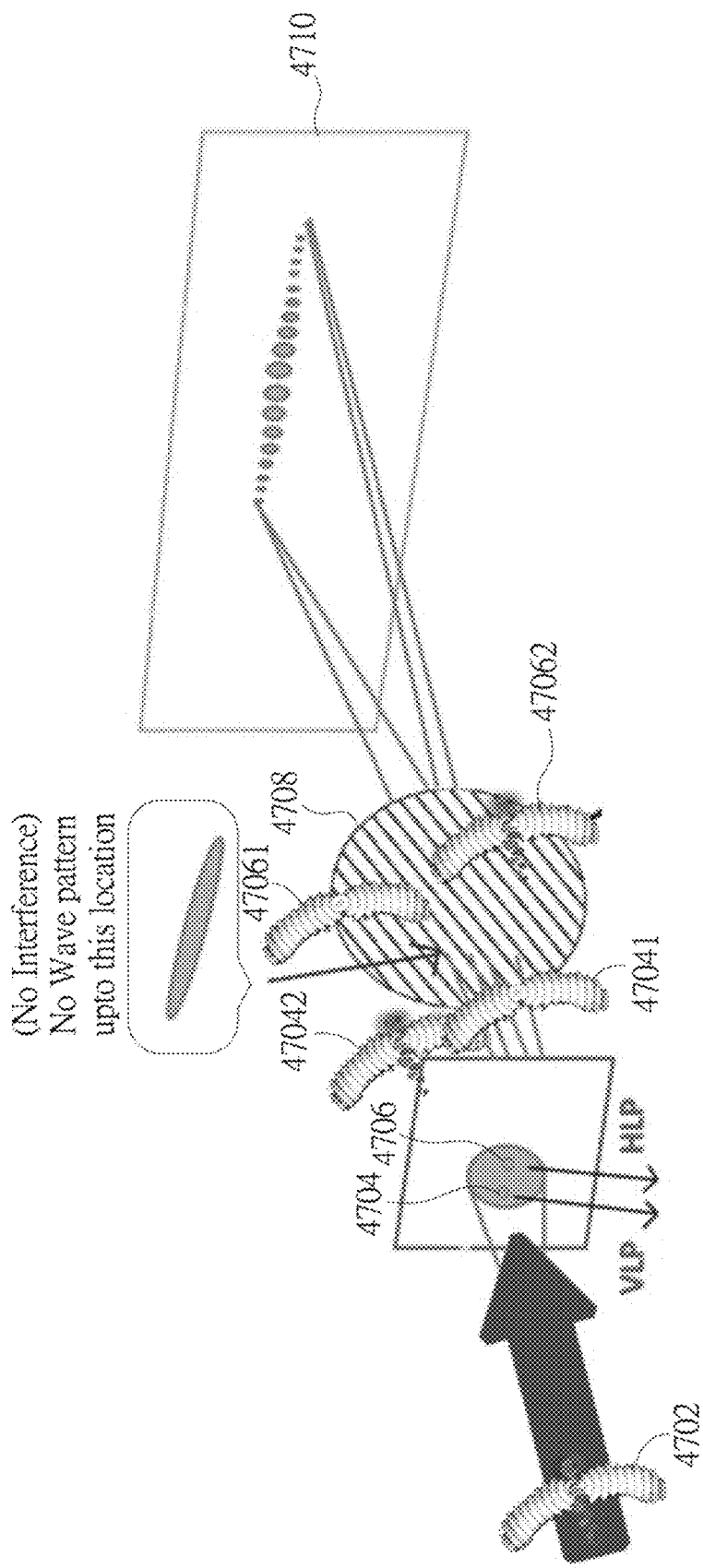
FIG. 47 is a diagram illustrating photons with HLP state and along with creating wavefront-split of the photons and MW thereof through vertical LP (Vertical linear polarization, VLP) being generated simultaneously after diagonal linear polarization (DLP) photons in 45° diagonal direction passing through horizon LP (HLP) slit.

Y. DSS-2 (Double-Single-Slit 2) Experiment Explains the Mysterious QM Eraser Effects The present invention discovers the complete theory to well explain the DSS-2 QM Eraser Experiment: As shown in FIG. 47, photon 4702 generated by laser source has diagonal linear polarization (DLP) in 45° diagonal direction. After the input terminal photon 4702 with diagonal linear polarization passes through horizon LP slit (horizontal linear polarization, HLP) 4706, it can generate photon 47062 with HLP state, and after the photon 4702 passes through vertical LP (Vertical linear polarization, VLP) slit 4704 it can generate another photon 47042 with VLP state, wherein H+V=H(0°)+V(0°), H−V=H(0°)+V(180°), (0°) or (180°) are the phase angle of a particular light beam.

Apparently, there is no interference patterns can be formed before or on the location of the 45 diagonal linear polarizer (DLP) 4708 (i.e. eraser) due to the joint photon states of the photon 47042 and the photon 47062 are orthogonal states. But, after the photon 47042 (VLP) and the photon 47062 (HLP) pass through the 45° diagonal linear polarizer (DLP) 4708, interference patterns can be resumed and formed on screen 4710.

The experiment DSS-2 of the present invention discovers that every single photon 4702, if it gets passed the slit 4704 to generate the VLP photon 47042 traveling toward the 45° DLP 4708, will generate simultaneously another orthogonal MW copy HLP wavefront 47041 versus VLP photon 47042 by passing a portion its DLP photon 4702 MWE spatial wavefront through the HLP slit 4706. Finally, the interference patterns can be resumed and formed on screen 4710 when copy HLP wavefront 47041 and VLP 47042 MWE packet pass through the 45° DLP 4708 by making them finally in the same DLP and coherent state. Similarly, as shown in FIG. 47, interference patterns can be resumed and formed on screen 4710 when copy VLP wavefront 47061 and HLP photon 47062 MWE packet pass through the 45° DLP 4708 by making them finally in the same DLP and coherent state. The present invention unveils; new light model illustrates that Malus Law combined with DSS-2 experiment can predict the Quantum Erase interference characteristics so as to be compliant with the Local-Realism and Causality theories.

Z. DSS Wavefront-Split Experiment Answers Different Traits of EM Wave Vs. Light (i.e. Photon) Wave DSS-1 and DSS-2 Experiments Reveal MWE packet of light and matters (e.g. Electron or Proton) can display characteristics of wave-particle duality while still can be obeying "Causality and Local Realism" theories supported by Einstein.

Over hundreds of years, DSS-1 and -2 experiment firstly answers the different characteristics in aspects of macro and microscopic wise, between EM waves and light Quanta (or Photon MWE packet) shown in TABLE 6.

TABLE 6

| Characteristics | EM waves | Light quanta | Remarks |
| --- | --- | --- | --- |
| A. Same or similar | | | |
| Geometrical optics | Reflection, refraction, TIR, λ-dispersion, etc. | Reflection, refraction, TIR, λ-dispersion, etc. | Both follow Snell's law, etc. |
| Wave optics | Interference, diffraction, coherence and polarization, etc. | Interference, diffraction, coherence and polarization, etc. | Both follow Huygens principle, Fourier and Fresnel theories, etc. |
| Black-body radiations | Follow Plank's distributions | Follow Plank's distributions | Radiation power density distribution follow Plank's law |
| B. Different or dissimilar | | | |
| Life-time governing rule | Traveling at speed of c, but | Traveling at speed of c with | EM wave decays while traveling and its |

TABLE 6-continued

| Characteristics | EM waves | Light quanta | Remarks |
| --- | --- | --- | --- |
| | is dispersive in Universe and governed by Maxwell's equation | stable invariant particle properties and governed by Dirac equation | energy submerge into the background state of Universe |
| Wave-particle duality | Only shows wave behaviors | Owns unique duality QM's spin, angular momentum, de Broglie matter wave behaviors | EM wave does not show QM spin, Compton's scattering effects, etc. |
| Polarizer materials | Showed up only with metallic slits (or meshes) only | Can be showing up with majority dielectric or metallic matters | EM polarized wave goes only with metallic matters, but light does not limit to that |
| Single slit and double slit experiments | Work only with conductive or metallic slits | Work with all kinds of metal, non-metal, or dielectric slits | EM waves penetrate dielectric and ruin interference effect of single slit and double slit experiments |

AA. DSS Wavefront-Split Experiment Answers Those Unanswered Behind Many Paradoxes As a short summary hereby, the present invention discovers DSS experiments (i.e. DSS-1 and -2) evidence light MWE convey wave-particle duality while obeying "Causality" and "Local Realism" theories. DSS experiments, firstly in human history, conceived that every single Photon owns a "defined-but-unknown or defined-but-known states" before entering the slits. It implied further, by following the movement of a Photon, "Arrow of time is unidirectional" by following the Theory of Causality. "Local Realism" theory is significant for classical mechanics, general relativity and electrodynamics, including QED theory. DSS Experiments evidence that all objects must objectively have a pre-existing Eigen-state or -Value for a measurement before the measurement being actually made.

"Decision had been made" when a Photon was just passing through either a single or double slits. DSS experiments predicted, there is no such thing such as, e.g., delayed decision, Quantum erase characters, etc. Simplicity of the Malus law shall take precedence over complicated Quantum Erase theory. In view of the new light model, there was no higher theory which is required to appeal to.

In viewing of the results of the present invention, one can answer those Unanswered Paradoxes accordingly:

The long lasting debatable EPR (Einstein-Podolsky-Rosen) Paradox: DSS experiments had evidenced what Einstein asserted one is indeed a right physical theory, i.e. "God does not play dice". On the other hand, QM is not complete and it is just quite the same as Einstein predicated a hundred years ago (Reference: Einstein, A; B Podolsky; N Rosen (1935-05-15). "Can Quantum-Mechanical Description of Physical Reality be Considered Complete?". Physical Review. 47 (10): 777-780.).

The Local Realism theory may defy the prior art of Wheeler's Experiment: DSS experiments evidenced "Locality and Realism" postulations, i.e. any object has a pre-existing Eigen Value or State for a measurement before people conducting a test (Reference: John Archibald Wheeler, "The 'Past' and the 'Delayed-Choice Double-Slit Experiment'," pp 9-48, in A. R. Marlow, editor, Mathematical Foundations of Quantum Theory, Academic Press 1978.).

Figure 48:
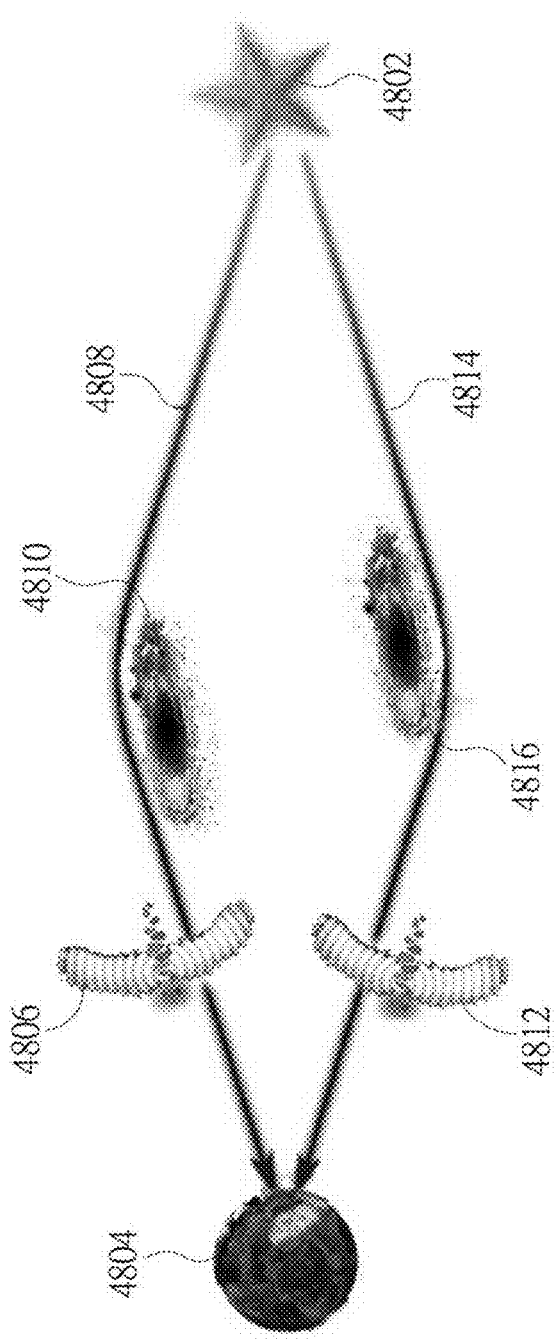
FIG. 48 is a diagram illustrating Wheeler's thought experiment getting disproved by DSS experiments when each Photon (generated by star) just passes through one of massive galaxies.

Also, DSS counter proved the results of Wheeler's thought experiment. The prior Wheeler's thought experiment had got disproved by DSS experiments; DSS experiments discover when each Photon (generated by star 4802) just passes through one of massive galaxy 4810 or galaxy 4816, each Photon MWE is diffracted primarily by gigantic MWF of the closest massive galaxy and is not diffracted a lot by another far distance massive galaxy before the Photon will be observed by an observer on earth 4804. That is, as shown in FIG. 48, each of photon 4806 and photon 4812 generated by the star 4802 only passes through only one of path 4808 or path 4814 before reaching the earth 4804. For example, the photon 4806 passes through the path 4808 to be diffracted by the galaxy 4810 before the photon 4806 arriving at the earth 4804, and the photon 4812 passes through the path 4814 to be diffracted by the galaxy 4816 before the photon 4812 arriving at the earth 4804.

AB. Huygens Principle Superposition of Spherical Wavefront

Figure 49:
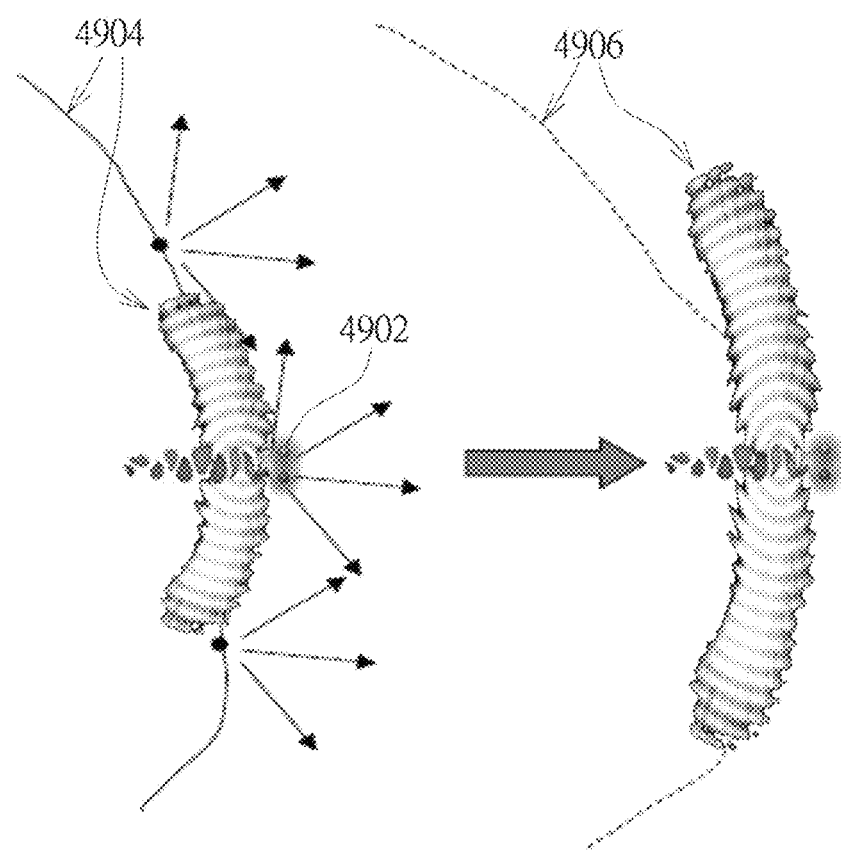
FIG. 49 is a diagram illustrating the new light model obeying the Huygens Principle.

As shown in FIG. 49, the Huygens Principle states that each point (e.g. point 4902 on first MW wavefront 4904) acts as a secondary light source emitting a spherical wave. Second MW wavefront 4906 after a short propagation distance is the result of superimposing all these spherical wavelets of the first MW wavefront 4904.

This summation of photon's MW wavefront needs to take into account the phase as well as the MW's amplitude of the individual wavelets. In viewing of the present invention, as shown in FIG. 49, the first MW wavefront 4904 is more spherical one and the second MW wavefront 4906 is diverged from a spherical toward the planar one.

AC. Prior Art "Classical" QM Model of Light Beam Splitter's Transmitting (TX) and Reflecting (RX) Wavefunctions The present invention discovers a better model to spell out the Photon's "Particle-and-wave" Views, and the "Wave-particle duality" is quite a comprehensible model that includes matter wave and Energy (MWE) packet model for Photon, e.g. the similar old pilot matter wave modeled by Louis de Broglie.

In view of another prior art, it is possible to detect the arrival of individual electrons, see the diffraction pattern emerge as a statistical made up of many small spots (Tonomura et al., 1989). Evidently, the present invention discovers all quantum particles are indeed particles embedded with energy packet and wave behaviors, but whose behavior is to be controlled by microscopic QM interactions of its MW wavefunction and object MWF which is very different from classical physics would have us to expect.

AD. New Light Model with MWE—the BS is a "Mass-Less" MW Generator

The present invention discovers the New BS Model is associated with the subtle characteristic of conjugate MW (or MW*) Generator.

Figure 50:
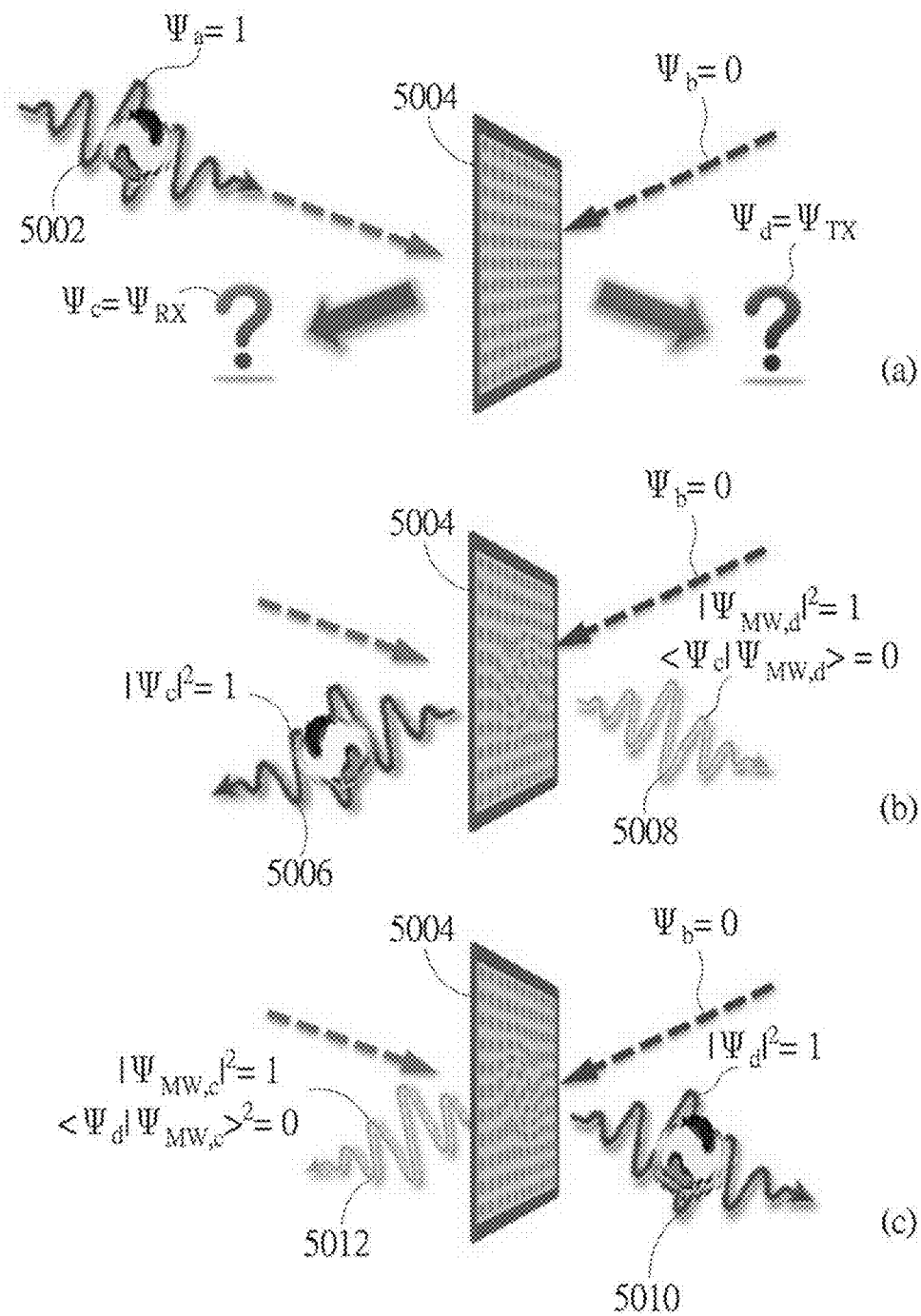
FIG. 50 is a diagram illustrating new modified transfer matrix which is characterized as modified QM beam-splitter matrix.

Modified Transfer Matrix BT2 can be characterized as Modified QM Beam-splitter Transfer Matrix of 50%: 50% BS, which is an Orthogonal (i.e. Conjugate) MW generator. An Orthogonal MW can be created inductively by QM Annihilation (â) and Creation (â⁺) subtle interactions between incident light MWE and MWF of beam splitter (BS) 5004 by following the Pauli Exclusion Principle. The inductive MW owns mass-less wave property and its spatial spread is bounded by the spatial distributions of both incident photon's MWE wavefunction and the MWF spread of the BS 5004. Therefore, as shown in FIG. 50($a$), when incident light 5002 (appearing at upper left corner) hits the BS 5004, reflected light (i.e. MWE packet) 5006 is generated in 50% probability and meanwhile an orthogonal MW 5008 (i.e. is mass-less by not including the energy core of a photon) is also created inductively by Annihilation (â) and Creation (â⁺) interactions between incident light (MWE) 5002 and the MWF of the beam splitter 5004 (shown in FIG. 50($b$)). Likewise, transmitted light 5010 is generated in 50% probability and meanwhile an orthogonal MW 5012 is also created inductively (shown in FIG. 50($c$)), wherein the BS 5004 has associated with the modified Transfer Matrix BT2.

As a typical Representation of MW packets, the MW wavefunction can denoted as $|\Psi MW, dc\rangle = |(\Psi MW, d, \Psi MW, c)\rangle$ which are in Phase-Entangled (e.g. orthogonal or conjugated) mode along with $|(\Psi c, \Psi d)\rangle$.

The present invention unveils that PBS (polarization Beam-Splitter) can fit similar rules, e.g. $\langle \Psi c | \Psi MW, d \rangle = 0$ by obeying the Pauli Exclusion Principle (PEP) while PBS creation (â⁺) process of photon MWE and associated Orthogonal polarization MW.

Figure 51:
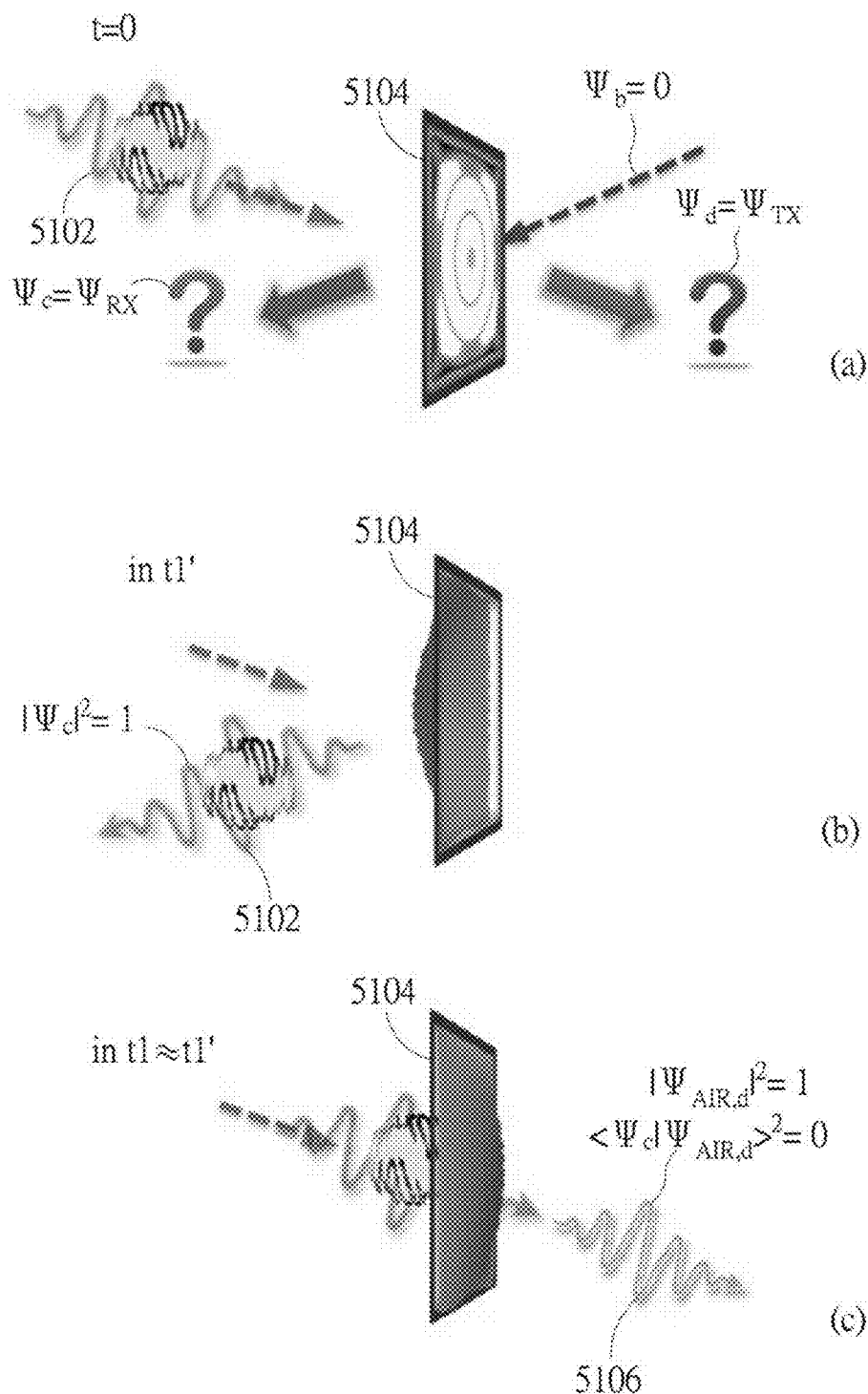
FIG. 51 is a diagram illustrating a semi-permeable transfer matrix analogous of a Membrane Splitter with MW generating function.

AE. New Light Model with MWE Analogous to Orthogonal Air Wave of a Base-Ball BS for a Classical Vibrating Ball:

The BT3 represents a Semi-permeable Transfer Matrix of a Membrane Splitter with MW generating function, i.e. $\Psi$AIR is created inductively by interactions in between a vibrating ball's wavefunction and BS membrane's MWF property. Therefore, as shown in FIG. 51($a$), when incident vibrating Ball 5102 (appearing at upper left corner) hits semi-permeable membrane 5104, owing to interaction in between the incident Ball 5102 and the Semi-permeable membrane 5104, the incident Ball 5102 may be reflected (shown in FIG. 51($b$)), and transmitted wave 5106 may be created (shown in FIG. 51($c$)), wherein the semi-permeable membrane 5104 has Semi-permeable Transfer Matrix BT3.

In $t1 \approx t1'$ instant, BT3 forms instantly the transmitted wave 5106 orthogonal to the reflected vibrating Ball 5102 while the ball hitting the semi-permeable membrane 5104.

AF. New Light Model—the MWE BS is "Mass-Less" MW Generating Matrix

Figure 52A:
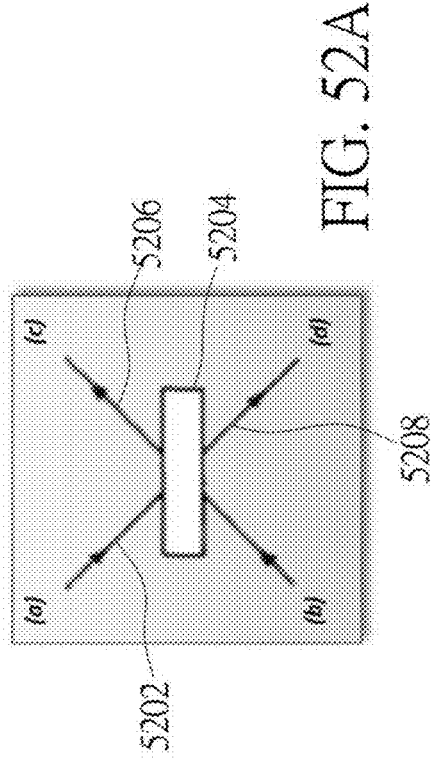
FIG. 52A is a diagram illustrating (a), (b), (c), (d) directions of BS.
Figure 52B:
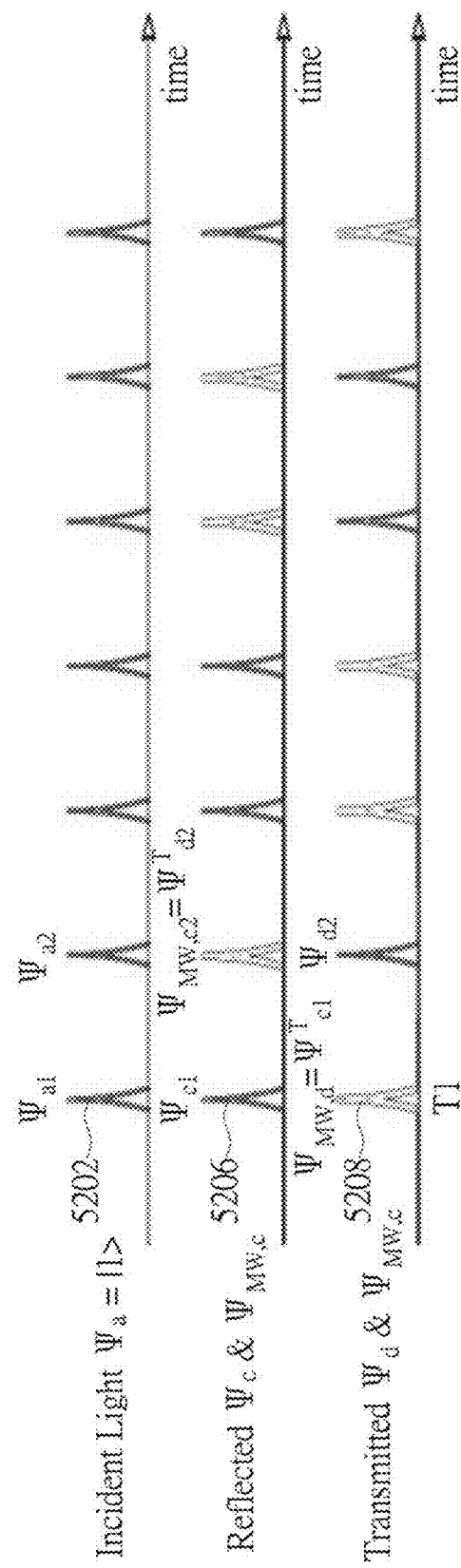
FIG. 52B is a diagram illustrating conjugated MW being created inductively by annihilation and creation processes of a BS in between incident light MWE and BS MWF tensors.

The present invention unveils, as shown in FIGS. 52A and 52B, conjugated (i.e. Orthogonal) MW can be created inductively by Annihilation (â) and Creation (â⁺) processes in between incident light MWE and BS MWF Tensors. The inductive MW is mass-less (i.e. energy-less) with its initial spatial spread bonded by the spatial distributions of BS MWF and the wavefunction spatial distribution of the incident Photon (MWE packet). Incident Photon's MWE and Its inductive MW spatial-temporal distribution have to be renormalized during the creation (â⁺) process, and it is conjugated wavefunction with each other by following Pauli Exclusion Principal. A PBS (polarization BS) can fit similar rules, e.g. $\langle \Psi c, d | \Psi MW, dc \rangle = 0$, wherein $|(\Psi_{Gw,dc})\rangle = |(\Psi_{GW, d}, \Psi_{GW,c})\rangle$ and $\langle (\Psi c, d)\rangle = |(\Psi_c, \Psi_d)\rangle$ by taking the conjugated polarization effects in between incident Photon MWE and the inductive conjugated Polarized MW wavefunction. For example, as shown in FIGS. 52A, 52B, when incident light 5202 from (a) direction hits BS 5204 at time T1, reflected light (MWE) 5206 appears at (c) direction and matter wave (MW) 5208 corresponding to the incident light 5202 being created inductively along (d) direction.

Hereby, to better tell the story behind the "mass-less" MW generating" BS matrix, a few BS' matrix operations as followings:

1) In one example, the input wavefunctions of BS' two ports is T a, b, then the BS (i.e. BS matrix) is able to create composite output states $|\Psi c, d, \Psi MW, dc\rangle$ via BS' mixing (i.e. entanglement) interactions with vacuum null (or null) states presenting at BS' input ports. (e.g. BS*$|\Psi a, b$, (null)$\rangle = |\Psi c, d, \Psi MW, dc\rangle$.
2) Given that the reflected inductive MW plus light MWE 5206 wavefunction can be represented by $\Psi RX$ in total and the transmitted inductive MW plus light MWE 5208 can be represented by $\Psi TX$ in total, then it will derive another format to represent the total composite output states by using 1) paired MWE vector wavefunctions $\Psi c, d = (\Psi c, \Psi d)$, and 2) paired MW vector wavefunctions $(\Psi MW, d, \Psi MW, c)$ (e.g. composite output states$= |(\Psi RX, \Psi TX)\rangle = |(\Psi c, \Psi d); (\Psi MW, d, \Psi MW, c)\rangle$, wherein the present invention discovers that $\langle \Psi c, d \Psi MW, dc \rangle = 0$ (i.e. $(\Psi c, d)$ and $(\Psi MW, dc)$ are orthogonal or conjugated states).
3) Similarly, inductive MW wavefunctions at output ports can be represented by paired MW vector wavefunctions (e.g. $|\Psi MW, dc\rangle = |(\Psi MW, d, \Psi MW, c)\rangle$) wherein paired MW vectors $|(\Psi MW, d, \Psi MW, c)\rangle$ are in "Temporal- or Spatial-conjugated along with $|(\Psi c, \Psi d)\rangle$ light (MWE) output states respectively, e.g. each other can be temporal or spatial orthogonal.
4) For ordinary skilled one can spell: if reflected light (MWE) 5206 $\Psi RX = \Psi c \rangle = |1\rangle$, then transmitted matter wave (MW) 5208 will be $\Psi MW, d\rangle$, and $\Psi MW, d\rangle = \Psi^T c\rangle = i \cdot |\Psi c\rangle$. The other way around, if transmitted light (MWE) is $\Psi TX$, then $\Psi TX = |\Psi d\rangle = |1\rangle$ and $|\Psi MW, c\rangle = |\Psi^T d\rangle = i \cdot \Psi d\rangle$ wherein the superscript "T" stands for "Transpose" operation of a given vector state.

AG. New QF Theory for BS—I New Vs. Old Models of BS Matrix

The present invention discovers BS is a secrete tensor to create temporal or spatial phase matched, conjugated and/or orthogonal pairs (i.e. duals) outputs for incident MWE photon and inductive MW. The spatial-temporalphase relationship of the TWOoutputs will obey Pauli Exclusion (Orthogonal) Principals, i.e. their Wavefunctions are conjugated and/or orthogonal to each other.

Figure 53A:
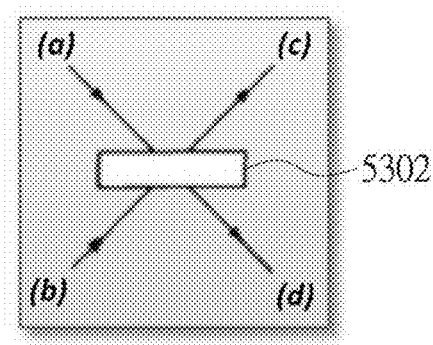
FIG. 53A is a diagram illustrating (a), (b), (c), (d) directions of BS.
Figure 53B:
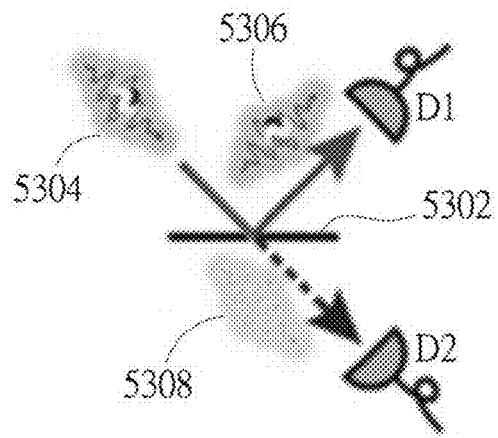
FIG. 53B is a diagram illustrating detector D1 detecting reflected light (MWE) and energy-less mater wave (MW) not clicking detector D2 which is orthogonal to the reflected light and vice versa.
Figure 53C:
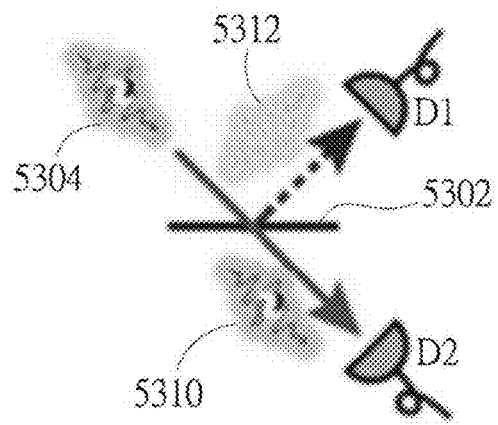
FIG. 53C is a diagram illustrating detector D2 detecting reflected light (MWE) and energy-less mater wave (MW) not clicking detector D1.

Therefore, the present invention discovers that FIGS. 53A-53C and TABLE 7 can be utilized to describe well of the relationships between incident light and BS. As shown in FIG. 53A, (a), (b), (c), (d) directions corresponding to BS 5302 have been defined. When incident light 5304 hits the BS 5302, detector D1 detects reflected light (MWE) 5306 and energy-less (or mass-less) mater wave (MW) 5308 (i.e. cannot click detector D2) orthogonal to the reflected light 5306 appears at the (d) direction in 50% probability (expt.-A1 shown in FIG. 53B), and the detector D2 detects transmitted light (MWE) 5310 and energy-less mater wave (MW) 5312 (cannot click the detector D1) orthogonal to the transmitted light 5310 appears at the (c) direction in another 50% probability (expt.-A2 shown in FIG. 53C).

Figure 53D:
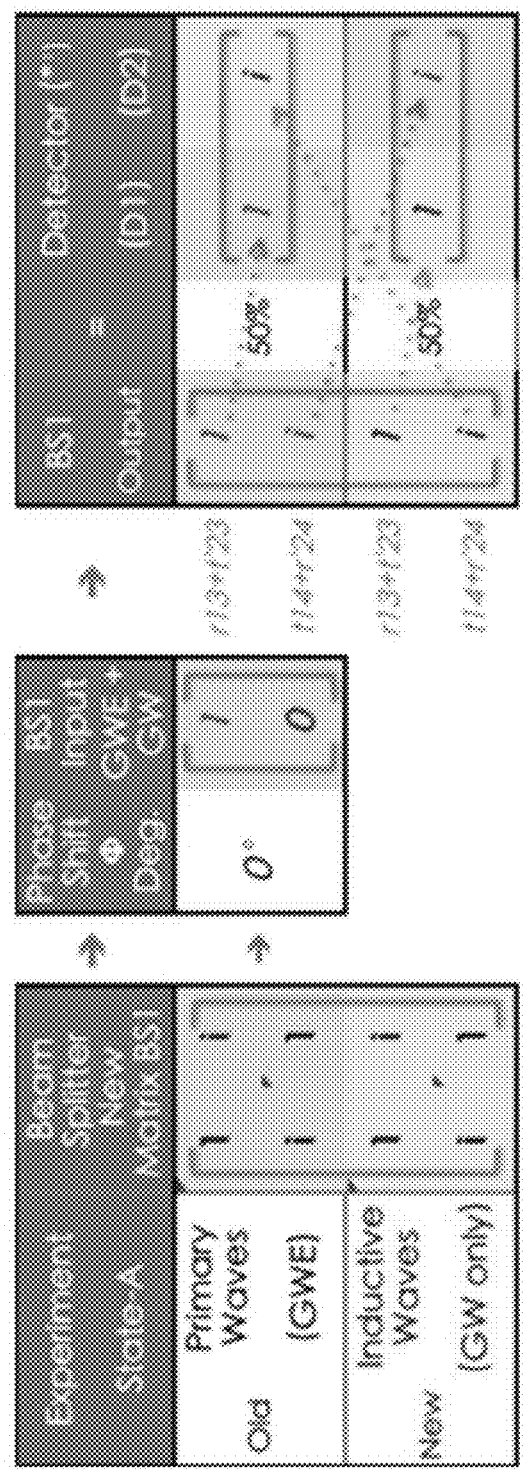
FIG. 53D is a diagram illustrating output of the BS being generated by simple matrix multiplication of the BS matrix and its input light vectors.

Output of the BS 5302 shown in FIG. 53D can be generated by simple matrix multiplication of the beam splitter matrix of the BS 5302 and its input light (photon) vectors.

Remarks corresponding to the expt.-A1 and the expt.-A2 are shown in TABLE 7.

TABLE 7

| | Remarks |
|---|---|
| expt.-A1 | 1) $\Psi c \approx |1\rangle$, 0° phase with ~50% probability to click the detector D1<br>2) $\Psi d \approx |i\rangle_{MW}$, 90° phase, is mass-/energy-less, without clicking the detector D2 |
| expt.-A2 | 1) $\Psi d \approx |i\rangle$, 90° phase with ~50% probability to click the detector D2<br>2) $\Psi c \approx |1\rangle_{MW}$, 0° phase, is mass-/energy-less, without clicking the detector D1 |

AH. New QF Theory for BS (II)— Mach-Zender (M-Z) Interferometer with Single Photon Input As shown in FIGS. 54A, B and C, photon 5406 entering BS 5402 (a1), created BS 5404 with MWE 5408 & MW 5410 inputs with their phase relationships being of $\Psi b2 = |i\rangle_{MW} = |1\rangle^T_{MWE} = (\Psi a2)^T$.

Phase shifter 5418 can be varied by a relative phase of different paths. The phase shifter 5418 can uncover the bunching and anti-bunching (i.e. constructive or destructive) interference effects among the coherent MWE and MW wavefunctions.

Figure 54A:
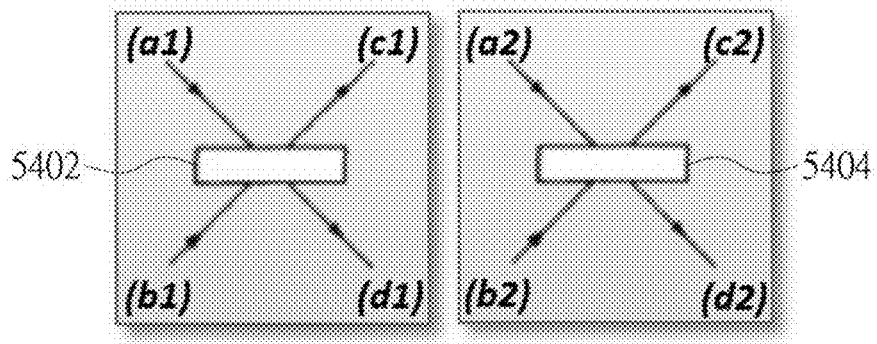
FIG. 54A is a diagram illustrating (a1), (b1), (c1), (d1), (a2), (b2), (c2), (d2) directions of two BS.
Figure 54B:
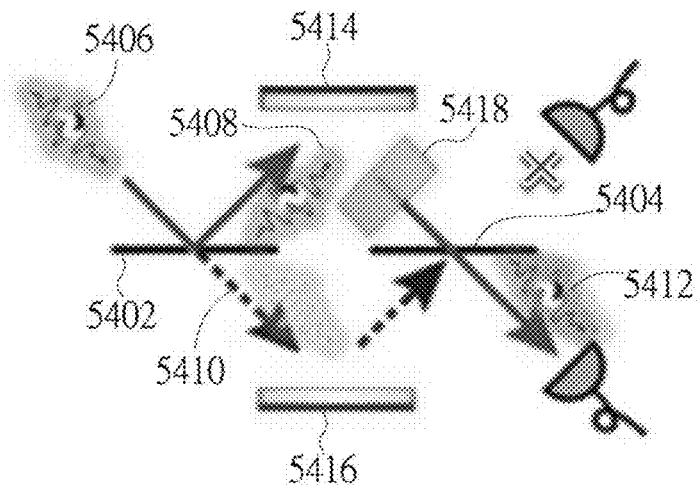
FIGS. 54B, 54C are diagrams illustrating the Mach-Zehnder (M-Z) Interferometer with single photon input associated with the new model of light.
Figure 54C:
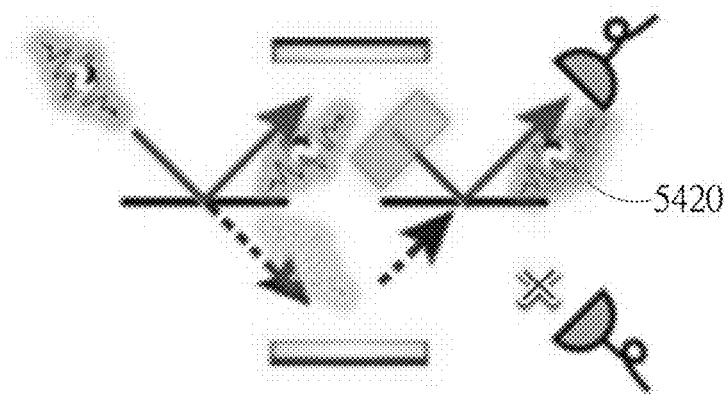
Figures 54D, 54E:
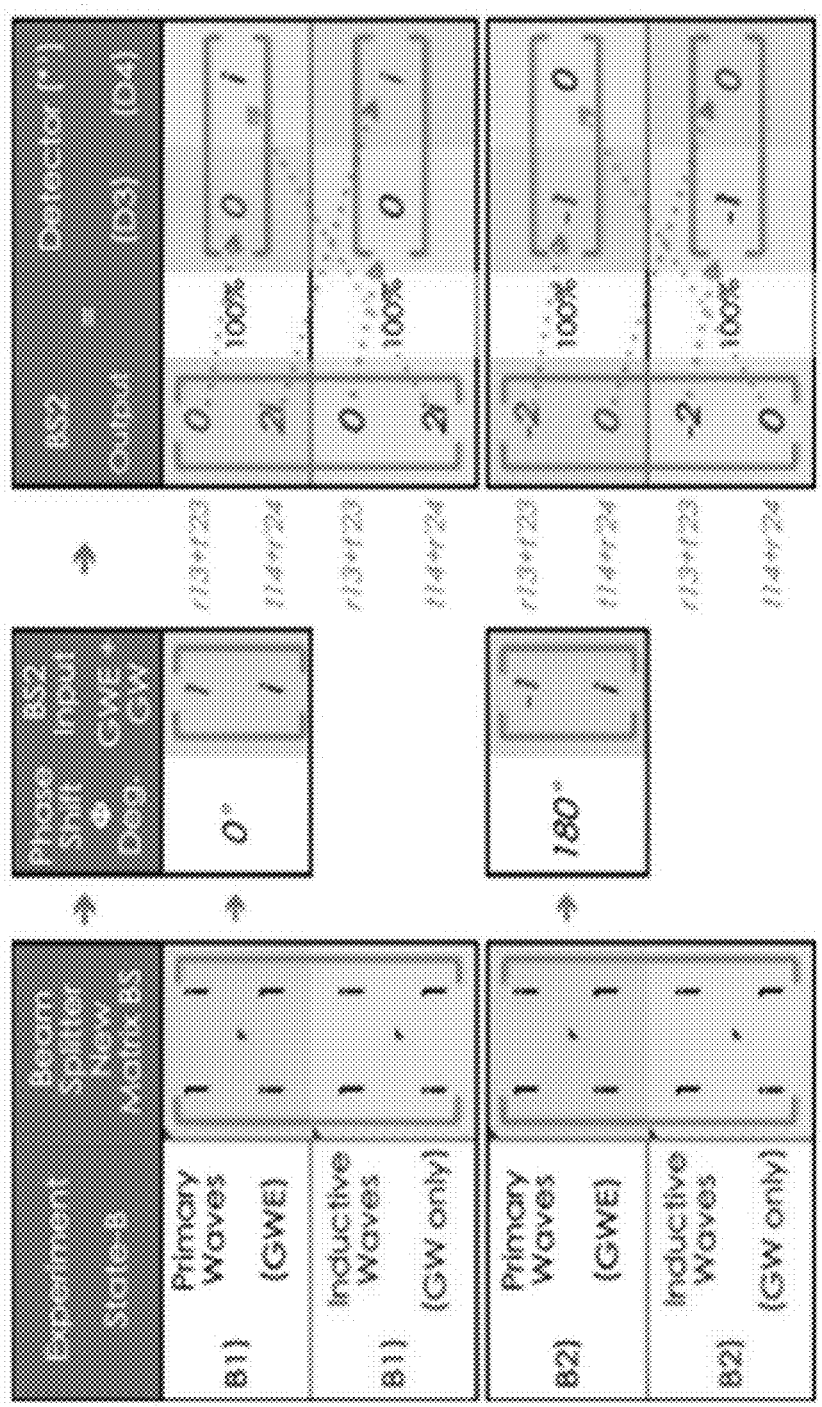
FIGS. 54D, 54E are diagrams being utilized to describe the relationships between incident light and BS outputs shown in FIGS. 54B, 54C.

Therefore, the present invention discovers FIGS. 54A-C and FIGS. 54D, 54E can be utilized to describe well of the relationships between incident light and BS. As shown in FIG. 54A, (a1), (b1), (c1), (d1) directions corresponding to the BS 5402 and (a2), (b2), (c2), (d2) directions corresponding to the BS 5404 have been defined. When MWE of the photon 5406 hits the BS 5402, if the reflected MWE 5408 and energy-less matter wave MW 5410 orthogonal to the reflected MWE 5408 appear at the (c1) direction and the (d1) direction respectively, detector D4 detects photon 5412 (i.e. MWE being bunching with energy-less MW mater wave) due to constructive-interference at output port (d2) and detector D4. There will be no photon MWE and energy-less MW mater wave will appear at the output port (c2) direction due to destructive-interference taking place after the reflected MWE 5408 is reflected by mirror 5414 to hit the BS 5404 and the energy-less mater wave 5410 is reflected by mirror 5416 to hit the BS 5404 (expt.-B1 shown in FIG. 54B), wherein phase shifter 5418 has Phase shift Φ degree 0°. As shown in FIG. 54D below, the present invention discovers that detector D3 and D4 output responses can be generated by simple matrix multiplications together with each component of the beam splitter matrices (i.e. BS 5402, BS 5404, mirrors, etc.), the input light (photon) 5406 and BS 5402 outputs (i.e. light MWE 5408, MW 5410, etc.) vectors.

Output of the BS 5404 shown in FIG. 54D can be generated by the bean splitter matrix of the BS 5404 and the BS 5404 input matrix.

A few remarks corresponding to the expt.-B1 are shown in TABLE 8 below.

TABLE 8

| | Remarks |
|---|---|
| The (c2) direction | 1) BS2 output $\Psi c2 \approx 0$ and is fully destructive at the detector D3,<br>2) Still, it followed the Law of Energy Conservation |
| The (d2) direction | 1) Inductive $\Psi d2$, MW $\approx |i\rangle$ > MW of the BS 5404 is mass-/energy-less<br>2) $\Psi d2 = |i\rangle$ & $\Psi d2$, MW = $|i\rangle$ > MW are bunching together and with 100% click at the detector D4 |

Similarly, if the phase shifter 5418 has make the photon 5406 with Phase shift Φ degree 180°, detector D3 detects photon 5420 (i.e. MWE being bunching with energy-less MW mater wave) due to constructive-interference and no light and energy-less mater wave appears at the (d2) direction due to destructive interference taking place at output port (d2) and detector D4 after the reflected MWE 5408 is reflected by the mirror 5414 to hit the BS 5404 and the energy-less MW mater wave 5410 is reflected by the mirror 5416 to hit the BS 5404 (expt.-B2 shown in FIG. 54C).

Output of the BS 5404 shown in FIG. 54E can be generated by the beam splitter matrix of the BS 5404 and each of the input MWE and MW vectors corresponding to Phase shift Φ degree 180°. As shown in FIG. 54E below, with a Phase shift Φ degree 180°, detector D3 and D4 output responses can be generated by simple matrix multiplications together with each component of the Phase shifter 5418, beam splitter matrices (i.e. BS 5402, BS 5404, mirrors, etc.), the input light (photon) 5406 and BS 5402 outputs (i.e. light MWE 5408, MW 5410, etc.) vectors.

A few remarks corresponding to the expt.-B2 are shown in TABLE 9 below.

TABLE 9

| | Remarks |
|---|---|
| The (c2) direction | 1) Inductive $\Psi c2$, MW $\approx |-1\rangle$ > MW of BS 5404 is mass-/energy-less<br>2) $\Psi c2 = |-1\rangle$ & $\Psi c2$, MW = $|-1\rangle$ > MW are bunching together and with 100% click at the detector D3 |
| The (d2) direction | 1) BS2 output $\Psi d2 \approx 0$ and is fully destructive at the detector D4<br>2) Still, it followed the Law of Energy Conservation |

AI. Two-Photon HOM Effects (I)— Interference of Photon Pairs with Same Polarization Beam splitter (BS) performs secrete actions of being a "Wavefunction Mixer or Entangler" while TWO photons entering at a space-temporal location within the ranges of its coherence time and/or coherent length. Also, the Reverse-HOM effect (Reference: Jian-Wei Pan, et al. "Experimental entanglement purification of arbitrary unknown states." Nature 423.6938 (2003):417-422) is best explained by new light model and its QFT (Quantum Field Theory) of the present invention.

Figure 55A:
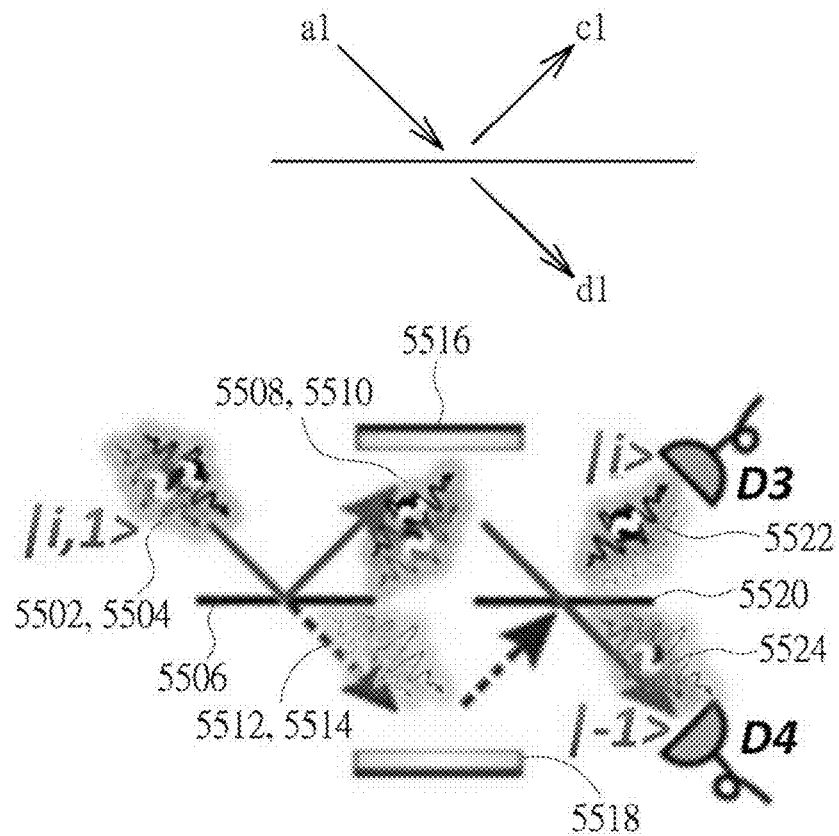
FIGS. 55A, 55B are diagrams illustrating HOM two-photon effects, wherein the input photons associated with same polarization and vice versa.

As shown in FIG. 55A (corresponding to expt.-C1), when temporal orthogonal pair of photons 5502 |i>, 5504 |1> (with same spatial polarization) hit BS 15506 from (a1) direction (that is, the photons 5502, 5504 hit the BS1 5506 from single end), reflected photons 5508, 5510 (corresponding to the photons 5502, 5504, respectively) and energy-less inductive matter wave MW 5512, 5514 (corresponding to the photons 5502, 5504, respectively) appear at (c1) direction and (d1) direction respectively. After mirrors 5516, 5518 reflect the reflected photons 5508, 5510 and the energy-less matter wave MW 5512, 5514 to hit BS2 5520, detector D3 detects photon 5522 (i.e. MWE of the photon 5502 or 5504 being bunching with inductive energy-less MW matter waves 5512 or 5514) and detector D4 detects photon 5524 (i.e. MWE of the photon 5502 or 5504 being bunching with energy-less MW matter wave of the photon 5502 or 5504), wherein the temporal phase of the light 5522 |i> is orthogonal to the light 5524 |−1> and each BS' matrix mathematical operation of the expt.-C1 can be referred to and well explained by FIG. 56.

Figure 55B:
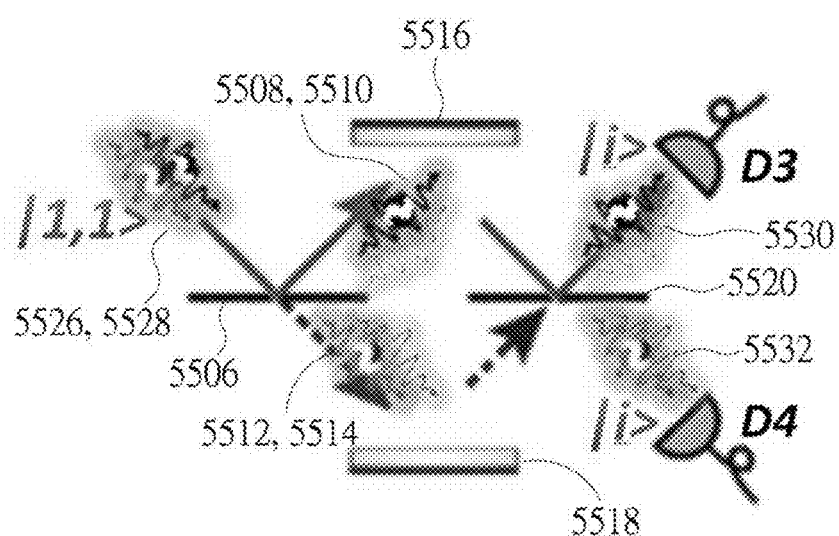
Figure 56:
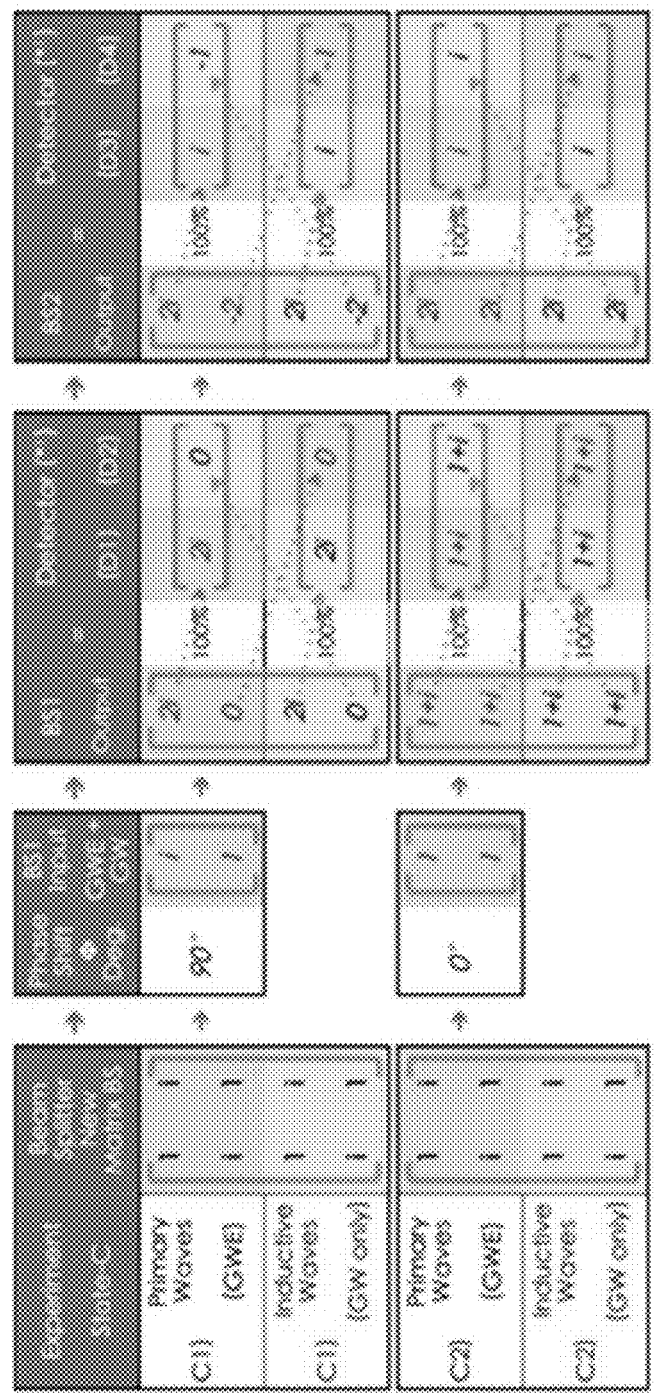
FIG. 56 is a diagram illustrating matrix mathematical operation of HOM two input photons getting bunching with inductive energy-less MW matter waves associated with the new model of light.

Similarly, the present invention unveils, as shown in FIG. 55B (corresponding to expt.-C2), when temporal in-phased pair of photons 5526 |1>, 5528 |1> (with identical polarization) hit the BS1 5506 from the (a1) direction (that is, the photons 5502, 5504 hit the BS1 5506 from single end), the detector D3 detects photon 5530 (i.e. MWE of the photon 5526 or 5528 being bunching with energy-less MW matter wave of the photon 5526 or 5528) and the detector D4 detects photon 5532 (i.e. MWE of the photon 5526 or 5528 being bunching with energy-less MW matter wave of the photon 5526 or 5528), wherein the temporal phase of the light 5530 |i> is identical to the light 5532 |i> and each BS' matrix mathematical operation of the expt.-C2 can be referred to and well explained by FIG. 56.

In addition, overall summary corresponding to expt.-C1 and expt.-C2 is shown in TABLE 10.

TABLE 10

| | |
|---|---|
| expt.-C1 | 1) Interference of photon pairs in BS1 and BS2 follows theory of superposition for all states generated with each of incident "MWE + MW" Wavefunctions or states<br>2) Two Photons |1 > + |i > (i.e. the temporal orthogonal photons 5502, 5504) will be Bunching at the BS1 5506, but anti-Bunching at the BS2 5520 due to MWE and MW interference or mixtrue effect associated with BS physical properties |
| expt.-C2 | 1) Exchange (Mixer) symmetry properties of the incident photon pair forces wavefunction with equal probability at BS1 5506 and BS2 5520 outputs<br>2) The MWE and/or MW Interference effects (the theory of superposition) suppress the possibility of seeing two photons at same output port under such condition<br>3) Anti-bunching state is 100% definite output state if and only if a BS input is associated with a pair of temporal in-phase (or temporal identical) photons, e.g. |1 > + |1 > |

AJ. Two-Photon HOM Effects (II)— BPP Photon Inputs with Orthogonal Polarizations The new BS model of the present invention can explain better for those experiments being associated with the anti-bunching Reverse HOM effect (Reference: M. Medic, J. B. Altepeter, M. A. Hall, M. Patel, and P. Kumar, -Fiber-based, telecom-band source of degenerate entangled photons, Optics Letters, Vol. 35, No. 6, Mar. 15, 2010, pp. 802-804) of Kumar et al.).

Figure 57:
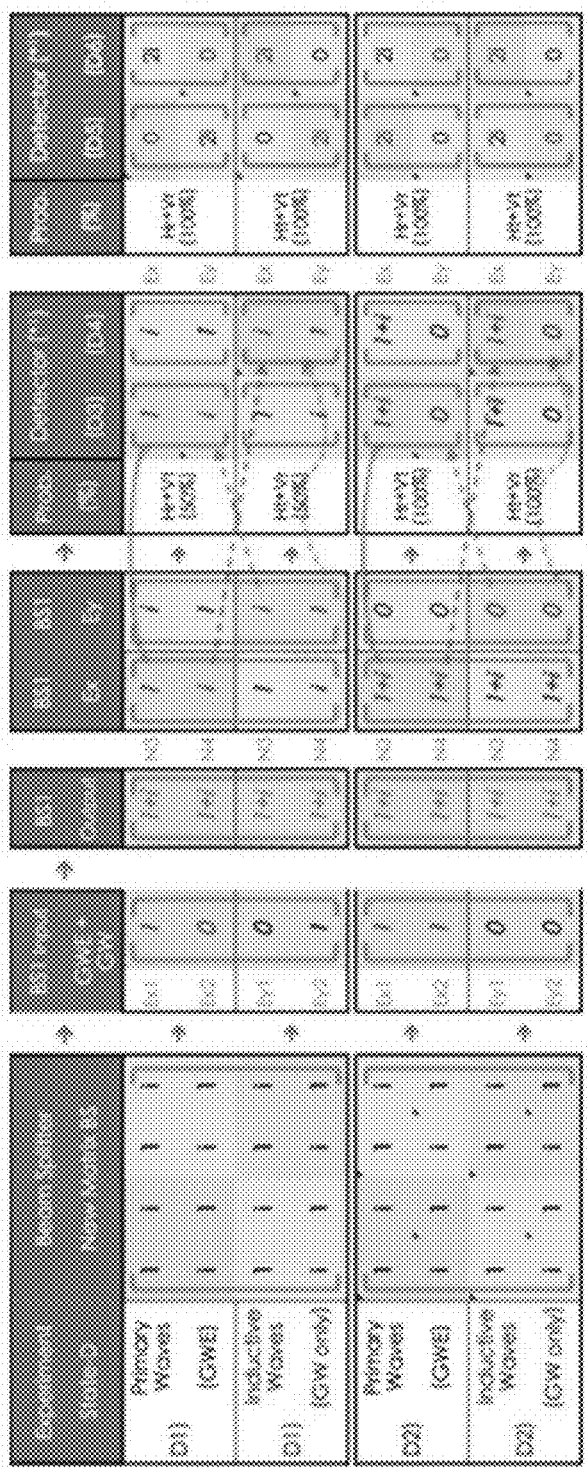
FIG. 57 is a diagram illustrating each BS' matrix mathematical operation of the expt.-D1/-D2.

Expt.-D1, when two photons (with H and V orthogonal polarizations) hit BS from the (a1) direction and the (b1) direction respectively, 50% state is bunching at detector D3, i.e. Horizontal polarization photon clicks D3$x$=|1> with a relative temporal phase shift of zero degree, and at the same time, Vertical polarization photon clicks D3$y$=|i> with a relative temporal phase shift of 90 degrees. The bunching photons at the detector D3=(D3$x$, D3$y$) form a Left Circular polarization light wave or photon pairs via the BS' quantum mixture effects, wherein each BS' matrix mathematical operation of the expt.-D1 can be referred to FIG. 57. Similarly, the present invention unveils that another 50% state is bunching at detector D4=(D4$x$, D4$y$), i.e. Horizontal polarization photon clicks D4$x$=|i> with a relative temporal phase shift of 90 degree, and at the same time, Vertical polarization photon clicks D4$y$=|1> with a relative temporal phase shift of zero degrees. The bunching photon pairs at the detector D4=(D4$x$, D4$y$)=(|i>,|1>) form a Right Circular polarization light wave or photon pairs via the BS' quantum mixture effects.

Figure 58:
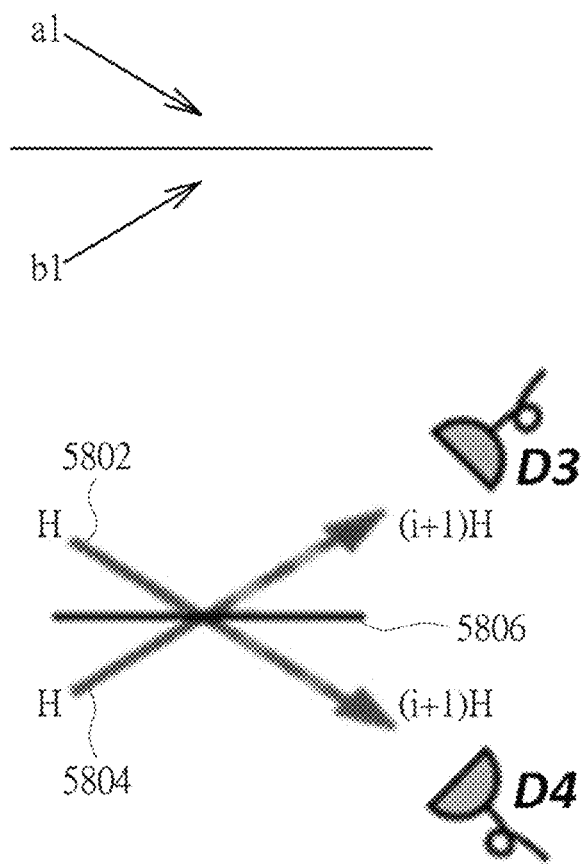
FIG. 58 is a diagram illustrating HOM two photons with same polarizations getting bunching or anti-bunching along with inductive energy-less MW matter waves under the M-Z interferometer.

As shown in FIG. 58 (corresponding to expt. -D2), a photon pairs with exchange symmetry forces equal probability at BS1/2 outputs by forming anti-bunching photons due to that Photon's MWE+MW Interferences (the theory of superposition) suppress the bunching possibility at BS output nodes. Anti-bunching is 100% if photons 5802, 5804 hit BS 5806 from the (a1) direction and the (b1) direction respectively with same polarization paired photons, e.g. paired Photon=|H>a+|H>b, wherein each BS' matrix mathematical operation of the expt.-D2 can be referred to FIG. 57.

In addition, the overall summary of expt.-D1 and expt.-D2 is shown in TABLE 11.

TABLE 11

| | |
|---|---|
| expt.-D1 | The New QFT predictions of the present invention:<br>1) Probability wavefunction at detectors D3, D4 will show:<br>50% bunching of \|H>a reflected and the other \|V>b transmitted photons (Hr + Vt) will be forming with an effective LCP wavefunction at D3 direction for the paired particular photons.<br>50% bunching Ht + Vr (i.e. \|H>a transmitted and the other \|V>b reflected photons) will be forming with an effective RCP wavefunction at D4 direction<br>2) In view of one more cascading BS3 associated with output detectors D5, D6, its output photons' quantum states indicate that the anti-bunching effect or anti-HOM effect of Kumar et al. experimental result is self-evident by the new QFT of the invention. |
| expt.-D2 | The New QFT predictions Exchange (Mixer) symmetry input photon pairs will force wavefunction showing up with equal probability at BS1/2 two output nodes:<br>1) Photon's MWE + MW Interference effects (the theory of superposition) suppress the Possibility of bunching at BS output nodes.<br>2) Anti-bunching is 100% state at BS outputs if the pair of photons 5802, 5804 have same polarization \|H>a + \|H>b and the like. |

AK. Reverse HOM Effects—BS with Photon Pairs in Signac Loop

Figure 59A:
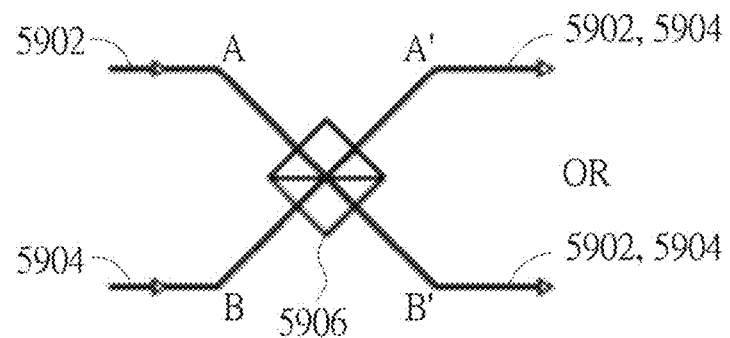
FIGS. 59A, 59B are diagrams illustrating the Sagnac loop and BS entanglement effects when a pair of H/V spatial orthogonal photons input to and output from the Sagnac loop.

As shown in FIG. 59A, when a pair of H/V spatial orthogonal photons, i.e. photon 5902 inputs at port A and photon 5904 inputs at port B together to hit 50%:50% Beam splitter 5906, the new QFT of the present invention self-evident that MWE and inductive MW interferences (the theory of superposition) suppress the possibility of seeing two separate photons at output ports in A' and B', and the outputs A' and B' contain either 1) the two photons 5902, 5904 or 2) none, if ignored the temporal phase shift of those photons.

Figure 59B:
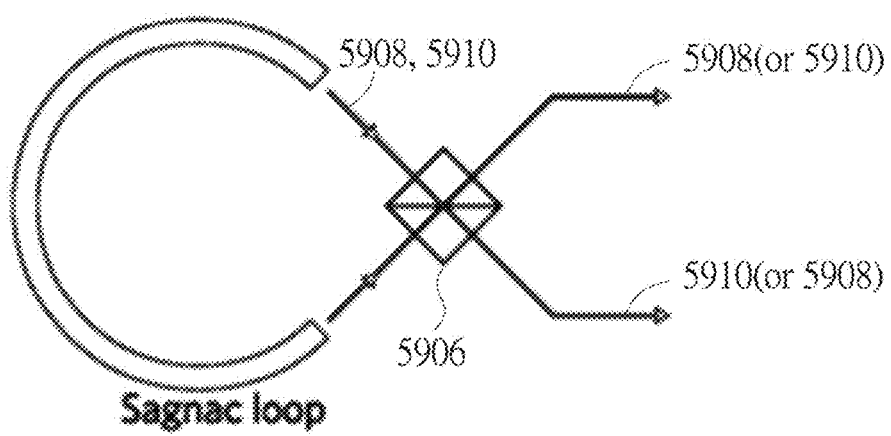

As shown in FIG. 59B, the Beam splitter 5906 performs secrete actions of being a "Wavefunction Mixer or Entangler" while a pair of orthogonal polarized photons entering a Sagnac Loop. The present invention discovers the theory behind of such reverse HOM experiment, i.e. by allowing two photons 5908, 5910 being inputted in either port (A or B) of their Sagnac loop at first. Then, the new QFT of the present invention self-evident that MWE and inductive MW interference effect can prove the reverse HOM effect by creating a pair of single photons leaving each of the separate ports (A' and B') respectively of the Beam splitter 5906 with certain temporal and/or spatial phase shift between output photons.

Figure 60:
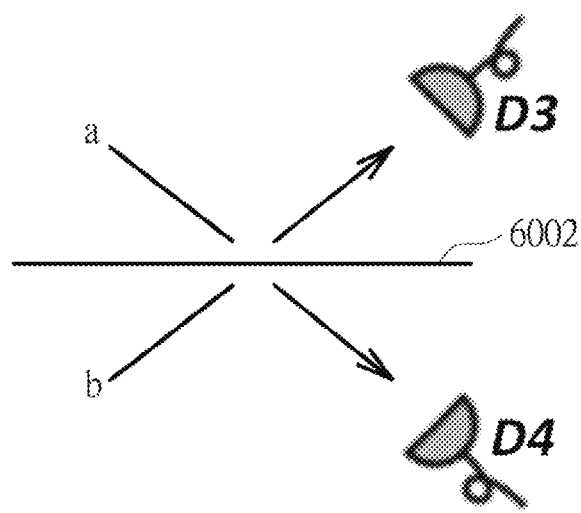
FIG. 60 is a diagram illustrating the direction of polarization beam splitters (PBS) interference of photon pairs at 45° angles.

AL. Polarization Beam Splitters (PBS) Interference of Photon Pairs at 45° Angles As shown in FIG. 60, polarization BS (PBS) 6002 performs secrete actions of being a "Wavefunction polarization Mixer" if incident photon with orthogonal polarization and with 45° polarized against the PBS 6002.

Figure 61:
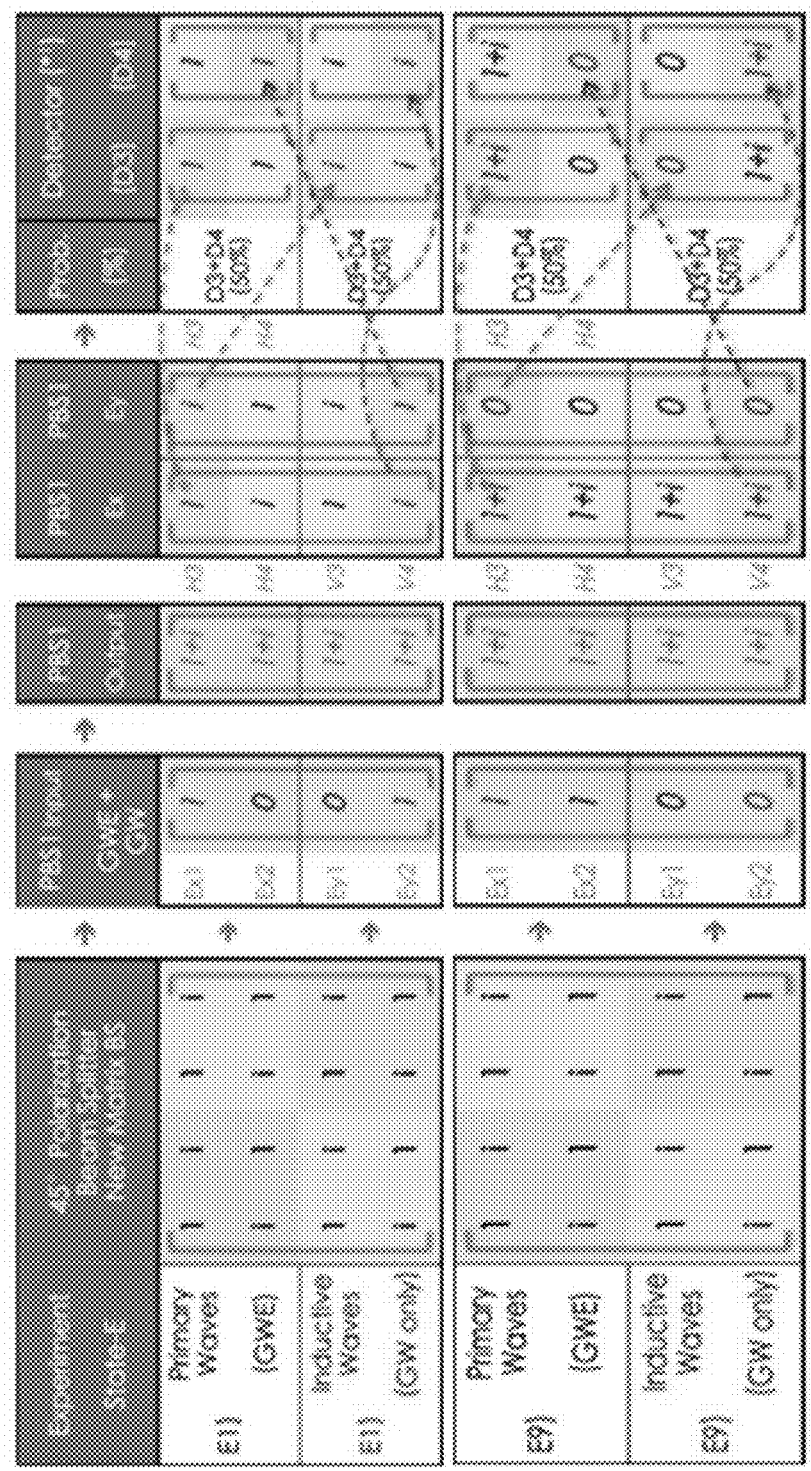
FIG. 61 is a diagram illustrating the PBS matrix mathematical operation of the expt.-E1.

Expt. E1: A pair of Input Photons are one |45° H> (at (a) direction) and another |45° V> (at the (b) direction) to hit the PBS 6002, new QFT model of the present invention predicates: 50% output state is anti-bunching state at the detector D3=|H> and the detector D4=|V>, and another 50% output state is anti-bunching with 90-degree temporal shift at the detector D3=|iH> and the detector D4=|iV >, wherein the PBS matrix mathematical operation of the expt.-E1 can be referred to FIG. 61.

Similarly, Expt. E9: a pair of Input Photons are one |45° H> (at the a direction) and another |45° H> (at the (b) direction) to hit the PBS 6002, this new QFT model predicates its output state will be with 50% bunching of TWO photons at the detector D3=|(1+i)*H> and with other 50% bunching of TWO photons at the detector D4=|(1+i)*V>, wherein the PBS matrix mathematical operation of the expt.-E9 can be referred to FIG. 61.

In addition, the overall summary of expt.-E1 and expt.-E9 is shown in TABLE 12 below.

TABLE 12

| | |
|---|---|
| expt.-E1 | The New QFT predicts:<br>1) Probability of wavefunctions at the detectors (D3, D4) will be:<br>About 50% anti-bunching with (\|H>, \|V>)<br>About 50% anti-bunching with (\|iH>, \|iV>)<br>2) The PBS new theory needs to be verified with experimental results if needed |
| expt.-E9 | The New QFT predicts:<br>1) Probability wavefunctions at the detectors (D3, D4) will be:<br>About 50% bunching with two temporal orthogonal photons \|(1 + i)H> at the detector D3 output node<br>About 50% bunching with two temporal orthogonal photons \|(1 + i)V> at the detector D4 output node<br>2) The PBS new theory needs to be verified with experimental results if needed |

AM. Ken's MZ Polarization Wavefront-Split Experiment—can it Evidence Photon Path Information?

Figure 62:
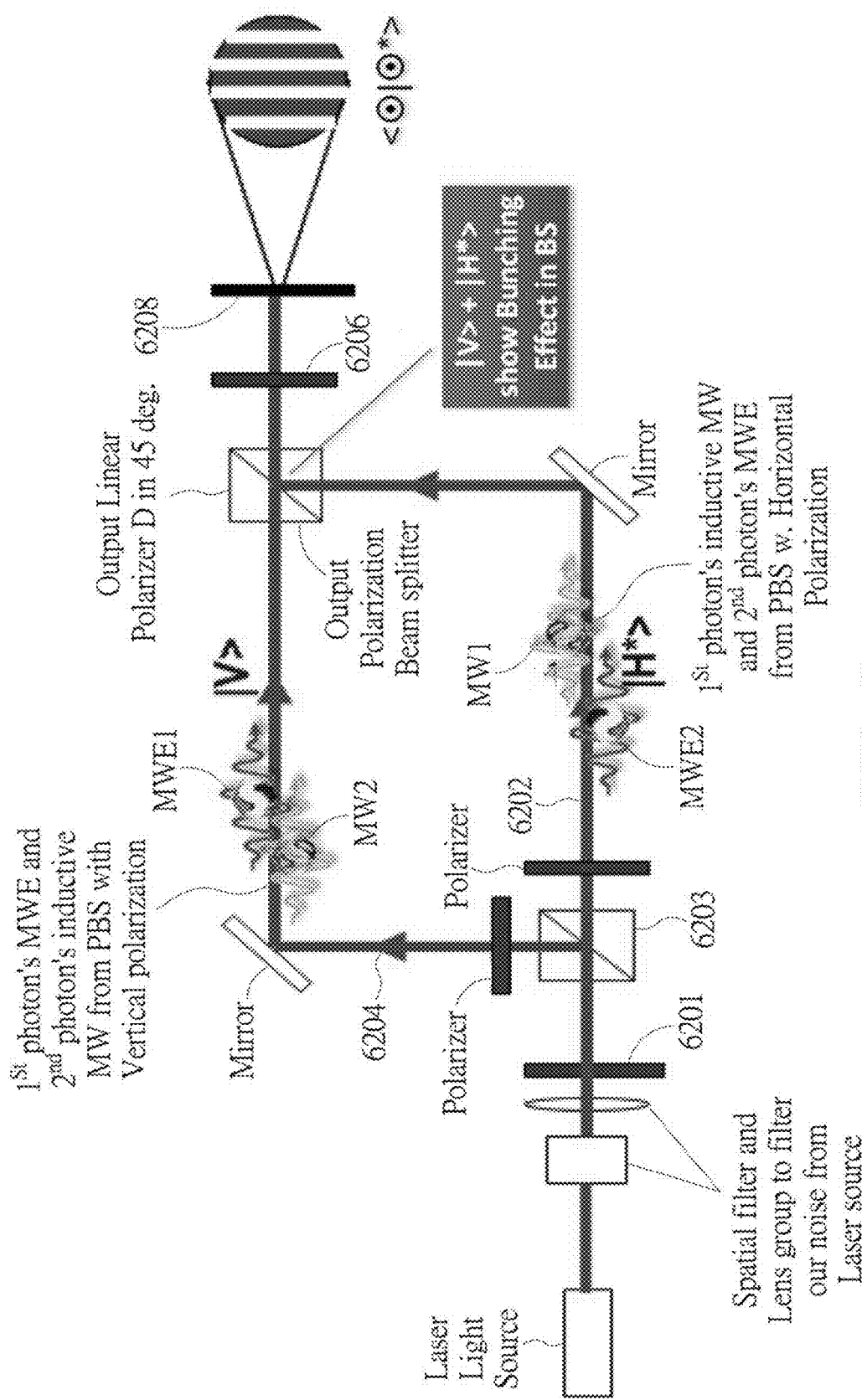
FIG. 62 is a diagram illustrating Ken's MZ polarization amplitude/phase-split (MZP) experiment which can evidence photon path information.

As shown in FIG. 62, in addition, a linear polarizer 6201 is displaced in 45 degrees orientation versus PBS 6203 V (Vertical) or H (Horizontal) polarization directions. The 45 degrees input photons work together with the PBS 6203 can perform MWE splitter function such that MWE2 of second photon=|H> in path 6202 or MWE1 of first photon=|V> in path 6204 and the orthogonal/conjugated inductive matter-wave (MW) generator for Vertical MW* in the path 6204 or Horizontal MW* in the path 6202 respectively at the same instance of time by following the PEP (Pauli Exclusion Principle). The MWE2=|H> of the second photon (with horizontal polarization) and MW1=|H> of the first photon (with horizontal polarization) show at the path 6202, and MW2 of the second photon (with vertical polarization) and MWE1 of the first photon (with vertical polarization) show at the path 6204.

Therefore, following the Malus Law of Polarizer, after MWE2 of the second photon (with horizontal polarization) and MW1 of the first photon (with horizontal polarization) pass through output polarizer 6206 associated with polarization angle 45° versus |H> or |V> directions, and after MW2 of the second photon (with vertical polarization) and MWE1 of the first photon (with vertical polarization) pass through the output polarizer 6206, MWE1 of the first photon projected by the polarizer 6206 is interfered with coherent inductive MW1 of the first photon projected by the polarizer 6206. And the like, MWE2 of the second photon projected by the polarizer 6206 is interfered with coherent inductive MW2 of the second photon projected by the polarizer 6206 to form interference (the theory of superposition) intensity patterns (i.e. <⊙|⊙*> or <↕|↕*> stands for the inner product or intensity of output photon's wavefunction) on the screen 6208 accordingly.

Figure 63:
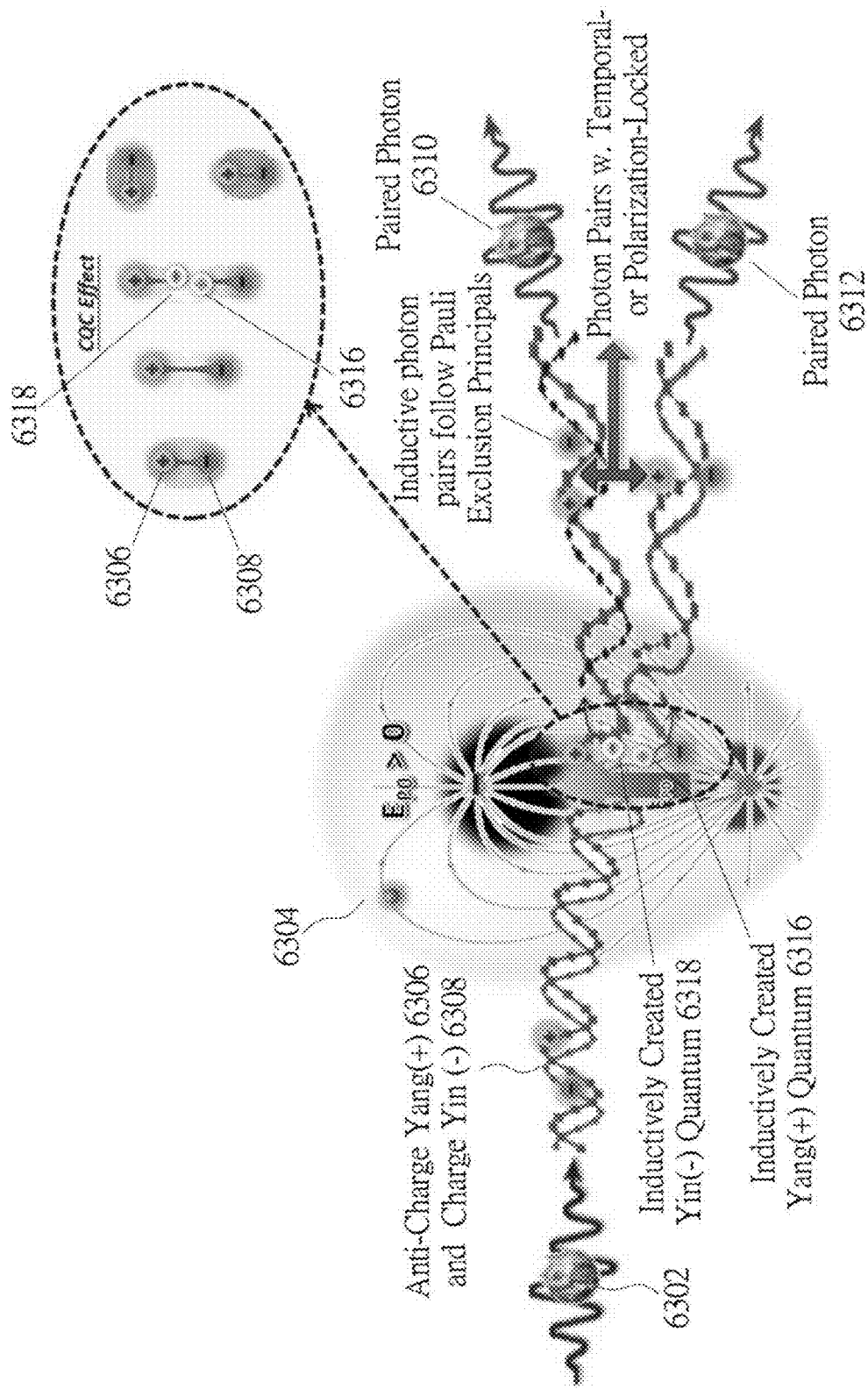
FIGS. 63, 64 are diagrams illustrating the new MWF model for SPDC properties and explaining the new BPP theory and phase-matching fundamentals by using PEP and Charge Quanta Confinement (CQC) effect.

AN. New MWF Model for SPDC (I)— Boson Pair Production (BPP) Theory for Phase-Matching Fundamentals As shown in FIG. 63, when incident photon 6302 (e.g. UV or blue photon is comprised of Yang(+) 6306 and Yin(−) 6308 Quanta) transmits through boson-Pair Production (BPP) non-linear MWF material 6304 (e.g. KDP (Potassium Dihydrogen-Phosphate), BBO (Beta barium borate) or PPLN (Periodically-Poled Lithium Niobate) crystals), the non-linearity (i.e. a secrete property of the BPP non-linear MWF material 6304) will attribute certain % of probability to inductively create Yang(+) Quantum 6316 corresponding to Charge Yin(−) Quantum 6308 of the photon 6302. At the same instance of time, by following the Pauli Exclusion Principle, the BPP non-linear MWF material 6304 will inductively create Yin(−) Quantum 6318 corresponding to Anti-Charge Yang(+) Quantum 6306 of the photon 6302. Those inductive Yang(+) and Yin(−) Quanta may be created owing to the subtle interactions among the electrical dipole EP0 of the BPP non-linear MWF material 6304, incident UV Photon's MWE wavefunction and Yang(+) 6306 and Yin(−) 6308 Quanta induced electric dipole of photon 6302, wherein the inductively created Yang(+) Quantum 6316 and the Charge Yin(−) quantum 6318 get together with the Yang(+) 6306 and Yin(−) 6308 Quanta of the incident photon 6302 so as to form a pair of lower energy photons (i.e. paired red photon 6310 and 6312) instantly by obeying General Conservation Laws of Physics (e.g. energy, momentum and angular momentum). The paired red photons 6310 (i.e. comprising 6306, 6318) and 6312 (i.e. comprising 6308, 6316) are spatially or temporally orthogonal (or conjugate) to each other by following the Pauli Exclusion Principle as well.

Figure 64:
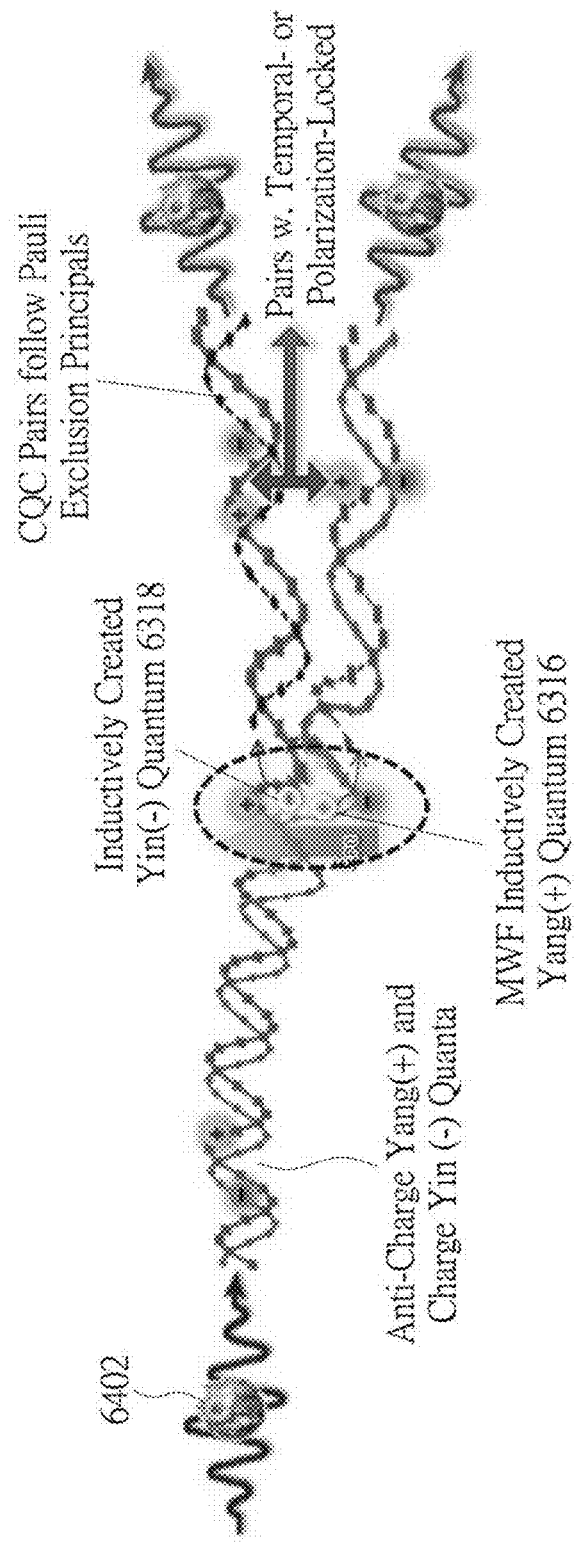

AO. New MWF Model for SPDC (II)— BPP and Charge Quanta Confinement (CQC) Effects As shown in FIG. 64, nonlinear crystal material (SPDC material) can form Asymmetric MWF and energy beam splitter function (e.g. asymmetric Polarized E/B fields) in Space-time. Under no external E/B bias, MWF distribution of the nonlinear crystal material causes asymmetrical non-zero electric dipole polarization $E_{P0}$ for certain % of incidence photons microscopically.

Following Pauli Exclusion Principals in temporal (Type-I) or spatial (Type-II) aspects, the nonlinear crystal BPP material performs an action of being Energy Beam Splitter within atomic-level structure under confined tiny region within space-time. When incident high energy photon 6402 (e.g. UV photon) transmits through the nonlinear crystal BPP material, asymmetrical non-zero electric dipole polarization $E_{P0}$ will create a few different types of conjugated or phase-matched photon pairs, including temporal phase-matched (Type-I) or spatial correlated H/V polarizations (Type-II) for each Signal-photon and idler-Photon pairs due to secrete boson's "charge quanta confinement (CQC)" effect.

In another aspect, the present invention unveils fermion's Stern-Gerlach effect is another analogous to the QEO (Kerr) Effect. Also, the Gluon (i.e. MWE packet) bunches or Quark jets formed during Large Hadron Collider (LHC) events which can be attributed to the chain-reactions of plurality of asymmetrical MWF Beam-Splitter incidences in space-time that associated with the "Quark confinement" and "Particle Jets" events.

It is well known, all particle exhibits DEP (Dielectrophoresis) Effect in presence of non-uniform or non-symmetrical E/B fields, the deflection force ($F_{DEP}$) depends strongly on a few physical properties, including (medium+particle)'s atomic fine structures, orientation of dipole polarizations and frequency of E/B field as well, e.g. DEP deflection force $(F_{DEP})=P_1*Grad(E_{P0})>0$.

AP. New MWF Model for SPDC (III)—BPP Theory and the Phase-Matching Postulates However, the temporal timing overlap or coherent is difficult for typical SPDC photon generation since the SPDC photon has a small coherent time about a ns to a few 100 fs, quite shorter than the time resolution of typical single photon detector, e.g. APD, etc.

BPP source, e.g. SPDC and the like, is a coherent or partially coherent due to temperature, MWF temporal and spatial non-uniformity effects. The coherent time is about ns~100 fs typically.

Figure 65A:
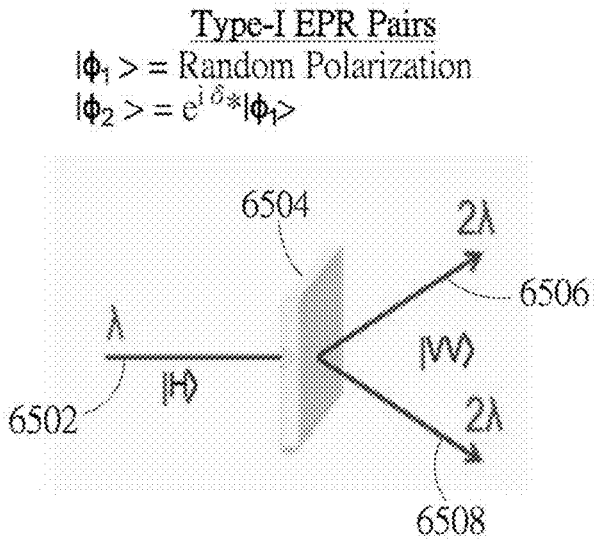
FIGS. 65A, 65B are diagrams illustrating the phase-matching fundamental properties of SPDC type-I and type-II matters by using the new light model.
Figure 65B:
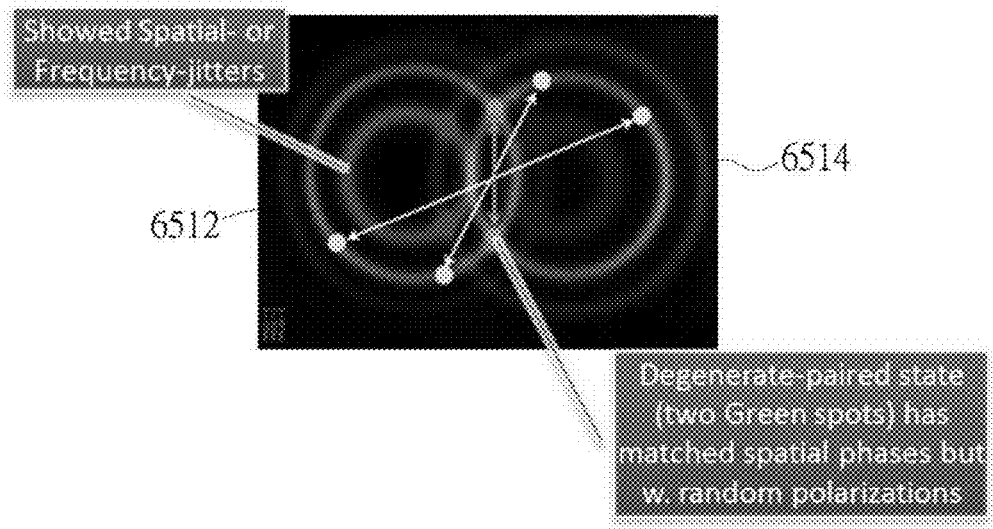

For SPDC Type-I, while blue or UV photon 6502 with wavelength λ transmits through BPP non-linear MWF materials 6504, two red photons 6506, 6508 are generated. As shown in FIG. 65A, $|\phi_1>$ is a Random polarization Photon MWE and $|\phi_2>=e^{i\delta}*|\phi_1>$ is characterized as having the same polarization but showing a temporal phase-matched (or temporal phase shift) with $\delta=+/-\pi/2$. For SPDC Type-II, as shown in FIG. 65B the smeared circles disclose spatial or temporal jitters (i.e. partial de-coherence) of a SPDC source. For those non-degenerated photon pairs, the spatial phases of first red circle 6512 and second red circle 6514 are matched, i.e. the pair of photons own definite H/V polarization states of its own, and if first red circle's photon is H polarization then second red circle will be V polarization, etc. For those degenerated photon pairs, e.g. two photons emitting out from cross points of the first and second red circles, the pair of photons will be associated with unknown but definite H/V-matched states. Also as shown in FIG. 65B, it can be expressed by $|\Psi_1>=H1$ or V1 wherein H1=(Cos(ωt+α), 0) and V1=(0, Sin(ωt+α)) with random temporal phase offset α, $|\Psi_2>=+/-R_{90}*|\Psi_1>$ is $+/-\pi/2$ spatial phase-matched with $|\Psi_1>$. In addition, an overall summary of Type-I is shown in TABLE 13.

TABLE 13

| Phase-matching | Pump axis | Signal axis | Idler axis | Temporal Phase E VS. o | Spatial polarization | Polarized direction | BS output |
|---|---|---|---|---|---|---|---|
| Type-I | e | o | o | ~90° | Same | Random | Bunching at BS outputs |
| Type-II | e | o | o | ~0° | \|H1, V2> or \|V1, H2> | Orthogonal | Bunching at BS outputs |

AQ. New SPDC Type-I Model—BPP Experimental Results for Phase-Matching Effect Type-I Phase-Matching: Following BPP Pauli Exclusion Principle (PEP) in temporal, SPDC photons (Signal and idler) shall have temporal orthogonal (π/2) or conjugated phase-matched with the same but random spatial polarization states. By obeying PEP in temporal, temporal phases of SPDC type-I Paired Photons creation are associated with the new theory of Paired Charge Quanta Confinement (i.e. CQC) effect and their quantum states have to be renormalized during SPDC BPP creation process by following PEP requirement in temporal.

Figure 66A:
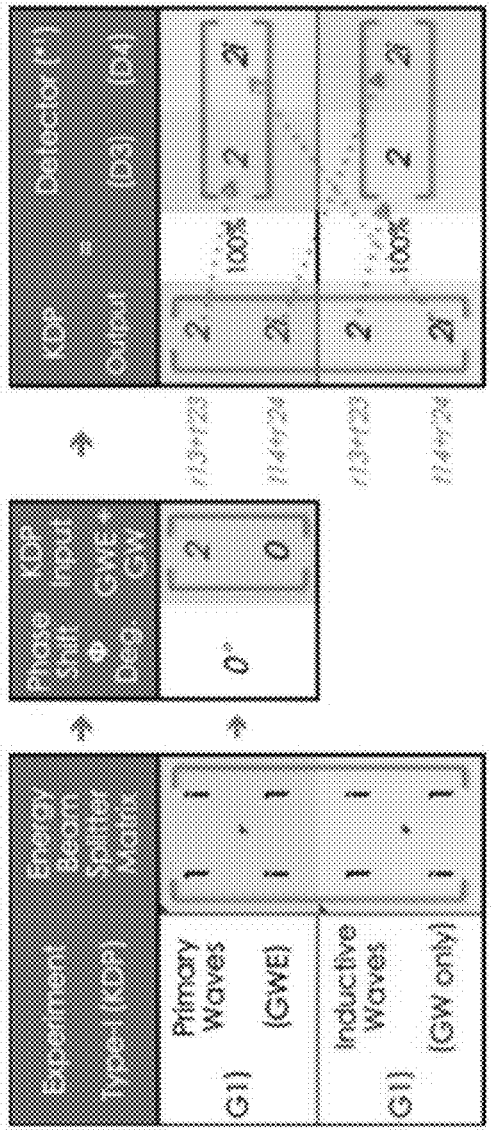
FIGS. 66A, 66B are diagrams illustrating experimental proof of SPDC Type-I new Model by using BS entanglement effect for temporal phase-matching matrix mathematical operation analyses.
Figure 66B:
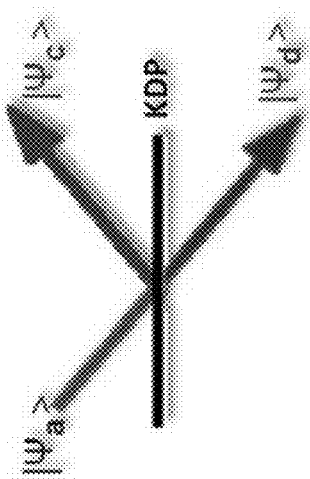

The present invention discovers SPDC type-I material such as KDP, etc. has been playing the energy- or beam-splitter role associated with a beam splitter with TWO inputs (a & b) and TWO outputs (c & d). The Expt.-G1 manifests that output state of $\Psi c=1>+\Psi d=i>$ is the ONE allowed SPDC type-I energy splitter output state for KDP e+o ray's conjugated phase-matching in temporal. Bunching of $\Psi c=2>$, or $\Psi d=2i>$ is not allowed due to violation of Momentum conservation, wherein the energy (Photon MWE packet) BS matrix mathematical operation of Expt.-G1 can be referred to FIGS. 66A and 66B. The Pump photon plays the role of two phase-matched (i.e. temporal and spatial paired) input photons while pump photon entering and interacting with the nonlinear optic materials, e.g. KDP, etc. In addition, the overall summary of expt.-G1 is shown in TABLE 14.

TABLE 14

| Expt.-G1 Theory | 1) Pump photon plays the creation role of two temporal and spatial phase-matched input photons while entering the nonlinear optic energy splitting SPDC materials, e.g. KDP, etc. |
|---|---|
| Expt.-G1 Output State | 1) It output state follows the Laws of Energy and Momentum Conservations<br>2) Bunching of TWO photons with $\Psi c = |2\rangle$ or $\Psi d = |2i\rangle$ is not allowed state due to Momentum conservation violations |

AR. New SPDC Type-II Model—BPP Experimental Results for Phase-Matching Effect

Figure 67A:
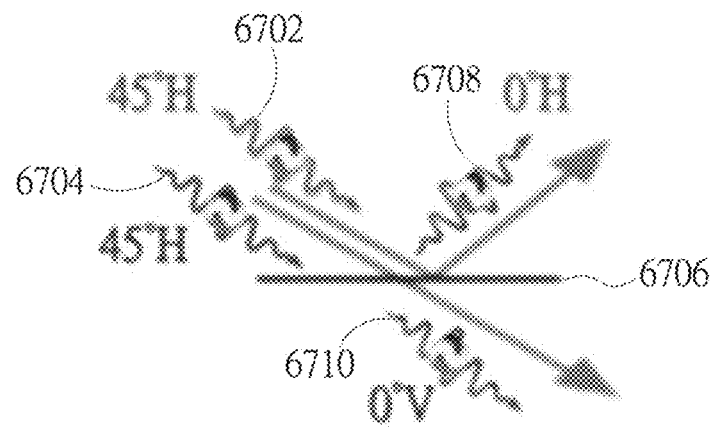
FIGS. 67A, 67B are diagrams illustrating experimental proof of SPDC Type-II new Model by using BS entanglement effect for H/V spatial phase-matching analyses.
Figure 67B:
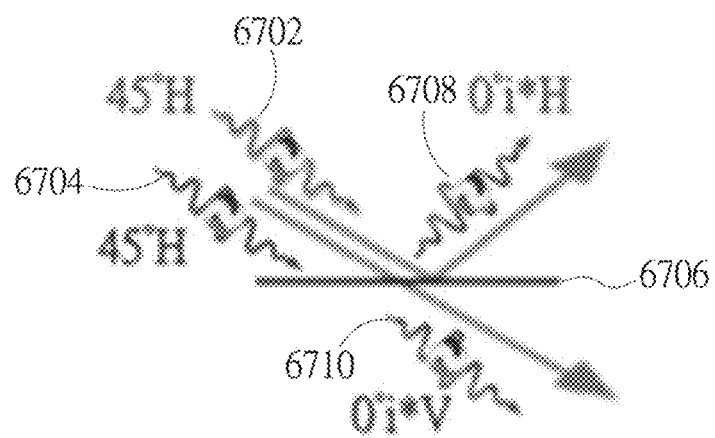

Type-II Phase-Matching: Following BPP Pauli (Spatial) Exclusion Principle (PEP) in spatial shown in FIGS. 67A and 67B, pump UV photon (i.e. equivalent to two entangled identical red photons 6702, 6704) hit nonlinear polarization BS material 6706 (e.g. BBO, etc.), SPDC signal 6708 and idler 6710 have conjugated polarizations (shown in FIGS. 67A, 67B), but have unknown but definite temporal phases. Their (i.e. CQC Quanta) Spatial relationship has to be re-Normalized (Orthogonal and conjugated) during photon pair's annihilation and recreation process. Also, the overall summary of Type-II is also shown in TABLE 15.

Expt. -G2: The allowed Anti-bunching states, including $\Psi c=|H\rangle+\Psi d=V\rangle$ or $\Psi c=|iH\rangle+\Psi d=|iV\rangle$, etc. are the possible output states for BBO SPDC type-II photon creation process. Bunching of $\Psi c=|2H\rangle$ or $\Psi d=|2iV\rangle$ is not allowed due to Momentum conservation violation. The typical SPDC photon pairs are in non-degenerated states, wherein the Spatial polarization is in a fixed direction for non-degenerate SPDC photon pairs and is in random but spatial-matched (i.e. HV matched or conjugated) directions for degenerated SPDC photon pairs at the cross-point locations of the two photon emitting circles as shown in FIG. 65B.

In addition, an overall summary of expt. -G2 is shown in TABLE 15.

TABLE 15

| expt. -G2 Theory | UV Pump photon can play the role of two entangled (phase matched) and identical red input 0photons 6702, 6704 while entering the nonlinear polarization BS material 6706, e.g. BBO, etc. |
|---|---|
| expt. -G2 Output State | 1) It follows the Laws of Energy and Momentum Conservations<br>2) Output Bunching of $\Psi c= | 2H\rangle$ or $\Psi d= | 2V\rangle$ is not allowed due to Momentum conservation violations" |

AS. Experimental Proofs of EPR Pair's Bell States (I)— can be Well Predicated by Malus Law (Reference: C. H. Thompson, "the Tangled Methods of Quantum Entanglement Experiments." Accountability in Research 6.4 (1999): 311-332)

EPR experiment with laser excited light source with time-varying method (Reference: A. Aspect, et. al. "Experimental test of Bell's inequalities using time-varying analyzers." Phy. Rev. Letter 49.25 (1982)):

QM (prior art) predicted Singlet States: $|\Psi 12\rangle=|HH\rangle+/-|VV\rangle$ for phase-matched and exchange symmetry photon pairs. Coincident curves can be with ~100% visibility, if subtracting (offsetting) incidental coincident events by free proof. It is shown, prior art's actual raw data(*1) was associated with ~50% visibility just met Bell Inequality and obeyed the EPR predication. EPR Local Realism well predicated the same ~50% visibility using classical "Malus +Superposition Laws", e.g. The first arm EPR photon is with $|\phi_1\rangle=H$ or V or random polarizations, and then the second arm EPR photon will be with $|\phi_2\rangle=e^{i\delta}*|\phi_1\rangle$ wherein the photon pairs are phase-matched (orthogonal or conjugated) in temporal with a factor $\delta=+/-\pi/2$ (90 degrees) phase shift.

Figures 68A, 68B:
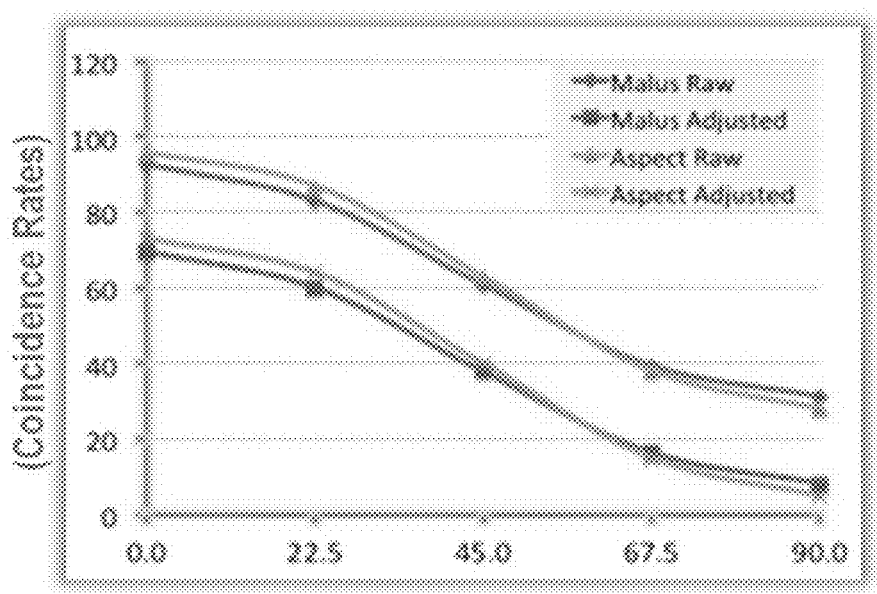
FIGS. 68A, 68B are diagrams illustrating new experimental proofs of EPR pairs not violating the Bell States, with which can be well predicated by Malus Law.

The local realist theory assumed 1) the observed correlations originate from commonly shared properties that had been acquired or given at the particle source, 2) the observer's detection events are independent of the particle given states while particle pairs being created, and 3) A small p-value (≤0.05) of prior art's vs. Malus Law's test data indicate the strong evidence against a null (QM) hypothesis (as shown in FIGS. 68A, 68B), so QM's mysterious model is to be rejected and it not the truth.

Figure 69A:
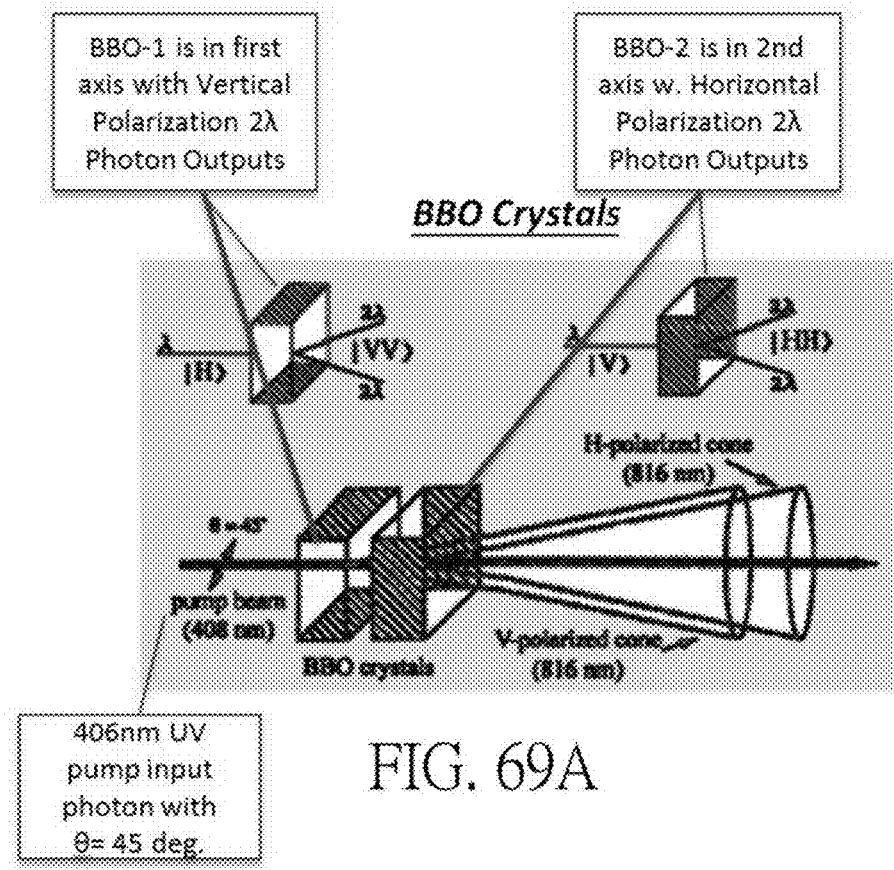
FIGS. 69A, 69B are diagrams illustrating new experiment proving that EPR pair is not violating the Bell States and the high brightness EPR light sources can be predicted simply by Malus law.

AT. Experimental Proofs of EPR Pair's Bell States (II)—can be Well Predicated by Malus Law Another prior art tested BBO sandwich sources of SPDC type-I experiment (Reference: Kwiat, Paul G., et al. "Ultra-bright source of polarization-entangled photons." Physical Review A60.2 (1999)) R773):

The prior art QM (prior art) predicted Singlet States: $|\Psi 12\rangle=|HH\rangle+/-|VV\rangle$ can be associated with ~100% visibility coincident curves as shown in FIGS. 69A, 69B.

Figure 69B:
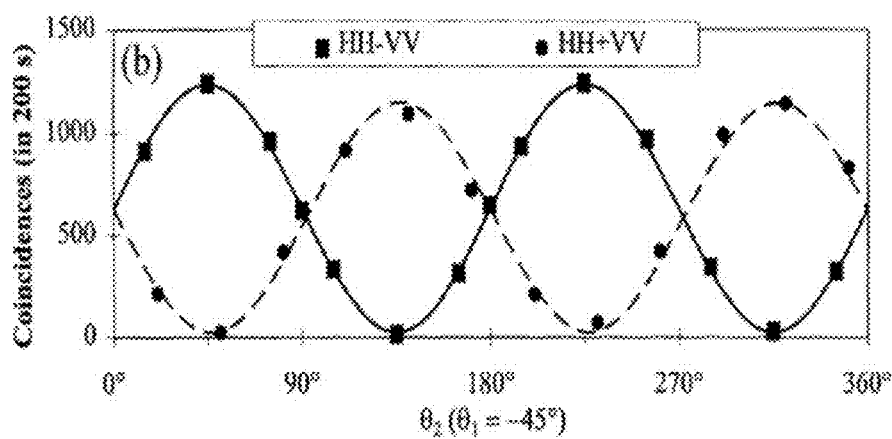

The present invention discovers that EPR Local Realism Paired Photon States predicate the same ~100% visibility using classical "Malus+Superposition" Laws (as shown in FIG. 69B).

The present invention discovers, in one case, EPR first-arm photon's wavefunction is associated with $|\phi_1\rangle=|H_1\rangle$ and EPR $2^{nd}$-arm photon's wavefunction is to be $|\phi_2\rangle=e^{i\delta}*|\phi_1\rangle=e^{i\delta}*|H_1\rangle$ and Temporal phase-matched with $\delta=+/-\pi/2$. In another case, EPR first-arm photon's wavefunction associated with $|\phi_1\rangle=|V_1\rangle$ and EPR $2^{nd}$-arm photon's wavefunction is to be $|\phi_2\rangle=e^{i\delta}*|\phi_1\rangle=e^{i\delta}*|V_1\rangle$ and with temporal phase-matched factor $\delta=+/-\pi/2$.

Apparently, the finding of the present invention evidences that there is no practical needs for Scientist inventing QM's mysterious "Entanglement Theory" or "Hidden Variables" so as to interpret the % visibility which can be fully understood and derived by the local realist Malus Law with such a classical and commonly known theory (Reference: C. H. Thompson, "The tangled methods of quantum entanglement experiments." Accountability in Research 6.4 (1999)).

AU. Formalism of Classical 4-Force Theories—Classical EM and QM Force Models

As prior arts said, while Maxwell equations and classical EM theories are successful at explaining variety applications of EM wave, light and other Physics phenomena, they are indeed not exact but known as approximations for many other cases.

In some cases, they can be noticeably inaccurate or even with wrong predictions. For various physical phenomena in the world, account Maxwell equations for predicting them to be impossible, including but not limited to under strong fields or extremely short distances (e.g. vacuum polarization in tiny space and in a short instance); any cases involving individual photon, like the other particles, such as the photoelectric effect, Planck's law, single-photon light detector or diffraction, etc; and it would be more difficult or impossible to explain, if Maxwell equations were true, as Maxwell equations do not involve any properties regarding light Quanta or SPDC photon "Particle" phase-matching effects and more.

For most accurate particle's EM behavior predictions in all cases, Maxwell equations must be superseded by QED. In addition, the summary properties of classical EM and QM force models can be referred to TABLE 16.

TABLE 16

| Characteristics | Electric Field | Magnetic Field |
|---|---|---|
| A. Nature of Source | +/− Charge (Scalar source) | +/− Current-loop (Vector source) |
| B. Potential Field | Scalar ($U_e$ Voltage) potential field | Vector (A) potential field |
| C. Spatial Direction of Field-line | Radius vector joining the source and all field points | Perpendicular to current-loop radius vectors and its source (J) vectors |
| D. Temporal Evolution | Static, if Charge is static. Dynamic, if Charge is moving | Proportional to Current flow (J) vectors, but its Divergence is "null" |
| E. Source Movement Force in Field | Perpendicular to the Magnetic Field lines | Perpendicular to the Electric Field lines |
| F. Unit or Dimensions | Newton/Coulomb | Tesla or Kg/(s^2*Amp) = Kg/(s* Coulomb) |

AV. New Concise Grand Unified Theory (GUT) and Postulates to Unify Matter Wave and Strong Interactions One has been knowing well with predictions in most cases that can be done by QED (Quantum E electrodynamics) along with many dozens of fitting parameters, the present invention unveils a Concise Grand Unified Theory (GUT) along with its simple postulations. The Concise GUT unifies the Matter Wave and Strong interactions so as to complement and comply with the duality essence of QM probabilistic "Wave Mechanics" together with the "Particle Physics".

The present invention discovers what can be most noticeably useful for various phenomena which either 1) cannot be predicted by classical EM theory or 2) can be predicted by QED theories together along with sophisticated fitting parameters, including: under strong fields or extremely short distances (e.g. in tiny squeezed vacuum, atomic scale or Taiji (e.g. Universe) polarization effects); any cases involving individual photon, like the other fundamental particles, such as the photoelectric effect, Planck's law, single-photon light detectors, particle diffractions or interferences, Beam splitters, energy packet splitters and Compton effect etc; and any cases involve boson particles such as BBP SPDC photon pairs phase-matching, or fermion particle interactions and proliferation of pair productions in LHC high energy Physics regimes and more. In addition, the summary properties of New Concise Grand Unified Theory (GUT) and Postulations can be referred to TABLE 17. Along the human civilization development process, the new Concise GUT will be eventually experimental proven by someone on someday in the future.

TABLE 17

| Characteristics | Matter Wave Field | Inductive Vector (W) Field |
|---|---|---|
| A. Nature of Source | +/− Mass object (Scalar source) | +/− Mass flow-loops (Vector source) |
| B. Potential Field | Scalar ($U_g$) potential field | Vector (X) potential field |
| C. Spatial Direction of Field-line | Radius vector joining the source and all field points | Perpendicular to Mass curling radius vectors and its source ($J_E$) vectors |
| D. Temporal Evolution | Static, if Mass unit is static. Dynamic, if Mass unit is moving | Proportional to Mass flow ($L_E$) vectors, but its Divergence is "null" |
| E. Source Movement Force in Field | Perpendicular to the Inductive W Field lines | Perpendicular to the Matter Wave Vector "W" Field lines |
| F. Unit or Dimensions | Newton/Kg | Kg/(s^2*$J_E$) = Kg/(s*E), E = m*c^2 |

AW. New Concise GUT Vs. Classical Maxwell Equations to Unify Gravitation and Strong Interactions Concise GUT Theory indicated "Energy (Mass equivalent Energy)" is a Dual Party of "Charge" associating with the set of Maxwell equations, wherein E represents the spatial "Energy density", it matched with Charge density ρ in Maxwell equations, $J_E$ represents the "Energy curling density", it matched with Current curling density J in Maxwell equations, G is the Matter Wave (Gravitational) Field arouse from interactions in between "mass density m" and space-time varying Energy forms, and W is the Inductive Vector Field arouse from "Energy density $J_E$" interaction with time varying G scalar potential.

The present invention theorized that Schrodinger and Dirac wave (Spinor) equations can be either the traveling or confined tensor solutions of matter waves in our Space-time (i.e. Universe) so as to satisfy the new Concise GUT and its most fundamental equations. The New Concise GUT manifests the relationship between Mass and Energy and it general predicts relativistic Mass-Energy equivalence principle (E=mc^2) formulated by Einstein, which states a Mass has an equivalent Energy counterpart, and vice versa. In addition, the summary properties and its mathematical relationships between New Concise GUT and Classical Maxwell equations can be referred to TABLE 18.

TABLE 18

| Field\Type | Source Nature | Static Interaction | Dynamic Interaction | Remarks |
|---|---|---|---|---|
| Electrical Field | +/− Charges | $\nabla \cdot E = \dfrac{\rho}{\varepsilon_0}$ | $\nabla \times E = -\dfrac{\partial B}{\partial t}$ | Ue is Scalar Potential |
| Magnetic Field | +/− Current Loops | $\nabla \cdot B = 0$ | $\nabla \times B = \mu_0 \left( J + \varepsilon_0 \dfrac{\partial E}{\partial t} \right)$ | A is Vector Potential |
| Matter Wave Field | +/− mass | $\nabla \cdot G = \dfrac{m}{\varepsilon_0}$ | $\nabla \times G = -\dfrac{\partial W}{\partial t}$ | Ug is Scalar Potential |
| Inductive Vector (W) Field | +/− Energy Flow Loops | $\nabla \cdot W = 0$ | $\nabla \times W = \mu_0 \left( J_E + \varepsilon_0 \dfrac{\partial G}{\partial t} \right)$ | X is Vector Potential |

AX. Summary and Perspectives—God is Subtle, but Plays Matter Simple and Classical Having borrowed wisdom from ancient Human civilizations, the present invention is dared to open a new page in the area of new Concise GUT which can unite the "Four" Fundamental Forces (*1) into "TWO" Forces, i.e. Electro-Weak and Gravita-Strong along with a set of new improved conservation laws of physics. The modified general conservation laws of physics can be describing as shown in following statements of Law #1~6.

Overall speaking, in all closed physical system or many-body particle interactions, the energy/mass, linear momentum, angular momentum and charge are relativistic conserved in either "macroscopically or microscopically".

Law #1) All elementary particles follow local-realism theory and possess classical-quantized angular momentum if it is in stationary state (not in motion) relative to the observer.

Law #2) All elementary particles possess classical-quantized linear and angular momentum if it is in motion state relative to the observer.

Law #3) Conservation of relativistic-energy/mass: The total sum of relativistic-energy/mass, including scalar field or vector field potentials in all its forms (e.g. E, B, G, W field potentials), is conserved.

Law #4) Conservation of linear momentum: In the absence of external force, relativistic linear momentum is conserved.

Law #5) Conservation of angular momentum: In the absence of external torque, relativistic angular momentum is conserved.

Law #6) Conservation of charge: Electric charge is quantized and conserved.

As a novel embodiment to be utilized for controlling the nuclei decay rate, e.g. neutron decaying to proton, the present invention teaches one (skilled person in the art) theoretically and experimentally on how a neutron life time can be controlled by changing the scalar or vector field potential energy of a particular neutron beam such that the neutron beam will be decaying slower (e.g. has longer life time under the external fields such as electric, magnetic, gravitational or W fields) than the other neutron beam may decay under the null or weak external field conditions. Hope it can be helped with research works on how to control nuclear power reactor more effectively and efficiently, and can contribute to the greener living environment of human being in future.

Under the blessing of the secrete nature, one can perform a neutron decay experiment and get its life-time of LT-1 under a sort of free space, e.g. showing weak, null or free of E/M fields environment, such that one would not need to consider the Relativistic potential field energy effects. On the other hand, the another neutron decay test does get longer life-time of LT-2 while its decay environment involved with high E/M field or gravitational field along with the pathway of the neutron movement. Based on Relativity Theory's prediction, the "Relativistic potential field latent energy" shall introduce the time dilation effect to those neutrons encountering such E/M field during tests. Also, in view of the great teaching of the present invention and the time dilation effect, one can predict that a standard time interval for a precision clock (e.g. super-fine atomic clock) will be slowing down a certain amount while it has been immersing into a location or environment which possesses with higher Gravitational or matter wave W fields.

Having known QED can explain the positronium pair annihilation and photon pair production interactions ($e^+ + e^- \rightarrow 2\gamma$) by generating of entangled eigen-states; this invention unveils the new theory behind the most famous annihilation of the positronium and photon pair production (PPP) interactions. (Ref: The Feynman Lectures, Vol III, page 18-5) Like a binary-star system exactly in the local realism space-time of our universe, as shown in Table 19, the new Concise GUT theory indicates that "atom of positronium" is made up of an electron and a positron orbiting and spinning to each other by possessing "classical-quantized" paired spin angular momentum and paired orbital angular momentum, wherein the paired spin and orbital angular momentum are Quantized and respect all the classical conservation laws of physics. Positronium is a rotating and bound state of an e+ (Positron) and an e– (Electron), like a hydrogen atom, except that a positron replaces the proton.

The annihilation process and photon pair production interactions are comprised of 1) The positron is the antiparticle of the electron; they can annihilate each other in a very short period to time, 2) The two paired antiparticle-particle disappear completely and converting (transforming) their total energy (e.g. rest mass and kinetic/potential energies) into TWO γ-rays (photons) moving in opposite directions by following all kinds of conservation laws of physics in both macroscopically and microscopically.

Figure 70A:
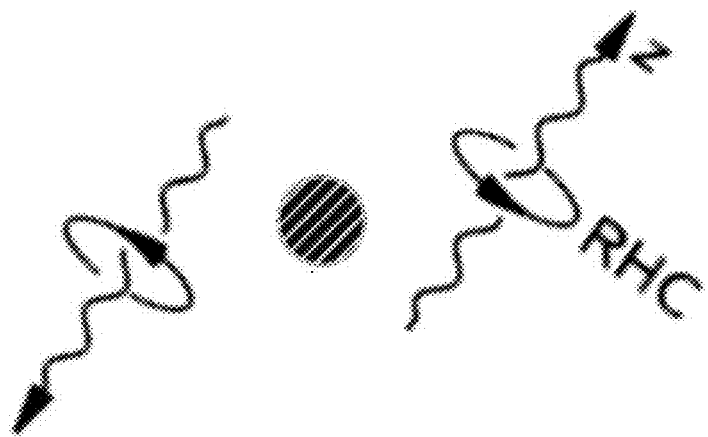
FIG. 70A is a diagram illustrating positronium decay model corresponding to old QM theory.
Figure 70B:
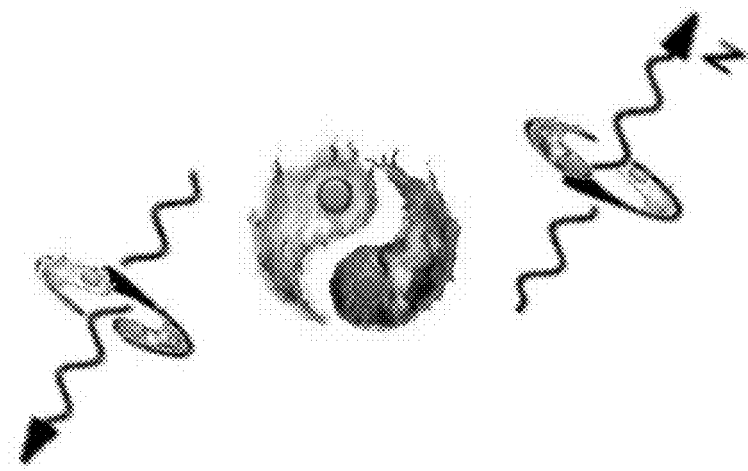
FIG. 70B is a diagram illustrating positronium decay model corresponding to new Concise GUT theory.

In the positronium annihilation interaction, it disintegrates into two γ-rays with a lifetime of about 10 to the minus 10 seconds. If the photon going upward is RHC (as shown in FIGS. 70A, 70B and TABLE 19, 20, wherein FIG. 70A corresponds to old QM theory, and FIG. 70B corresponds to new GUT theory), then the classical total angular momentum can be conserved ONLY if the downward going photon is LHC in contrast (i.e. the new concise GUT theory predicts that classical law of angular momentum conservation demands that $e^+ + e^- \rightarrow \gamma_{RHC} + \gamma_{LHC}$). Each photon will carry ½ unit of original total angular momentum (A) with respect to its original angular momentum direction (z), which means each photon spinning or rotating about the z-axis. On contrary to the prediction of QED (Old QM Theory), the new Concise GUT theory predicts the total angular momentum will be remaining with the same amount of "A" (i.e. it is non-zero and given amount) after the disintegration will be the same as before. Moreover, the present invention discovers that the positronium annihilation interaction is parity symmetry in all directions which means the behavior of annihilation and γ-ray PPP outcomes will be the same for Right-handed coordinate system versus a mirrored Left-handed coordinate system as always.

TABLE 19

| Positronium Experiment States & Models | Total Angular Momentum (J) | Magnetic Spin (MS) | Remarks |
|---|---|---|---|
| Old QM Theory Representation | \|0> | \|0> | Point-like with total J = 0, Ms = 0 |
| New GUT Theory Representation | A (Classical-Quantized, non-zero value) | 0 | Respects local-realism in space time by given that angular momentum A is finite and Ms = 0 |

TABLE 20

| Positronium States & Models | Output Vectors | Total Angular Momentum (J) | Magnetic Spin (MS) | Remarks |
|---|---|---|---|---|
| Old QM Theory Representation | \|RR> − \|LL> | \|0> | \|+1, −1> = \|0> | Hypothetical entangled-states (FTL speed) with J and Ms conserved |
| New GUT Theory Representation | \|R, L> or \|L, R> | A/2 + A/2 = A (Classical-Quantized) | 0 + 0 = 0 | It is determined, local realism and respects Pauli Exclusion Principle and all kinds of classical conservation laws |

Also in another particle Physics, this invention unveils the theory of how the Neutron Decay can be violating the parity conservation, i.e. Known Parity Asymmetry Effects for neutron decay. A few prior arts articles observed experimentally, beta particles were emitted preferentially (i.e. polarized emissions) in the opposite direction of the neutron polarization (Nuclear spin direction aligned by external B field), which indicated that parity conservation law might be violated, i.e. the beta ray decay rate (or cross section) changes under parity operation, then the parity is discerned not conserved.

While in B field, the neutron-neutron interaction (i.e. the strong interaction of boson W— and nuclear total angular momentum Jn) will derive beta-decay inside of nuclei, the beta-particle generating rate (G) is parity conserved due to the nature of strong interactions. On the contrary, the beta-ray may get diverged out and/or recombined back under the asymmetrical E/B field's forces, e.g. $F=q(E+v\times B)$, of nuclei which make the recombination (R) interaction of Pe (electron momentum)×Bp (B field of proton) being an odd-parity (asymmetric) state:

To respect the General Conservation Laws, this invention unveils; the Helicity is in opposite directions for beta particles moving in parallel and anti-parallel to external B field so as to make total angular momentum conserved during neutron's beta decay process.

The net beta particle emission rates (i.e. G-R) does not respect Parity Conservation owing to the Right-handed and Left-handed states are in different parities in the whole process of beta decay.

Figure 71B:
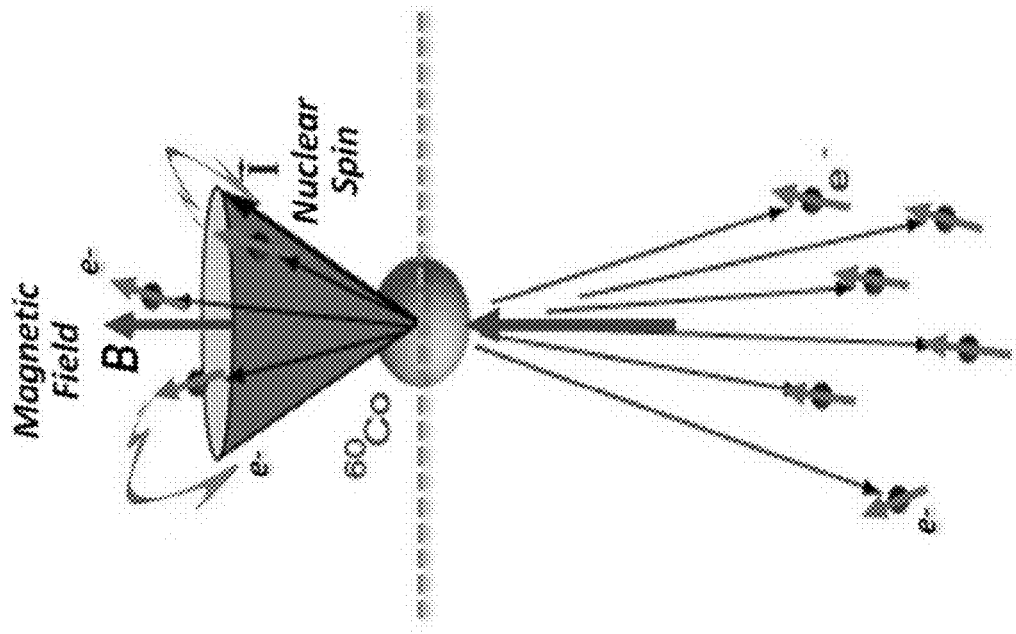
FIGS. 71A, 71B are diagrams illustrating new model representation of neutron decay parity asymmetry effect in Co-60 beta-decay.
Figure 71A:
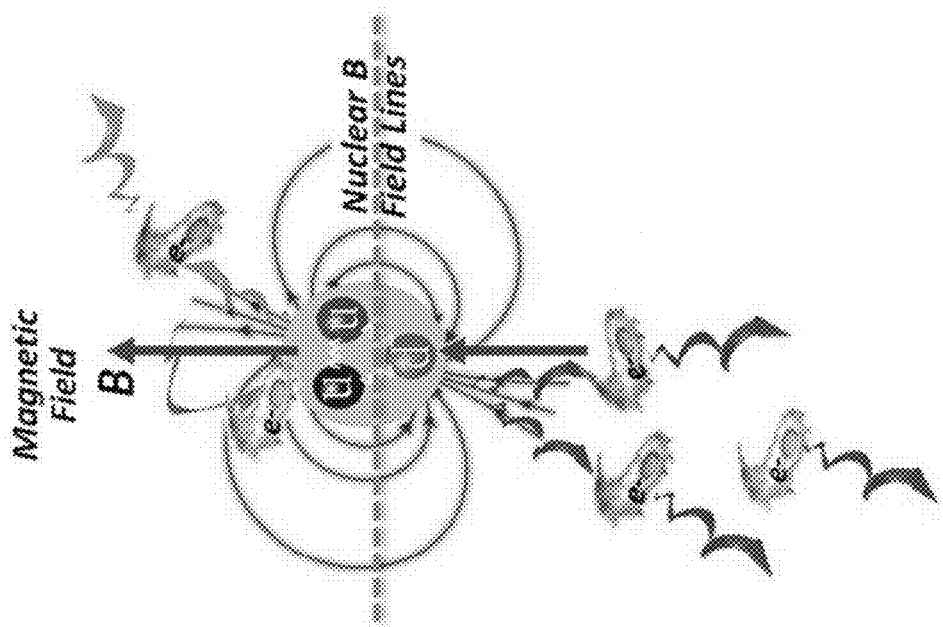

As shown in FIGS. 71A, 71B, their microscopic QM states are not in symmetrical (even) Parities, while mirroring beta particles net emission rate (G-R) through the dashed line. In one state of moving in the anti-B field direction, beta particles will get confined by B field automatically and prefer moving anti-parallel to B field (i.e. anti-neutron spin polarization) direction. In another state of moving along B field direction, beta particles get diverged by EM interaction of B field around the Proton and prefer moving diverged away from B field direction, or will even get folded back and recombined with nuclei by lowering the net emission rate (G-R) in along B field direction.

As shown in FIGS. 71A, 71B, while mirror Electron pairs going through dashed lines, their states are not in symmetrical (even) Parity states vs. B or W fields. Parity Asymmetry Effect in Space-time spells out the New Model of Neutron Decay and the story why neutron decay can be violating Parity Conservations.

Figure 72A:
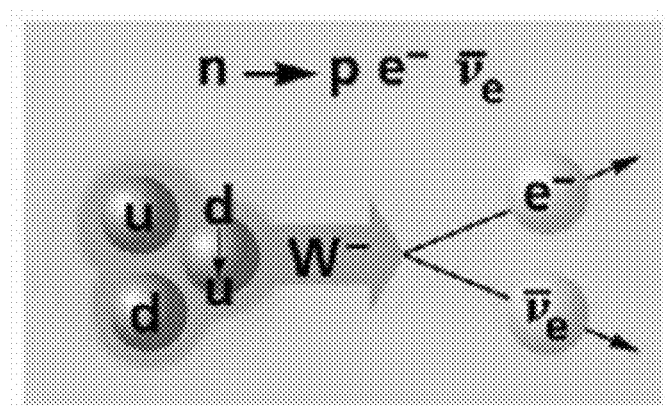
FIGS. 72A, 72B are diagrams illustrating neutron and proton possessing classical-quantized angular momentum and being comprised of a group of 3 massless fractional anti-Charge or Charge Quanta along with 3-in-1 paired rotating "Energy or anti-Energy threads".
Figure 72B:
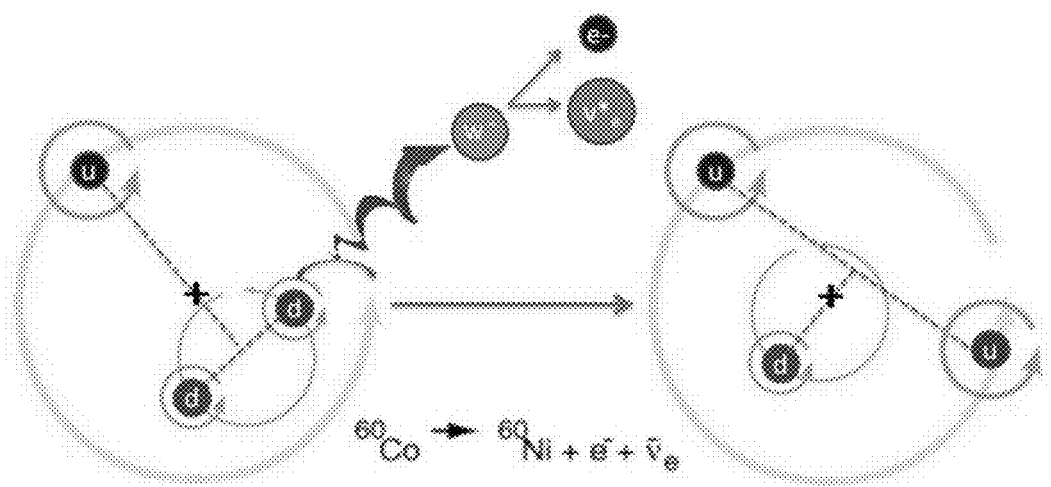

As shown in FIGS. 72A, 72B, similarly to trio-star (triple-star) system, Neutron and Proton possess classical-quantized angular momentum and are comprised of a group of 3 massless fractional anti-Charge or Charge Quanta along with 3 rotating Quark's "Energy or anti-Energy threads", wherein the bonding force of Quarks is associated locally with its Gravita-Strong (i.e. MW tensor) force within such tiny space-time of nuclei.

In a physical triple star system, each Quark orbits the center of mass of the system. Usually, two of the Quarks form a sub-closed binary system, and the third Quark orbits this pair at a distance much different than that of the binary orbit. The Quark group of nuclei is called hierarchical triple-Quark system. The reason for this is that if the inner and outer orbits are comparable in size, the triple-Quark system may become dynamically unstable, it can be leading to a Quark being ejected from the system or to violate the General Conservation Laws of Physics under the environment of Gravita-strong MW field interactions inside of nuclei.

In another aspect of this invention, the General relativity (also known as the general theory of relativity or GTR) is the geometric theory of gravitation published by Albert Einstein in 1915 and the basic principle of Cosmology in gravitational aspect in modern physics. On the other hand, the present invention unveils that GTR and Newton's law of universal gravitation is a nature consequence of the new Concise GUT of this invention that provides a unified description of gravity as a geometric property of both static mass/energy (e.g. fermion) and motion mass/energy (e.g. boson or light).

In particular, the curvature of space-time is directly related to the potential field energy in all its forms and relativistic momentum of whatever matter (e.g. fermion) and radiation (e.g. boson or Light) are present. The relation can be specified by the Gravita-Strong field equations of the new Concise GUT, a set of amicable partial differential equations teaching by the present invention in aforementioned. Examples of early science theories being able to manifest by such Concise GUT include gravitational and E/M potential field induced time dilation, gravitational and E/M potential field induced energy/mass lensing effect, the gravitational and E/M potential field induced redshift of light, and the gravitational and E/M potential field induced time delay.

The predictions of Concise GUT have been confirmed in plurality of observations and experiments in past, it is the simplest theory that is consistent with experimental data. Though other unanswered questions remain, the most fundamental theories and matters can be reconciled with the laws of new Concise GUT of physics to produce a complete and self-explained theory of quantum field theory. For instance, the bending of light by gravity potential field can lead to the phenomenon of gravitational lensing, in which multiple images of the same distant astronomical object are visible in the sky. Also, in following embodiments of the present invention, the new Concise GUT also teaches the existence of gravitational waves (i.e. matter waves), which have been observed since directly by our daily life. In addition, the Concise GUT is the universe basis of current cosmological models of a consistently expanding or to-be-collapsing universe.

Among hundreds of known particles, Mass-equivalent Energy coupled with "Mass-less" charge (Yang, +) and anti-charge (Yin, −) Quanta are the most elementary ones that constitute most of fundamental particles including bosons and fermions. The present invention has evidenced new mechanisms for forces that can contribute to human civilization and understanding of the origin of fundamental Forces in both grand (Universe) and subatomic (particles) scales. The present invention has set up a few ground-breaking Realist experimental methods that enable us to reveal the subtle interactions of each individual quantum systems consisting of boson or fermion. Discover the mechanism of BPP and FPP which follows strictly Pauli Exclusion principles in temporal or spatial space associated with subatomic physics, such as SPDC and LHC, etc. Finally, more Mother Natures are about to understand by Human Beings beyond this invention in near future as it was going always.

In addition, relationships between 4-force model can be referred to TABLE 21.

TABLE 21

| Interaction | ElectroWeak | | GravitaStrong | | Remarks |
|---|---|---|---|---|---|
| Property Acts on | Electromag Electric Charge | Weak Flavor | Gravitational Mass Energy | Strong Color-Charge Energy | New GUT Theory |
| Sources of Mediating | QED & EM Field Potentials | | GarvitaStrong Potentials | Field | No particle's Mediating needed |
| Particles involving | Photons, +/−e, +/−p, EM waves | Quarks, Leptons | bosons (e.g. Photons), fermions | Photons Quarks, Gluons Hardrons | Listed particles with reasonable stable life times |
| Strength at Quark | 1 | $10^{-4}$ | $10^{-41}$ | 60 | (*1) |
| Strength in Nuclei | 1 | $10^{-7}$ | $10^{-36}$ | 20 | (*1) |

Reference: (*1) "Standard model of particles and interactions". Contemporary Physics Education Project. 2000. Retrieved 2 Jan. 2017.

AY. New Model for Electron and Positron—Dared with Breath-Taking Postulates

The present invention unveils the new model for electron, as shown in FIGS. 73A, 73B, 74A, 74B, and 75 in following pages.

Taiji is literally: "great pole" is a Chinese cosmological term for the "Supreme Ultimate" state of undifferentiated absolute and infinite potential, the oneness before duality, from which Yin (−) and Yang (+) originate, in contrasted with the Wuji (without Ultimate) !

Figure 73A:
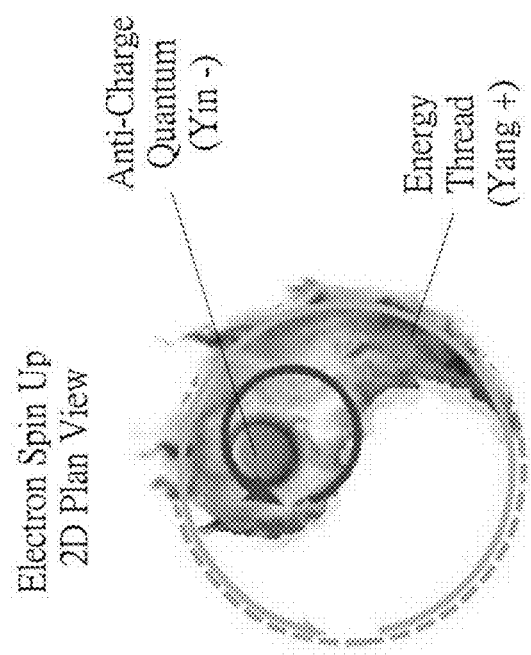
FIG. 73A is a diagram illustrating an orbiting and spinning representation of electron being comprised of a Yin (−) anti-Charge Quantum and a single rotating strand of energy equivalent mass packet (i.e. MWE).

As shown in FIG. 73A, electron is comprised of a paired Yin (−) anti-Charge Quantum and a single rotating strand of energy equivalent mass ($m_e$) packet which is associated with a finite size and locally condensed matter (or gravitational) wave (MW), wherein the wavefunction (Eigen-state) solution of the electron is with stable life-time in Universe, i.e. in the space-time.

Figure 73B:
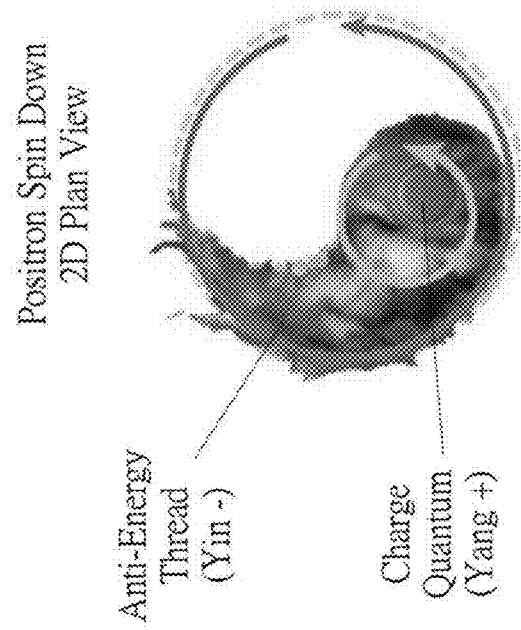
FIG. 73B is a diagram illustrating an orbiting and spinning representation of positron being comprised of a Yang (+) Charge Quantum and a single rotating strand of anti-energy equivalent mass energy packet (i.e. MWE).

As shown in FIG. 73B, positron is comprised of a paired Yang (+) Charge Quantum and a single rotating strand of anti-energy equivalent mass (me+) energy packet which is associated with a finite size and locally condensed matter (or gravitational) wave (MW), wherein the wavefunction (Eigen-state) solution of the positron is with stable life-time in Universe, i.e. in the space-time.

While creating fermion pair production (FPP) in vacuum, electron and positron pairs can see instantly Solar system and perhaps the entire Universe, via the wavefront (phase velocity) of its MW tensor wavefunction at the Light speed in space-time.

The "single strand" of mass-equivalent+/−energy (Em) represents the "+/−energy (mass) polarization state" of the vacuum, entangled with a condensed massless anti-Charge or Charge Quantum so as to forming the structure of an electron or positron respectively associated with the finite space-time locality, i.e. the electron and positron are not the point-like elementary particles.

While electron (position) being created, its MWE packet propagating at a speed of classical EM waves, i.e. "c" in Vacuum. Electron (positron) energy +Em (−Em) reveals its particle-like or ballistic-mass behavior in macroscopic space, e.g. shadow, impact or pressure behaviors, photoelectric effects, etc.

In addition, electron or positron MW wavefunction conveys the wave behavior in space-time, e.g. reflection, transmission, interference, refraction, diffraction or magnetic spin polarizations/quantization, etc.

Figures 74A, 74B:
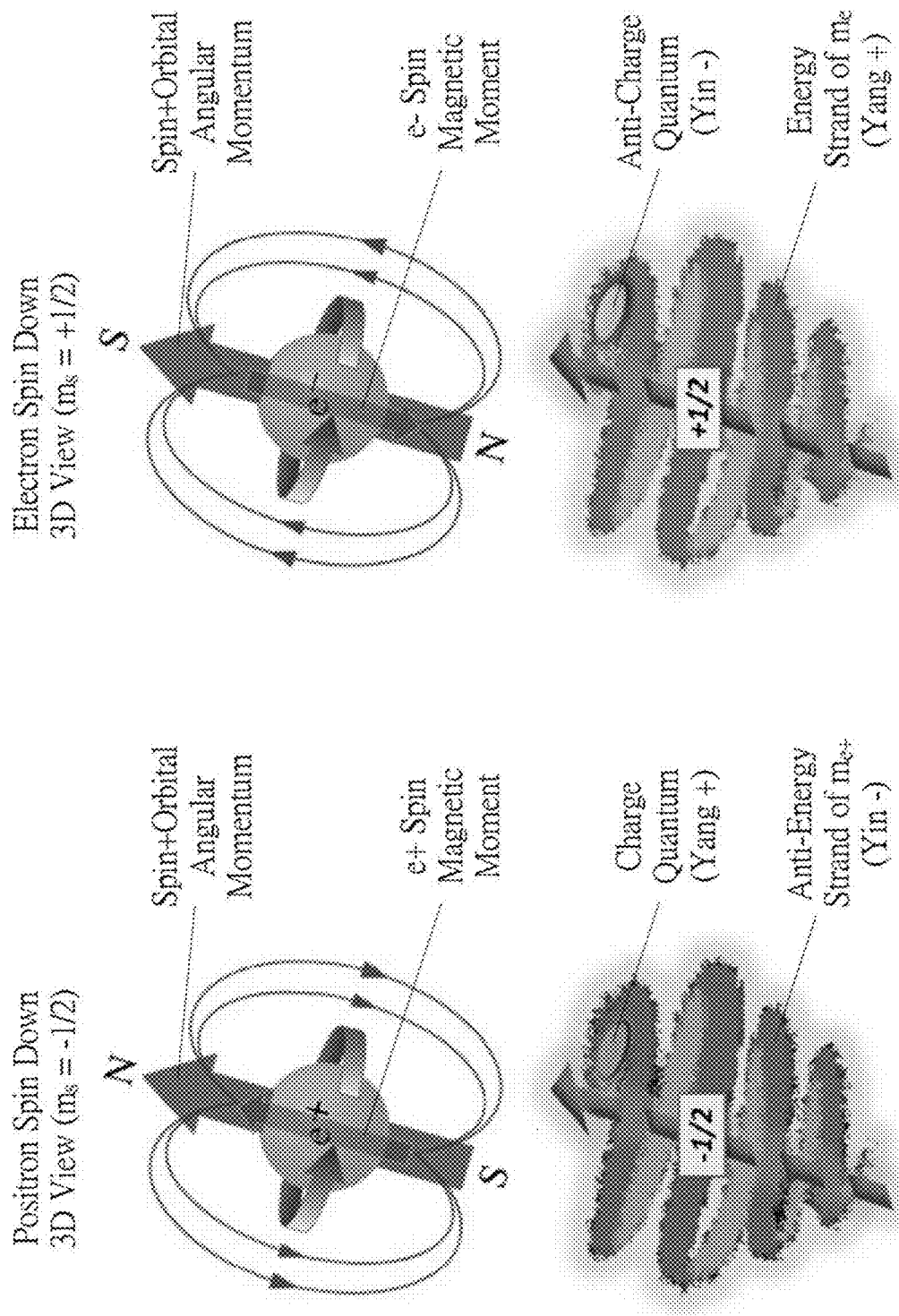
FIG. 74A is a diagram illustrating another representation of electron being comprised of a paired Yin (−) anti-Charge Quantum with a single rotating strand of "Energy thread".
FIG. 74B is a diagram illustrating another representation of positron being comprised of a paired Yang (+) Charge Quantum with a single rotating strand of "anti-Energy thread".

Similarly, as shown in FIGS. 74A, 74B, while forming a pair of "fermions" in vacuum, each of anti-fermion and fermion is comprised of a condensed massless anti-Charge or Charge Quantum along with a single rotating strand of "Energy or anti-Energy thread", wherein the single rotating strand of "Energy or anti-Energy thread" is associated with an MW tensor wavefunction in finite space-time, and FIG. 74A shows a fermion particle (e.g. electron) and FIG. 74B shows an anti-fermion particle (e.g. positron).

Figure 75:
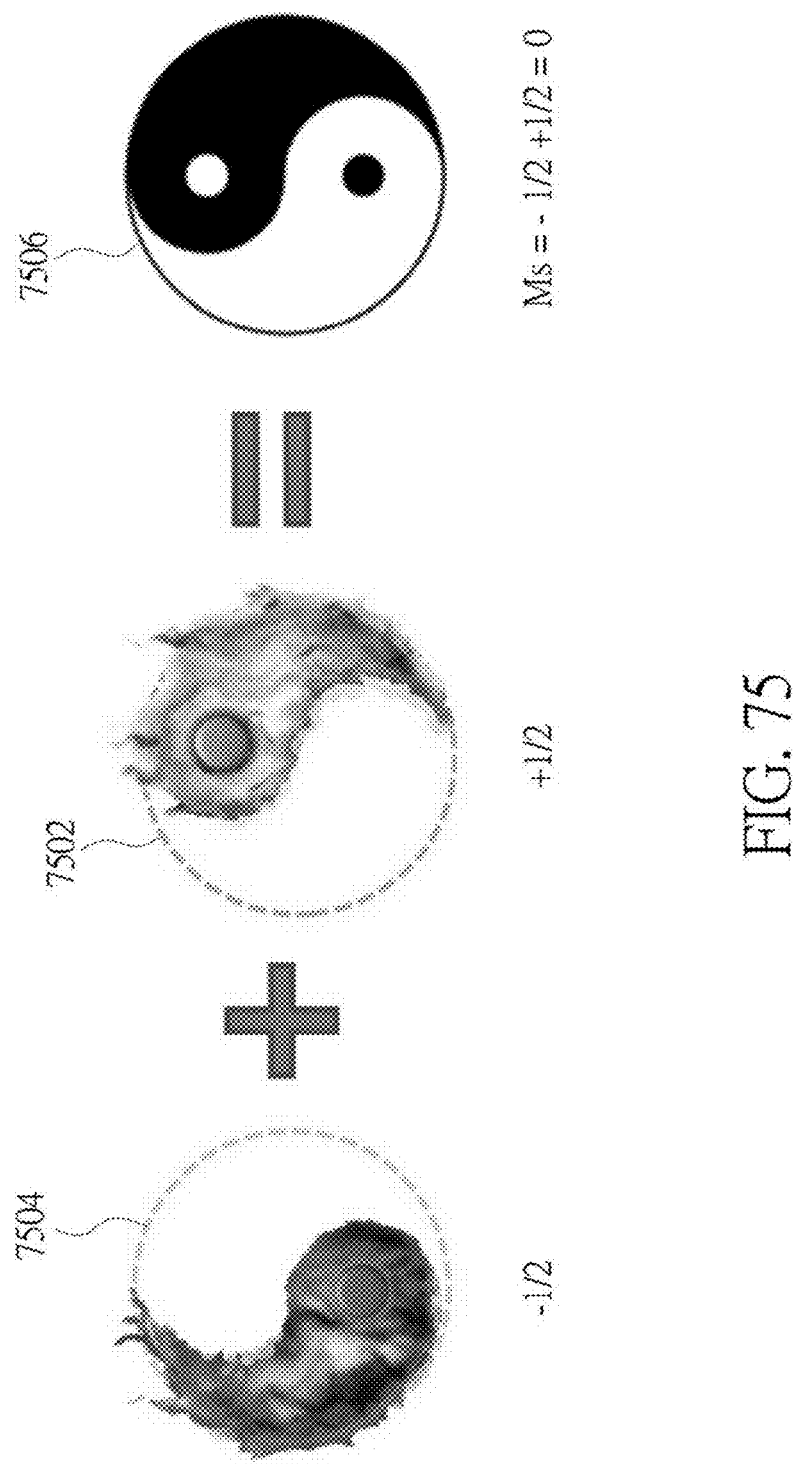
FIG. 75 is a diagram illustrating a photon like Tai chi being generated when an electron hits a positron in space-time.

In addition, as shown in FIG. 75, when an electron 7502 (spin =+½) hits a positron 7504 (spin=−½), there is a certain probability that the electron-positron pair can be annihilated and a photon 7506 (spin=0) will be generated by obeying the necessary conservation laws, e.g. energy, momentum and the like conservation laws.

While interacting with other particles, the rotating strand of mass carries the finite and relativistic properties (or eigen-states) and obeys classical-quantized Energy and Momentum Conservation Laws, including:

1) Momentums: Linear, self-orbiting (precession) angular, spin angular and TOTAL momentums.

2) Relativistic Kinetic and rest mass energies.

3) Electromagnetic E/B Scalar and Vector potential Energies.

4) New discovered Garvita-strong interaction G/W scalar and Vector potential Energies.

5) Second order interactions (Forces or Potential energies) via O(E/B, G/W, etc.) associated with many-body system, wherein O(E/B, G/W, etc.) means a negligible term that is equal or beyond the second order, etc.

As shown in TABLE 22, a set of "MW/GW Equations in Space-time" associated with moving fermion and boson mass-equivalent energy +/−EM reconciles the two viewpoints, through the articulate "MW/GW and Energy (MWE)" Packet, as shown in TABLE 22 wherein $$\left(W = \text{Curl}(X) \text{ and } G = -\text{Grad}(Ug) - \frac{\partial X}{\partial t}\right).$$

TABLE 22

| Field\Type | Source Nature | Static Interaction | Dynamic Interaction | Remarks |
|---|---|---|---|---|
| Gravitational Field | +/− mass | $\nabla \cdot G = \dfrac{m}{\varepsilon_0}$ | $\nabla \times G = -\dfrac{\partial W}{\partial t}$ | Ug is Scalar Potential |
| Inductive Vector (W) Field | +/− Energy Flow Loops | $\nabla \cdot W = 0$ | $\nabla \times W = \mu_0\left(J_E + \varepsilon_0 \dfrac{\partial G}{\partial t}\right)$ | X is Vector Potential |

Figure 76:
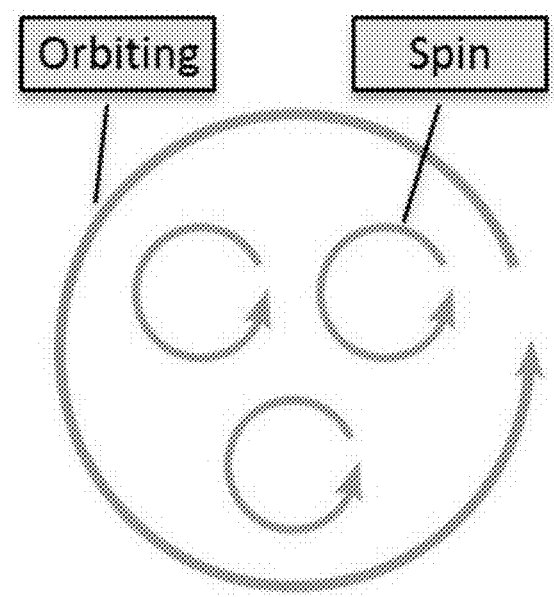
FIG. 76 is a diagram illustrating another orbiting and spinning representation of neutron and proton including a group of three-in-one massless fractional anti-Charge or Charge Quanta along with another three-in-one rotating strands of "Energy or anti-Energy threads".

AZ. New Models for Stationary-States of Neutron and Proton Stationary-State in Free Space Also, as shown in FIG. 76, the present invention unveils, similarly to trio-star system, neutron and proton include a group of three massless fractional anti-Charge or Charge Quanta along with three rotating strands of "Energy or anti-Energy thread", wherein the rotating strands of "Energy or anti-Energy thread" are associated with a standing-wave solution of its own Gravita-Strong MW tensor wavefunction in finite space-time.

Figure 77A:
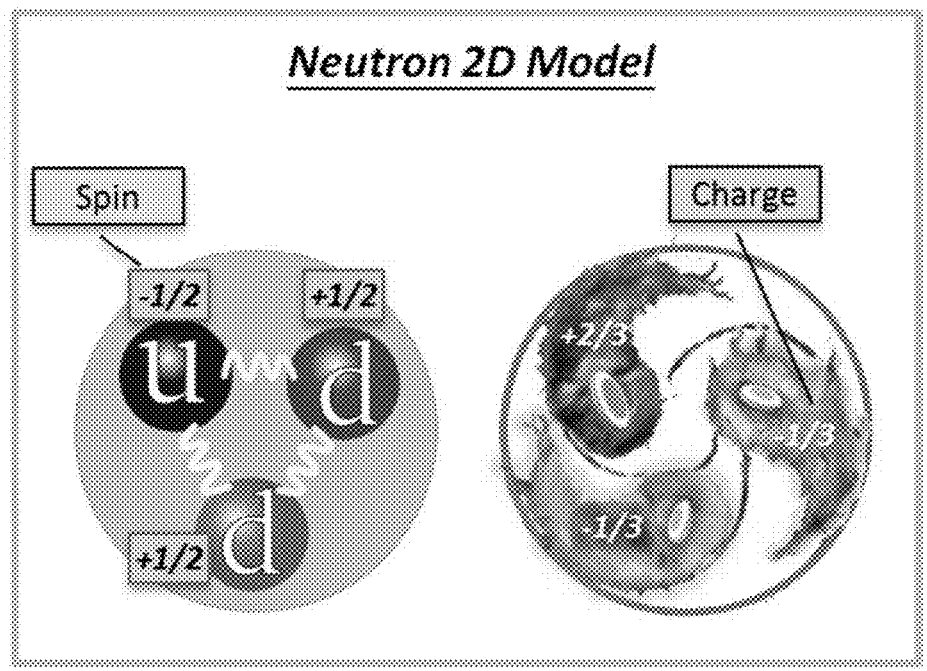
FIG. 77A is a diagram illustrating a 2D orbiting and spinning model representation of a proton being composed of two u quarks and one d quark.
Figure 77B:
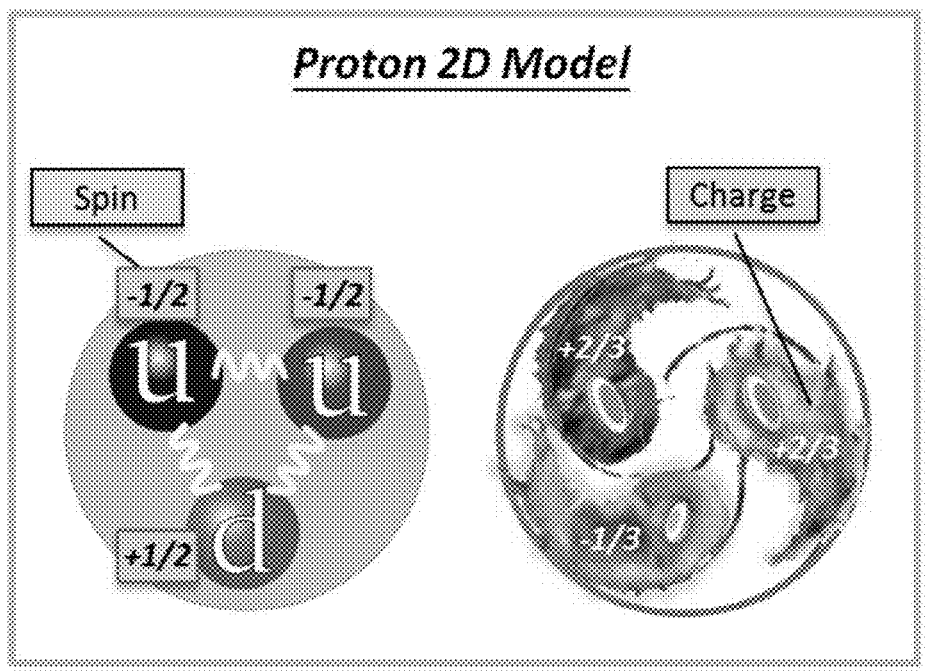
FIG. 77B is a diagram illustrating a 2D orbiting and spinning model representation of a neutron being composed of two d quarks and one u quark.

As shown in FIG. 77A, a neutron is composed of two d quarks (spin and charge of each d quark are equal to +½ and −⅓, respectively) and one u quark (spin and charge of u quark are equal to −½ and +⅔, respectively), so total spin and charge of the neutron are equal to ½ and 0, respectively. In addition, as shown in FIG. 77B, a proton is composed of two u quarks and one d quark, so total spin and charge of the proton are equal to −½ and 1, respectively.

While interacting with other particles, the rotating strands of energies carry finite and relativistic properties (or eigen-states) and obey "Classical-quantized" Energy and Momentum Conservation Laws, including:

1) Momentums: Linear, self-orbiting (precession) angular, spin angular and TOTAL momentums.
2) Relativistic Kinetic and rest mass energies.
3) Electromagnetic E/B Scalar and Vector potential Energies.
4) New discovered Garvita-strong interaction G/W scalar and Vector potential Energies.
5) Second order interactions (Forces or Potential energies) via O(E/B, G/W, etc.) associated with many-body system, wherein O(E/B, G/W, etc.) means a negligible term that is equal or beyond the second order, etc.

BA. New Model for Electron Spins in Free Space—More Stories about Stern-Gerlach Atomic Spin Quantization The Stern-Gerlach apparatus comprising of an oven of atom source 7802 was developed in 1922. Atom beams is collimated by collimator 7804 and sent in between two asymmetrical magnets (i.e. non-uniform S & N magnets), wherein the atom beams have random spins, the S & N magnets can form a non-uniform magnetic field (B), and spins of the atom beams can be realigned by magnetic polarization generated by the non-uniform magnetic field (B). The inhomogeneous or non-uniform magnetic field (B) bends atom trajectories proportional to the amount of spin $\mu_s$ and the Gradient of Magnetic field $B_z$ in z-axis which it is associated with deflection force $F_D$ ($=\mu_s \cdot \nabla(B_z)$), wherein as shown in FIG. 78, shift distance Z on screen (or detector) 7806 can be calculated or derived by that well-known formula for an ordinary-skilled person in the art, so further description thereof is omitted for simplicity.

Figure 78:
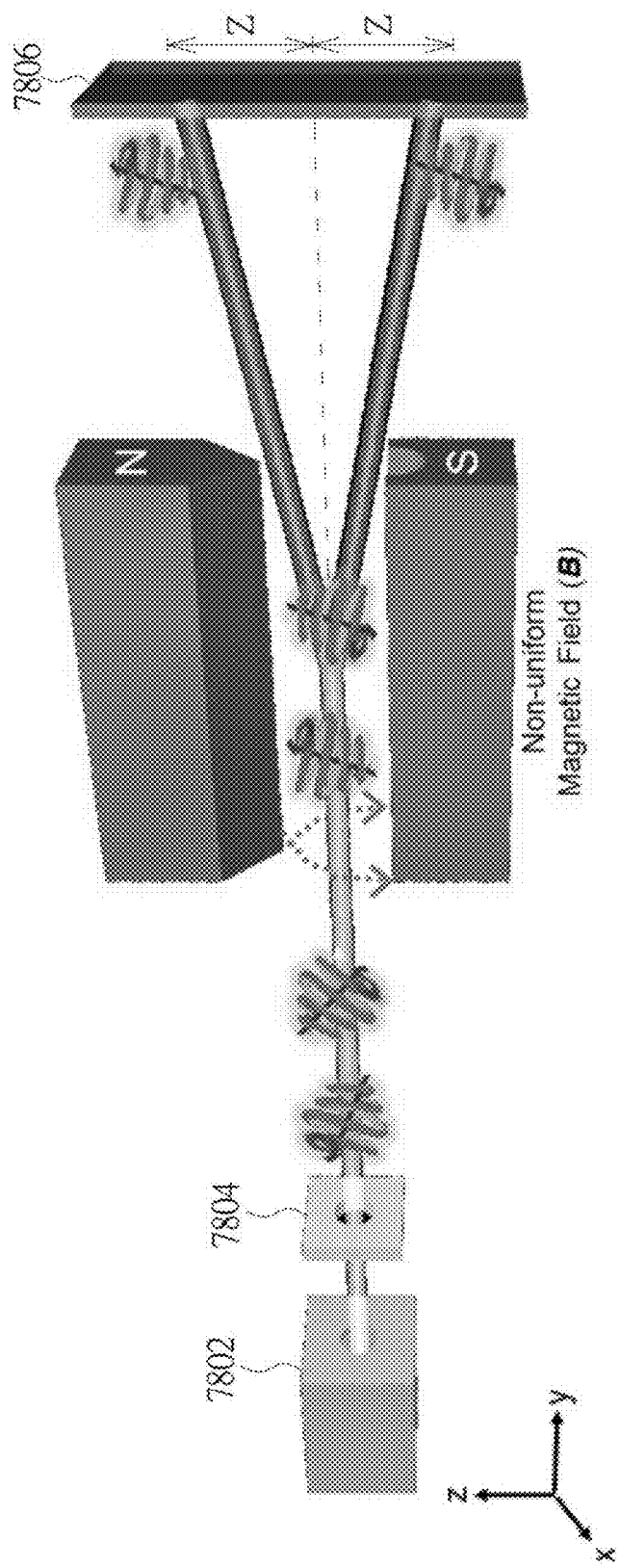
FIG. 78 is a diagram illustrating new model representation for electron spins in free space when electrons transmit Stern-Gerlach apparatus.

As shown in FIG. 78, particles' spins of the atom beams are classical-quantized, wherein the incident atom beams are with random magnetic spin directions and half the particles' spins (corresponding to spin=½) are deflected upward, the other half (corresponding to spin=−½) deflected downward by a discrete amount as to prove the existence of "Space or Spin quantization".

The new model of electron (positron) can self-explain well of the quantization of spins for an ordinary person in the art, perhaps better than most of known QM theories or models of nowadays. Also, this new model sheds some bright lights on resolving the historical problem of Quantum spin state (or spin Eigen value) measurement.

Figure 79:
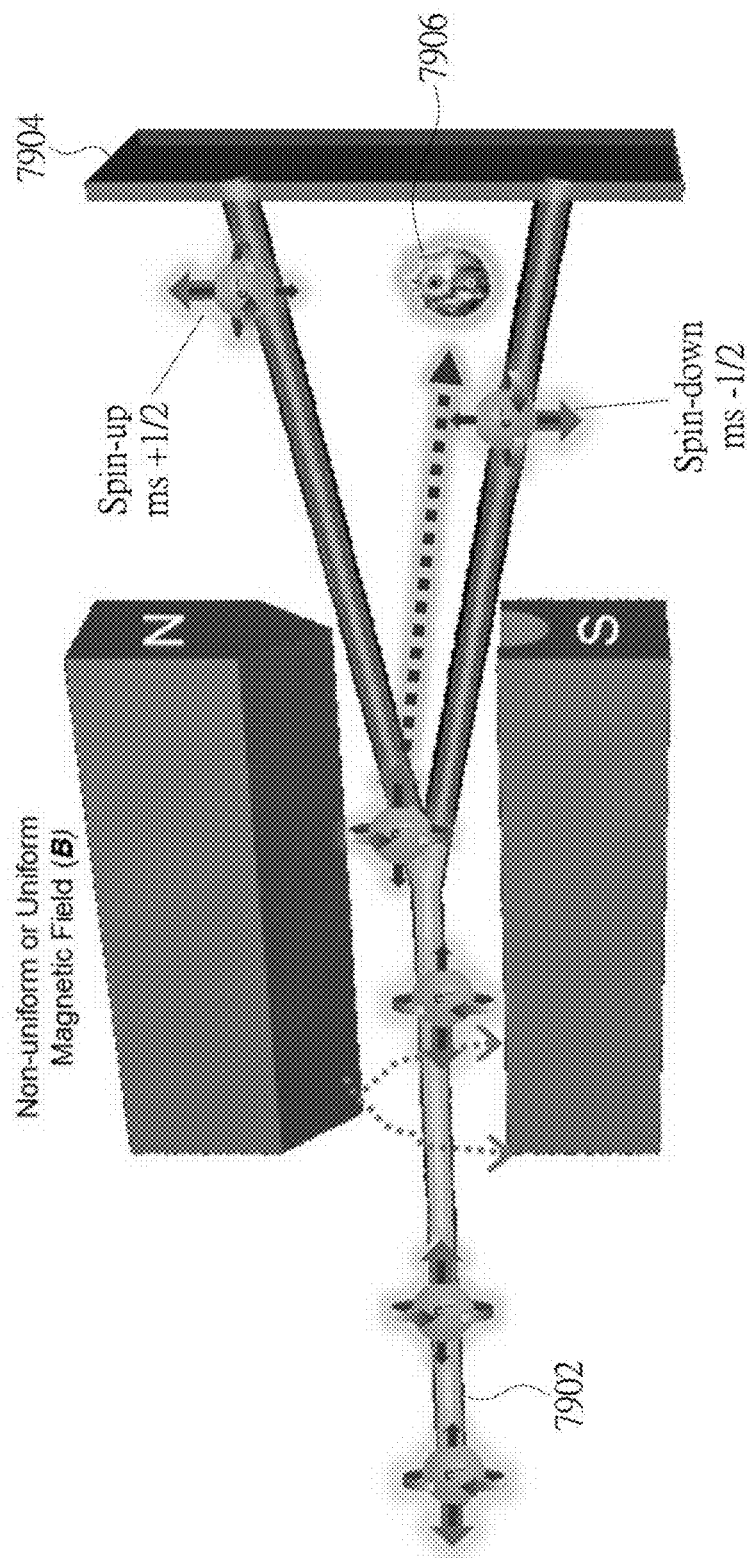
FIG. 79 is a diagram illustrating electrons getting into a spin-up state while they releasing instantly a corresponding photon when traveling within the non-uniform or partially uniform magnetic field.

As show in FIG. 79, incident electrons 7902 (or fermions and the like) with random spins and high relativistic kinetic energy move toward a non-uniform or partially uniform magnetic field (B) and a screen (or detector) 7904 behind the magnetic field (B). While the electrons 7902 traveling within a spatial region of the non-uniform or partially uniform magnetic field (B), some electrons get into a spin-up state while they release instantly a corresponding photon 7906 moving toward a lower part of the screen 7904. On the other hand, for those electrons getting into a spin-down state, they will seldom release an accompany photon toward the screen 7904.

The present invention discovers a new model for Parity Asymmetry (or violation) under the B field mirror reflection coordinates that:

A spin-up output electron coming out from incident electrons 7902, if is associated with input total energy Ein of horizontal spin input state, it output state will possess a QM Eigen-state energy Eout associated with relatively lower B field potential energy (i.e. Eout−Ein<0) while traveling within or coming out of the non-uniform or partially uniform magnetic field (B). By following the Energy Conservation Law, excess potential energy of the incident electrons 7902 can be released by Photon decay (i.e. emission or generation or the like) interaction at the same instance while the electron converting its spin direction, for instance, from a horizontal spin input state (higher energy) into a spin-up output state (lower energy) by making its magnetic moment is in parallel with the external B field. Also, the direction of such Photon's emission shall obey Momentum Conservation in relativistic Linear and Angular momentum aspects toward the opposite side of the screen.

Spin-down output electron coming out from incident electrons 7902, if is associated with input total energy Ein of horizontal spin input state, will possess a QM Eigen-state energy Eout associated with relatively higher B field potential energy (i.e. Eout−Ein>0) while traveling within or coming out of the non-uniform or partially uniform magnetic field (B). By obeying Energy Conservation law, its kinetic energy will get decreased some so as to neutralize the increasing amount of its relativistic potential energy of any kinds, e.g. magnetic moment potential energy in the B field, or other scalar/vector potential energies of all kinds, etc. by making its magnetic moment is in anti-parallel with the external B field Therefore, as shown in FIG. 79, while the electrons are in the non-uniform or uniform magnetic field (B), the spin-up and -down electrons are literally a pair of mirror particles each other. Apparently, the mirror pair of electrons violate the Parity Conservation law, i.e. their decay or interaction modes with the physical world or the external B field are different, though Parity Conservation Law requires that their (e.g. Right-handed vs. Left-handed coordinate systems) decay or interaction modes with outside physical world should be the same ones under the external B field mirror reflection.

While moving speed of the pair of mirror particles (e.g. electrons) is close to light speed c, the relativistic term β (=v/c) shall be included in order to calculate the related physical energy (or eigen) states, e.g. relativistic term for each physical properties including velocity (v), mass/energy (M/E), finite rotation inertia (I), linear momentum (P), Quantized angular momentum (L), and magnetic moment (μ), etc. For an ordinary skilled person in viewing of the present invention, it can indeed be self-explained why the pair of electrons (i.e. Right-handed vs. Left-handed coordinate systems) can be violating the well-known Parity Symmetry or Parity Conservation Law accordingly.

BB. New Model of Fermions Electron Linear Motion in Free Space

Figure 80A:
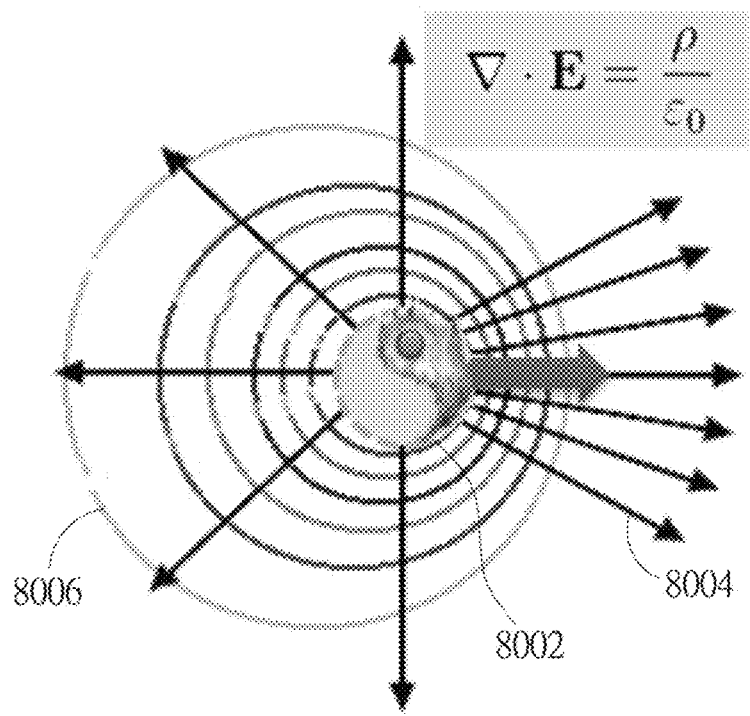
FIGS. 80A, 80B, 81A, 81B are diagrams illustrating new model representations of fermions (e.g. electrons) linear motion in free space.
Figure 80B:
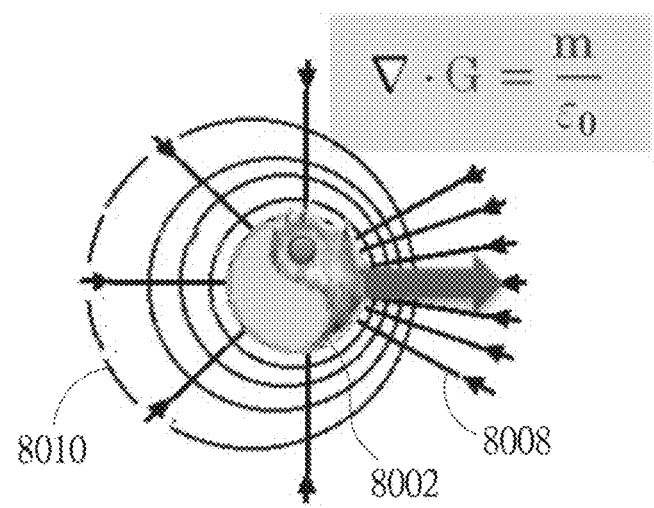

As show in FIG. 80A, when an electron 8002 moves in free space with high kinetic energy, electric E field lines 8004 and equal potential circles 8006 of the E field are shown in FIG. 80A (2D plan view), respectively. In addition, as show in FIG. 80B, when the electron 8002 moves in free space with high kinetic energy, gravitational G field lines 8008 and equal potential circles 8010 of the G field are shown in FIG. 80B (2D plan view), respectively.

Figure 81A:
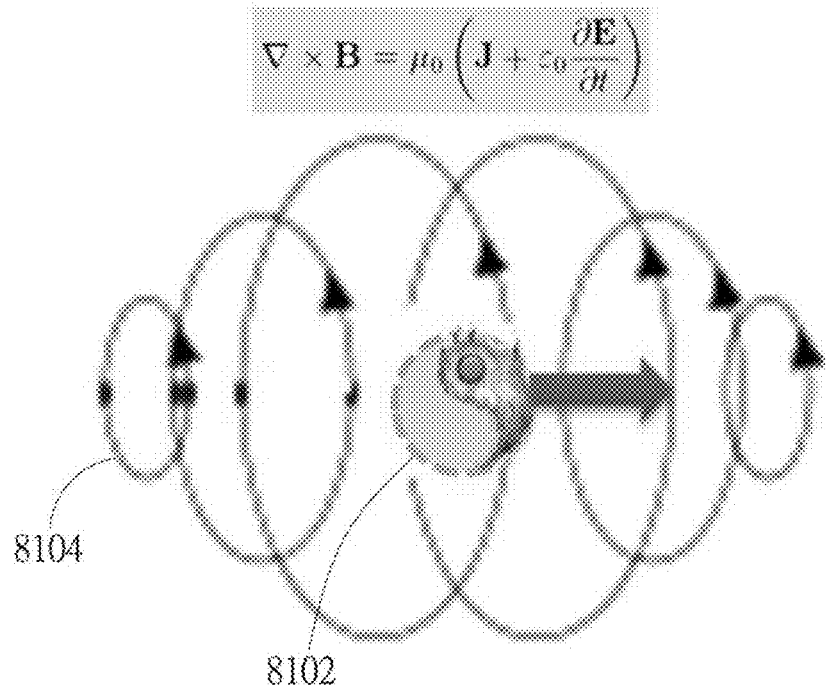
Figure 81B:
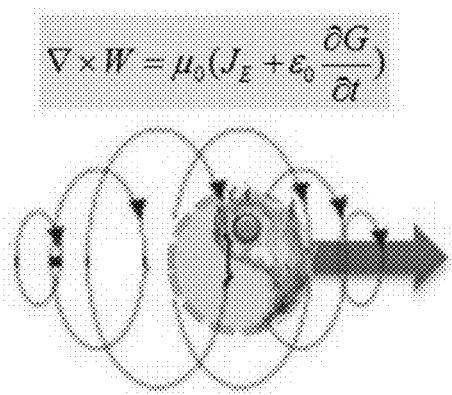

As show in FIG. 81A, by obeying the Concise GUT of the present invention, when electron 8102 moves in free space, magnetic B field circle lines 8104 of the electron 8102 and MW W field circle lines of the electron 8102 are shown in FIGS. 81A, 81B (3D plan view), respectively. It is evidenced by the present invention; all elementary particles (e.g. Electron or the like) possess classical-quantized linear and angular momentum if it is in motion state relative to the observer in outside world.

Figure 82:
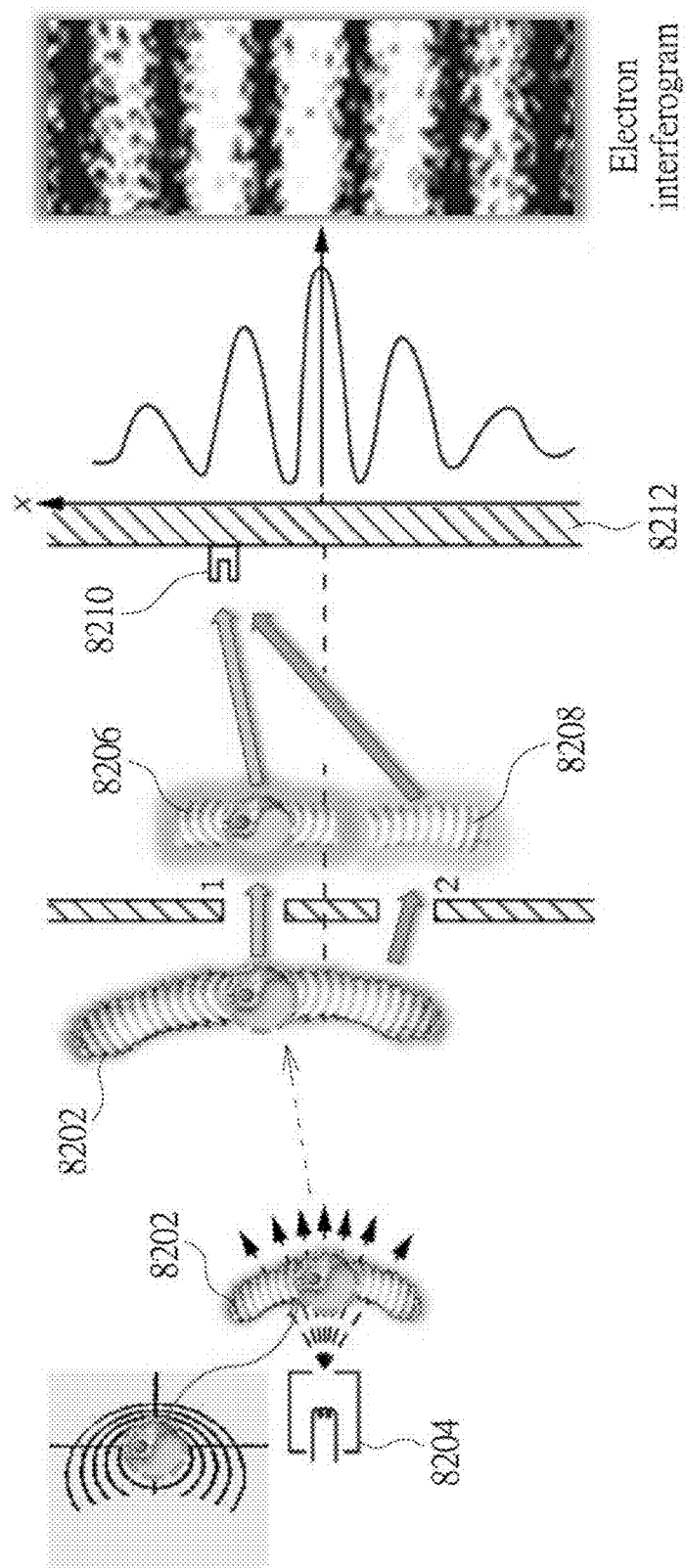
FIG. 82 is a diagram illustrating new model for electron double slits evidencing MW properties of fermions (e.g. electrons).

BC. New Model for Electron Double Slit (EDS) Evidences MW and MWE Duality Properties of Fermions As show in FIG. 82, after a plurality of single electron 8202 emitted by electron source 8204, EDS experiment reveals MWE packet 8206 of the electron 8202 can pass through only one slit of two slits 1, 2 (e.g. the MWE packet 8206 of the electron 8202 passes through the slit 1 and its coherent or partially coherent MW wavefront-split 8208 of the electron 8202 will pass through the another slit (that is, the slit 2), respectively.

Electron's interference pattern is occurred in near field location of the two slits 1, 2 within its coherence length or time, wherein the electron's interference pattern of plurality of single electron is detected by detector 8210 and shown in screen 8212 in the far field at where the location of the screen cannot have further interaction with regard to the electron interferences. The far-field MW diffraction patterns will be developing over space-time just by following the evolution of the near-field diffraction patterns always. In view of the teaching of this invention, it is evidenced that, for an ordinary skilled person, one can legitimately disprove the Schrodinger's Cat, Wheeler's delayed decision and Quantum Erase theories via the EDS new theory. It DOES reveal that Electron's interference pattern is occurred and well defined by the near field path within its coherence length by obeying Huygens-Fresnel Principle as followings:
1) Wavefront-Split:

EDS allows electron MWE packet to forming a MW wavefront-split spatially into two separate ones that get combined later on to create interference patterns on a screen by obeying the Huygens-Fresnel Principle.
2) Amplitude- or Phase-Split:

Michelson or Mach-Zehnder interferometers can split an incident MWE wavefront into two separate coherent copies (i.e. the incidence electron's MWE wavefront and its inductive MW wavefront) via 50%-50% electron beam splitter by following the Energy Conservation, Momentum Conservation Laws and Pauli Exclusion Principle.

Figure 83:
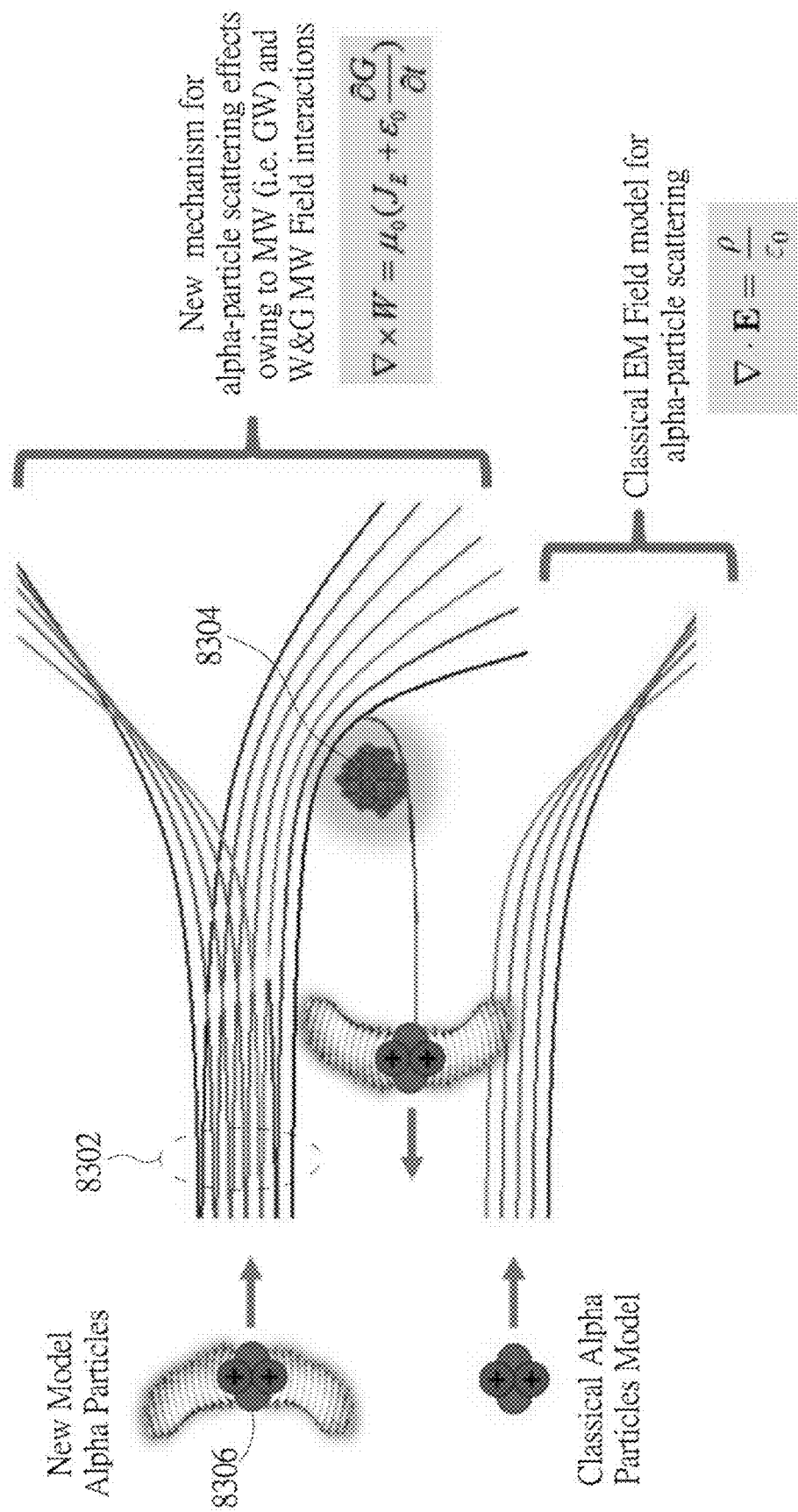
FIG. 83 is a diagram illustrating new model for Rutherford scattering evidencing MW properties of matters.

BD. New Model for Rutherford Scattering Evidences MW and MWE Interaction Properties of Matters New MW (i.e. GW) Model for spin-0 Alpha-particles vs. Nuclei Scattering Effect:

As show in FIG. 83, classical EM Field (or Force) induced particle scattering (i.e. Rutherford scattering) while a charged particle hitting target nuclei (e.g. a gold foil or the like), the new element of the present invention is the essential MW Field view for the "short-range and strong interaction" in between elementary particle objects (e.g. incident charged particles and target nuclei) in space-time.

As a results of that a MWE wavefunction of incident particles (e.g. fermion or boson) interacts strongly with Gravita-Strong MW Field, the MWE wavefunction 8302 of the incident particle is either transmitted, reflected, refracted, diffracted, or scattered, etc. while it encounters an MW Field of the target 8304 (e.g. Gold foil, Nuclei and the like).

The responses of such scattering interaction depend on the composition of the target 8304, incident path and MW wavelength of incident particle 8306, etc. The NEW Gravita-Strong interaction and scattering effects are conveyed by elastic MW and MWF interactions, e.g. refraction or diffraction effects among incident particle's MWE of the incident particle 8306 and MW Field tensors of the target 8304 that are associated with the all kinds of Scalar or Vector Potentials in atomic scale or even macroscopic scale disclosed by the present invention.

Figure 84:
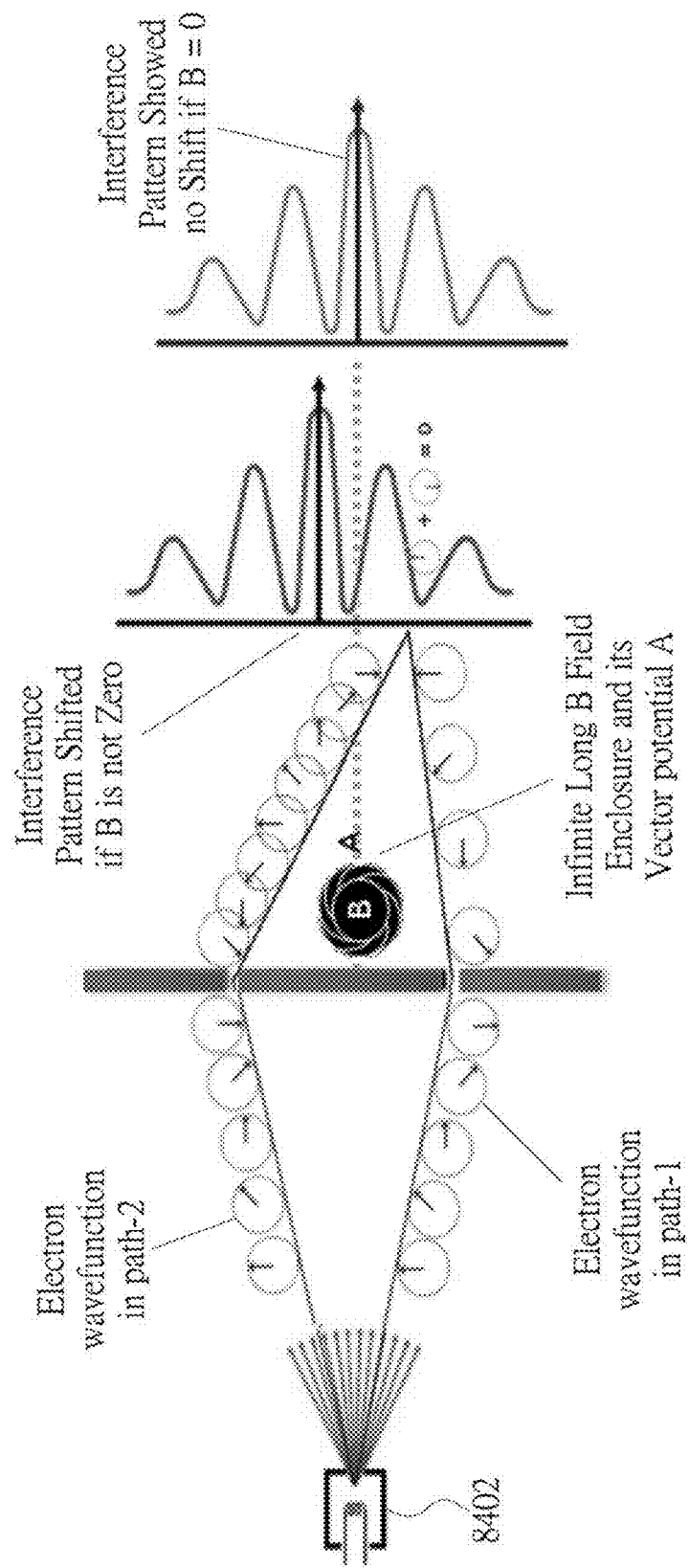
FIG. 84 is a diagram illustrating hypothetical vector potentials of prior arts being utilized to explain Aharonov-Bohm QM effect.

BE. Aharonov-Bohm QM Effect can be Explained by Hypothetical Vector Potentials As shown in FIG. 84, The Aharonov-Bohm effect disclosed by the prior art (also called the AB effect), is a QM phenomenon in which an electrically charged particle generated by coherent or partially coherent electron source 8402 is affected by an electromagnetic potential (V, A), despite the moving path of the charged particle being confined to a region in which both the magnetic field B and electric field E are zero or null. The prior art theory postulated the underlying mechanism is originated from electromagnetic potential (V, A) influencing or interacting with the complex phase of a charged particle's wavefunction from path-1, path-2, and the AB effect has been illustrated by EBEAM interference experiments in past years.

Figure 85:
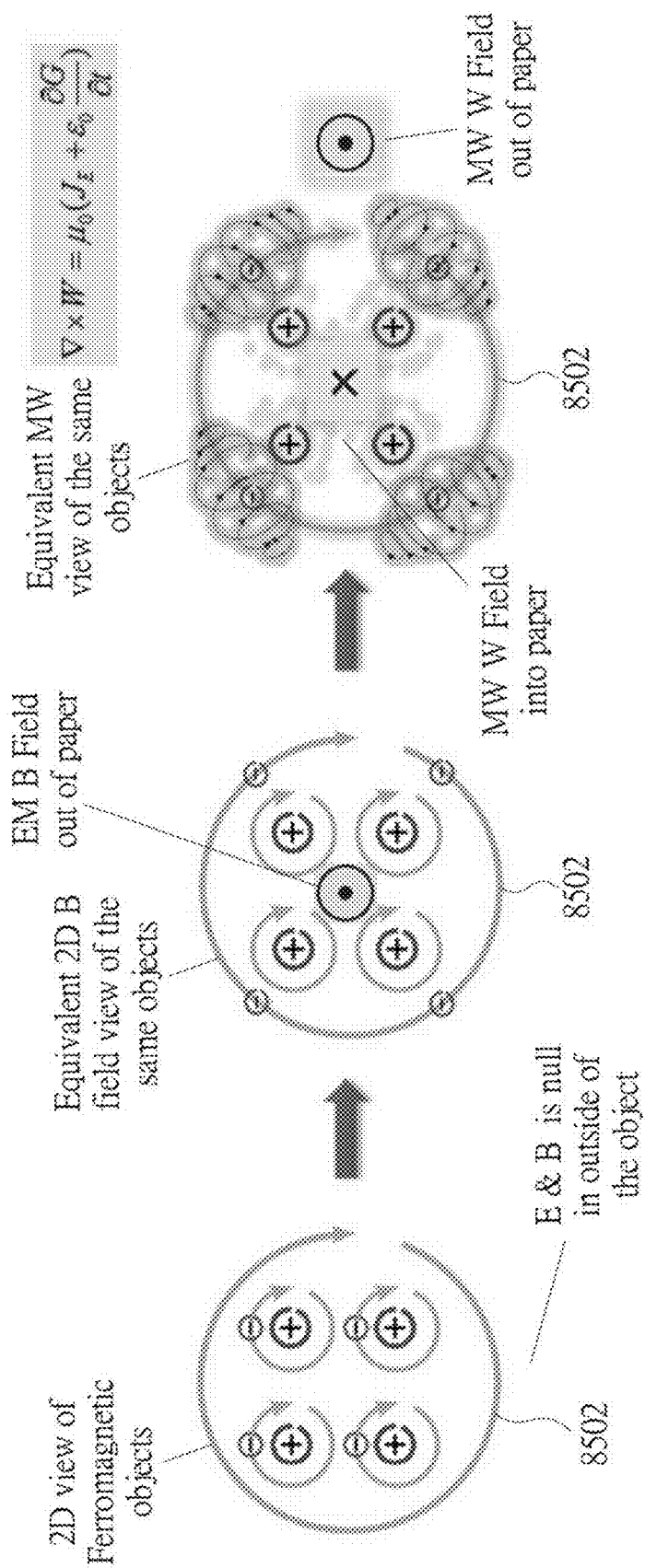
FIGS. 85, 86, 87 are diagrams illustrating new model of MW properties of magnetic matters (e.g. ring coil) being utilized to explain Aharonov-Bohm effect.

BF. New Model for Aharonov-Bohm Effect (I)— Evidences MW and MWE Properties of Magnetic Matters New QM view of Aharonov-Bohm effect:
The essential element of the present invention is that the Gravita-strong MW Field view of the same Ferromagnetic objects can be self-explained well for the AB effect. As shown in FIG. 85: E field of infinite long Ferromagnetic object (e.g. a long tube of current carrying coils, a ring magnet, a toroid magnet and the like.) 8502 is with charge neutralized state in atomic and macroscopic scales, and the B field of the infinite long Ferromagnetic object 8502 is confined within inside of the infinite long Ferromagnetic object 8502 such that the E & B field is null (i.e. V, A=constants in space-time) in external space outside of the infinite long Ferromagnetic object 8502.

Despite long range force of E and B field is null in outside of the infinite long Ferromagnetic object 8502, short range MW Field (or force) is not zero in outside of the infinite long Ferromagnetic object 8502 due to shielding, dispersion or dissipation effects for the infinite long Ferromagnetic object 8502 (e.g. its nuclei structures, atomic shielding effect etc.) against the MW or MWF. The infinite long Ferromagnetic object 8502 has been forming a gigantic or giga-scale infinite long nuclei surrounding by a plurality of electrons being in circular motion outside, as shown in FIG. 85.

Figure 86:
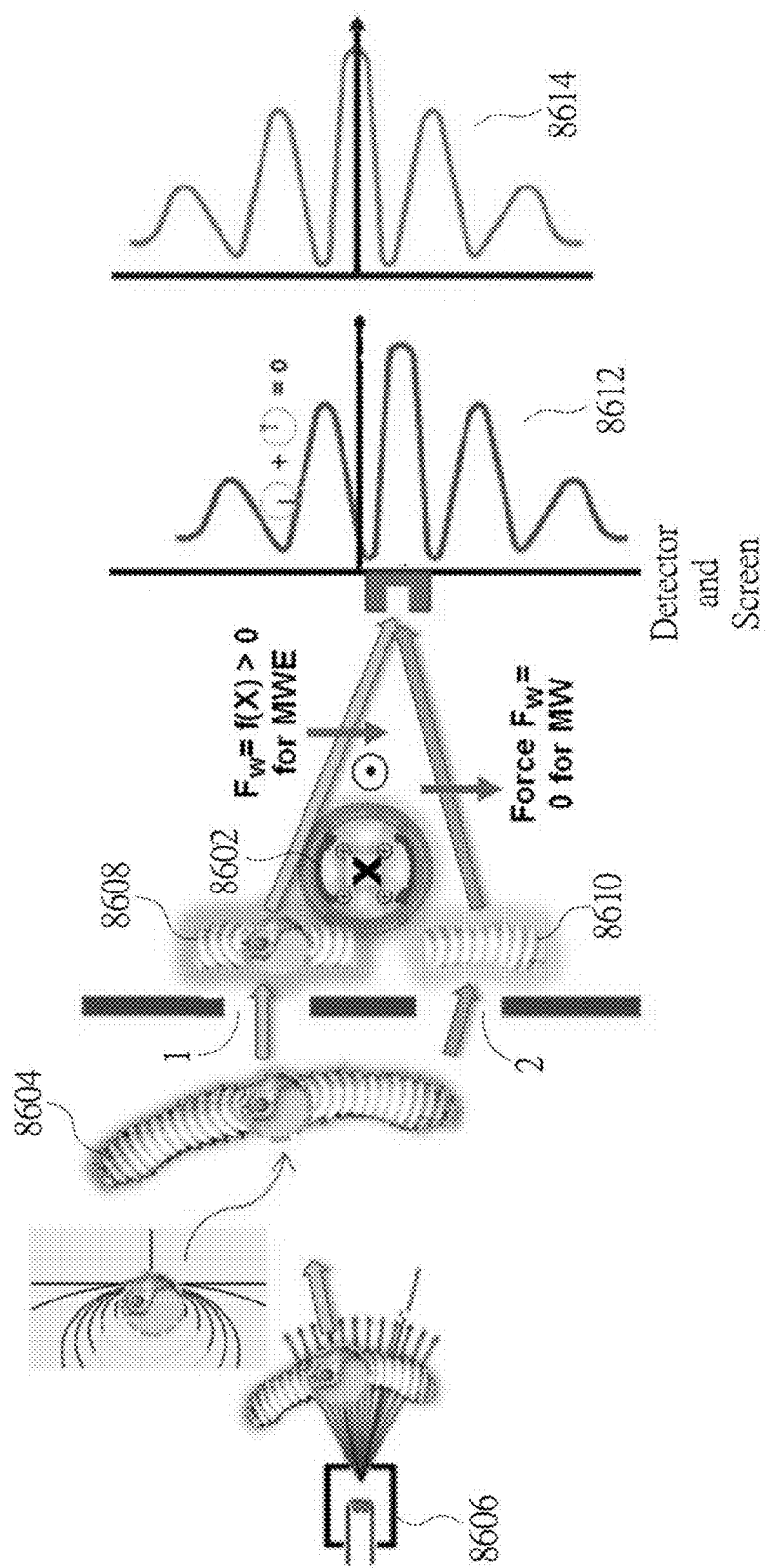

BG. New Model for Aharonov-Bohm Effect (II)—Evidences MW and MWE Properties of Magnetic Matters New model and representation for Aharonov-Bohm effect:

As shown in FIG. 86, in regard to the new Gravita-Strong MW Field view of the same experimental Magnetic coils or objects, E field of magnetic object (e.g. an infinite long tube of current carrying coils, a toroid magnet and the like) 8602 is neutralized gigantic nuclei in both atomic and macroscopic scales, and its B field is confined within the center region of the object, wherein the E & B field is null (i.e. V, A=constants in space-time) in external region of the magnetic object 8602. Despite long range E and B field is null in outside of the magnetic object 8602, the short range MW W-Field W=f(X) and its interaction force $F_W$=Curl-Force of f(X) of the Gravita-strong interaction is not zero in outside space of the magnetic object 8602 due to the shielding, dispersion or dissipation effect for the magnetic object 8602 (e.g. its nuclei structures, etc.) against the MW Field, wherein the X (function of space, time) is the Vector potential of MW Field W. The magnetic object 8602 can be creating a gigantic or giga-scale infinite long "macroscopic nuclei" surrounding by plurality of Electrons being in circular motion around the nuclei.

Therefore, after incident electron 8604 emitted by electron source 8606, MWE packet 8608 of the electron 8604 can pass through only one slit of two slits 1, 2 (e.g. MWE packet 8608 of the electron 8604 passes through the slit 1) and coherent MW wavefront-split 8610 (that is, a copy or a piece of mass-less and energy-less MW front) of the electron 8604 will pass the another slit (that is, the slit 2), respectively, wherein the W field Curl-Force (Curl of f(X)) of the magnetic object 8602 will impact and interact with the MWE packet 8608 of the electron 8604, rather than impacting or interact with the coherent MW wavefront-split 8610 (that is, mass-less MW front) of the MWE packet of electron 8604. For an ordinary skilled person, it is self-explained as followings: 1) if W≠0, interference Pattern 8612, composed of the MWE packet 8608 and the coherent MW wavefront-split 8610 of the electron 8604, is to be shifted either downward or upward on the screen, and 2) if W=0 or null, then interference Pattern 8614, composed of the MWE packet 8608 and the coherent MW wavefront-split 8610 of the electron 8604, is not to be shifted.

Figure 87:
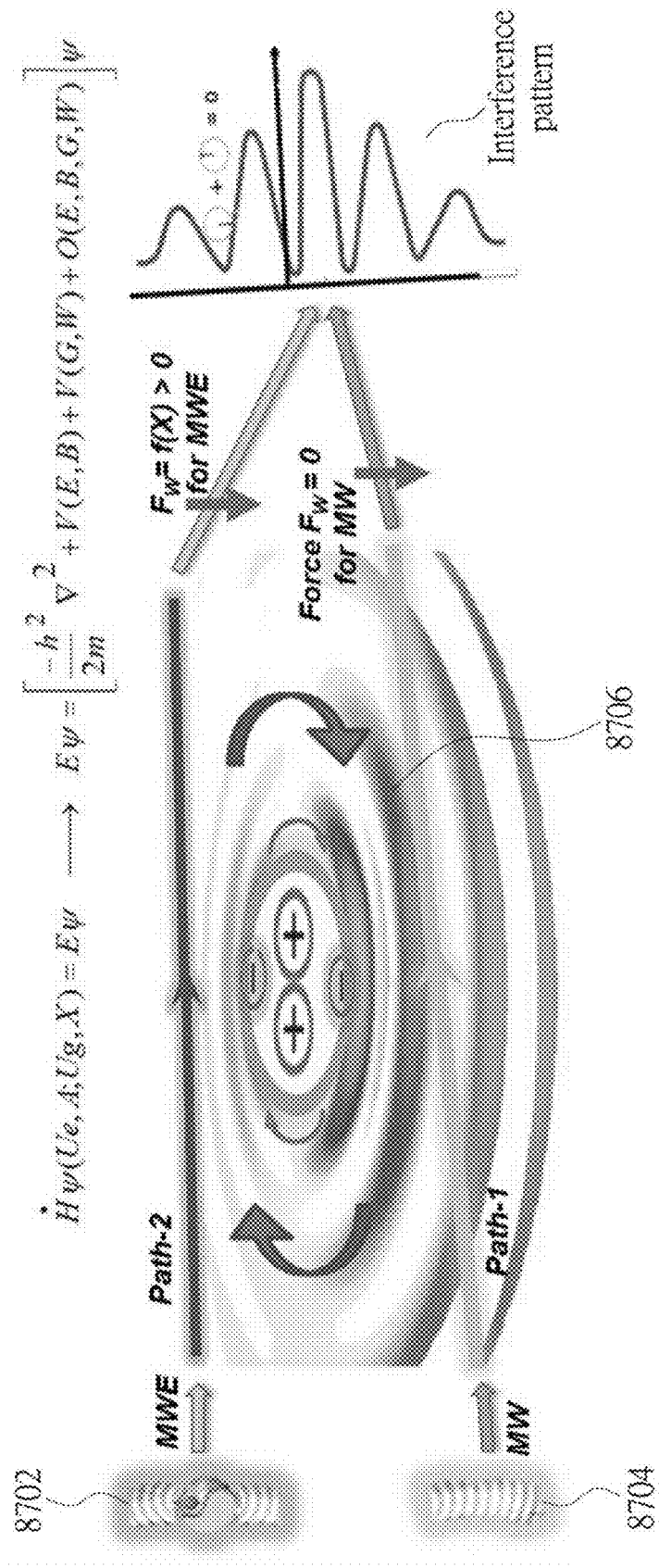

BH. New Model for Aharonov-Bohm Effect (III)—Evidences MW and MWE Properties of Magnetic Matters On top of classical potential field energy-states (e.g. Gravitational G field, Mirror charge E field, Magnetic B field, Spin/moment interaction energies, etc.), the present invention discovers, MWE packet 8702 and MW wavefront-split 8704 of free electron in FIG. 87 sees MW force $F_W$ (i.e. curl force of W field) and MW Vector potential (i.e. X) of infinite long Ferromagnetic object 8706 at the same instance, by changing its own X-vector potential energy state from a null, to higher, then to lower and finally back to null potential energy states along path-2, as shown in FIG. 87 below. The MW wavefront-split 8704 will not get its energy state changed due to intrinsic characteristics of mass-less energy-less MW is transparent to all the known scalar or vector potential fields in terms of energy perspective, though its wavelength of MW wavefront-split can be changed in accordance of the scalar or vector field potentials. Along the path-2, a path integral of its W field potential (integral of X*dS) over space-time is not zero (not being cancel out) which can introduce a definite phase shift (e.g. phase change, wavelength change, or energy shift or the like) for MW wavefunction of the MWE packet 8702 of the free electron moving in the path-2 while it is even under null external B field conditions.

The present invention unveils; a new Hamiltonian analysis is able to determine a new force acting on those electron or neutron in variety of variations of AB effect experiments. A new energy operator (H) ought to be renovated and refined by including the W field potential energy component for both the non-relativistic version for v<<c, or the relativistic version for V~c, as shown in formula below, wherein the O(E, B, G, W) stands for the 2nd order negligible cross-interaction terms in low field environments:

$$H\psi(Ue, A; Ug, X) =$$
$$E\psi \to E\psi = \left[\frac{-\hbar^2}{2m}\nabla^2 + V(E, B) + V(G, W) + O(E, B, G, W)\right]\psi$$

For an ordinary skilled person, one can prove that variety of variations of AB effect experiments (e.g. electron, neutron or the like) can be explained and predicted well by the new Hamiltonian analysis in order to determine the hidden force acting on those moving particles under such experiments.

BI. Parity Violation in K⁺ Meson (or τ-θ) Puzzle is a Big Scientific Blunder?

The present invention also discovers a new decay model for τ-θ Puzzle or Kaon (K+) 8802 (shown in FIG. 88A). In view of the teaching of the present invention, one can spell out the theory behind the Parity violations of what had been observed in science history. Two different decays were found for K+ meson's degenerated multiplets (i.e. paired or mirrored particles) as shown in FIG. 88B, with different energy associated with spin/orbital scalar and vector potentials:

1) As shown in FIG. 88C, left-circular (e.g. a left-handed system or view against B Field 8804) low energy K+ meson decay path: Θ+→π++π0;

2) As shown in FIG. 88C, right-circular (e.g. a right-handed system or view against B Field 8804) high energy K+ meson decay path is the another one with τ+→π++π++π−, which had been proven the decay mode is quite different from that of low energy K+ meson;

3) Physical interactions and decay modes of Right-circular (right-handed) coordinate vs. Left-circular (left-handed) coordinate are not the same;

In summary, it indicated apparently the Parity Symmetry has been violated due to initial Eigen-state Energies are different for different coordinates systems. In reality, Parity is conserved so long as their initial energy states are with the same energy state. Alternatively speaking, Space Inversion is symmetry associated with most of the physical properties of Nature in case of that their initial Eigen-states (Energies) are the same to each other.

For an ordinary skilled person, one can prove that there is no simple method which can distinguish paired (chirality) matter of one Left-handed from the other Right-handed, e.g. K+ (τ-θ) mesons. It can be distinguished only through a chiral sensitive or polarizer-filter environment if available. In general, the magnetic moment of paired K+ mesons (left-handed vs. right-handed) is so small that it is not measurable by current available B Field, such that their (e.g. τ-θ or K+ Mesons) interactions to physical world are identical and cannot be distinguished in an achiral B field environment of previous experimental setups in science history.

BJ. Evidences Light Wave-Particle Duality with MZ Interferometer (BS) New Experiments Along the human civilization development process in the future, the present invention has set up a few ground-breaking experimental apparatus and methods that enable us to reveal the subtle interactions of each individual quantum systems consisting of boson or fermion. Also, it will unveils the mechanism of BPP and FPP QM process which follows strictly Pauli Exclusion principles in temporal or spatial space associated with all of subatomic physics.

One significant and exemplary case is that the present invention shall evidence New Photon and Particle Models via a series of MZ-KC experiments. In the field of matter-wave interferometry, beam splitters have so far been constructed successfully for various particles, including electrons, neutrons and a number of different atoms and molecules. From the viewpoint of classical physics, a beam splitter is a rather simple device and understanding of its physical properties is obvious. But, its operation becomes highly non-trivial when we consider quantum behavior such as some embedded hidden variables behind a BS.

Hereby the question is simple, this invention shall be targeting to what happens to an individual particle incident on a semi-reflecting beam splitter? What will be the behavior of two particles or photons incidents simultaneously on a beam splitter? How can one understand the behavior of one- or two-particle systems in a series of beam splitters (e.g. series of Mach-Zehnder interferometers)? Is Causality and locality valid or not?

Following BS, Michelson and MZ interferometer experiments shall give us the foremost answers that we had never known in past hundreds of years. In a local realistic description both EPR particles have fixed intrinsic polarizations given by its nature source. For a reliable Bell test that the measurements at EPR arms A and B are completely independent and, in particular, that the polarizer(s) should be set well after the moment that the particles left the source (Reference: Thompson, Caroline H. "The tangled methods of quantum entanglement experiments." Accountability in Research 6.4 (1999): 311-332.).

Figure 89:
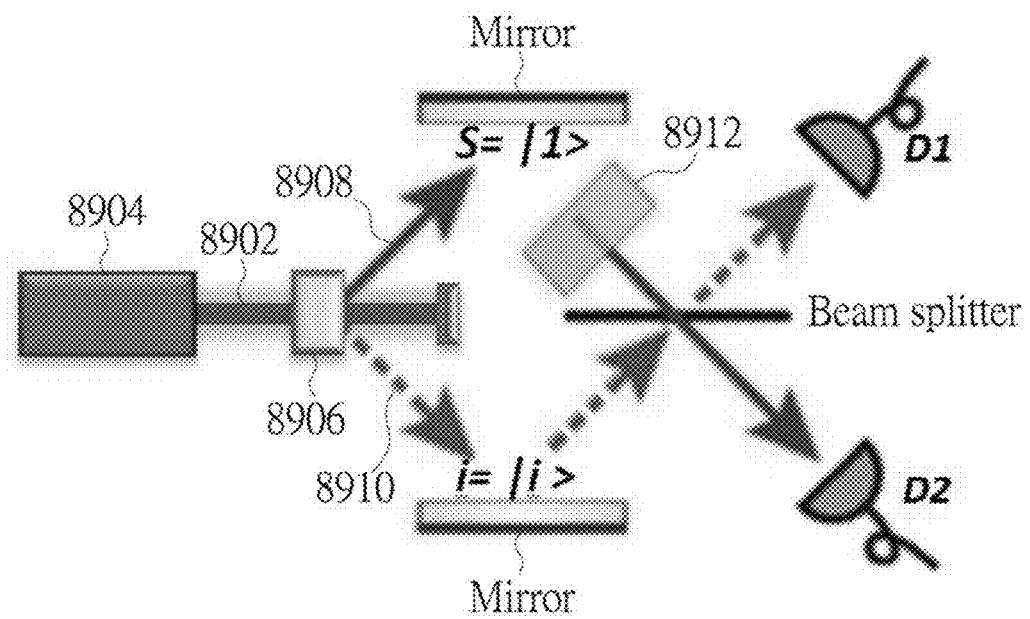
FIGS. 89, 90 are diagrams illustrating the experimental proof corresponding to the phase-matching of SPDC type-I being phase-paired or phase-locked in temporal.

BK. Experimental Proof—Phase-Matching (I)— SPDC Type-I is "Temporal" Phase-Matched, Phase-Paired, or Phase-Locked Type-I phase-matching pairs followed BPP Pauli Exclusion Principle (PEP) in temporal:

SPDC Type-I:

as shown in FIG. 89, when photon 8902 (e.g. UV photon) generated by laser source 8904 transmits through BPP Non-linear MWF Materials 8906 (e.g. BBO type-I crystal), signal photon 8908 (e.g. a red photon) and idler photon 8910 (e.g. another red photon) are generated, wherein the signal photon 8908 and the idler photon 8910 are with π/2 orthogonal or conjugated "Temporal phases" by keeping the same Spatial polarization each other with random polarization directions.

The present invention discovers that Expt. SPDC-1: $\Psi a=|1>+\Psi b=|i>$ is an allowed state for type-I BBO "o+o" ray's temporal phase-matching output results. The BPP SPDC type-I paired photons ($\omega_s$, $\omega_i$) can be a coherent or partially coherent pairs depending on the emission orientation, incident orientation, environmental condition (e.g. temperature, etc.), source material/structure and its working conditions.

Given an emission angle, if signal photon 8908=|1> & idler photon 8910=|i>, BS output photon detector's visibility (corresponding to the signaler photon 8908 or the idler photon 8910)~100% in changing the 0π toward 2π (i.e. 0° toward 360°) phase-shift cycles of phase-shifter (PS) 8912, wherein visibility can be referred to equation (1) and many other prior arts:

$$\text{visibility} = \frac{I_{max} - I_{min}}{I_{max} + I_{min}} \quad (1)$$

Figure 90:
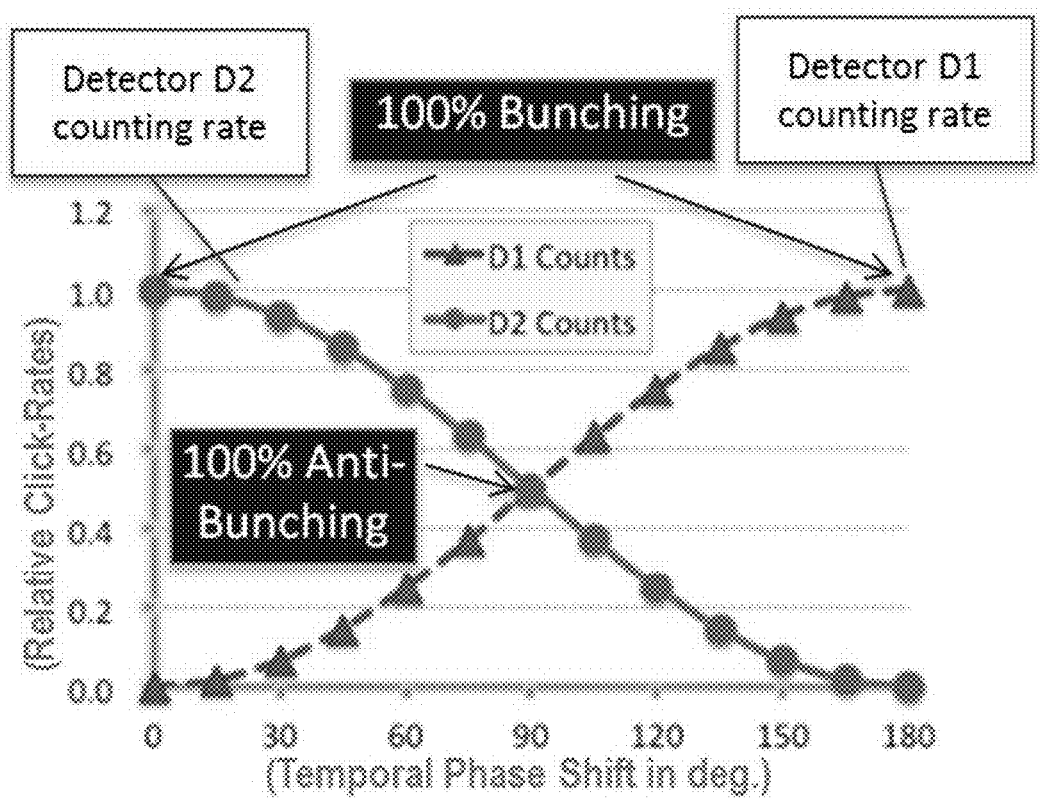

As shown in equation (1), Imax and Imin can be referred to photon counting/click rate fluctuations while changing the PS cycles (shown in FIG. 90). As shown in FIG. 90, the relative click-rate is corresponding to Expt. SPDC-1 shown in FIG. 89, detector D1 has minimum click-rate~0 at phase-shifter 0°, then ~0.5 at 90° and ~1.0 at 180°; and detector D2 has maximum click-rate~1.0 at phase-shifter 0°, then ~0.5 at 90° and ~0 at 180° of PS cycles.

Figure 91:
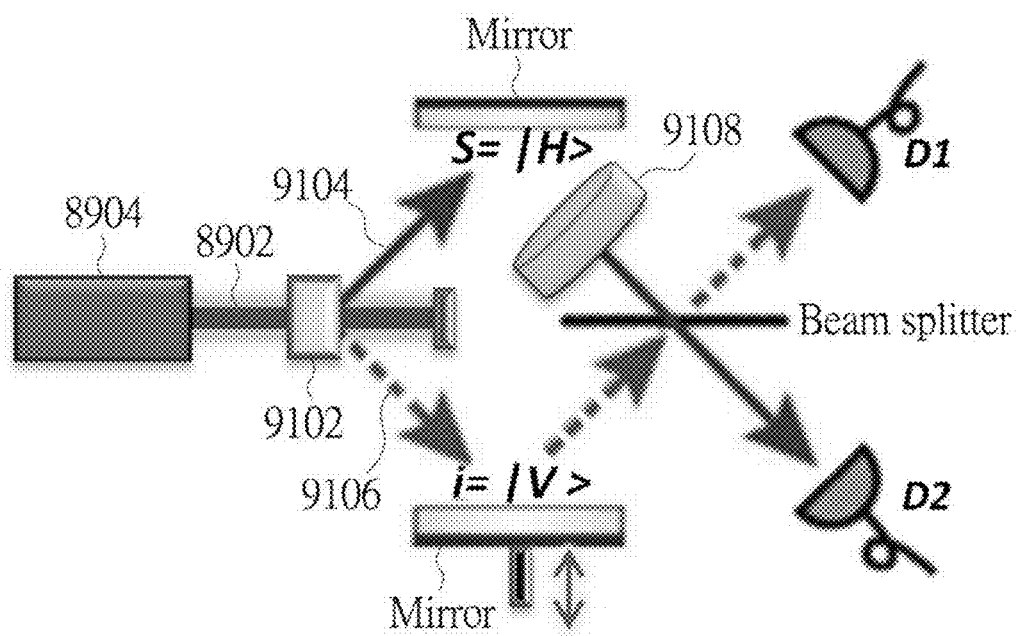
FIGS. 91, 92 are diagrams illustrating the experimental proof corresponding to the phase-matching of SPDC type-II being phase-paired or phase-locked in H/V spatial polarizations.

BL. Experimental Proof—Phase-Matching (II)— SPDC Type-II is "Spatial" Phase-Matched, Phase-Paired, or Phase-Locked Type-II phase-matching pairs followed BPP Pauli Exclusion Principle (PEP) in Spatial:

SPDC Type-II: as shown in FIG. 91, when photon 8902 (e.g. UV photon) generated by laser source 8904 transmits through BPP Non-linear MWF Materials 9102 (e.g. Beta barium borate (BBO) type-II crystal), signal photon 9104 (e.g. a red photon) and idler photon 9106 (e.g. another red photon) are generated, wherein the signal photon 9104 $|\Psi_a>=(\Psi_X, \Psi_Y)=(\cos(\omega t+\alpha), 0)$ or $(0, \sin(\omega t+\alpha))$ (i.e. the signal photon 9104 can be horizontal polarization state or vertical polarization state) and the idler photon 9106 $|\Psi_b>=+/-R_{90}*|\Psi a>$ are shown π/2 spatial orthogonal or conjugated "Spatial phases" each other, wherein $R_{90}$ is 90° polarization rotation matrix and a is a random or fixed phase offset parameter.

The SPDC type-II photon pairs can be a coherent or partially coherent pairs in temporal depending on the emission orientation, incident orientation, environmental condition (e.g. temperature, etc.), source material/structure and its working conditions.

Expt. SPDC-2: BPP SPDC type-II paired photons ($\omega_s$, $\omega_i$) can be either coherent or partially coherent in temporal. Given an emission angle, if the signaler photon 9104=|H> & the idler photon 9106=|V>, its output detector click-rate (i.e. intensity) is varying in accordance with polarization "rotator's angles" in rotator 9108.

Figure 92:
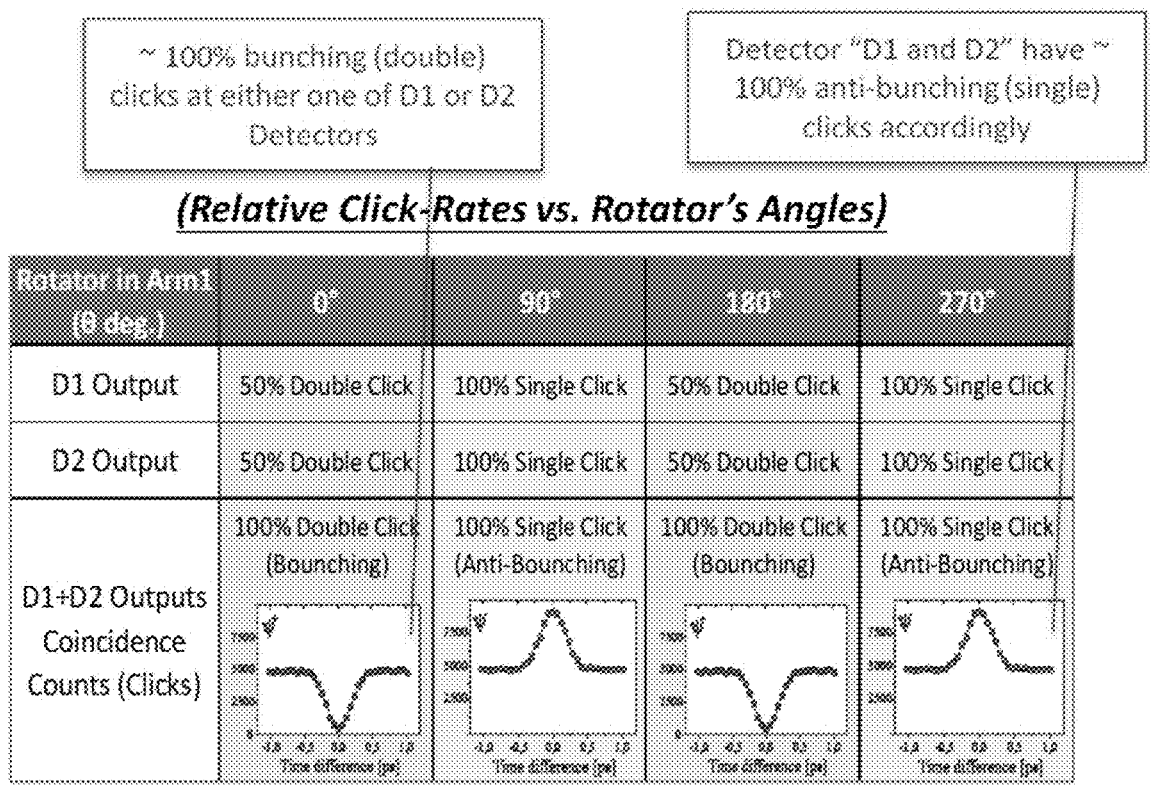

As shown in FIG. 92, if the rotator 9108 is with rotating angles 0° and 180°, the present invention discovers there are 100% bunching (double) clicks at either one of the detectors D1 or D2; and if the rotator 9108 are with angle 90° and 270°, then detectors D1 and D2 have ~100% anti-bunching (single) clicks accordingly. The present invention discovers, if the rotator 9108 is set with angle 45° the detectors D1 and D2 will show up with ~50%-50% of bunching vs. anti-bunching counts and it will be associated with minimum visibility (e.g. a flat line of coincidence count) accordingly.

Figure 93:
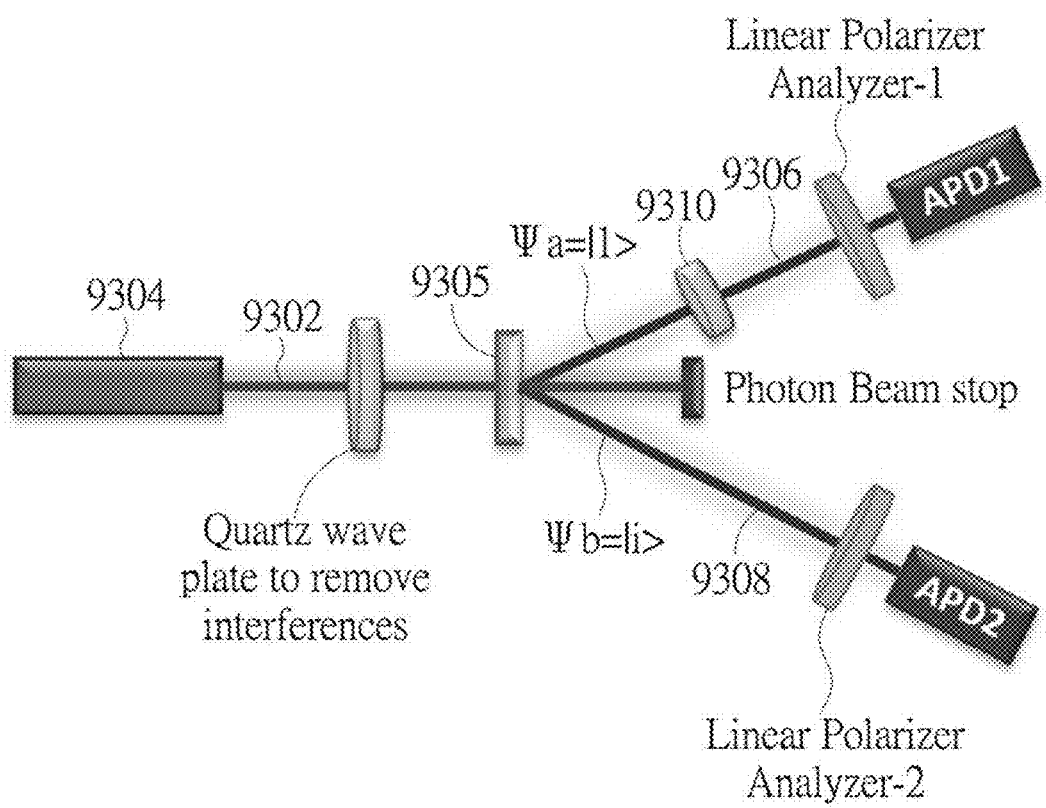
FIGS. 93, 94 are diagrams illustrating the experimental proof which discloses QM entanglement does not happen, EPR+Rotator (EPRR) experiment proves local realism prevail and QM reality cannot be considered complete.

BM. QM Entanglement does not Happen! New EPRR (EPR+Rotator) Experiment Says QM Reality Cannot be Considered Complete As shown in FIG. 93, when photon 9302 (e.g. UV photon) generated by laser source 9304 transmits through BBO (Beta barium borate) Non-linear MWF Materials 9305 (SPDC type-II), signal photon (e.g. a red photon) appears in arm 9306 and idler photon (e.g. another red photon) appears in other arm 9308.

QM Theory (prior art) predicted a "Null Effect" in between the signal photon and the idler photon, if the arm 9306 with 90° Faraday (polarization) rotator 9310 before APD (Avalanche Photon detector) 1, 2 "detecting and collapsing" either one of EPR pair's wavefunctions. However, EPR Theory predicted 90° shift in APD1 outputs, if the arm 9306 with 90° Faraday rotator 9310 before detecting their local realist wavefunctions. In addition, Einstein ever said that was the moon still there while you did not look at it? The present invention confirms about what Einstein was asking in 100 years ago.

Figure 94:
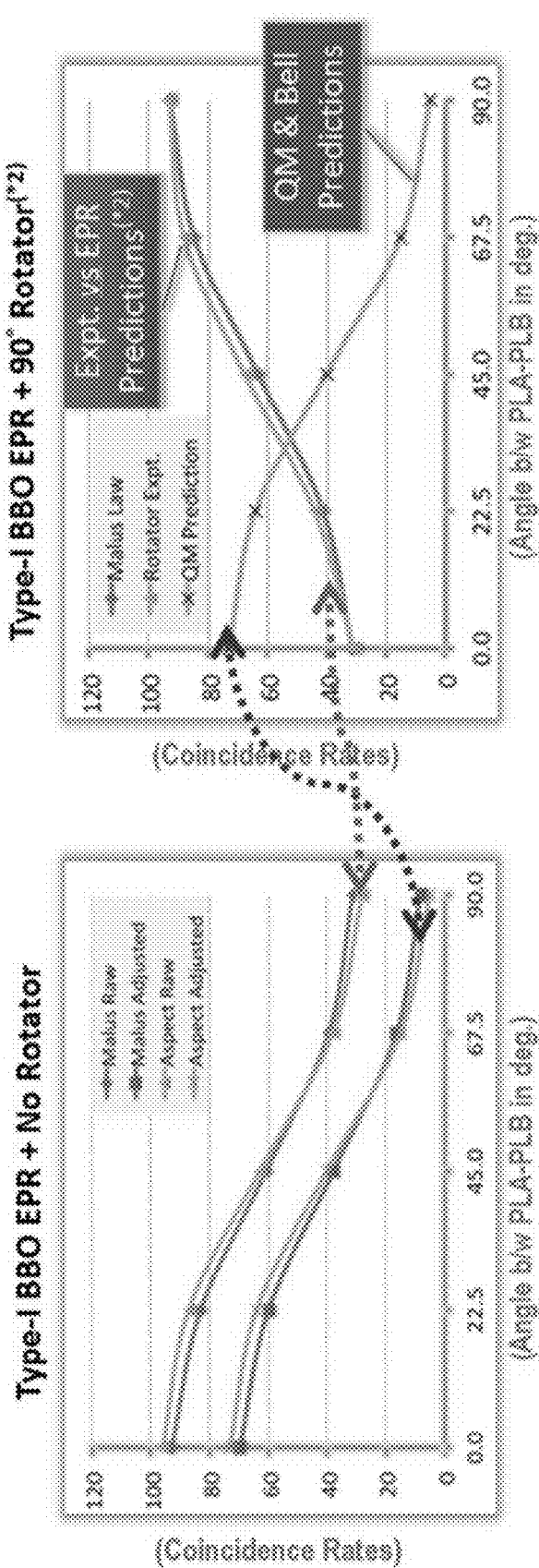

As shown in FIG. 94, the newly invented EPRR (EPR rotator) Expt. has literally disproved QM Quantum Entanglement (i.e. Bell Inequality violation) paradox by the rotator 9310 in the arm 9306. "Given polarization decision" had been made by "God" while emitting the signal photon and the idler photon pairs out from the BBO MWF object (i.e. SPDC type-II matter) by obeying PEP.

BN. Ken's Michelson Rotator (KMR) Experiment—KMR's Amplitude Split Evidences New Light Model Before describing FIG. 95 to FIG. 101, assumption conditions are shown as follows: 1) it is assumed incident Photon intensity is normalized to 100% for Expt. State A to D. Hereby, the intensity % is relative to incident photon intensity % as always; 2) it is assumed intensity degradation along the optical paths due to reflection, scattering and absorption is negligible; and 3) the incident Photon (Laser) input is associated with a predetermined Linear polarization direction as to control the well-behaved refraction index or its MWE/MW deflection properties.

Figure 95:
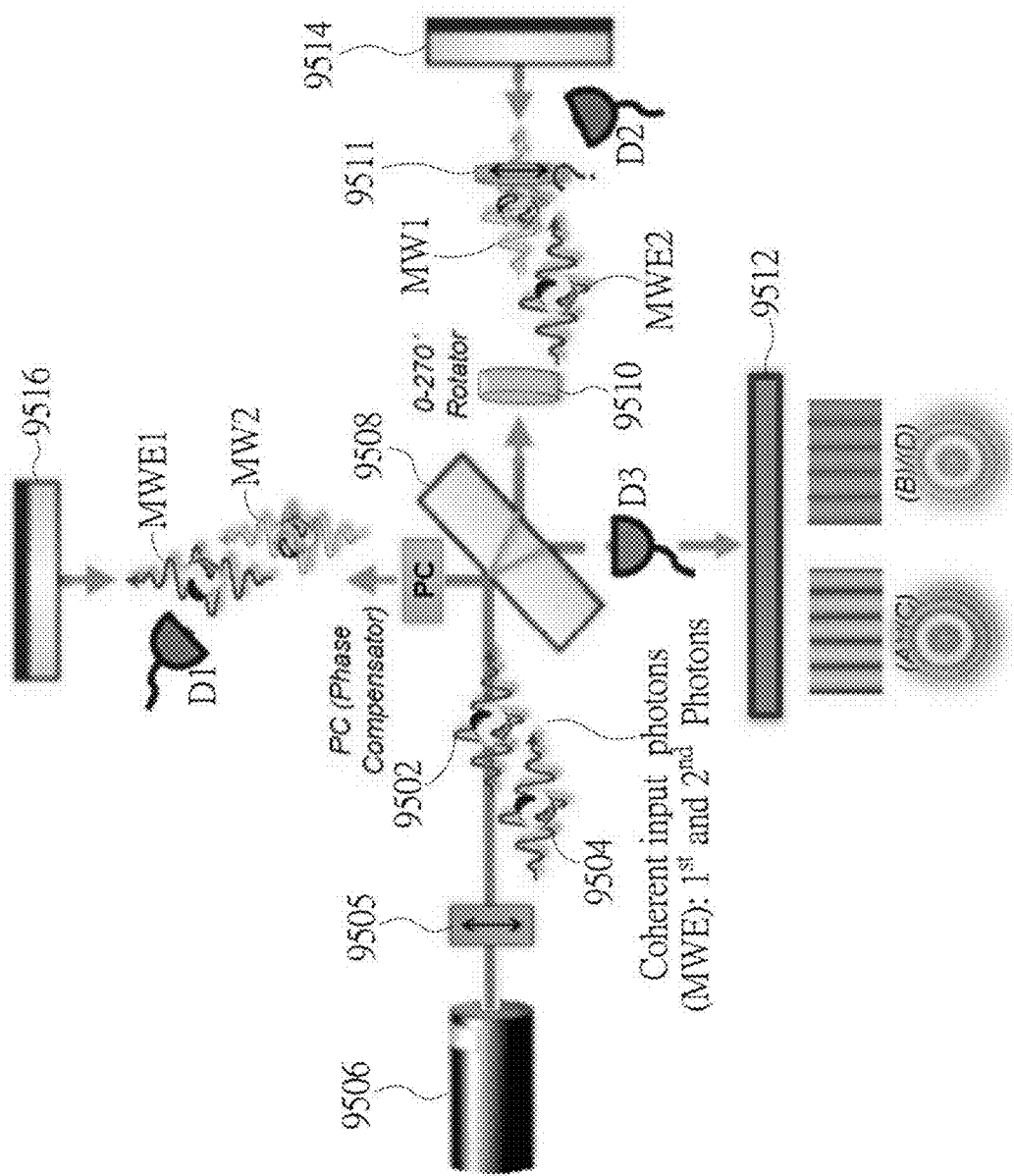
FIGS. 95, 96, 97, 98 are diagrams illustrating different embodiments proving the new light model by Ken's Michelson Kerr-Cell (MKC) experiments.

As shown in FIG. 95, when two spatially separate photons 9502, 9504 generated by laser source 9506 associated with vertical polarization of linear polarizer 9505 hit BS 9508. Having unveiled by the present invention that the BS 9508 performs MWE splitter and inductive MW generator at the same instance of time, MWE1 of the photon 9502 and MW2 of the photon 9504 appear toward upper arm direction, and MW1 of the photon 9502 and MWE2 of the photon 9504 appear toward right arm direction, wherein there is rotator 9510 in the right arm direction, the rotator 9510 and vertical polarization plate linear polarizer 9511 are used for 1) filtering MWE2 energy packet out from the Laser beam in right arm 2) while leaves the MW1 passing through the right Arm in back and forth directions, and wherein a distance between the photons 9502, 9504 is supposed to be greater than its coherence length or coherence time.

Experiment results corresponding to FIG. 95 are shown in TABLE 23. The present invention discovers, in states B, D, because the rotator 9510 has angle 90° and 270°, the rotator 9510 and the linear polarizer 9511 together can filter out MWE2 of the photon 9504, resulting in that intensity of detector D2, if being placed right after the linear polarizer 9511 and before mirror 9514, is almost 0. Therefore, in states B, D, only MWE1 of the photon 9502 is interfered with its own coherent inductive MW1 of the photon 9502 so as to form weaker interference patterns (e.g. stripe or circular ones, etc.) on screen 9512.

In addition, as shown in TABLE 23, in states A, C, because the rotator 9510 has angle 0° and 180°, the rotator 9510 and Linear polarizer 9511 cannot filter out MWE2 of the photon 9504, resulting in intensity of the detector D2, if being placed right before mirror 9516 is ~50%. Therefore, in states A, C, not only MWE1 of the photon 9502 is interfered with its own coherent inductive MW1 of the photon 9502, but also MWE2 of the photon 9504 is able to get interfered with its own coherent inductive MW2 of the photon 9504 together to form stronger interference patterns on the screen 9512 with higher intensity.

TABLE 23

| State | Angle θ of rotator 9510 | detector D1 intensity | detector D2 intensity | detector D3 intensity |
|---|---|---|---|---|
| A | 0° | ~50% | ~50% | ~50% |
| B | 90° | ~50% | ~0% | ~25% |
| C | 180° | ~50% | ~50% | ~50% |
| D | 270° | ~50% | ~0% | ~25% |

BO. Ken's Michelson Kerr-Cell (KMC) Experiments—MKC-1 Amplitude Split Evidences New Light Model As shown in FIG. 96, differences between FIG. 95 and FIG. 96 are that there is no rotator in FIG. 96, but there is a Kerr cell 9602 in the upper arm direction, and there is a Kerr cell 9604 in the right arm direction, wherein the Kerr cells 9602, 9604 are used with external bias voltages (+V) for deflecting MWE energy packet while leave MW passing through without major disturbance on MW property wherein the conjugated inductive MW being generated by the BS at the same instance while MWE energy packet getting split or redirected by BS toward either upper or right arms.

Figure 96:
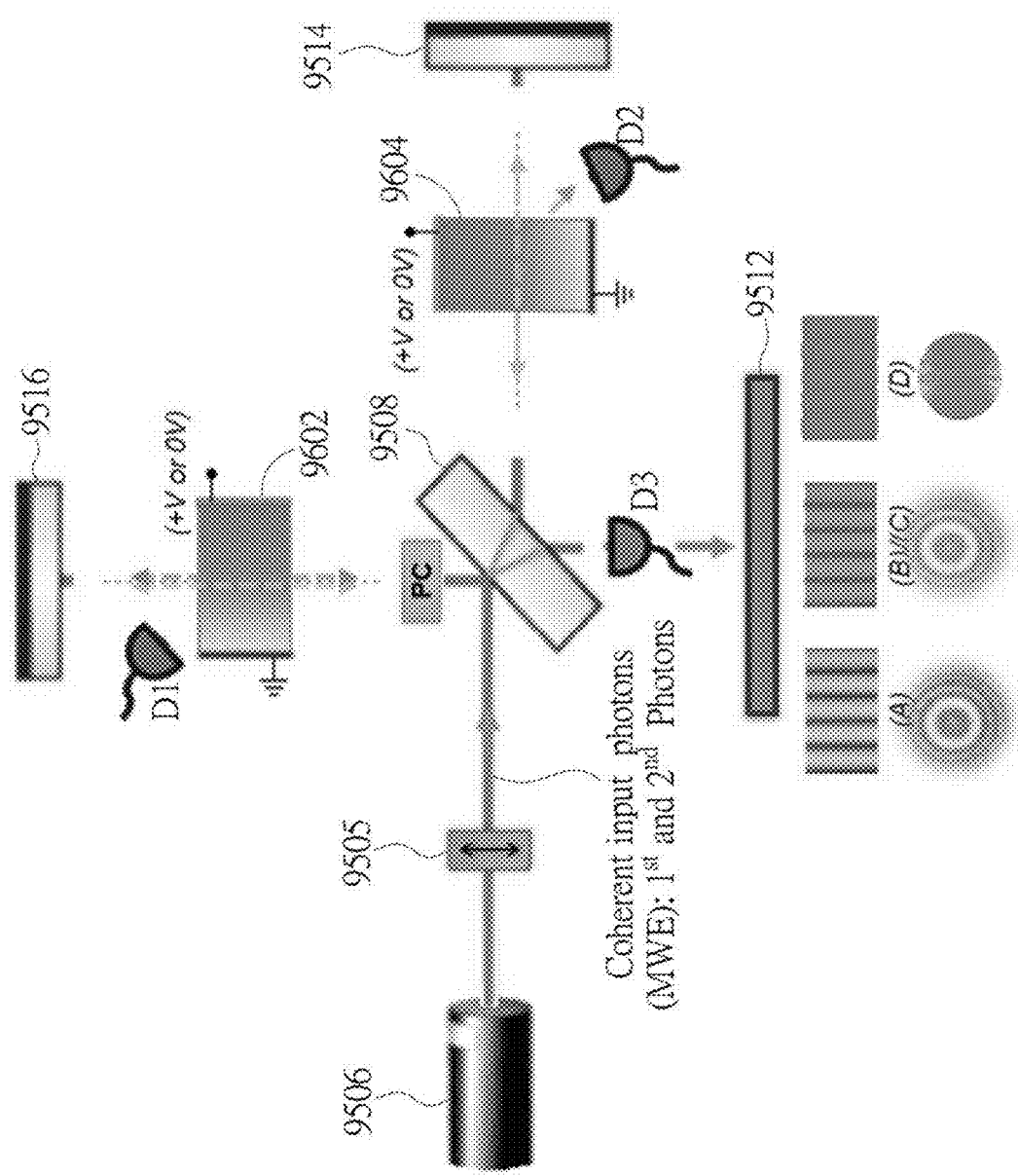

Experiment results corresponding to FIG. 96 are shown in TABLE 24. The present invention discovers, in state A, because the both Kerr cells 9602, 9604 are turned off (i.e. external bias voltage is null), the Kerr cells 9602, 9604 cannot deflect MWE1 of the photon 9502 and MWE2 of the photon 9504 respectively, resulting in MWE intensity of the detectors D1, D2 being almost 0. Therefore, in state A, MWE1 of the photon 9502 is interfered with its own coherent inductive MW1 of the photon 9502 and MWE2 of the photon 9504 is able to get interfered with its own coherent inductive MW2 of the photon 9504 to form stronger interference patterns (e.g. stripe or circular ones, etc.) on the screen 9512.

In addition, as shown in TABLE 24, in state B, because the Kerr cell 9602 is turned on (with +V) and the Kerr cell 9604 is turned off (with zero bias), the Kerr cell 9604 cannot deflect MWE2 of the photon 9504, resulting in MWE intensity of the detector D2 being almost 0. Therefore, in state B, only MWE2 (right arm) of the photon 9504 is able to get interfered with its own coherent inductive MWE2 (upper arm) of the photon 9504 to form weaker interference intensity patterns on the screen 9512, resulting in intensity of the detector D3 being reduced to 25%, if it was placed before the screen 9512.

In addition, as shown in TABLE 24, in state C, because the Kerr cell 9604 is turned on and the Kerr cell 9602 is turned off, the Kerr cell 9602 cannot deflect MWE1 of the photon 9502, resulting in MWE intensity of the detector D1 being almost 0. Therefore, in state C, only MWE1 (upper arm) of the photon 9502 is able to get interfered with its own coherent inductive MWE1 (right arm) of the photon 9502 to form weaker interference intensity patterns on the screen 9512, resulting in intensity of the detector D3 being reduced to 25%, if it was placed before the screen 9512.

In addition, as shown in TABLE 24, in state D, because the both Kerr cells 9602, 9604 are turned on, the Kerr cells 9602, 9604 can deflect MWE1 of the photon 9502 and MWE2 of the photon 9504 respectively, resulting in MWE intensity of the detectors D1, D2 being almost 50% for each one. Therefore, in state D, no interference patterns are able to shown on the screen 9512, resulting in MWE intensity of the detector D3 being reduced to 0% accordingly.

TABLE 24

| State | Kerr cell 9602/Kerr cell 9604 | detector D1 intensity | detector D2 intensity | detector D3 intensity |
|---|---|---|---|---|
| A | Off/off | ~0% | ~0% | ~50% |
| B | On/off | ~50% | ~0% | ~25% |
| C | Off/on | ~0% | ~50% | ~25% |
| D | On/on | ~50% | ~50% | ~0% |

Figure 97:
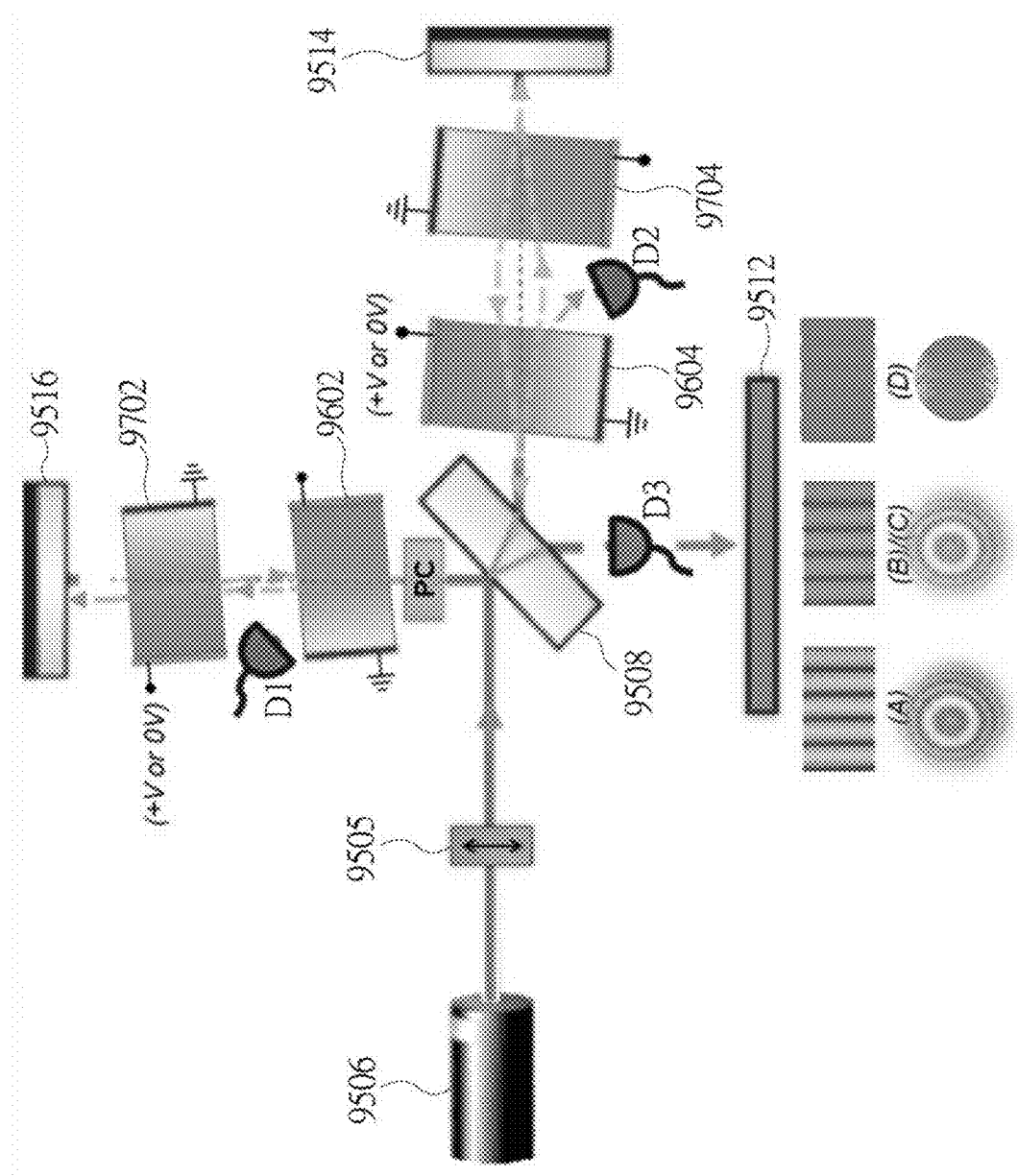

BP. Ken's Michelson Kerr-Cell Experiments—MKC-2 Amplitude Split Evidences New Light Model As shown in FIG. 97, differences between FIG. 97 and FIG. 96 are that FIG. 97 includes optical path compensation plate 9702 in the upper arm direction, compensation plate 9704 in the right arm direction. The compensation plates 9702, 9704 are used for compensate tiny deflection or non-linear disturbance of the Kerr Cells 9602, 9604 for MW1 of the photon 9502 and MW2 of the photon 9504, respectively, wherein the compensation plates 9702 and 9704 can be with biased or without biased conditions. As shown in FIG. 97, the Kerr cell 9602 and the compensation plate 9702 are tilted a predetermined angle of less than 3 or 5 degrees, and the Kerr cell 9604 and the compensation plate 9704 are tilted the predetermined angle of less than 3 or 5 degrees to reduce unwanted interference effect due to surface reflections for each of the optical elements used in these experiments while it can be improving the sensitivity or visibility of the interference intensity/phase patterns. In addition, subsequent operational principles of FIG. 97 are the same as those of FIG. 96, so further description thereof is omitted for simplicity. In addition, overall summary corresponding to FIG. 97 is shown in TABLE 25.

TABLE 25

| State | Kerr cell 9602/Kerr cell 9604 | detector D1 intensity | detector D2 intensity | detector D3 intensity |
|---|---|---|---|---|
| A | Off/off | ~0% | ~0% | ~50% |
| B | On/off | ~50% | ~0% | ~25% |
| C | Off/on | ~0% | ~50% | ~25% |
| D | On/on | ~50% | ~50% | ~0% |

Figure 98:
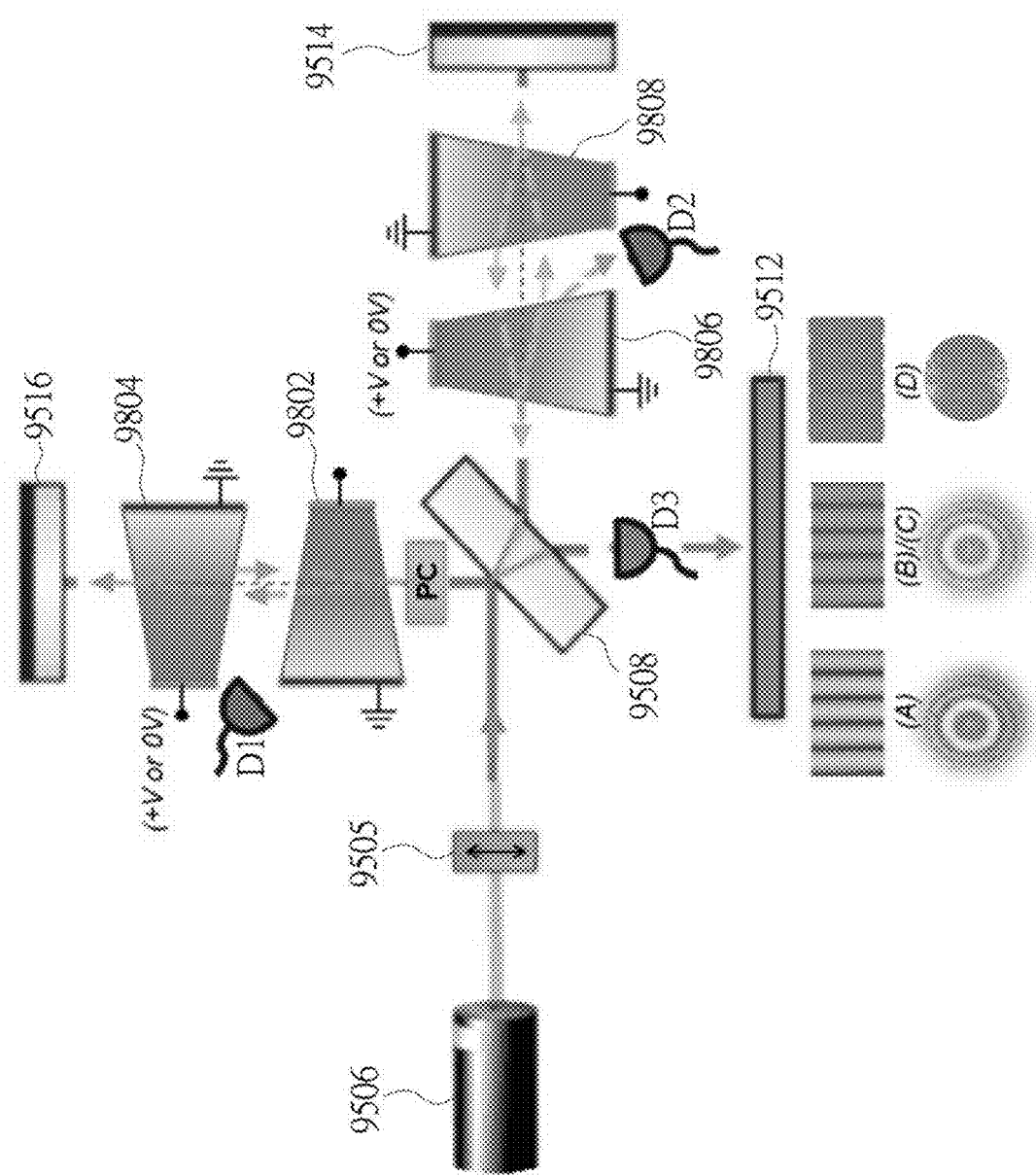

BQ. Ken's Michelson Kerr-Cell Experiments—MKC-3 Amplitude Split Evidences New Light Model As shown in FIG. 98, differences between FIG. 97 and FIG. 98 are that Kerr cell 9802 and optical path compensation plate 9804, and Kerr cell 9806 and compensation plate 9808 have trapezoidal shapes of less than 5 or 10 degrees to reduce unwanted interference effect due to surface reflections for each of the optical elements used in these experiments while it can be improving the sensitivity or visibility of the interference intensity/phase patterns, wherein the compensation plates 9804 and 9808 can be with biased or without biased conditions. In addition, subsequent operational principles of FIG. 98 are the same as those of FIG. 97, so further description thereof is omitted for simplicity. In addition, overall summary corresponding to FIG. 97 is shown in TABLE 26.

TABLE 26

| State | Kerr cell 9802/Kerr cell 9806 | detector D1 intensity | detector D2 intensity | detector D3 intensity |
|---|---|---|---|---|
| A | Off/off | ~0% | ~0% | ~50% |
| B | On/off | ~50% | ~0% | ~25% |
| C | Off/on | ~0% | ~50% | ~25% |
| D | On/on | ~50% | ~50% | ~0% |

Figure 99:
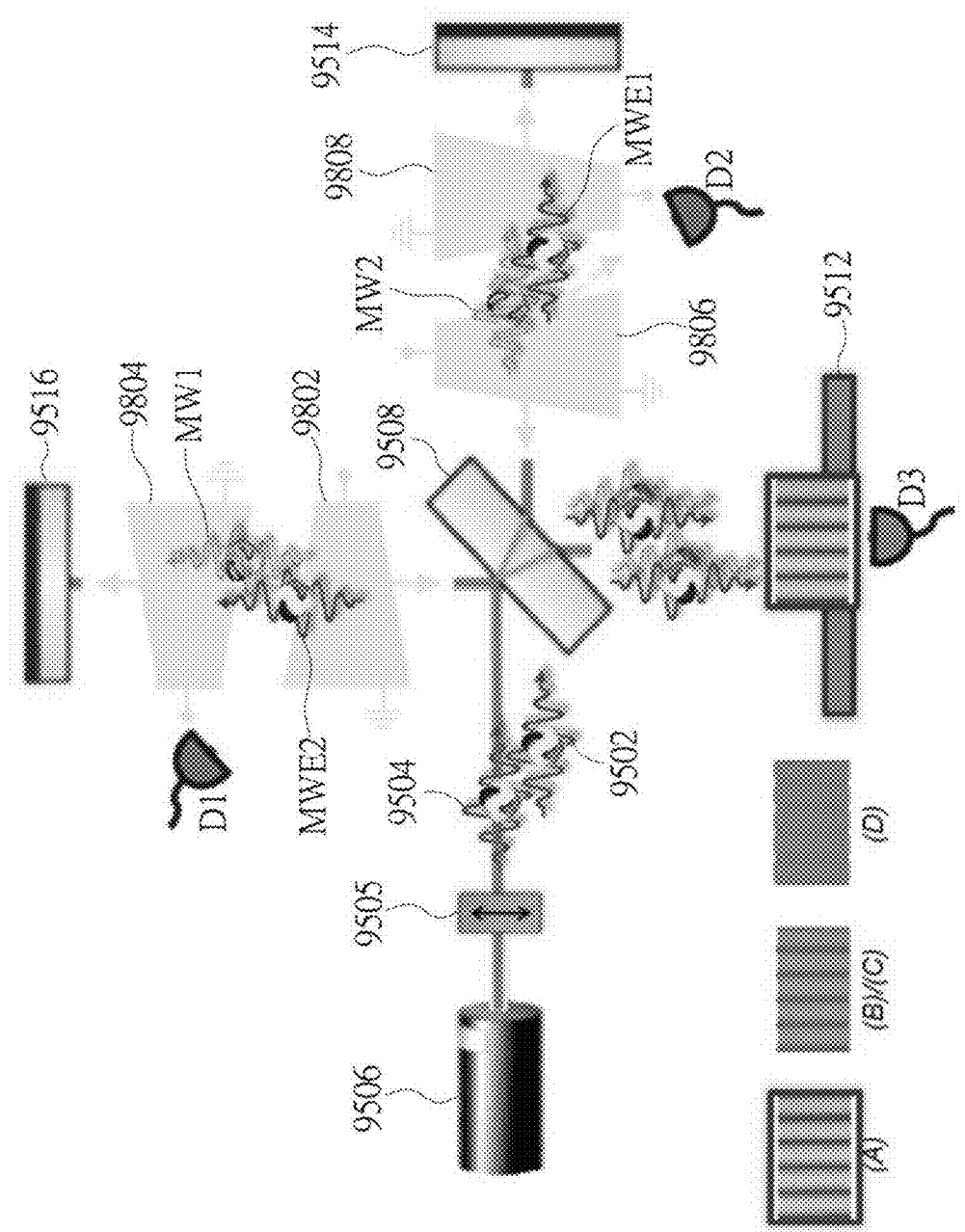
FIG. 99 is a diagram illustrating the theory and working principle for state A of FIG. 98.

BR. Ken's Michelson Kerr-Cell Experiments—MKC Expt.3-A with the Both Kerr Cell 9802 & Kerr Cell 9806 Off FIG. 99 describes the theory and working principle for state A of FIG. 98. The present invention discovers, as shown in FIG. 99, the both Kerr cells 9806, 9802 are turned off, the Kerr cells 9802, 9806 cannot deflect MWE1 of the photon 9502 and MWE2 of the photon 9504 respectively, resulting in MWE intensity of the detectors D1, D2 being almost 0.

Therefore, in state A, MWE1 (right arm) of the photon 9502 is interfered with its own coherent inductive MW1 (upper arm) of the photon 9502 and MWE2 (upper arm) of the photon 9504 is able to get interfered with its own coherent inductive MW2 (right arm) of the photon 9504 to

Figure 100:
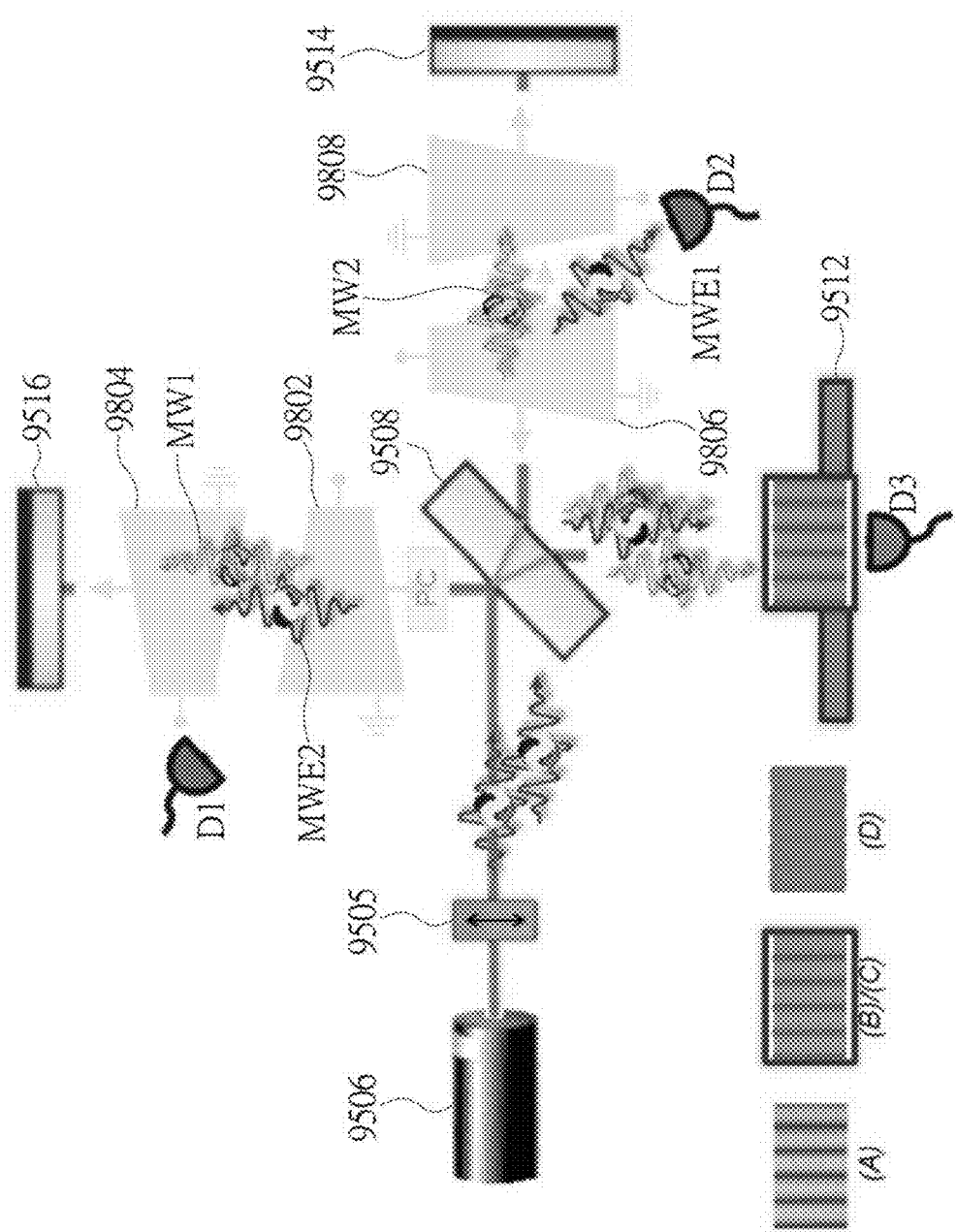
FIG. 100 is a diagram illustrating the theory and working principle for state C of FIG. 98.

BS. Ken's Michelson Kerr-Cell Experiments—MKC Expt.3-C with the Both Kerr Cell 9802 Off & Kerr Cell 9806 on FIG. 100 describes the theory and working principle for state C of FIG. 98. As shown in FIG. 100, because the Kerr cell 9802 is turned off, and the Kerr cell 9806 is turned on, the Kerr cell 9802 cannot deflect MWE2 of the photon 9504, resulting in MWE intensity of the detector D1 being almost 0.

Therefore, in state C, because the Kerr cell 9802 is turned off and the Kerr cell 9806 is turned on, only MWE2 of the photon 9504 is able to get interfered with its own coherent inductive MW2 of the photon 9504 to form weaker interference intensity patterns on the screen 9512, resulting in intensity of the detector D3 being reduced to 25% if the detector D3 was placed before the screen 9512.

Figure 101:
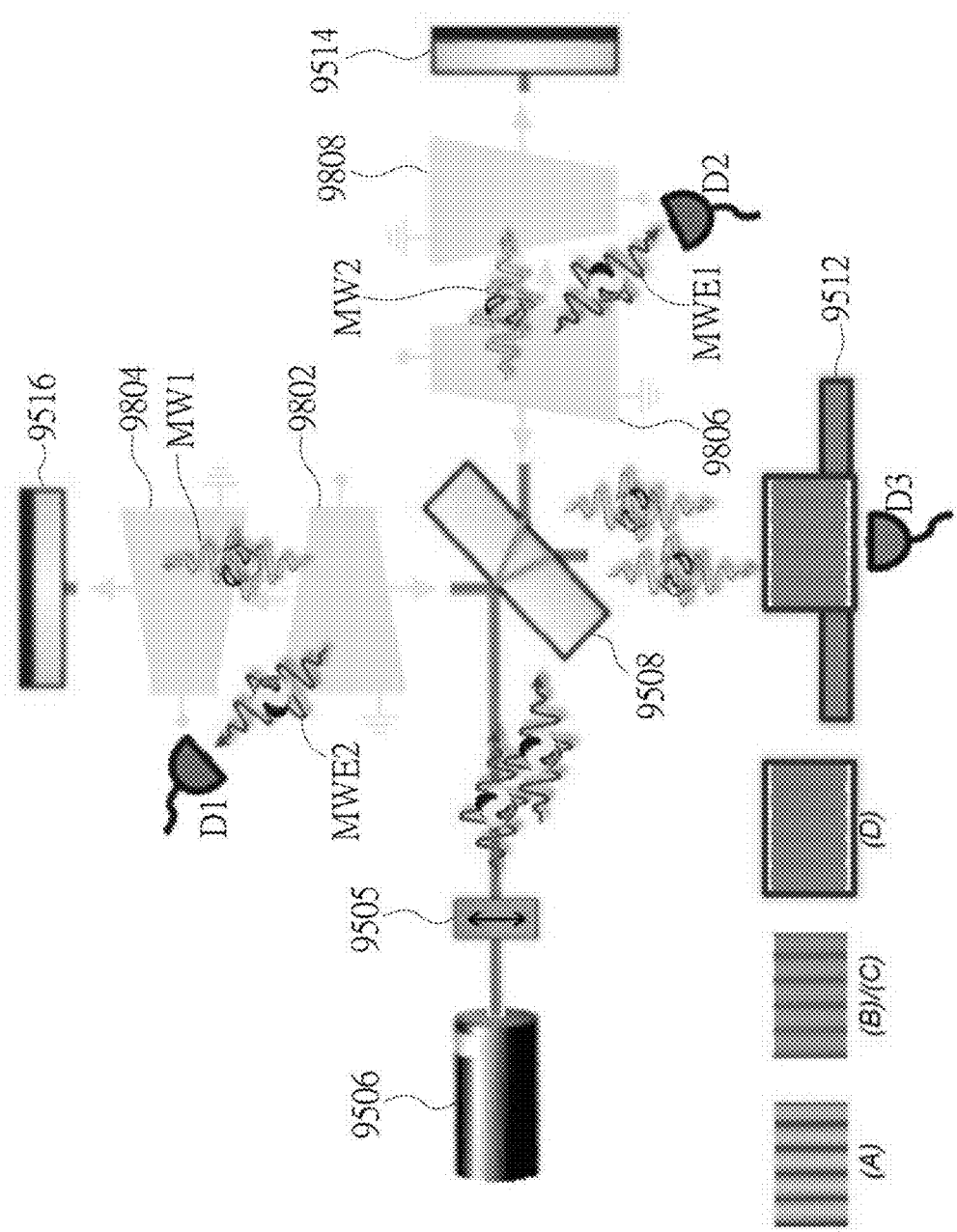
FIG. 101 is a diagram illustrating the theory and working principle for state D of FIG. 98.

BT. Ken's Michelson Kerr-Cell Experiments—MKC Expt.3-D with the Both Kerr Cells 9802, 9806 on FIG. 101 describes the theory and working principle for state D of FIG. 98. As shown in FIG. 101, because the Kerr cells 9802, 9806 are turned on, the Kerr cell 9802 and 9806 can deflect MWE2 of the photon 9504 and MWE1 of the photon 9502 respectively, resulting in MWE intensity of each of the detectors D1, D2 being almost 50% equally owning to the 50%:50% beam splitter effects. Therefore, in state D, no interference intensity pattern can be shown on the screen 9512, resulting in intensity of the detector D3 being reduced to 0% if the detector D3 was placed before the screen 9512.

BU. Ken's MKC Amplitude-Split Experiments Evidences the New Light Model with MWE+MW*

Summary of MKC phase-split evidences new light model:

EPR local realism theory had asserted 100 years ago, the "Decision had been made" when a Photon was just passing through BS 9508. The present invention evidences, Instantly, a "mass-less amplitude-conjugate or orthogonal" copy MW* for incident Light MWE was created inductively via interaction between incidence Photon(s) and MWF tensors of BS 9508 by following Pauli Exclusion Principles (PEP).

MKC Expt. of this invention reveals there is no such things, e.g. Delayed decision or Quantum erase characters mentioned in past prior arts. The present invention has reaffirmed "EPR's Locality with Realistic" postulations, i.e. any object has its pre-existing Eigen-Value or -State for a measurement before measuring being actually conducted.

MKC Expt. reveals a Kerr-Cell with non-linear optical property (e.g. QEO, Quadratic Electro-Optic effect) can be distilling the MW* (i.e. Conjugate MW of Light MWE Quanta) out from a beam associated with mixture of Photon MWE and MW*, etc. The present invention unveils and answers many paradoxes among those unanswered and have been lasting there for hundreds of years.

BV. Ken's MZKC Amplitude-Split Expt.-1a—Single Photon Evidences MWE+MW* Model Before describing FIG. 102 to FIG. 105, assumed conditions are shown as follows:

1) it is assumed incident Photon intensity is normalized to 100% for Expt. State A to D. Hereby, the intensity % is relative to incident photon intensity % as always;

2) it is assumed intensity degradation along the optical paths due to reflection, scattering and absorption is negligible; and 3) The incident Photon (Laser) input is associated with a predetermined linear polarization direction as to control the well-behaved refraction index or its MWE/MW deflection properties.

Figure 102:
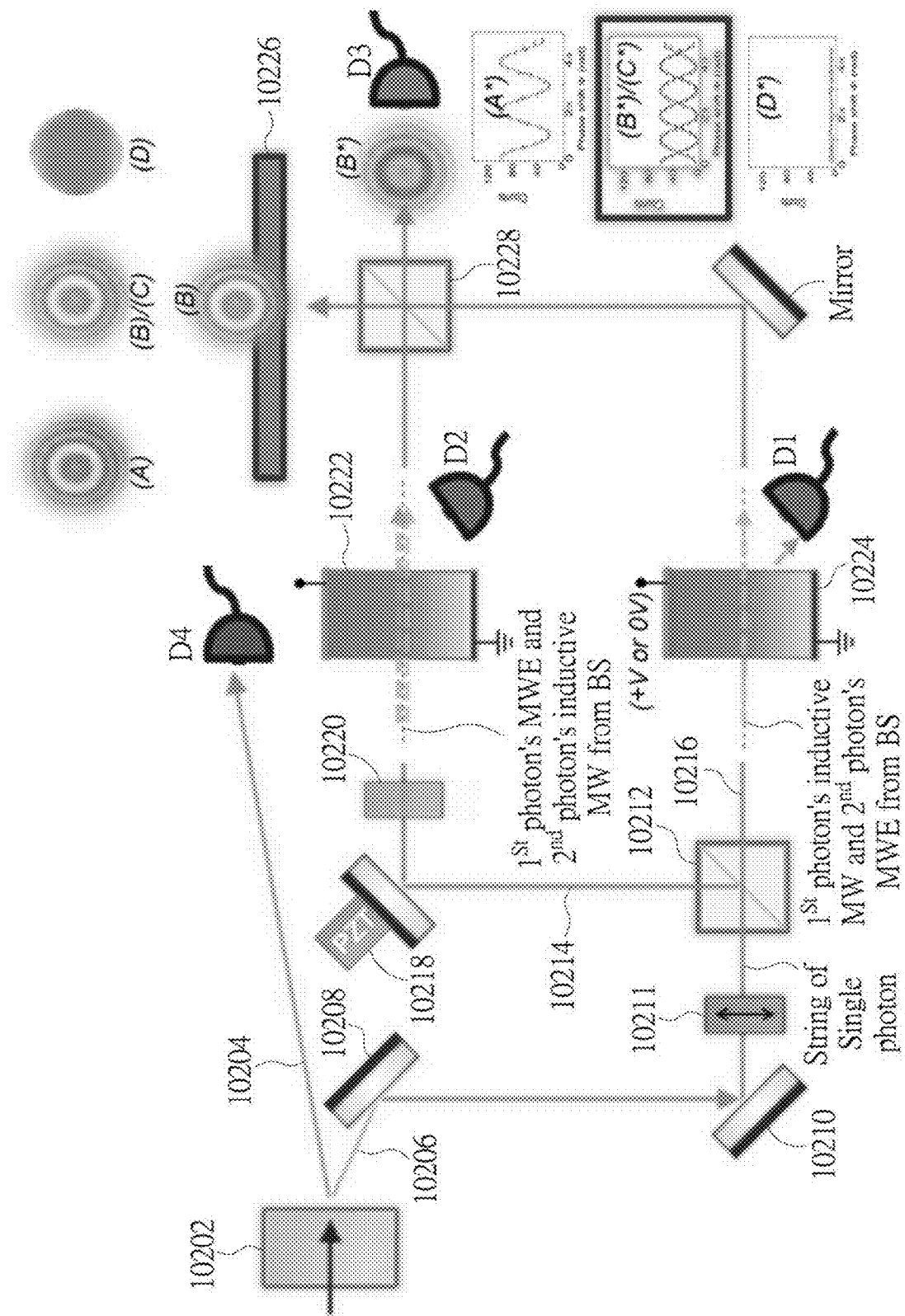
FIGS. 102, 103 are diagrams illustrating two different embodiments proving the new light model by Ken's MZKC amplitude- or phase-split experiments along with single photons to evidence new light model.

As shown in FIG. 102, after pump photons (e.g. UV photon) generated by laser light source or Single Photon Source (SPS), wherein the laser light source is nitrogen-vacancy center (N-V center) with one point defects in diamond, the pump photons (e.g. blue or UV light) hit BBO 10202 (SPDC type I), plurality of paired two red photons (signal and idler) corresponding to some among UV photons are generated due to interaction of non-uniform electrical dipole MWF of the BBO 10202, wherein plurality of one red photon of the two red photons passing through path 10204 is detected by detector D4 for synchronizing BBOevents, and plurality of the other red photon of the two red photons passing through path 10206 is reflected by mirrors 10208, 10210 to hit BS 10212 via a Liner Polarizer 10211. Therefore, 50% plurality of red photons hitting the BS 10212 will pass through path 10214, and plurality of other 50% red photons hitting the BS 10212 will pass through path 10216, wherein PZT 10218 (i.e. Lead Zirconate Titanate, when an external electric field is applied, it can physically change its shape and can be useful for actuator applications) and phase compensator 10220 are used for adjusting temporal phase difference in between the paths 10214, 10216, and detectors D1, D2 are associated with non-linear Kerr Cells 10222, 10224 respectively and have been installed at the paths 10216, 10214, respectively.

As shown in TABLE 27 and FIG. 102, in state A, because the both Kerr cells 10222, 10224 are turned off, the Kerr cells 10222, 10224 cannot deflect MWE1 of first photon passing through the path 10214 and MWE2 of second photon passing through the path 10216 respectively, resulting in Photon MWE intensity of the detectors D1, D2 being almost 0. Therefore, in state A, MWE1 of the first photon is interfered with its own coherent inductive MW1 of the first photon passing through the path 10216 and MWE2 of the second photon is interfered with its own coherent inductive MW2 of the second photon passing through the path 10214 to form stronger interference patterns (e.g. stripe or circular ones, etc.) on screen 10226, and its average intensity of detector D3 is also stronger (as shown in A*). In addition, in another embodiment of the present invention, the Kerr cells 10222, 10224 can be tilted with 3 to 5 degrees to reduce unwanted interference effect due to surface reflections for each of the optical elements used in these experiments, while it can be improving the sensitivity or visibility of the interference intensity or phase patterns.

In addition the present invention discovers, as shown in TABLE 27 and FIG. 102, in state B, because the Kerr cell 10224 is turned on and the Kerr cell 10222 is turned off, the Kerr cell 10222 cannot deflect MWE1 of the first photon, resulting in MWE intensity of the detector D2 being almost 0. Therefore, in state B, only MWE1 of the first photon is interfered with its own coherent inductive MW1 of the first photon to form weaker interference intensity patterns on the screen 10226, resulting in average intensity of the detector D3 being reduced to 25% (as shown in B*), wherein the detector D3 is placed in the second arm of output BS 10228 of such MZKC interferometer to display the orthogonal or conjugated interference patterns as those showing on the screen 10226.

In addition, as shown in TABLE 27 and FIG. 102, instate C, because the Kerr cell 10224 is turned off and the Kerr cell 10222 is turned on, the Kerr cell 10224 cannot deflect MWE2 of the second photon, resulting in MWE intensity of the detector D1 being almost 0. Therefore, in state C, only MWE2 of the second photon is able to get interfered with its own coherent inductive MW2 of the second photon to form weaker interference intensity patterns on the screen 10226, resulting in average intensity of the detector D3 being reduced to ~25% (as shown in C*) relatively.

In addition, as shown in TABLE 27 and FIG. 102, instate D, because the both Kerr cells 10222, 10224 are turned on with external bias (V+), the Kerr cells 10222, 10224 can deflect MWE1 of the first photon and MWE2 of the second photon respectively, resulting in MWE intensity of the detectors D1, D2 being almost ~50%. Therefore, in state D, no interference intensity pattern is on the screen 10226, resulting in intensity of the detector D3 being reduced to 0% (as shown in D*) accordingly. In addition, overall summary corresponding to FIG. 97 is shown in TABLE 27.

TABLE 27

| State | Kerr cell 10222/Kerr cell 10224 | detector D1 intensity | detector D2 intensity | detector D3 intensity |
|---|---|---|---|---|
| A | Off/off | ~0% | ~0% | ~50% |
| B | Off/on | ~50% | ~0% | ~25% |
| C | On/off | ~0% | ~50% | ~25% |
| D | On/on | ~50% | ~50% | ~0% |

BW. Ken's MZKC Amplitude-Split Expt.-1b—Single Photon Evidences MWE+MW* Model-I

Figure 103:
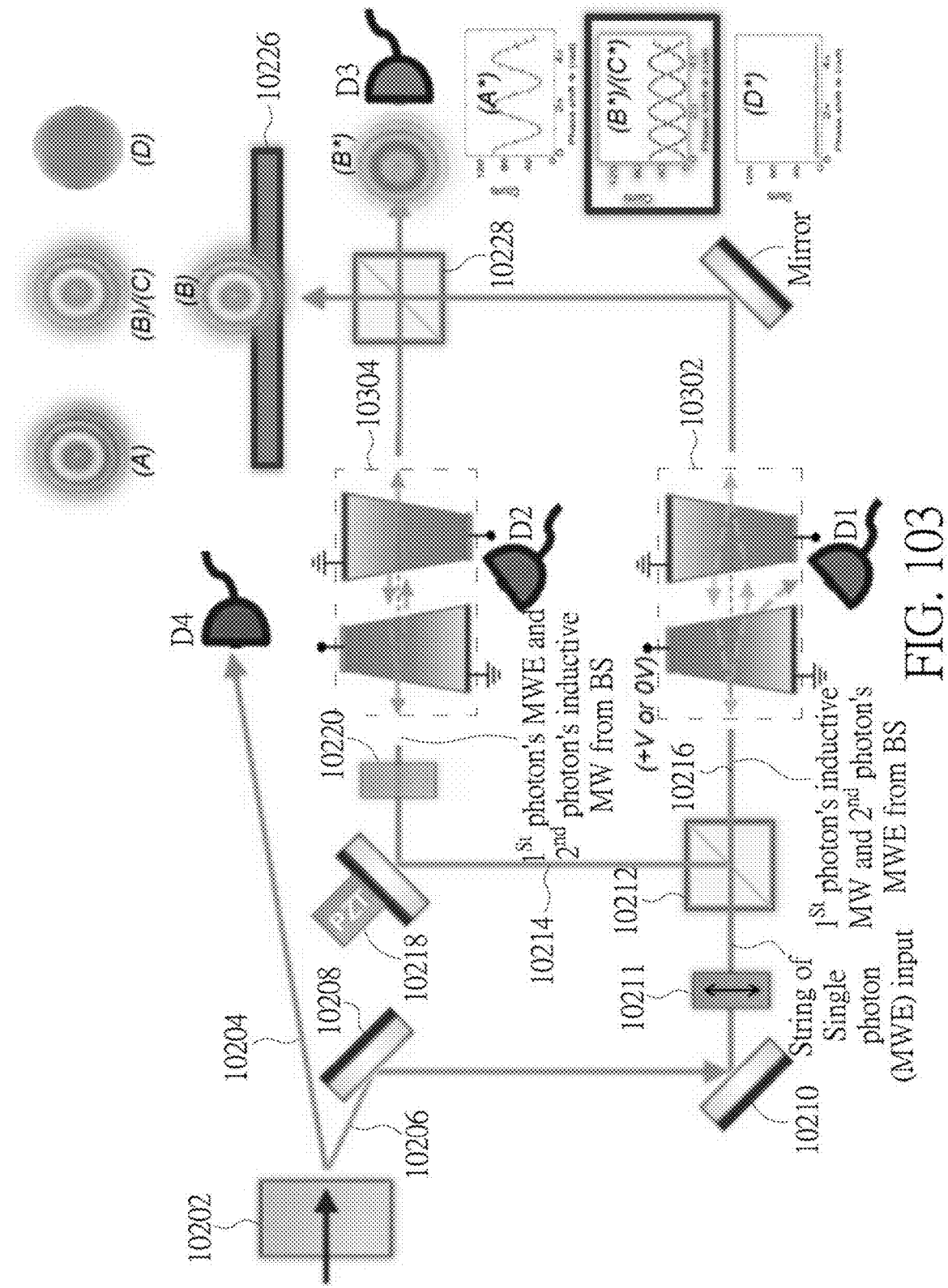

As shown in FIG. 103, a difference between FIG. 103 and FIG. 102 is that Kerr cell groups 10302, 10304 have trapezoidal shape associated with surface tilting angle about less than 5 to 10 degrees to reduce interference effect due to surface reflections for each of the optical elements used in these experiments, while it can be improving the sensitivity or visibility of the interference intensity or phase patterns. Therefore, in state B, because the Kerr cell group 10302 is turned on and the Kerr cell group 10304 is turned off, the Kerr cell group 10304 cannot deflect MWE1 of the first photon, resulting in MWE intensity of the detector D2 being almost 0. Therefore, in state B, only MWE1 of the first photon is able to get interfered with its own coherent inductive MW1 of the first photon to form weaker interference intensity patterns on the screen 10226, resulting in average intensity of the detector D3 being reduced to 25% (as shown in B*).

BX. Ken's MZKC Amplitude-Split Expt.-Lb—Single Photon Evidences MWE+MW* Model

Figure 104:
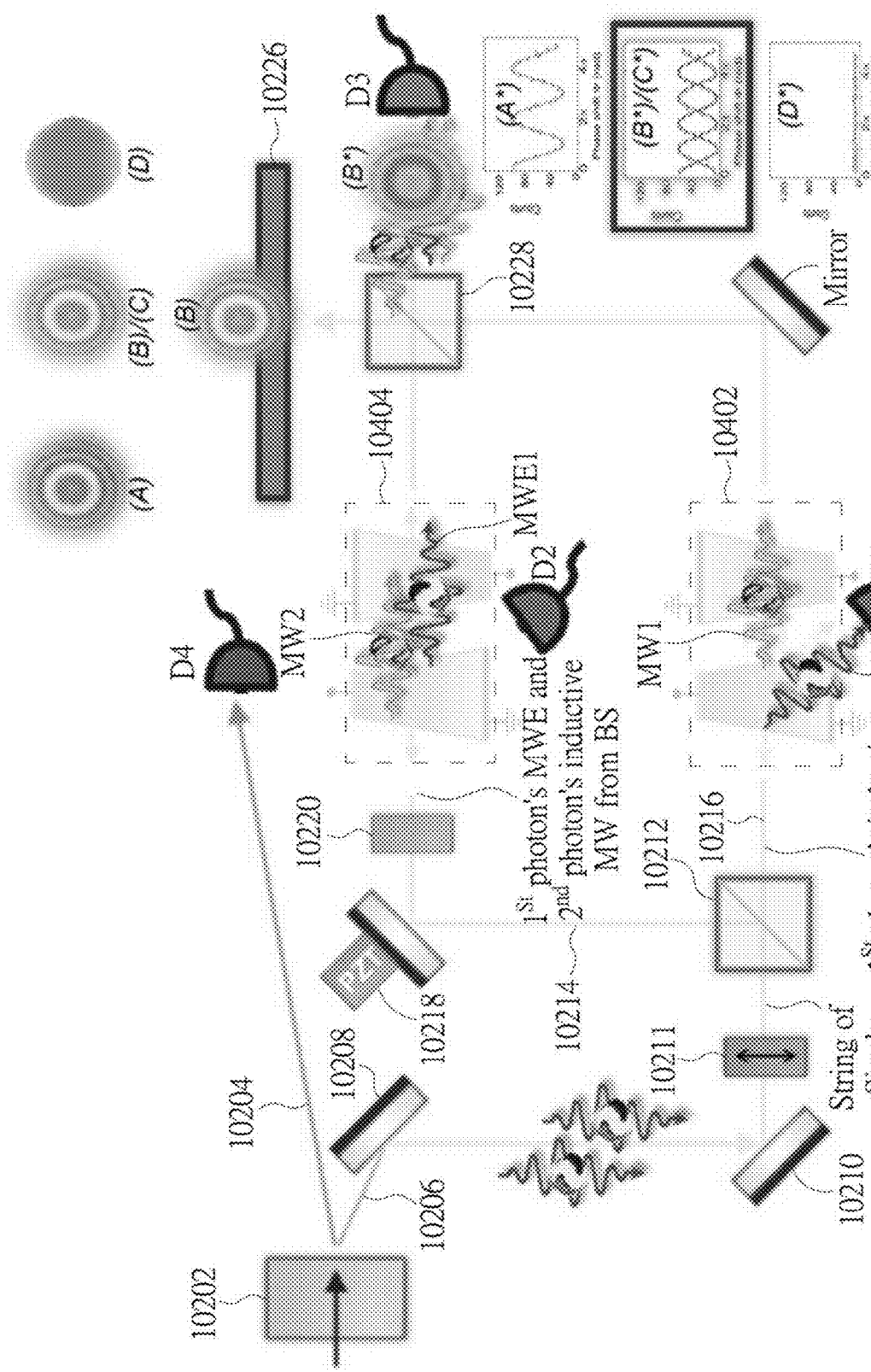
FIG. 104 is a diagram illustrating the theory and working principle for FIG. 103.

As shown in FIG. 104, in state B, because Kerr cell group 10402 is turned on and Kerr cell group 10404 is turned off, Kerr cell group 10402 can deflect MWE2 of the second photon and Kerr cell group 10404 cannot deflect MWE1 of the first photon, resulting in MWE intensity of the detector D2 being almost 0 and intensity of the detector D1 being almost 50%. Therefore, in state B, only MWE1 of the first photon is able to get interfered with its own coherent inductive MW1 of the first photon to form weaker interference intensity patterns on the screen 10226, resulting in average intensity of the detector D3 being reduced to 25% relatively (as shown in B*).

BY. Ken's MZKC Amplitude-Split Expt.-2—can EOM Evidence Photon Path Information?

Before describing FIG. 105, assumed conditions are shown as follows:
1) For exemplary purpose, it is assumed incident Photon intensity of PBS 10504 is normalized to 400% for Expt. State A to D. Hereby, the measuring intensity % is relative to incident photon intensity % as always;
2) It is assumed intensity degradation along the optical paths due to reflection, scattering and absorption is negligible small; and
3) The polarization (s=perpendicular and p=parallel to photon incident plane) property of plurality of incident Photons (i.e. generated from BBO via pump Laser or SPS sources) in PBS 10504 input port is associated with the given polarization directions in one of two BBO entangled outputs.

Figure 105:
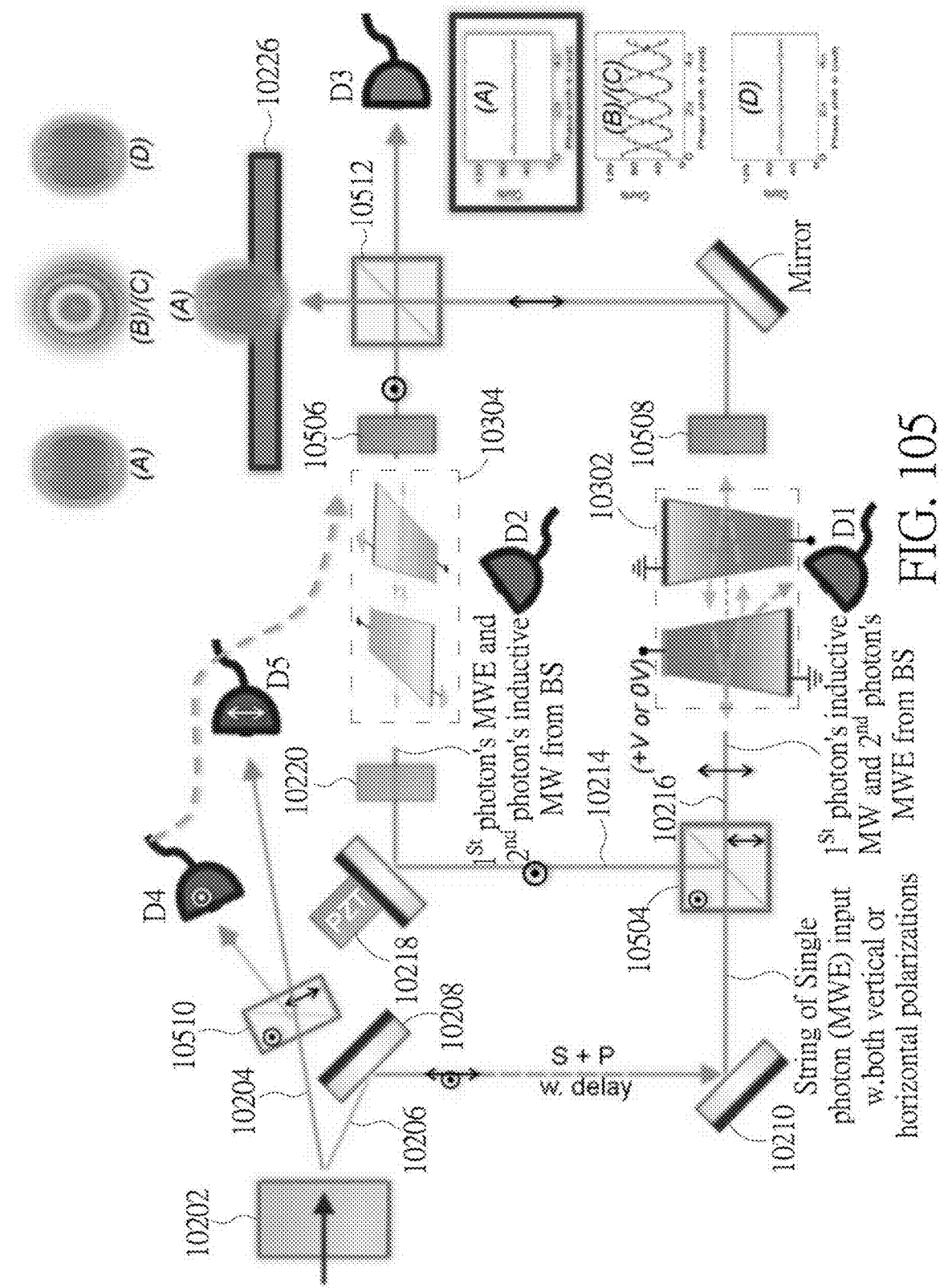
FIG. 105 is a diagram illustrating the theory and working principle for another embodiment of FIG. 103 associated with PBS in input beam splitter.

As shown in FIG. 105, differences between FIG. 105 and FIG. 103 are that BBO 10502 (SPDC type II with two entangled outputs) and polarization BS 10504 substitute for BBO 10202 (SPDC type I) and non-polarized BS 10212 in FIG. 103; and rotators 10506, 10508 are installed at the paths 10214, 10216 respectively, wherein the Kerr Cell group 10302 working axis is arranged for vertical polarization photon in the path 10216 and the Kerr Cell group 10304 working axis is arranged for horizontal polarization photon in the path 10214 (i.e. it is orthogonal to photon in the path 10216), and wherein the rotators 10506, 10508 can be replaced with polarization Electro-Optical Modulator (EOM) to modulate the polarization by external electric field when it is needed. In addition, polarization of the BS 10504 is placed in 45 degrees orientation versus the S (Vertical) or P (Horizontal) polarization directions of BBO output photons to perform the S & P photon MWE splitter and the inductive MW generator at the same instance of time. In one case, MWE1 of S-polarization of first photon appears toward upper arm direction on the path 10214, and then its orthogonal/conjugated inductive MW1 of the first photon will appear toward right arm direction on the path 10216 by following the PEP (Pauli Exclusion Principles). In another case, MWE2 of p-polarization of second photon appears toward right arm direction on the path 10216, and then its orthogonal/conjugated inductive MW2 of the second photon will appear toward upper arm direction on the path 10214 by following the PEP relatively. As shown in FIG. 105, Wallason Plate (WP) 10510 can be used for distinguishing photons with vertical polarization (hitting the detector D4) from photons with horizontal polarization (hitting the detector D5), wherein a distance between consecutive plurality of paired photons, e.g. (the first photon+the second photon)= (s+p) or =(p+s), is supposed to be greater than their coherence length or coherence time generating by Laser or SPS pump photon sources.

Experiment results corresponding to FIG. 105 are shown in FIG. 106. As shown in FIG. 106, because the Kerr Cell group 10302 is turned on and the Kerr Cell group 10304 is turned off, the Kerr Cell group 10302 can deflect MWE2 of plurality of the second photon (with horizontal polarization) and the Kerr Cell group 10304 cannot deflect MWE1 of plurality of the first photon (with vertical or s-polarization), resulting in MWE intensity of the detector D1 being almost 200%, intensity of the detector D2 being almost 0%, and average intensity of the detector D3 and the screen 10226 being almost 100% for each once the plurality of second photons passing through output of 50%:50% BS 10512.

The present invention discovers, because the Kerr Cell group 10302 can deflect MWE2 of the second photon (with horizontal or p-polarization), only MW1 of the first photon (with horizontal or p-polarization) passes through the rotator 10508. In addition, Therefore, MWE1 of the first photon appears at the path 10214 has vertical or s-polarization relatively.

Also, because MW1 of plurality of the first photon appears at the path 10216 has horizontal p-polarization and MWE1 of plurality of the first photon appears at the path 10214 has vertical s-polarization, when in state B, the rotator 10506 is turned on (with rotation angle 90°) and the rotator 10508 is turned off (with rotation angle 0°), and in state C, the rotator 10506 is turned off and the rotator 10508 is turned on, spatial interference patterns can be shown on the screen 10226, and the like, temporal interference curves can be shown at the detector D3 if changing the temporal phase or optical length on the path 10214 by using PZT electrical knob 10218 or the phase compensator 10220 respectively. In another case, as shown in State A, both the rotators 10506, 10508 are turned off, there will be no spatial interference intensity patterns (e.g. ring or circle ones, etc.) that can be shown on the screen 10226 owing to that the paired MWE1 in the path 10214 and MW1 in the path 10216 are orthogonal in its spatial polarization, and the like, the paired MWE2 in the path 10216 and MW2 in the path 10214 are orthogonal. On the other hand, as shown in FIG. 105, the average intensity received by both the screen 10226 and the detector D3 is still about 100% in value.

BZ. Ken's MZKC Amplitude-Split Experiments—can Evidences the New Light Model with Path Information MZKC first and second phase-split (Reference: Ken's first MZKC experiment Laser input is with unknown polarizations, it can be with or without D4 synchronization) Expt. evidences new light model (Reference: Ken's first MZKC experiment Laser input is with unknown polarizations, it can be with or without D4 synchronization, and Phase compensator (PC) can make up the optic path/phase differences between on-Kerr and off-Kerr cells):

"Decision had been made" while a Photon was just passing through the PBS. Instantly, mass-less MW*, a "polarization-conjugate" copy (i.e. $|\updownarrow *>$) of MW of incident Light (i.e. $|\odot>$) was generated inductively via the interaction between incident Photon and PBS' MWF tensors.

PBS input: $|\odot> \rightarrow$PBS output: $|\odot>$ and $|\updownarrow *>$

PBS input: $|\updownarrow> \rightarrow$PBS output: $|\updownarrow>$ and $|\odot *>$ The present invention revealed there is no such things, e.g.

Delayed decision or Quantum erase characters and such experiment reaffirms "locality and Realistic" postulations of Einstein, i.e. an object or matter has its own pre-existing Eigen Value or State for a measurement before conducting the measurement. MZKC 2nd Expt. disprove the Quantum Erase postulation of path information, it reveals PBS with 45 degrees photon inputs can generate inductively a polarization-conjugate MW* of MW of incident Light Quanta in no time.

Figure 107A:
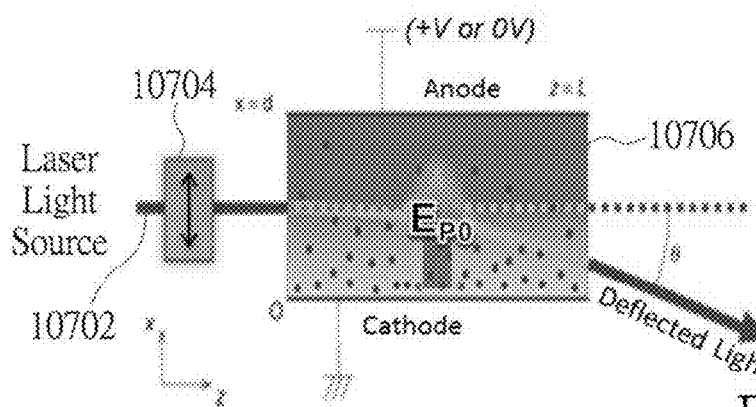
FIG. 107A is a diagram illustrating the photon being deflected by electrical dipole of the KTN with external bias >0V when photon hits vertical polarizer and then KTN.

CA. New Model of KTN Nonlinearity Attributes to Non-Uniform Polarization and MWF Scalar/Vector Potential As shown in FIG. 107A, when photon 10702 generated from laser light source hits vertical polarizer 10704 and then KTN 10706, the photon 10702 will be deflected by electrical dipole $E_{P0}$ of the KTN 10706 with non-zero external bias+ V>0V, wherein θ represents deflected angle of photon output direction vs. incidence direction. The present invention discovers that the KTN 10706 has larger DC Kerr Effect due to comprising of high % of asymmetric electric polarization centers, and its output light is not fully coherent light in spatial wise.

In state A, when electric field applied to the KTN 10706 is null or zero, most object's MWF tensor of the KTN 10706 show integral symmetric electric-dipole polarization (i.e., the KTN 10706 will create a uniform refraction by following Snell's law). Therefore, θ is equal to zero (shown in FIG. 107B) and "leakage current" through the KTN 10706 is equal to zero (shown in FIG. 107C).

Figure 107B:
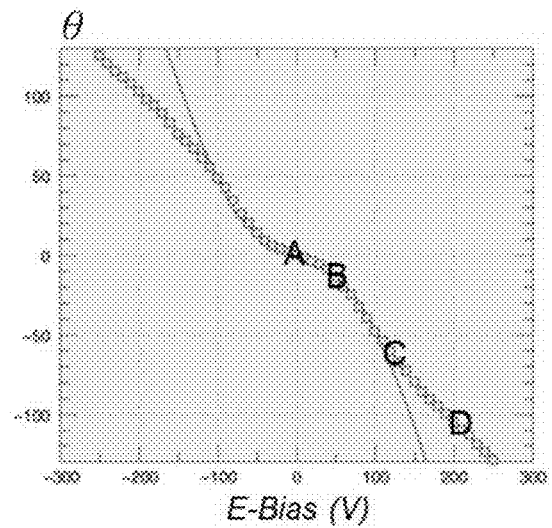
FIGS. 107B, 107C are diagrams illustrating new model of KTN nonlinearity non-uniform electric dipole polarization and MWF vector potential vs. deflection angle of light and leakage current properties.
Figure 107C:
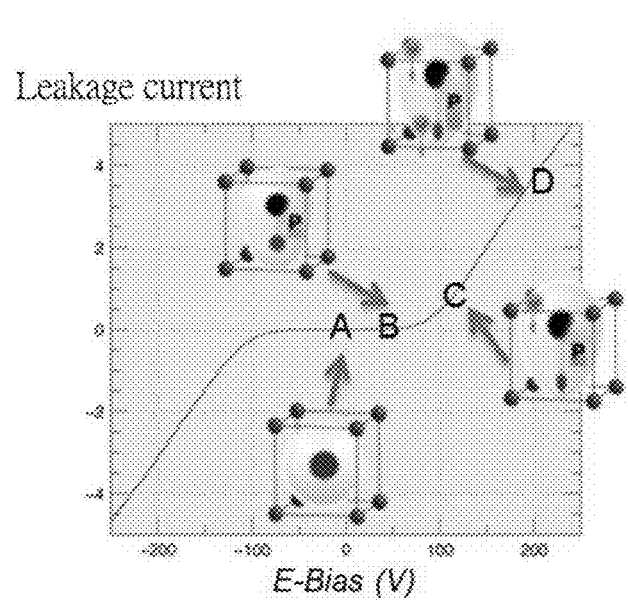

In state B, when electric field applied to the KTN 10706 is in low level, asymmetric dipole polar-centers are fast and quadratic responded than symmetric polar-centers, resulting in showing quadratic or birefringence refractions property along with the external electric bias field, wherein, θ and leakage current corresponding to state B are shown in FIG. 107B and FIG. 107C, respectively.

In state C, when the electric field applied to the KTN 10706 is in medium level, asymmetric dipole polar-centers enter saturation, symmetric dipole polar-centers start following the electric field better relatively, wherein, θ and leakage current corresponding to state C are shown in FIGS. 107B, 107C, respectively.

Finally, In state D, when the electric field applied to the KTN 10706 is in high level, asymmetric polar-centers enter keep in saturated, symmetric dipole polar-centers following the electric field in the linear and symmetric refraction modes, wherein, θ and leakage current corresponding to state D are shown in FIGS. 107B, 107C, respectively.

Figure 108:
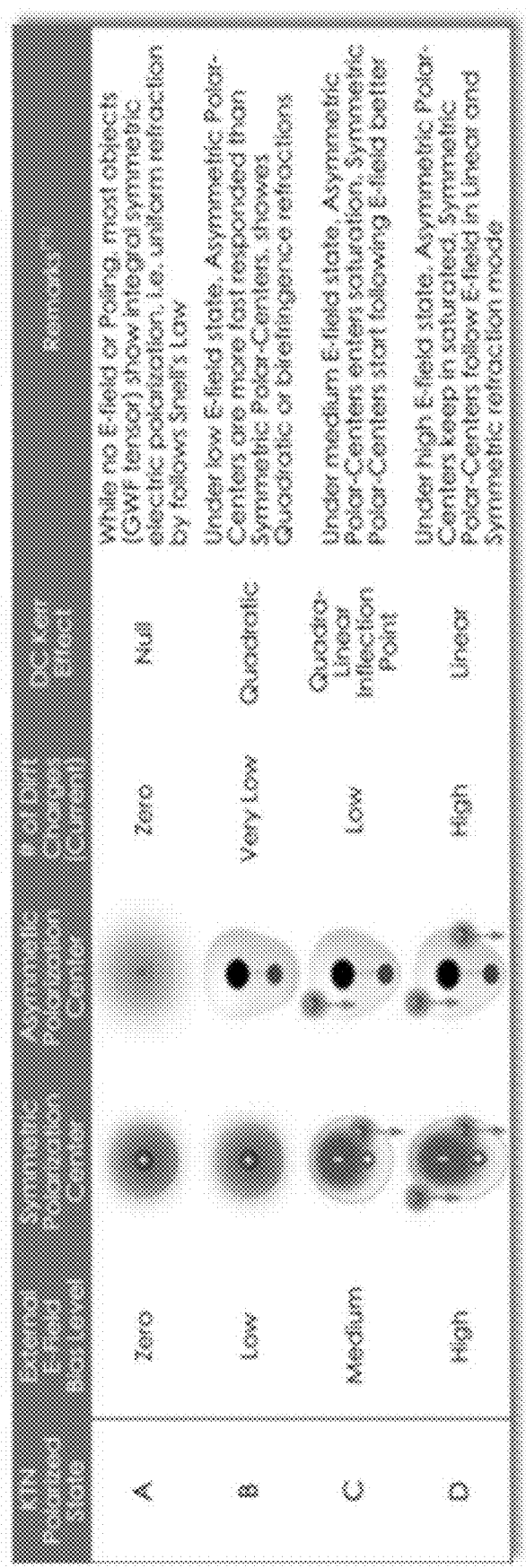
FIG. 108 is a diagram illustrating the remarks and overall summary corresponding to states A, B, C, D of FIGS. 107B, 107C.

In addition, remarks and overall summary corresponding to states A, B, C, D can be referred to FIG. 108.

Figure 109:
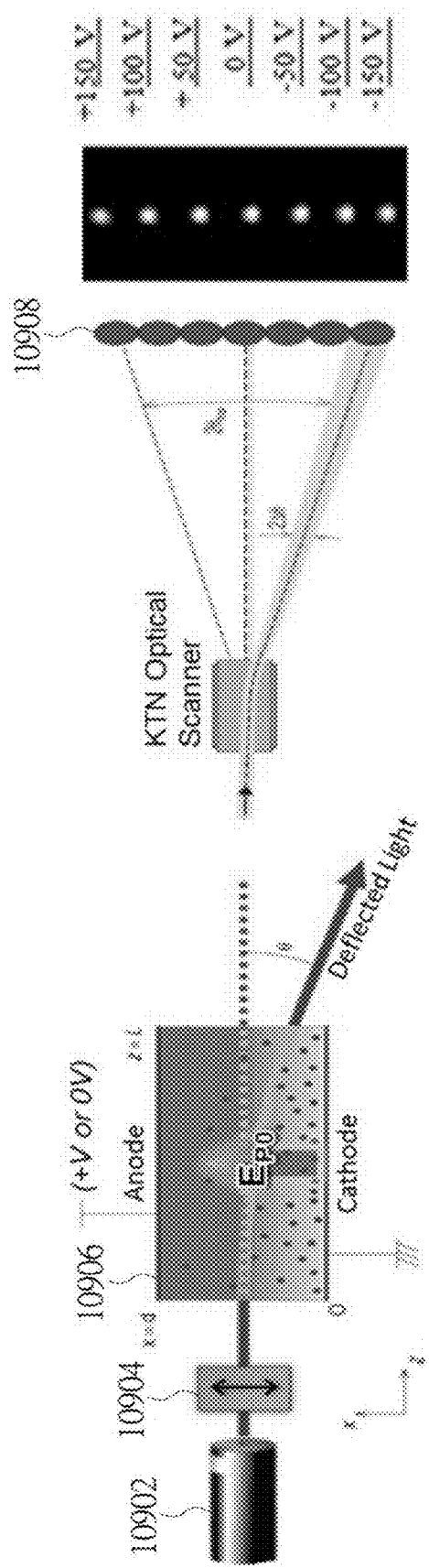
FIG. 109 is a diagram illustrating the second order QEO effects on spatial coherence evidencing the new model of light in Kerr media.

CB. QEO Gets Spatial Coherence Descrambled at its Output Port—Evidenced by New Model of Light in Kerr Media Light De-Coherence Under DC Kerr Effect:

As shown in FIG. 109, when input photon generated from laser light source 10902 (having strictly coherent input Light), hits vertical polarizer 10904 and KTN 10906, the input photon will be deflected by asymmetric electrical dipole polarization field of the KTN 10906. Thus, the present invention indicated, when output Light generated out from the KTN 10906 displayed on screen 10908, the output photon are partially coherent in spatial or temporal such that the KTN 10906 can be used as optical scanner function. Local Realism Postulation predicated, a De-coherent effect is associated with random scattering (i.e. dispersion) effect of asymmetric atomic Spatial asymmetric MWF (i.e. $EP0=P0/\varepsilon 0$) against Light Dipole P1 of the input photon (i.e. it is associated with Yin(−) and Yang(+) charge Quanta) while the input photon passing through the KTN 10906 due to that EP0 and P1 together being experienced spatial, temporal and thermal fluctuations at that given instance of time.

Total resolvable points of Kerr media N≈2Θ max: 2ΔΘ, where ΔΘ is revealed by ΔF (deflection force)=Δ[$P_1 \cdot \nabla(E_{P0})$] of Kerr dispersion wherein Δ is the difference or differential value of a variable and $\nabla$ is the spatial gradient or spatial differential mathematical operation of a variable. By taking Integration over the space and time spans of the Light (photon) path of Kerr device, e.g. the KTN 10906, If net ΔF is a non-zero term arising from the correlated quadratic "random" dispersion effects which cannot be cancelled out over the space-time, hereby it is able to get ΔF>0 and ΔΘ>0. Thus, for the first time in human history, the present invention unveils and discovers the Light De-coherence, photon deflection effect and its working principle behind the Kerr QEO deflection media.

The present invention unveils, light (Photon) deflection force is embedded with the tensor property of Kerr Media in space-time, i.e. the Photon deflection force ($F_{DEP}$) depends strongly on a few interactions of physical properties, including Kerr medium's atomic fine structures, orientation of its electric dipole polarization over space-time, etc. Typically, for Photon with right polarization states, Kerr Media's deflection force for photon will be able to expressed by ($F_{DEP}$)=$P_1$*Grad($E_{p0}$)>0, wherein the P1 is electric dipole polarization vector of photon and $E_{P0}$ is the electric dipole field strength under an external E field bias state.

The output photon of Kerr Media will show certain level of Spatial incoherent properties due to that the variation of deflection forces $\Delta F_{DEP}$ is not able to be cancelled out while integrated over space-time along with the optical path of particular incidence photon. The variation of deflection force, i.e. $\Delta F_{DEP}=\Delta[P_1 \cdot \nabla(E_{P0})]$, is a non-zero term arising from the uncorrelated quadratic "random" dispersion effects, hereby ΔΘ>0 and it has evidenced Light De-coherence effect in Kerr media's output state.

CC. Non-Contact Mode Angle Measuring Apparatus

Figure 110:
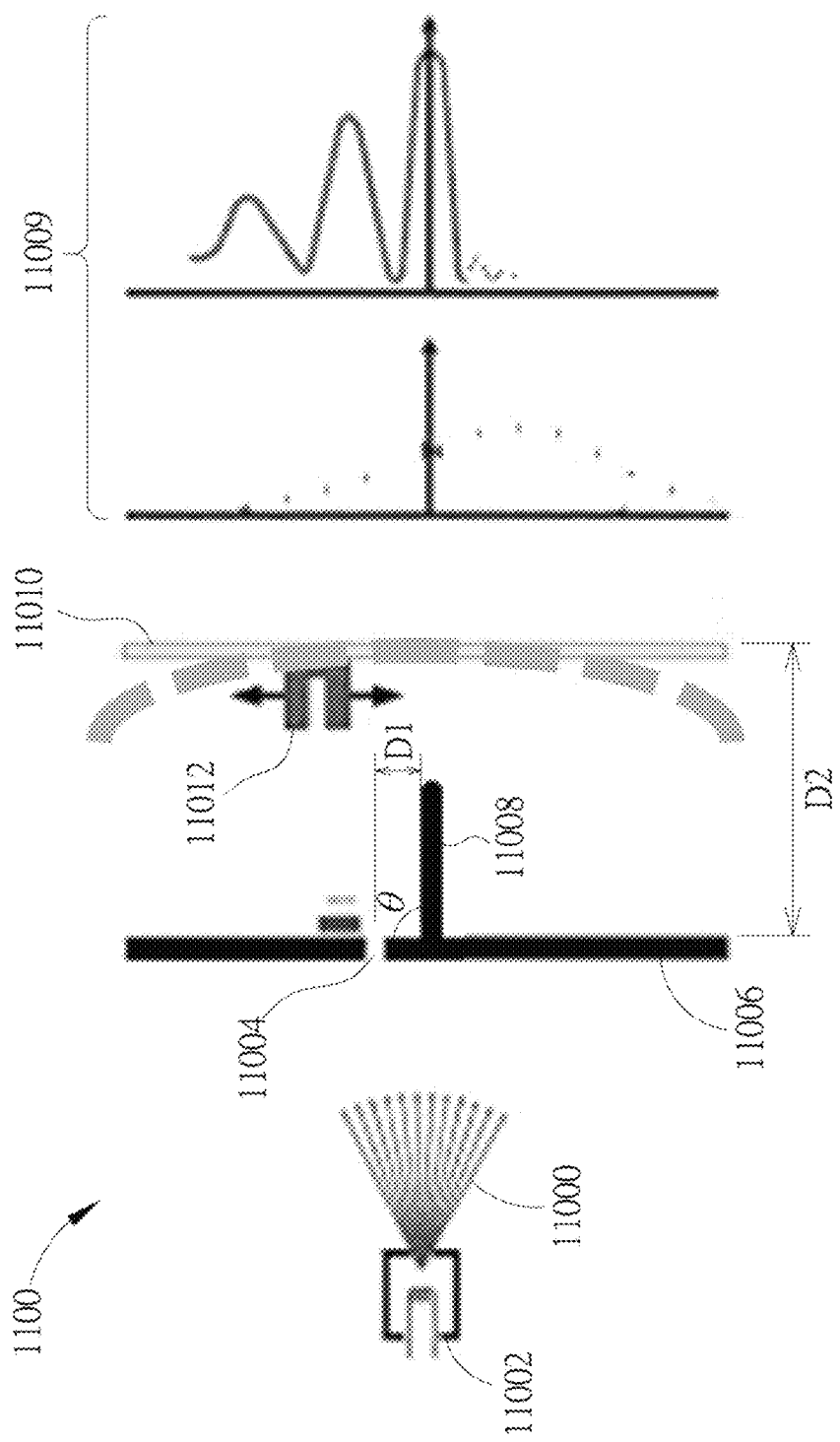

Please refer to FIG. 110, and FIG. 110 is a diagram illustrating a non-contact angle measuring apparatus 1100 according to a first embodiment of the present invention. When particle 11000 (e.g. Photon or fermion) generated by coherent source 11002 passes through slit 11004 (or hole of any shape) of object 11006, plane 11008 can reflect matter wave associated with the particle 11000, wherein as shown in FIG. 110, the object 11006 is placed along a first direction, and the plane 11008 is placed along a second direction, wherein an angle θ between the first plane and the second plane is defined by a joint region of the object 11006 and the plane 11008, the slit 11004 is spaced apart a first distance D1 from the joint region, the plane 11008 can be composed of transparent materials, dark materials, dielectric materials, semi-conductive materials, or conductive materials, and the second direction is different from the first direction. In addition, the angle θ is better for an angle measurement apparatus if it is in between 15° to 165° for getting the best accurate angle measurement result, wherein 1) "transparent material" means the incident Light particles' transmission rate is about larger than 50%, or the reflectance is less than 50% while light incidence angle is about normal to the plane, 2) "dark material" means the incident Light particles' absorption rate is about larger than 50%, or the reflectance is less than 50% while light incidence angle is about normal to the plane.

The coherent MWE particle source 11002 can be a particle source for generating boson or fermion particles, wherein the boson or fermion particles emitted by the matter-wave and energy (MWE) particle source 11002 are associated with one or multiple equivalent MW wavelengths (in between 0.1 to 400 nm).

Therefore, by following the Huygens principle, wavefront of reflected matter wave (i.e. MW reflected away from the plane 11008) of the particle 11000 can combine with original matter wavefront of the particle 11000 MWE packet so as to form substantially half double-slit interference pattern 11009 on screen 11010 and detector 11012, wherein the detector 11012 can be a boson or fermion intensity detector, the half double-slit interference pattern 11009 is boson interference patterns (when the coherent source 10902 is the boson particle source) or fermion interference patterns (when the coherent source 10902 is the fermion particle source), and the detector 11012 is spaced apart from the slit 11004 by a second distance D2. Therefore, the detector 11012 can decide the angle θ by detecting a plurality peaks or valleys of the half double-slit interference pattern 11009, wherein calculation of the detector 11012 deciding the angle θ can be referred to the well-known Yang's Double-slit Interference theory, so the further description thereof is omitted for simplicity.

In addition, the slit 11004 has a short side length with a third distance, wherein the one or multiple equivalent wave lengths is less than 1/10~1/20 of the first distance D1 or less than 1/5~1/10 of the third distance. In addition, as shown in FIG. 110, the detector 11012 can be located on a plane of the screen 11010 or along a linear, straight or an arc line direction.

In addition, the non-contact angle measuring apparatus 1100 needs to operate in a partial vacuum, low humidity, enclosed environment when 1) the coherent source 10902 is the fermion particle source, or 2) the high measurement accuracy is required for the boson particle source.

Figures 111A, 111B:
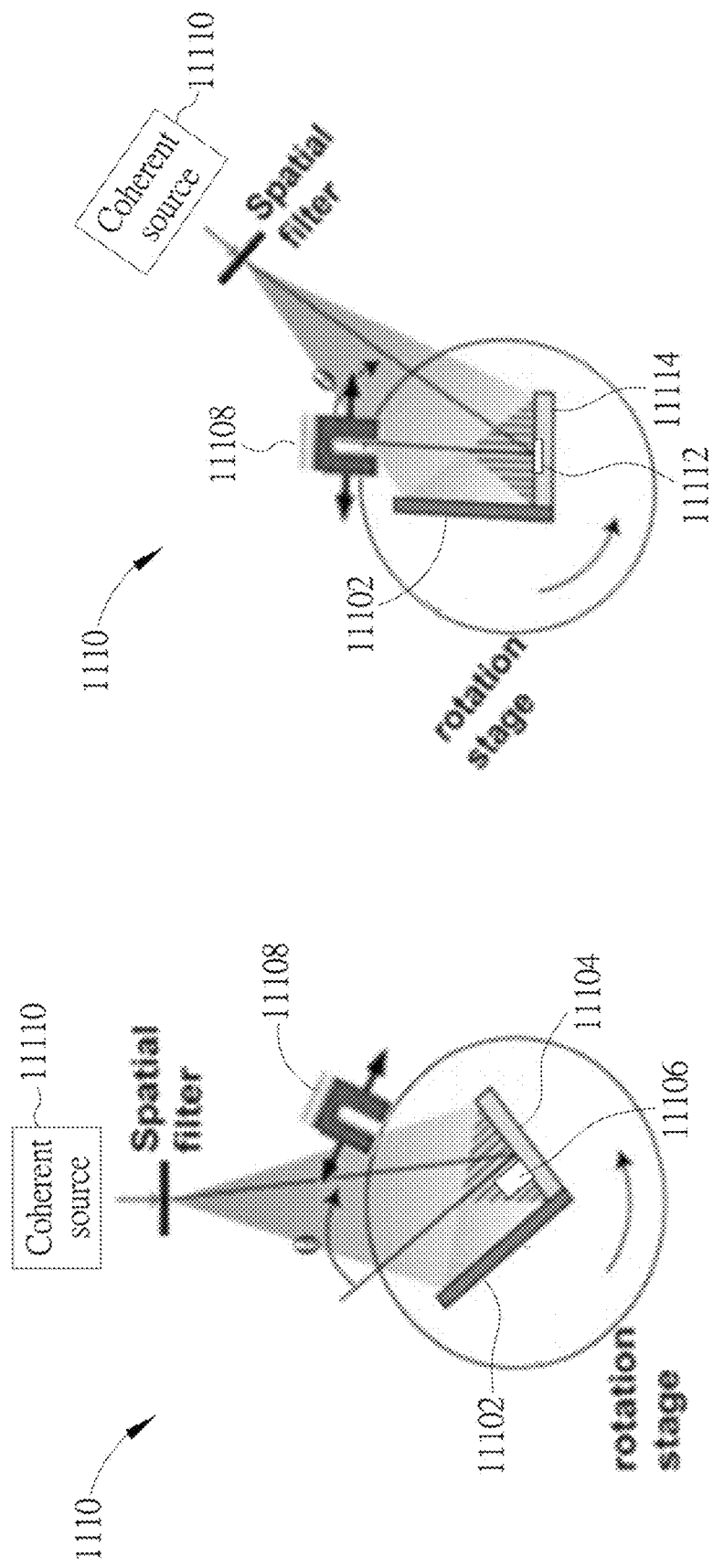

In addition, in another embodiment of the present invention, first plane 11102, and second plane 11104 of a non-contact angle measuring object or apparatus 1110 are shown in FIG. 111A, wherein sacrificial bump 11106 is located on the second plane 11104. Therefore, detector 11108 can detect a plurality MWE packet peaks or valleys of the interference patterns generated by boson or fermion MWE particles (i.e. generated by coherent source 11110 and got scattered corresponding to the sacrificial bump 11106) and matter waves (associated with the incident boson or fermion particles) reflected by the first plane 11102. Therefore, an angle θ shown in FIG. 111A can be determined by the plurality peaks or valleys of the MWE interference patterns.

Similarly, as shown in FIG. 111B, shallow dip (or hole) 11112 is located on third plane 11114. Therefore, the detector 11108 can detect a plurality peaks or valleys of the MWE interference patterns generated by boson or fermion MWE particles (generated by coherent source 11110) corresponding to the dip 11112 and the matter waves (associated with the incident boson or fermion particles) reflected by the first plane 11102. Therefore, an angle θ shown in FIG. 111B can be determined by the plurality peaks or valleys of the interference pattern.

Utilities for the non-contact angle measuring apparatuses 1100, 1110 of the present invention are shown as follows:

1) Can have ultra-fine accuracy for an angle measurement for all macroscopic scale or atomic level fine structures, with or without sacrificial layer or hole; 2) There is no needs for long base lines or target objects for alignments the incidence beam of particles; 3) There is no needs for using direct contact mode to determine the angle and its directions; 4) There is no needs for complicated optical alignment steps before measurement steps; 5) It can be fitting into a small space or object which target (sample or device under test) resided in; 6) The accuracy will be good enough and the measurement cycle time is short; and 7) Can be creating measurements in between many combinations of the points or edges of the 3D models or objects under test.

In addition, the non-contact angle measuring apparatuses 1100, 1110 also have some advantages as follows: as you move the pointer over the 3D model, the non-contact angle measuring apparatuses 1100, 1110 supports four types of measurements: perpendicular distance between two straight edges, linear distance between two points, the radius of circular edges, and the angle between two edges (or three points), you can associate the measurement apparatus with a 3D non-contact Holograph Image measurements tool along with specific x-section views. If the default view is active when a measurement is added, a new measurement view is created, and you can also display comments on the image display or screen while taking measurements. These comments (also called measurement markups) are preserved after the document is closed and saved back to a computer storage space.

CD. MW Distilling and Tomography Apparatus and Methods Inventions

The present invention has characteristics as follows:
1) Non-contact novel angle and profiling measurement tools and methods, with or without patterned sacrificial layer or hole;
2) High Power and high precision CD (Critical Dimensional) SEM and CT diagnosis plus treatment tools:

Those utilities of the present invention include as followings: Commercial 3D life-cell, atomic or molecular level inspections, atomic or molecular level 3D holograph imaging; field emission and spin nano-gate high bright MW sources; multi-focal plan scanning method and apparatus; multiple MW wavelength or phases (+ and −) measurement, inspection, diagnosis or treatment; multi-slit scan, x-slit scan+y-slit scan tools and methods; multi-beam with single column or multi-beam with multi-columns; multi-spatial frequency or multi-matter wave length (frequency) interference method; multiple Guns with FE (field emission) Gun or MEMS for inspection, holograph, diagnosis or treatment; holograph measurement with Spatial multiplexed beam sources; holograph measurement with Time domain multiplexed beam sources; anti-reflection anti-residual interference methods; spin or polarization phase-entangled or -matched, coherent and de-coherent high brightness MW sources; spin coupled fermions (beams) spin up+spin down; MW or Laser guided cool fermions beams~0° Kelvin, and compressed sensing randomization method.

CE. MW Distilling and Tomography-2 Apparatus and Methods Inventions (II)

The present invention also has the other utilities which can be characterized as follows: including side-wall tilt angle measurement, noncontact and non-deformation CD (critical dimension) measurement, non-noninvasive and non-energy transferring inspections, anti-stray light tilt angle test, anti-interference noise design by rotator or waveplate; MW distilling and purification new structure and method; EOM (Electric-Optical Modulation) scanning tool and method; spatial or temporal convolution and noise reduction method; multi- or single-magnetic devices for splitting MW out from MWE incidence beams; and mixed and adjustable coherence to have better edge-imaging and resolutions for SEM or other imaging technologies.

CF. Before illustrating another embodiment of apparatus and methods of the present invention, it needs to be noted that Second apparatus and methods Invention can solve 1) CD SEM and 2) Defect Review SEM major challenges that had been suffered by the prior arts.

Major challenges for the next 2-decade semiconductor inspection tool industry:

Over the past several decades, optical or confocal scanning microscopy has become an essential tool for examining a wide variety of biological molecules, pathways, and dynamics in living cells, tissues, human bodies, tumors and even for whole live animals.

In contrast to other techniques such as electron microscopy (e.g. SEM, TEM), fluorescence scan imaging is compatible with living cells that are being maintained in past years, which enables minimally invasive optical-based observations of events occurring on a large span of timescales.

In terms of spatial resolution for different imaging technologies, several techniques including positron-emission tomography, magnetic resonance imaging, and optical coherence tomography can generate images of animal and human subjects at resolutions between 10 centimeters and 10 micrometers, whereas electron microscopy and scanning probe techniques feature the highest spatial resolution, often approaching the molecular and atomic levels. On the other hand, SEM does create seriously a plurality of damaging effects and drawbacks on the living cells or biological molecules, etc.

Between these two extremes, the center-piece skill of best resolving power lies Matter-wave (MW) oriented optical microscopy. Aside from the benefits derived from that MW is able to image living cells without introducing damage due to exposing under energetic MWE particles such as fermions or Photons. Among the most significant valuable utilities to all forms are those features associated with the new MW microscopy technologies of this invention, including wide field, dark-field, laser scanning, spinning disk, multi-photon, multi-wavelength, and total internal reflection, etc. Meantime, there is no theoretical limit to the spatial or depth resolution that is to be first elucidated and described by quite a few embodiments of this invention.

CG. Another Embodiment of the Apparatus and Methods Invention—Solve Mission Critical CD and Defect Review Major challenges for the next 2-decade inspection tool semiconductor industry are shown as follows:
1) Requiring fine pitch, precision and non-disturbing critical dimension (CD) measurement innovations;
2) New measurement Metrology for Extreme CMOS after 15 to 20 year's horizon;
3) FEP (Front-end Process) pattern definition metrology, including CD test for etching and lithography metrologies;
4) Interconnect line-width CD test metrology in integrated circuits;
5) Metrology for beyond CMOS integrated circuits, such as 3D FINFET or Graphene devices' 3D line-width CD test and 3D defect imaging method and apparatus.

Challenges and known problems for critical dimensional metrology-Requires fine, precision and non-disturbing measurement innovations:
1) Multiple patterning lithography issues in integrated circuits: two or more sets of CD's pitch walking together prevent from the fine accuracy can be made by typical metrology method and apparatus;
2) Etching line edge roughness introduces extra CD measurement deviation from the ideal one;
3) Traditional 2D CD metrology cannot afford the right test metrologies for 3D Transistors, GaAs, Graphene and Interconnects;
4) DSA (Directed Self Assembly) 2D/3D metrology with block co-polymers;
5) USJ (ultra-super junction) depth test metrology Gap (profile and dose) has not been satisfied in past;
6) Defects review and identification in new semiconductor transistor channel materials, e.g. Ge and III-V's;
7) New type of semiconductor interconnects' CD or TSV (Through-Silicon Via) void defect characterization for R&D technology scaling beyond current generation;
8) Contact resistance defect review and CD measurement gaps and more.

CH. Another Embodiment of the Apparatus & Methods for Mask Tooling, Inspection and Mask Metrology Industry The present invention will disclose a few novel embodiments which can offer the best technological approaches to resolve those Major challenges for Future Mask tooling Mask Metrology industry:
1) Mask CD test metrology for optical and EUV Masks for semiconductor mass production use;
2) Mask blank quality inspection, mask raw substrate and patterned mask defect and quality inspections;
3) Mo—Si plating multi-layer mask or absorber layer glass mask inspection;
4) How to take the 3D holograph skill to project a 3D mask image onto a 3D detectors and 3D hologram display;
5) 3D hologram aerial imaging measurement system for fine line semiconductor manufacturing process and technology use;
6) Detection of the top-2 serious Mask defect types: phase and amplitude defects by NEW imaging method and apparatus.

CD Metrology Extendibility and its Potential Solutions:
1) It needs to have new method to detect defects below semiconductor device surface;
2) New imaging technology or metrology for lithography double patterning or multiple (2/3/4) patterning Issues: characterization of two sets of CD's, three sets of CD's and four sets of CD's;
3) There is limit for current lithography CD metrology methods: CD SEM, state of the art uses energy filtered imaging—scatterometry, ellipsometry of grating structures that are not satisfied by next generation semiconductor metrology needs.

CI. Another Embodiment of the Apparatus and Methods Invention for Complex Structures Inspection, Such as 3D FinFETs Semiconductor Metrology Requirements Besides, the present invention can solve Major challenges for Complex structures (suffered most by the prior art), such as FinFETs, that require 3D precision metrology shown as follows:

1) Many parameters are not accessible via current state-of-art metrology technologies, not mentioning top corner rounding, footing, or etch recess under fin;
2) Gate spacer fine line semiconductor process needs would increase the complexity and number of parameters;
3) One other example: FinFET is not able to be measured precisely by CD-SEM or AFM and results fed forward;
4) OCD (optical coherent diffraction) then can only simultaneously measure much fewer parameters with improved measurement uncertainty and higher measurement speed then it is needed;
5) 3D Transistor Dimensional Metrology Challenges: Require measurements of finFET CD, height, sidewall angle and roughness with fine resolutions, non-disturbing and short cycle-time measurement;
6) New SiGe Transistor Dimensional Metrology: SiGe layer strained along the length of the fin and partially relaxed perpendicular to it, etc.

CJ. Also, Another Embodiment to Solve Major Challenges for Future CD-SEM Extendibility and Semiconductor 3D Through Silicon Via (TSV) Metrology or Structure Inspections Major Challenges CD-SEM Extendibility:
1) Current CD-SEM technology is hard to cover those problems, such as image drift-correction, frame averaging, fast single frame, aberration corrected CD-SEM;
2) 3D modeling technology requires to determine all structure dimensions that is impossible for current apparatus available now;

Major Challenges TSV Metrology and Inspection:
1) The alignment accuracy is not enough for coming generation semiconductor technologies, including X-Ray microscopy, overlay alignment through silicon substrate—IR microscopy;
2) Inner layer's defect inspection is required: voids and delamination in TSV's inner structures, stress metrology around TSVs; bonding defects—SAM scanning acoustic microscopy;
3) Other device challenges for inspection: high carrier mobility and structural robustness have driven a considerable effort in Graphene research; defects in CVD Graphene, Quantum Hall effect, etc.

CK. Another Embodiment of the Present Invention—Mission Critical CD and Defect Review Tools and Methods To resolve those challenges and problems of current technologies, it is clear to find many Utilities for the second embodiments of tools and methods of the present invention. It can provide a novel fine, precision, non-invasive, non-disturbing 2D/3D projection or Hologram measurement with adaptive cycle-times. It is to be sufficient for Metrology for Extreme CMOS semiconductor industry in next 10-20 Year's Horizons. It can fit for either Scanning or Transmission modes tools/tests to cover the most demanding needs of semiconductor FEP (Front-End Process) Metrology, Lithography Metrology, Interconnect Metrology, Metrology for Beyond CMOS and the like.
1) In a current state-of-art CD-SEM, however, this artifice is not possible. For example, the need to manage DUT charging control, and if possible to minimize photoresist damage, by lowering the beam energy directly which conflicts with the requirement for ever better imaging resolution. Bu, one can see neither resolution nor charge control can be ignored in future metrology needs. Lower beam energies also result in a reduction in gun brightness and hence reduced beam currents, but smaller features and larger wafer sizes actually demand increased probe currents if throughput rates are hardly to be held constant or even be degraded.

2) Higher scan speeds improve throughput and alleviate many charging effects, but only at the expense of factors, such as decreased image quality and degraded signal to noise ratio, which are again crucial to future fine line metrology. This situation is occurring now because the CD SEM, in its current form, is faced with fundamental limitations rather than with shortcomings in design or execution.

3) The impact of pattern-size deviation from the design value on the device performance is becoming more and more serious in coming fine line semiconductor process technologies. If the CD-SEM/TEM is to have a useful future it will therefore be necessary to re-think the definition of what the tool does and how it does. Having innovative tools and methods of the present invention, it opens a new horizon that the conflicts discussed in TABLE 28 can be fixed or avoided, and the necessary improvements in performance can be obtained within the novel method and apparatus of this invention in near future.

TABLE 28

| Parameter | The present invention | Future needs | Current SEM or TEM |
|---|---|---|---|
| Beam energy | Close to null or very low damage | Free from Charging beam damage | High beam energy can Degrade electron-optical Performance, Diffraction limited or with Poor source brightness |
| Beam current | Spin, phase, spatial, temporal (time multiplexing) intensity or frequency is adaptive with Hi-dynamic ranges | Trade-off between high throughput rate, damage and charging needs to be further enhanced | Lower the beam current to introduce Marginal signal to noise ratio and lower the scan rate performance |
| Spot size | Close to null or the smallest in spatial wise | High Spatial and temporal Resolution "precision" is required | Lower beam current and spot size can Degrade signal/noise Decreased depth of field |
| Scan speed | Multi-beam multiplexed or higher image scan rate is possible | Demand High Throughput and free from charging control issue | Stress on video components and can show Poor imaging linearity |

4) If the CD-SEM/TEM is to be with the useful features, it will therefore be necessary to re-invent about what the tool does and how it does differently. Having innovative tools and methods of the present invention, it opens a new horizon that the conflicts discussed in TABLE 29 can be avoided successful and the necessary improvements in performance can be obtained with the self-evident reduction to practice in the near future.

TABLE 29

| Key issue | Solutions of the present invention | Current SEM/TEM problems and damages |
|---|---|---|
| Resolutions | Can do best Aberration correction with Higher MW frequency and negligible energy involved in DUT imaging (Device-under-Test) | Higher beam current into a smaller probe, but collapse of the Depth of Field and induce DUT charging damages |
| Charging Control | Still free from DUT charging with lower or higher beam energies in Low vacuum operation | Problem in maintaining optimal charging performance will be with loss in resolution and contrast Reduction in usable scan speed if beam current is mall |
| Beam induced damage | Free from charging damages from Ultra-low energy toward the High beam energies | Electron-optical charging performance needs to be improved but it is not proven |
| Contamination (carbon carry-over) | High scan rate, Low out-gassing and low vacuum operation along with In situ cleaning is capable for reduce to practice contamination | Possible loss in resolution and contrast by out-gassing Reduction in usable scan speed. Longer process Cycle Time is required if improved Cross contaminations |
| 3-D information | Can have 3D stereo imaging Modeling by MW plus MWE Holograph method | Requires two exposures Limited geometries Needs extensive pre-computation Accuracy and usefulness may be limited by charging distortion and damaging effects |
| Throughput | Multiple columns or single column multi-MW plus MWE beam with temporal- or spatial-multiplex 3D Holographic high scanning rate methods | Complex technology and data compensation approximation handling needed Statistical rather than on the measurement spot site-specific data |
| Cost and delay in developing and delivering new tools | Can share the Common Platform for CD SEM/TEM and defect inspection tools | Needs difficult agreement on basic specifications and creativity in design different imaging column systems |

5) As large scale integration, such as EUV (extreme ultraviolet) 7 to 10 nm or smaller scale semiconductor devices become more miniaturized. Even in cases where the average critical dimension (CD) is in the limit of process margin, a slight variation in CD sometimes causes fatal degradation of device performance. In addition, the pattern edge roughness and deterioration of the two-dimensional pattern shape also can reduce production yield. Therefore, local and non-invasive measurements of patterns of several tens of nanometers are critical in advanced lithographic processing.

6) Under these circumstances, the CD scanning electron microscope (CD-SEM) plays an important role in the inspection process during semiconductor manufacturing. As for the metrology of lithographic features, it is well known that photoresist (PR) materials shrink due to electron-beam (EBEAM) irradiation during the acquisition of SEM images. The "line width slimming" caused by the SEM induced shrinkage has been an issue seriously because it causes an error in the CD measurements of PR patterns. The present invention can meet advanced device mass production non-invasive measurement requirements of working on the 7 to 10 nm and below generation devices, including CD inspection, mask inspection, defect inspection and mapping purposes. The a few embodiments of the present invention can be the core technology to form advanced extremely high resolution CD-SEM for those practical applications of the SEM that measures the dimensions of fine patterns or defects of semiconductors wafers or masks.

7) The present invention can also fit for either Scanning or Transmission modes measurement tools/tests, wherein the output image can be with 3D or Hologram stereo images. The Matter-wave (MW) plus MWE particle (e.g. electron) microscope column is able to select novel MW imaging or conventional SEM functions, such as SE (Secondary elec.) mode or BSE (backscattered electrons mode, and the like, from the material depending on the measurement target. The present invention can be enabling a higher resolution image to be obtained and high-contrast edge detection without having deteriorated of SEM edge blurring and static charging effect. In this way, the MW purified imaging system is able to measure the highest aspect-ratio bottom dimensions of a FINFET trenches and a very deep holes in via-in-trench BEOL process as well as 3D NAND and DRAM 3D processes.

In addition, a newly designed stage will be able to increase productivity with boost in scanning speed in terms of the number of wafers processed per hour, thereby reducing the "total" cost of ownership (TCO) to the ecosystem users. Moreover to meet the needs of device mass production, matching between the multi-column or single column multi-beam systems will be improved to realize stable long term stability. Also shall provide the industry with a clear, noise-free 2D or 3D images using multiple scanning methods including high-speed scanning such that can achieve the sub-atomic or molecular levels resolution (<1 nm) and inspections including real atomic or molecular level 2D or 3D holograph imaging technology.

Some of the core novel technologies of this invention are able to expand the capability and utility of such inspection or diagnosis system. It includes those innovations such as, Field emission and spin nano-gate high bright MW (Matter-wave) sources; Multi-focal plan scanning method and apparatus; Multiple phases (+ and −) measurement; temporal or spatial multiplex inspection, diagnosis or treatment; Multi-slit scan, x-slit scan+y-slit scan tools and methods; Multi-beam with Single Column or Multi-beam with multi-columns; Multi-spatial frequency or multi-matter wave length (frequency) method; Multiple Guns with FE Gun or MEMS for inspection; 3D holograph scanning, diagnosis or treatment; Holograph measurement with Spatial multiplexed beam sources, Holograph measurement with Time domain multiplexed beam sources; Anti-reflection anti-residual interference methods, Spin or Polarization Entangled; Coherent and de-coherent high brightness MW sources; MW and Electron source Spin coupled fermions (beams) spin up+spin down, MW or Laser guided cool fermions beams 0 deg. Kelvin for noise reduction and Compressed sensing randomization method to achieve extraordinary high scanning speed at ultra-high resolution of nm ranges.

The present invention can create measurements between combinations of points or edges of the 2D or 3D models or objects. As a user move the pointer over the 2D or 3D model, the 3D Measurement Tool supports four types of measurements: perpendicular distance between two straight edges, linear distance between two points, the radius of circular edges, and the angle between two edges (or three points). The user can associate 2D or 3D measurements with specific x-section views. If the default view is active when a measurement is added, a new measurement view is created. The user can also display comments while taking measurements. These comments (also called measurement markups) are preserved after the document is closed and saved to computer storage devices.

Figure 112A:
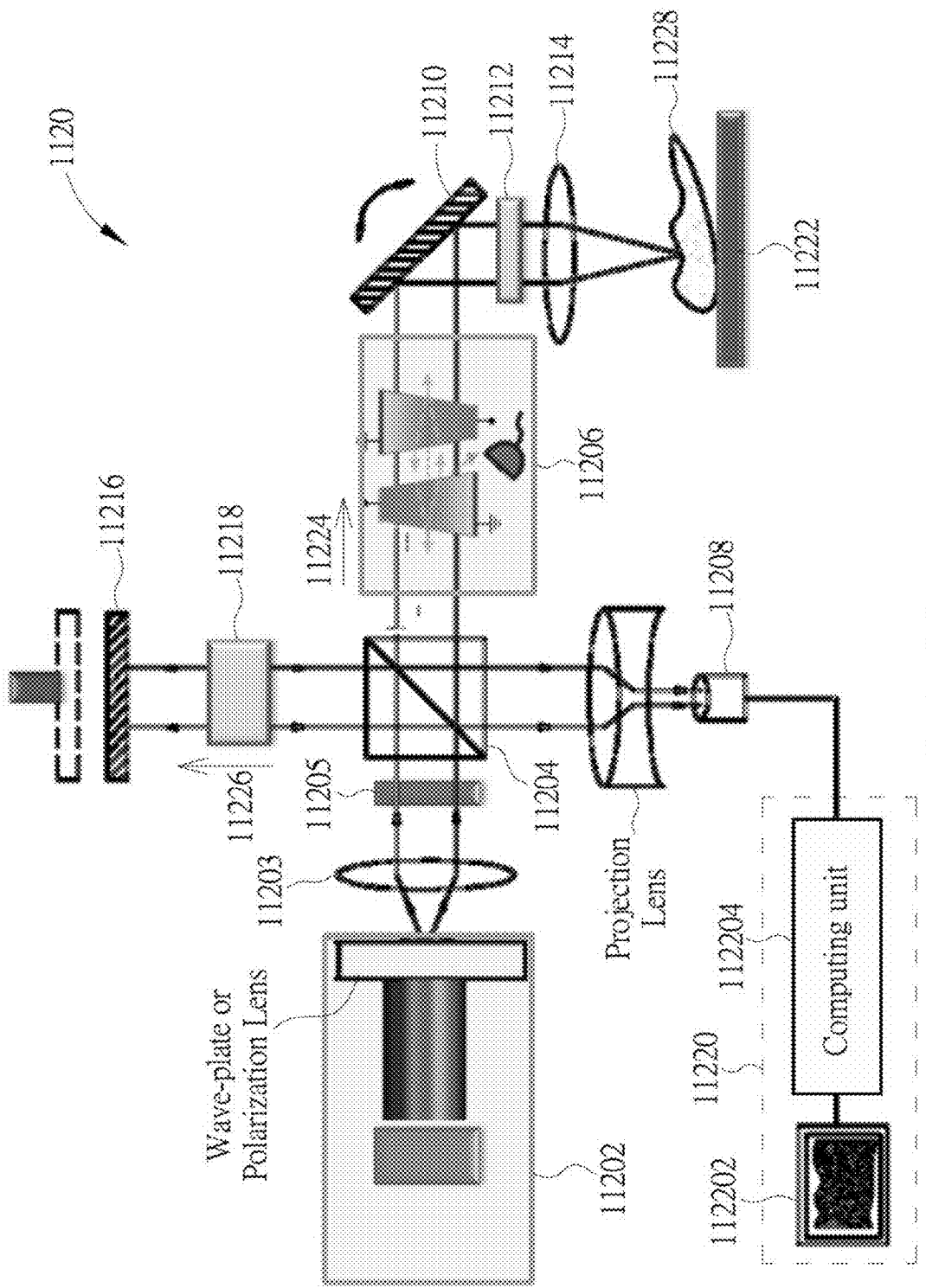

CL. Another Embodiment of the Critical Dimension (CD) Metrology and Defect Inspection Apparatus Please refer to FIG. 112A. FIG. 112A is a diagram illustrating a mission critical inspection apparatus 1120, that can be using for including the advanced semiconductor, mask tooling or and the like of fine-line manufacturing processes, according to a second embodiment of the present invention. As shown in FIG. 112A, the CD and defect inspection apparatus 1120 includes an MWE particle source 11202, a beam splitter 11204, an MW filter (or distiller) 11206, a detector (or sensor) 11208, a first mirror 11210, a first phase compensator 11212, an object lens 11214, a second mirror 11216, a second phase compensator 11218, a display and signal processing unit 11220, and a holder (or sample stage) 11222, wherein the display and signal processing unit 11220 includes a display 112202 and a computing unit 112204 to calculate, aggregate and display the temporal or spatial interference information of the inspection apparatus 1120. Besides, as shown in FIG. 112A, a QEO (Quadratic Electro-Optic) element, a Kerr-Cell Group KC-A/B 11206 and the like under a voltage bias or external electric field bias conditions, can be used for MWE boson particle source 11202 along with the MW filter (or distiller) 11206 to performing MW filter or distiller functions (or screen out MWE particles) for an incident boson's MWE particle beam mixing in with a component comprising of the energy-less mass-less MW beam. Besides, as shown in FIG. 112A, ordinary skilled one can exercise the features or structures of the present invention by using source comprising typical multi-wave length Laser light (Photon) sources, including typical electron E-gun source, including electron thermal emission source, field emission source or source having spin injection e-beam generator feature disclosed in the present invention. In addition, in another embodiment of the present invention, when the MWE particle source 11202 is fermion particle source, an MW filter for fermion particles (shown in FIG. 112B) can be substitute for the MW filter 11206.

The MWE particle source 11202 can be forming a continuous beam of particles, temporal- or spatial-multiplexed beam of particles via a time- or spatial-domain multiplexer and can further comprises multi-beam particle sources along with single column to emit and inject MWE multi-beam particles (but in another embodiment of the present invention, the MWE particle source 11202 includes multi-beam with multi-columns to emit or inject MWE particles), wherein when the MWE particle source 11202 is a boson particle source, the emitted MWE particles can be uncharged particles (e.g. photons or x-ray), when the MWE particle source 11202 is a fermion particle source, the emitted or injected particles can be charged or uncharged particles (e.g. electrons, positrons, proton or neutron), and the emitted particles randomly comprises a first particle beam and a second particle beam. In addition, the majority emitted particles can be coherent and associated with one or more equivalent MW wavelength, wherein the one or more equivalent MW wavelength is shorter than about 0.1-10 nm ranges. In addition, the particles emitted by the MWE particle source 11202 are temporal or spatial coherent and are associated with a single wavelength or a plurality of MW wavelengths. On the other hand, in another embodiment of the present invention, the majority particles emitted by the MWE particle source 11202 are partially coherent and are associated with a single wavelength or a plurality of wavelengths. In addition, the emitted particles can be forming a continuous beam of particles, temporal- or spatial-multiplexed beam of particles for inspecting the object or sample 11228 under test. In addition, the MWE particle source 11202 includes a wave-plate (i.e. MW phase retarder plate) or polarization unit, wherein the wave-plate or the polarization unit is used for adjusting polarization direction of the injecting particles before it can be split randomly into the first particle beam and the second particle beam through the first entanglement unit or beam splitter 11204. In another derived embodiment, the particles emitted by the MWE particle source 11202 can be corresponding to a matter wave (MW) along with multi-temporal frequency/wavelength or multiple-spatial orientations (polarizations or phases).

When the MWE particle source 11202 is a boson particle source, a source lens 11203 is located before the MWE particle source 11202 for making the majority emitted particles being nearly parallel movement particles. However, when the MWE particle source 11202 is a fermion source, the CD and defect inspection apparatus 1120 further utilizes fermion condense/scan module 11205 to substitute for the source lens 11203, wherein the fermion condense/scan module 11205 includes fermion x/y direction scan coil and electric or magnetic x/y direction condense lenses, and the MWE particle source 11202 is a thermal or FE (Field emission) gun particle emission source.

When the MWE particle source 11202 is a boson or fermion particle source, a beam splitter for making MW of a first particle beam and MWE of a second particle beam toward a first path, and making MW of the second particle beam and MWE of the first particle beam toward a second path; an MW filter located at the first path for tilting the MWE of the second particle beam and let the MW of the first particle beam passing through the first path to hit or transmit a sample, wherein 1) the MWE of the first particle beam and 2) the MW of the first particle beam being reflected from or transmitted through the sample are used forming an interference pattern; and a detector for detecting a plurality of peaks or valleys of the interference pattern. Alternatively speaking, the beam splitter 11204 can output instantly a counterpart MW1 (e.g. energy-less and mass-less conjugate or orthogonal counterpart matter wave) of the first particle beam toward a first path 11224 along with outputting simultaneously the MWE1 of the first particle beam toward a second path 11226, and can output simultaneously MWE2 of the second particle beam toward the first path 11224 along with making instantly a counterpart MW2 (e.g. energy-less and mass-less conjugate or orthogonal counterpart matter wave) of the second particle beam toward the second path 11226. In addition, one edge dimension of the beam splitter 11204 is larger than 1000 to 20000 times of the one or more equivalent MW wavelengths.

Figure 112B:
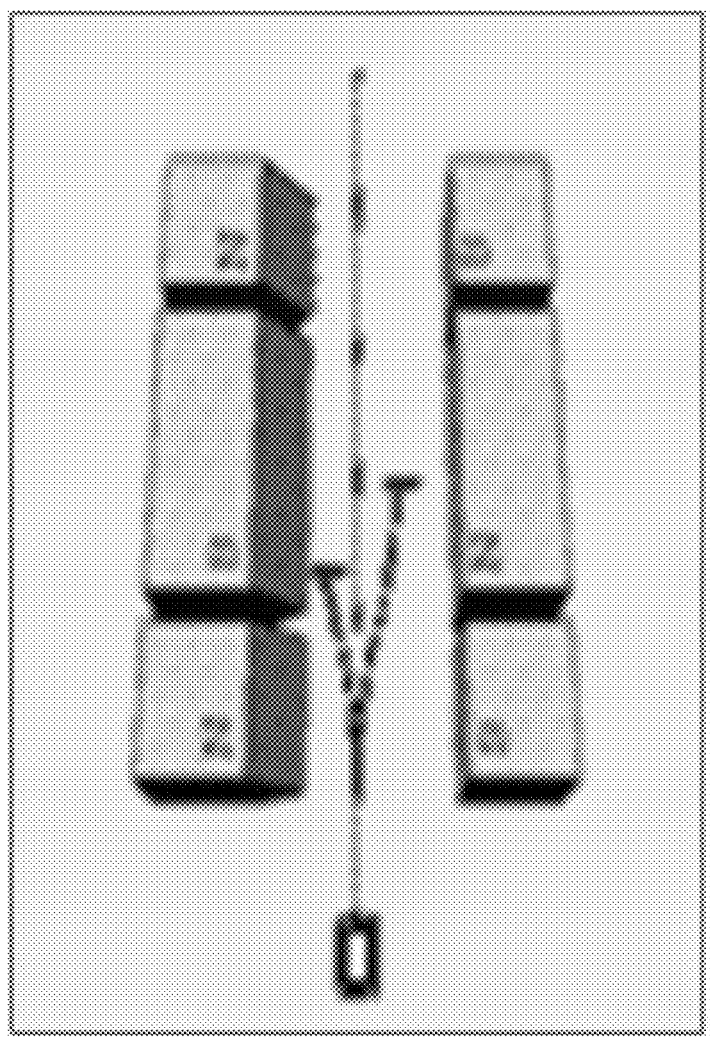

However, when the MWE particle source 11202 is a fermion particle source, the apparatus 1120 further includes the first beam splitter 11204 to making the counterpart MW1 of the first particle beam and MWE2 of the second particle beam toward the first path 11224, and some electric or magnetic material or structure forming non-uniform MAG (Magnetic) field over the first path 11224, wherein the non-uniform MAG field is used as a filter or distiller to pass selectively the counterpart MW1 of the first particle beam and to stop (or screen out) MWE2 of the second particle beam toward the first path 11224, and the beam splitter 11204 making the counterpart MW2 of the second particle beam and MWE1 of the first particle beam toward the second path 11226 accordingly. Besides, as shown in FIG. 112B, a non-uniform magnetic unit, a Magnetic filter group of MAG-A/B/C and the like, i.e. comprising non-uniform magnetic fields, can be used for MWE fermion particle source 11202 along with the MW filter (or distiller) 11206 to performing MW filter or distiller functions (or screen out MWE particles) for an incident fermion's particle beam mixing in with a component comprising of the energy-less mass-less MW beam.

In addition, when the MWE particle source 11202 is the fermion particle source, the MWE particle source 11202 includes a plurality or array of Field Emission (FE) tips and array of electronic gates to select a given QM spin configuration for a plurality of emitted fermions particle groups, and a part of the CD and defect inspection apparatus 1120 needs substantially to operate in a partial vacuum, low humidity, enclosed environment. In addition, when the MWE particle source 11202 is the fermion particle source, the particles emitted by the MWE particle source 11202 are with groups of particles associated with temporal- or spatial-multiplexed modes among multiple groups such that the nearest emitted groups of particles are with opposite QM spin states to get better 2D or 3D image resolutions in temporal or spatial wise.

In regard to the first path 11224, the MW filter 11206 is located at the first path 11224 for tilting (or moving) the MWE2 of the second particle beam substantially away from the first path 11224 and let the MW1 of the first particle beam passing through the first path 11224 to hit a sample 11228 when a bias condition (e.g. voltage, current, electric field, magnetic field or the like) is applied on the MW filter 11206, wherein the MW filter 11206 is further coated with one or more layers of anti-reflection coating to reduce scattered residual MW or MWE interference effects in an environment of the apparatus 1120, and to be able to reduce imaging defects by taking the advantage of a surface of the MW filter 11206 being not orthogonal (i.e. tilted angle of a few degrees) to an incident direction of the MWE2 of the second particle beam and the MW1 of the first particle beam. The first mirror 11210 is located at the first path 11224 for reflecting the MW1 of the first particle beam to or from the sample 11228 wherein the first mirror 11210 further comprises a moveable feature for doing the one or more dimensional (e.g. X, Y or Z direction) scanning for the sample 11228. The first phase compensator 11212 is also located at the first path 11224 for compensating a temporal or spatial phase difference in between 1) reflected MW1 of the first particle beam from the sample 11228 and 2) the MWE1 of the first particle beam (i.e. being moved toward and reflected from the second mirror 11216), wherein the MW1 of the first particle beam from or transmitted through the sample 11228 is partially or fully in temporal or spatial wise corresponding to the MWE1 of the first particle beam. The object lens 11214 is located between the first mirror 11210 and the sample 11228 for focusing the MW1 of the first particle beam on the sample 11228. The holder 11222 is used for holding the sample 11228, and a surface of the holder 11222 is a partial absorption plane (e.g. coating with ARC) or a partial/full reflection plane (e.g. coating with reflective material) or partial/full transmitting plane (e.g. transparent glass material or the like) to assist getting the better 2D or 3D image contrast for the sample 11222 under the test condition of apparatus 1120.

In regard to the second path 11226, the second mirror 11216 is located at the second path 11226 for reflecting the MWE1 of the first particle beam and the MW2 of the second particle beam being outputted by the first beam splitter 11204, wherein second mirror 11216 further comprises a moveable feature for doing the one or more dimensional (e.g. X, Y or Z directions) scanning for the sample 11228; and the second phase compensator 11218 is also located at the second path 11226 for compensating the temporal or spatial phase difference in between 1) reflected MW1 of the first particle beam from the sample 11228 and 2) the MWE1 of the first particle beam.

As shown in FIG. 112A, the MWE1 of the first particle beam and the reflected MW1 of the first particle beam from the sample 11228 are used to forming an interference pattern via an interaction with the beam splitter (i.e. entanglement unit) 11204, wherein the detector 11208 utilizes a boson or fermion sensitive materials or devices (such as microchannel photomultipliers for bosons and Fluorescence film for fermions) to detect a plurality of peaks or valleys of the interference pattern through an image projection lens 11230. In addition, the one or more equivalent wavelengths is shorter than about 0.1-10 nm for the detector 11208 getting better image resolutions of the interference pattern. Also, the one edge dimension of the beam splitter 11204 is larger than 1000 to 20000 times of the one or more equivalent wavelengths such that the detector 11208 will get better image resolutions of the interference pattern. In addition, the first phase compensator 11212 and the second phase compensator 11218 can also make the detector 11208 get better image resolutions of the interference pattern under the test condition of the apparatus 1120.

As shown in FIG. 112A, the display and signal processing unit 11220 is coupled to the detector 11208, wherein the computing unit 112204 can be used for processing, aggregating and magnifying and displaying the image of interference pattern to generate a 2D image or 3D Hologram image by optical film projection methods well-known in the prior art, or the display 112202 displays the 2D image or 3D Hologram image after the display 112202 receives the processed 2D or 3D image.

Therefore, a user can take time and utilize the 2D image or 3D Hologram image displayed on the display 112202 to execute CD and defect inspection thoroughly corresponding to the sample 11228.

Figure 113:
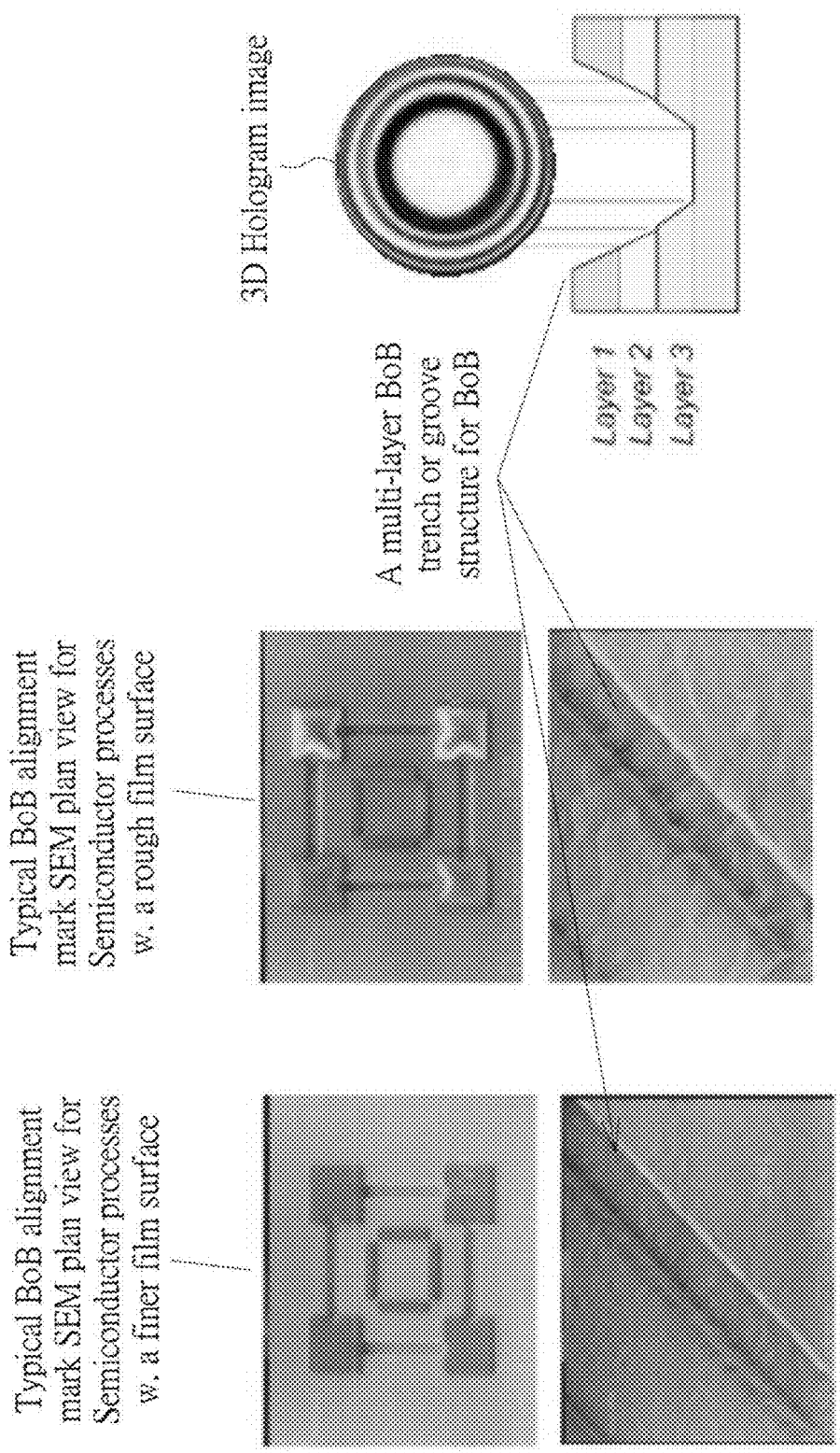

In addition, the CD and defect inspection apparatus 1120 can be a part of precision overlay measurement or alignment system which can inspect Box-in-Box (BiB) or Box-on-Box (BoB) patterns forming by different materials (shown in FIG. 113) for precision overlay or alignment purposes, e.g. the alignment for a semiconductor wafer versus photolithography masks. The CD and defect inspection apparatus 1120 can have better than ever before precision, repeatability for different substrates, higher matching properties between tools, machines, inspection Program portability of MAM (Machine-align-Machine) time in much less than a few seconds, high throughput aligner's overlay analysis, Real-time overlay analysis and good pattern recognitions.

Figure 114:
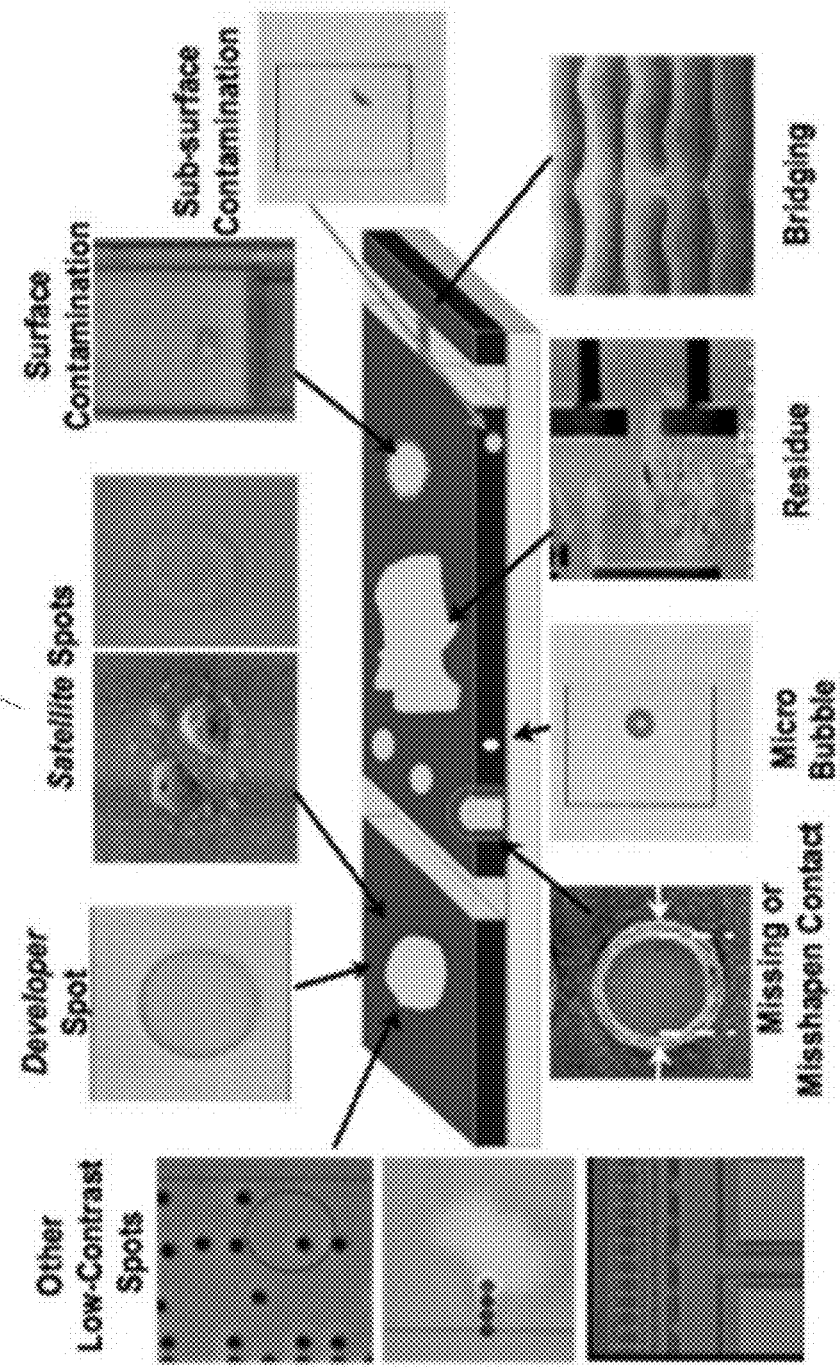

In addition, the CD and defect inspection apparatus 1120 can be a part of multiple systems, including semiconductor wafer, packaged integrated circuit (IC) or mask inspection/repairing systems as to provide users with Precision Defect Inspection and in-situ defect repairing features, wherein some of typical semiconductor wafer inspection defects (shown in FIG. 114) are characterized with ADI (After Developing Inspection) spots, Satellite spots, Surface contaminations, Substrate contaminations, Patterning bridging, Residues, Nano-bubbles, Miss-happen or missing contacts and via-holes, etc. Therefore, when the CD and defect inspection apparatus 1120 finds some defects on a semiconductor wafer, photo mask and the like, the user can turn off the MW filter 11206 to let the MWE1 of the first particle beam burn the exact same location defects to repair the defects showing on semiconductor wafer or photo mask.

Figure 115:
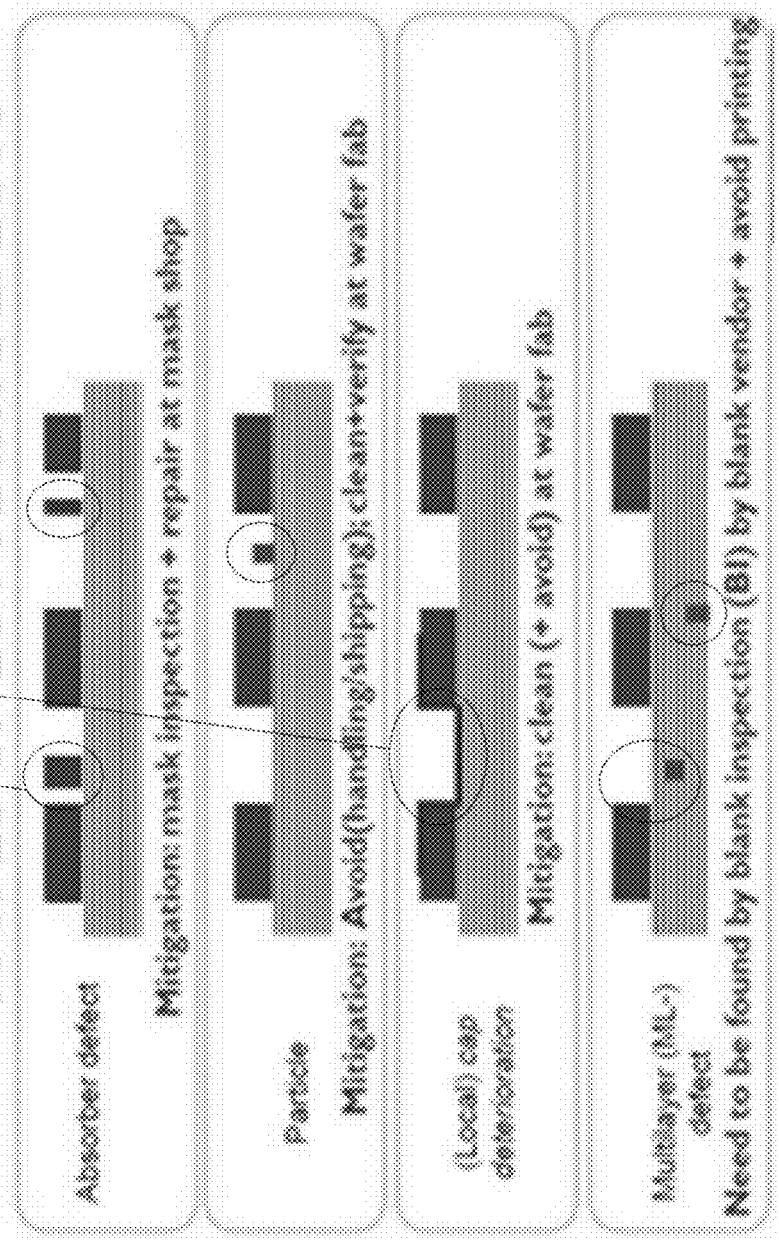

In addition, as shown in FIG. 115, basic photo mask defects can be inspected precisely by the CD and defect inspection apparatus 1120 include Absorber defects, Particle defects, Local-cap defects, Multi-layer inner defects which are essential for most advanced industrial process or technology use purposes, e.g. nm ranges of semiconductor manufacturing.

Therefore, the CD and defect inspection apparatus 1120 of the present invention can teach well and provide a novel non-invasive (i.e. energy-less and mass-less MW based) inspection tool and method, precision, cost effective in-situ mask inspection and repair features to best utilize the machine investment for advanced mask tooling purposes, wherein the present invention discloses a unique approach for filtering matter wave (MW) from a composite particle beam corresponding to aforementioned embodiments of this invention by following method: obtaining a composite particle beam along a first particle path that comprising a beam splitter or entanglement unit, a MWE particle component of boson/fermion particles and a MW component, wherein the MW component is not corresponding to or directly derived by the MWE particle component; directing the composite particle beam toward a unit having a non-uniform spatial field (e.g. electric, magnetic or the like); tilting or moving the MWE particle component of the composite particle beam away substantially from the first path; generating an output beam comprised of the MW component along the first path; and receiving the output beam for processing a plurality of following steps, including getting mixed or entangled with another coherent or partially coherent beam of MWE particle component (e.g. via a beam splitter, a bi-prism or the like) to form interference pattern, wherein the interference pattern can be detected by a detector.

Figure 116:
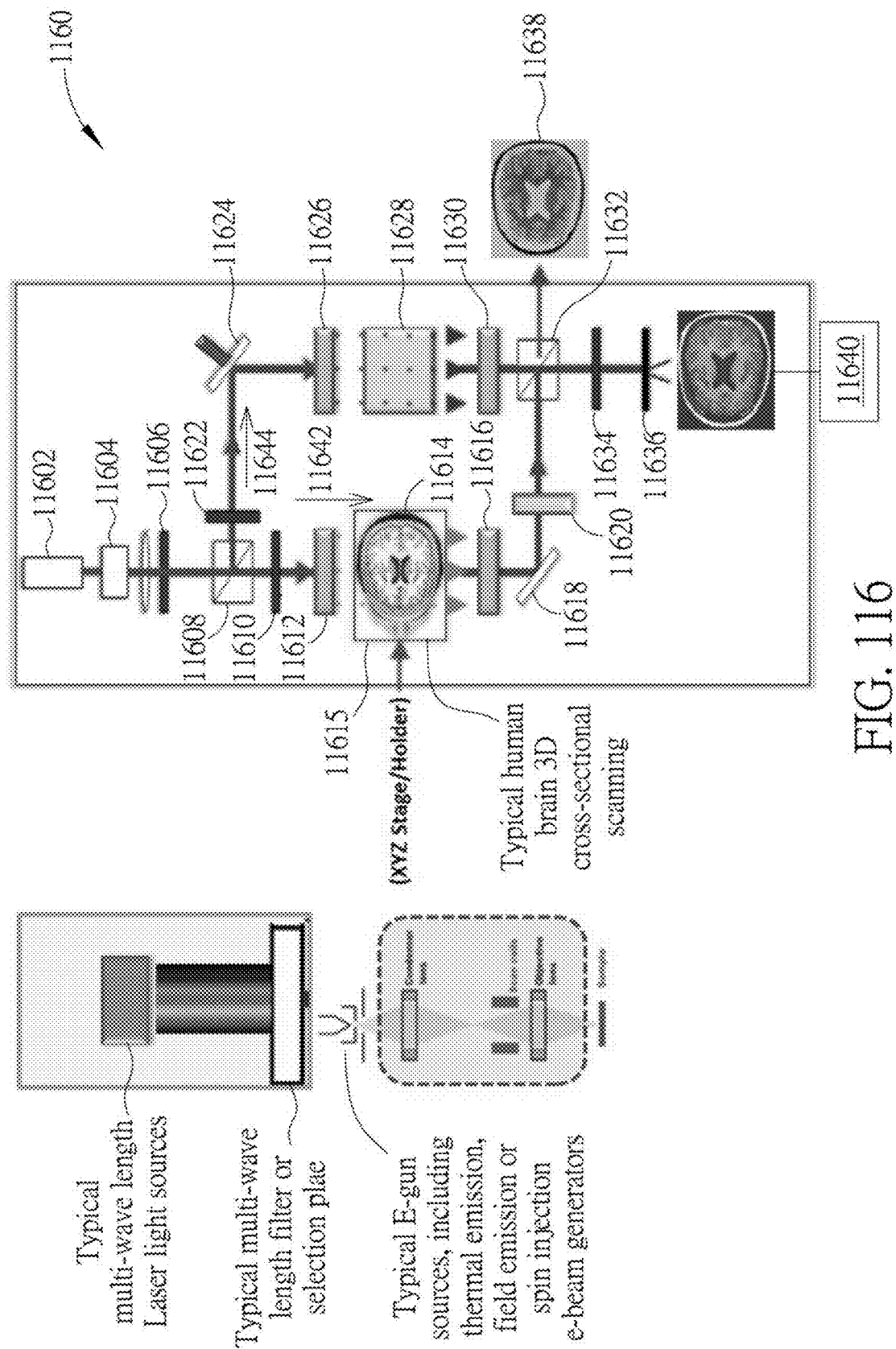

CM. Another Embodiment of the Transmission-Type Non-Invasive Diagnosis/Treatment Apparatus or System FIG. 116 is a diagram for illustrating a transmission-type non-invasive diagnosis/treatment apparatus 1160 according to a third embodiment of the present invention. As shown in FIG. 116, the transmission-type non-invasive diagnosis/treatment apparatus 1160 includes an MWE particle source 11602 associated with one or more equivalent MW wavelengths, a first x/y/z direction scan unit 11604, a first wave-plate (e.g. phase shift or polarization shift plate) unit 11606, a first beam splitter (or entanglement unit) 11608, an MW filter 11610, a first scan lens unit 11612, a holder (e.g. XYZ scan stage) 11614, an first lens unit 11616, a first mirror 11618, a first compensator 11620, a second wave-plate unit 11622, a second mirror 11624, a second x/y/z direction scan unit 11626, a second compensator 11628, a second lens unit 11630, a second beam splitter (or entanglement unit) 11632, a projection lens 11634, a first detector 11636, a second detector 11638, and a display and signal processing unit 11640. As shown in FIG. 116, the MW filter 11610, the first scan lens unit 11612, the holder 11614, the first lens unit 11616, the mirror 11618, and the first compensator 11620 are located at a first path 11642, and the second wave-plate unit 11622, the mirror 11624, the second x/y/z direction scan unit 11626, the second compensator 11628, the second lens unit 11630 are located at a second path 11644.

As shown in FIG. 116, major differences between the CD and defect inspection apparatus 1120 and the transmission-type non-invasive diagnosis/treatment apparatus 1160 are that a sample 11615 placed on the holder 11614 is a living organ, a living tissue, or living cells (e.g. as shown in FIG. 116, the sample 11642 is a human brain by not showing the living body); the first beam splitter 11608 can output instantly a counterpart MW1 (e.g. energy-less and mass-less conjugate or orthogonal counterpart matter wave) of the first particle beam toward a first path 11642 along with outputting the MWE1 of the first particle beam toward a second path 11644, and can output MWE2 of the second particle beam toward the first path 11642 along with making instantly a counterpart MW2 (e.g. energy-less and mass-less conjugate or orthogonal counterpart matter wave) of the second particle beam toward the second path 11644. In addition, one edge dimension of the beam splitter 11608 is larger than 1000 to 20000 times of the one or more equivalent MW wavelengths; the MW1 (i.e. energy-less and mass-less) of the first particle beam transmit the sample 11615; the second beam splitter 11632 outputs a first interference pattern and a second interference pattern, wherein the first interference pattern and the second interference patterns are substantially composed of 1) transmitting MW1 of the first particle beam from the sample 11642 and 2) the MWE1 of the first particle beam, and the first interference pattern and the second interference pattern are conjugate ones to each other by obeying energy conservation law. In addition, the first x/y/z direction scan unit 11604 and the second x/y/z direction scan unit 11626 can let particles scan in 3 dimensional x, y, z directions to forming better image spatial resolutions. Also, the transmission-type non-invasive diagnosis/treatment apparatus 1160 is comprised of the second mirror 11624 having a moveable feature for doing the one or more dimensional scan, and is further comprised of the first mirror 11618 having a moveable feature for doing the one or more dimensional scan.

Because the novelty of the transmission-type non-invasive diagnosis/treatment apparatus 1160 utilizes the mass-less MW1 of the first particle beam to transmit (i.e. see through) the sample 11642, and the first interference pattern and the second interference pattern are comprised of transmitting MW1 of the first particle beam from the sample 11642 along the path 11642 and the MWE1 of the first particle beam along the path 11644, the transmission-type non-invasive diagnosis/treatment apparatus 1160 has advantages as follows: the transmission-type non-invasive diagnosis/treatment apparatus 1160 can improve treatment quality and protection of patient. Among those essential utilities, the present invention can teach the better approaches that can be most beneficial to the life quality of the patients, including reduction of pain, reduction of side effects, no risk of infection or general anesthesia, no requirement for head/body frame, short treatment course, and minimal recovery time), and the transmission-type non-invasive diagnosis/treatment apparatus 1160 can improve treatments (e.g. having less damage and risk to healthy tissue, single and multiple sessions (2-5 fractions) available, treat larger lesions than traditional radiosurgery, treat complex, previously judged untreatable lesions, access to lesions in all parts of a body, delivery of a large single dose of energy-less and mass-less MW radiation to a small target in a brain with great accuracy, very important role in treatment of both benign and malignant brain tumor, alternative to surgery, outperforming to radiotherapy, belong to a new class of non-invasive radiotherapy techniques: Image-Guided Radiotherapy (IGRT), able to shape the appropriate energy-less and mass-less radiation profile to conform to patients' individual anatomy, much more spatially and temporally precise in delivering energy-less and mass-less radiation, and maximal preservation nearby normal tissue).

In addition, when a tumor or disease regions of a patient detected by the transmission-type non-invasive diagnosis/treatment apparatus 1160, the tumor or the disease regions of the patient can be treated in real-time basis by using the MW's MOT (Magneto-Optical Trap) cooling and scanning method/apparatus. The MW's MOT in-situ repairing features of the present invention is to be the most essential method for living organ treatments, wherein one can turn on the MW's MOT apparatus comprising cooling and scanning functions to cure or burn out (i.e. ashes) while diagnosing the exact same disease location presented in the body of patients.

In addition, functions of the MWE particle source 11602, the first x/y/z direction scan unit 11604, the first wave-plate unit 11606, the first beam splitter 11608, the MW filter 11610, the first scan lens unit 11612, the holder 11614, the first lens unit 11616, the first mirror 11618, the first compensator 11620, the second wave-plate unit 11622, the second mirror 11624, the second x/y/z direction scan unit 9626, the second compensator 11628, the second lens unit 11630, the second beam splitter 11632, the projection lens 11634, the first detector 11636, the second detector 11638, and the display and signal processing unit 11640 can be referred to corresponding elements of the CD and defect inspection apparatus 1120, where in those are the similar embodiments with sharing the same novelty and methods of the present invention, so further description thereof is omitted for simplicity.

Figure 117:
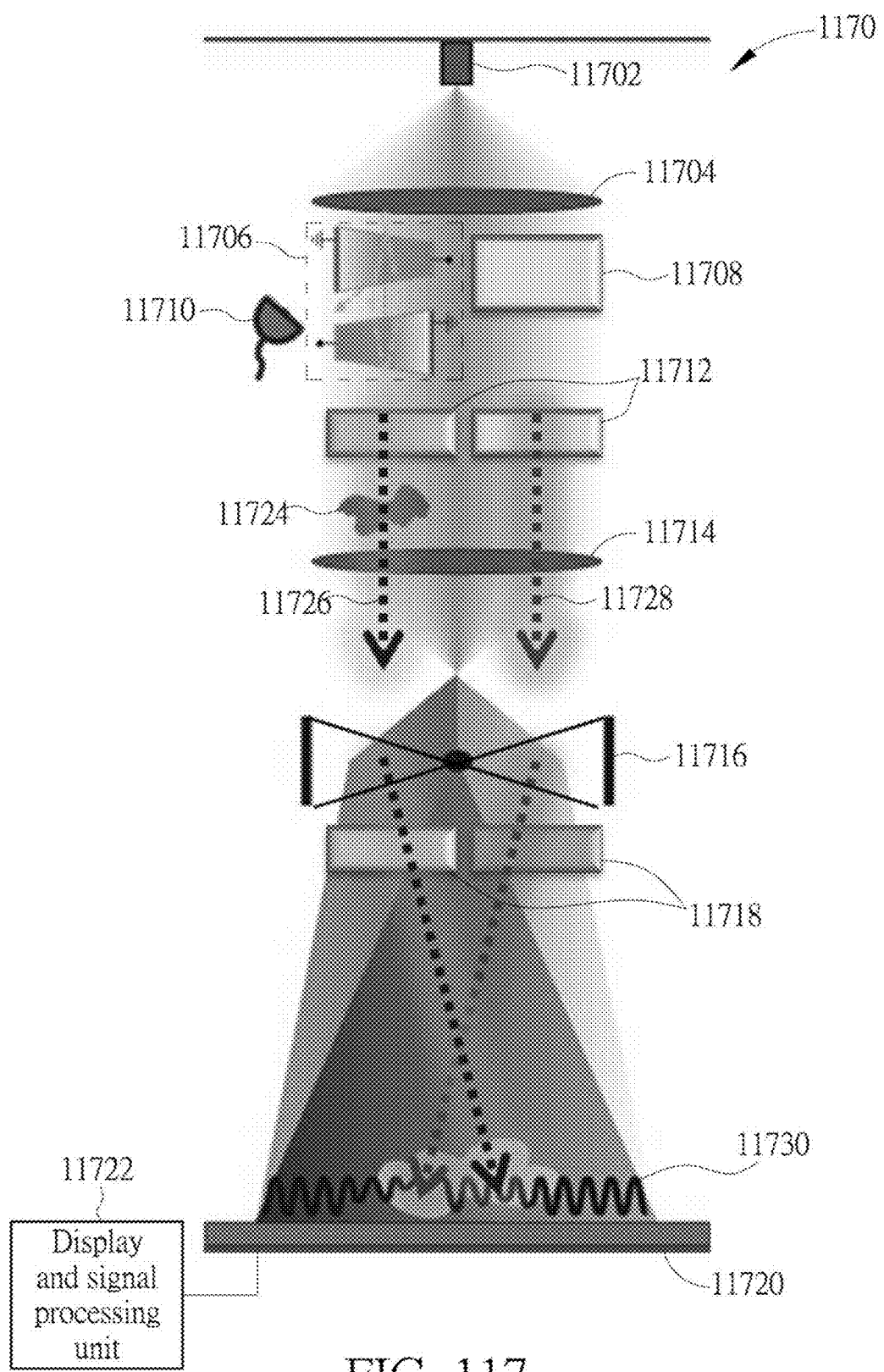

CN. Another Embodiment of the Transmission-Type Non-Invasive Measuring Apparatus or System Please refer to FIG. 117. FIG. 117 is a diagram illustrating a transmission-type non-invasive measuring apparatus 1170 according to a fourth embodiment of the present invention. As shown in FIG. 117, the transmission-type non-invasive measuring apparatus 1170 includes an MWE particle source 11702, a source lens 11704, an MW filter 11706, a first compensator 11708, an MWE detector 11710, a second compensator 11712, an object lens 11714, an entanglement device 11716, a third compensator 11718, an interference detector (or exposure film) 11720, and a display and signal processing unit 11722. As shown in FIG. 117, the MW filter 11706 and a sample 11724 are located at a first path 11726, and the first compensator 11708 is located at a second path 11728. In addition, the source lens 11704, the object lens 11714, and the entanglement device 11716 are across the first path 11726 and the second path 11728, wherein the second compensator 11712 can be displaced in the first or second path and the third compensator 11718 can be displaced in the first or second path as well.

As shown in FIG. 117, differences between the transmission-type no-invasive diagnosis/treatment apparatus 1160 and the transmission-type non-invasive measuring apparatus 1170 are that the former one uses MW amplitude splitting method to form a conjugate MW copy of the MWE particles emitted from a MWE particle source and the latter one uses MW wavefront splitting method to form a coherent or partially coherent MW wavefront copy of the MWE particles emitted from a MWE particle source.

As shown in FIG. 117, MWE particles emitted by the MWE particle source 11702 are associated with one or more equivalent wavelengths, wherein the one or more equivalent wavelength is shorter than about 0.1 to 10 nm; one edge dimension of the entanglement device 11716 is larger than 10 times to 20 times the one or more equivalent wavelengths; when the MWE particle source 11702 is a boson source, the entanglement unit 11716 includes an optical bi-prism forming by transparent materials with refraction index greater than 1.0 corresponding to the MW wavefront or the emitted MWE particle, or when the MWE particle source 11702 is a fermion source, the entanglement unit 11716 includes a magnetic/electric bi-prism forming by electric or magnetic field in spatial, and the entanglement device 11716 is used for coupling an interaction between 1) an MW wavefront of a first particle beam emitted toward the first path 11726 and 2) an MWE particle of the first particle beam emitted toward the second path 11728 so as to generate an interference pattern 11730; and when the MW filter 11706 tilts MWE of a first particle beam emitted toward the first path 11726, the MWE detector 11710 is used for collecting the energy and monitoring intensity of MWE of the first path first particle beam tilted from the first path 11726.

In addition, in another embodiment of the present invention, the entanglement unit 11716 is a double slit or circular shapes when the MWE particle source 11702 is a boson source or fermions source.

In addition, the particles emitted by the MWE particle source 11702 are associated with multi-spatial frequency (e.g. a plurality of spatial geometry) or multiple matter wavelength (frequency) and the equivalent matter wave of MWE particle is a temporal/spatial coherent or partially coherent.

In addition, the detector (or exposure film) 11720 can detect a plurality of temporal/spatial phase shifts, or a plurality of peaks or valleys of the interference pattern 11730 through a mechanism including fluorescent, exposure film, or particle multiplication methods, and transmit information of the plurality of temporal/spatial phase shifts, or the plurality of peaks or valleys of the interference pattern 11730 to the display and signal processing unit 11722, wherein the detector 11720 includes an energy sensitive film or sensing device to detecting interference pattern 11730 of a plurality of boson or fermion, and the interference pattern 11730 deriving from the sample 11724 is developed on the energy sensitive film or the sensing device. In addition, the sensitive film can form a 3D hologram image of the sample 11724 by having irradiated with a second coherent MWE particle source (not shown in FIG. 117) to reconstruct the 3D hologram image of the sample 11724. Then, after the display and signal processing unit 11722 can generate a final magnified 2D or 3D image of the sample 11724 accordingly.

Figure 118:
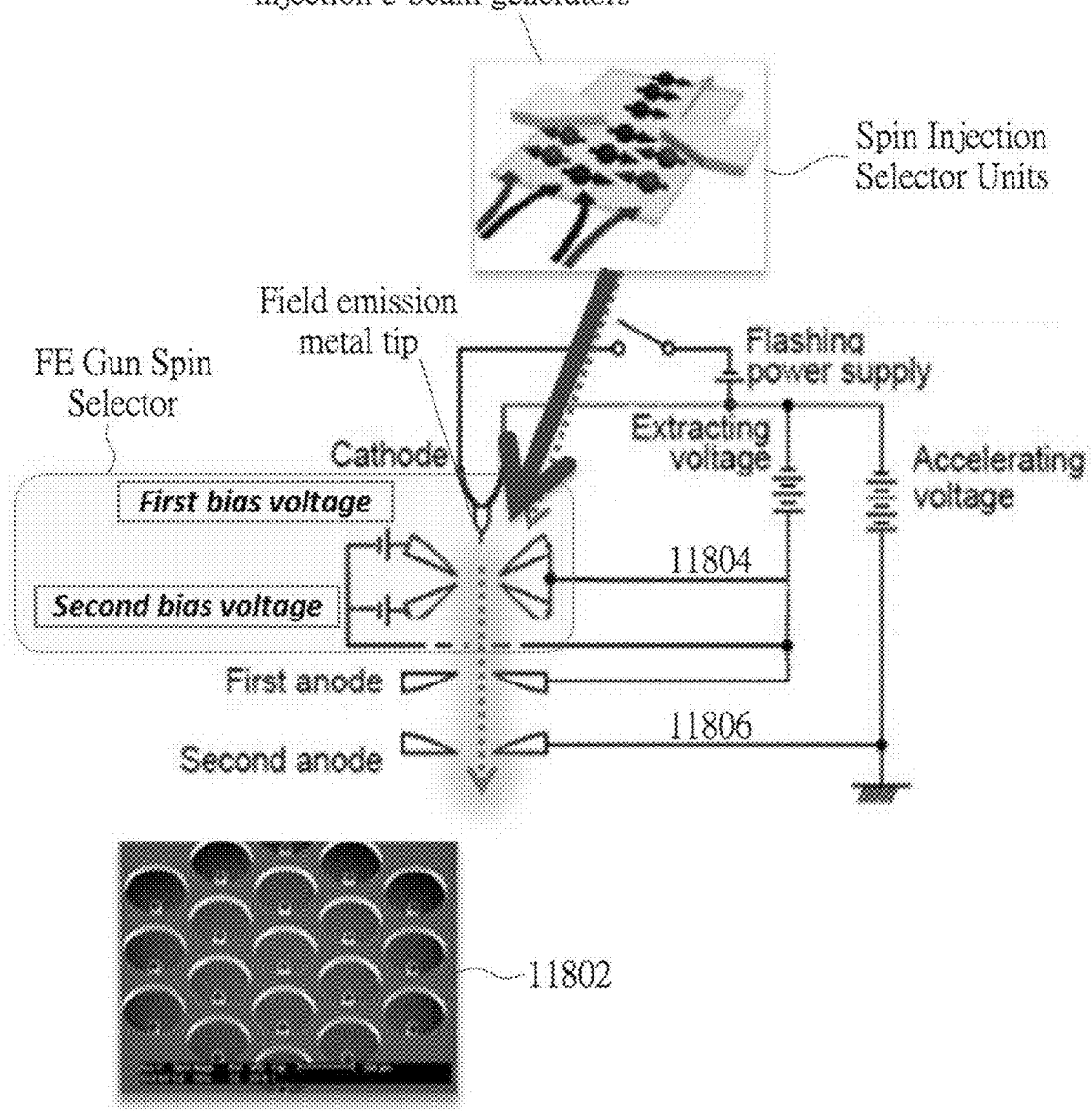

In addition, as shown in FIG. 118, when the MWE particle source 11702 is the fermion source, the MWE particle source 11702 includes a plurality or array of Field Emission (FE) tips 11802, wherein each of the FE tips 11802 is coupled with a plurality of bias voltages and electrodes to select desired QM spins states for each FE tips to forming a selected QM spin configurations for each groups of the particles, wherein a first electrode 11804 provides an extracting voltage to pull a fermions (e.g. electrons) out of a tip structure, and a second electrode 11806 utilizes an accelerating voltage to accelerate the fermions (e.g. electrons) to about 10V to 100 kV or more for irradiating or inspecting the sample under test.

Figure 119:
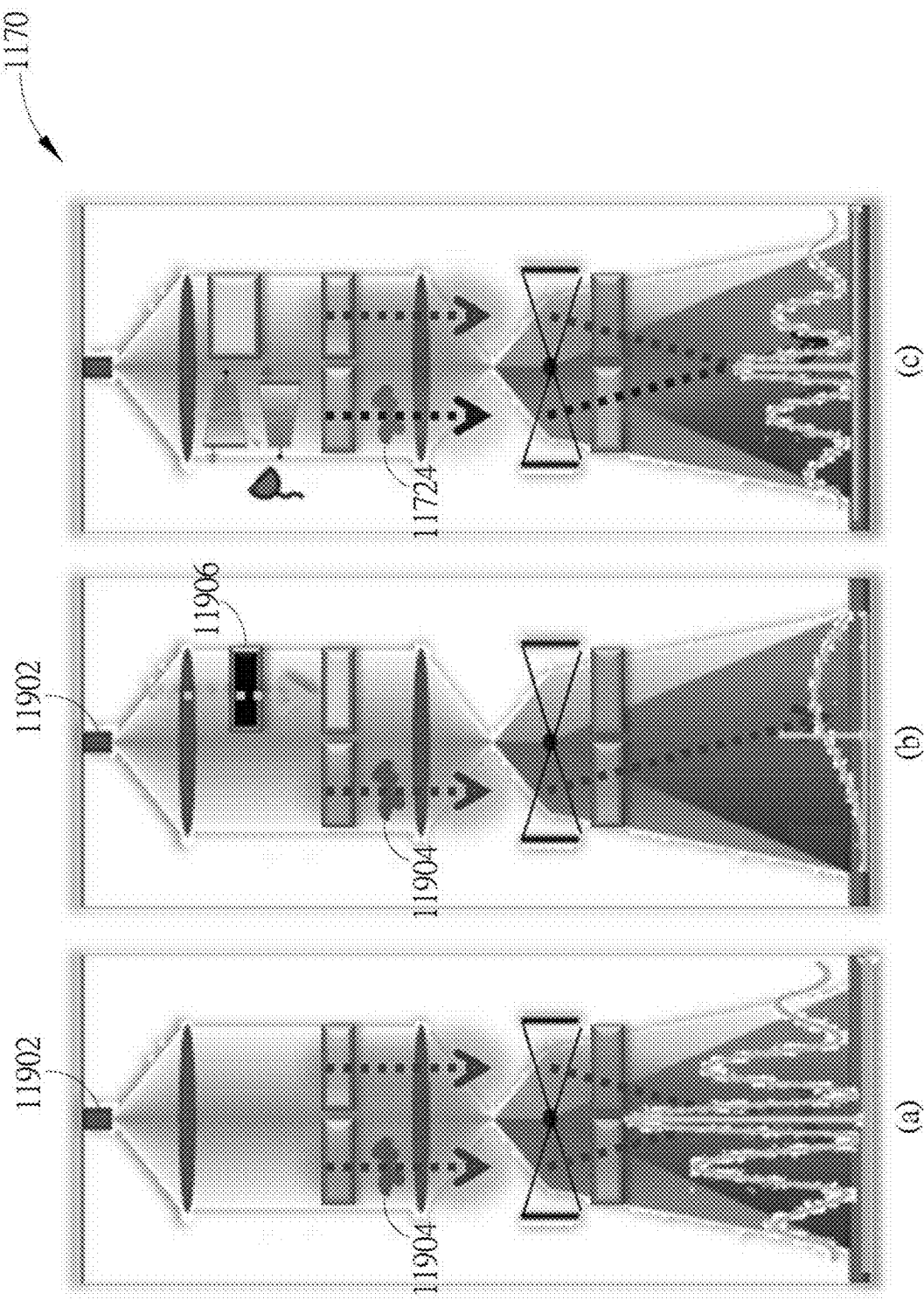

In addition, please refer to FIG. 119, wherein FIG. 119 (a), (b) are prior arts or other methods will show unwanted damages on a sample under test. As shown in FIG. 119 (a),(b), because an MWE of a first particle beam toward a first path emitted by an MWE particle source 11902 directly transmits a sample 11904, as shown in FIG. 119 (a),(b) will still damage the sample 11904, wherein a block 11906 is used for blocking a first particle beam toward a second path emitted by the MWE particle source 11902. However, the non-invasive measuring apparatus 1170 shown in FIG. 119 (c), because only the MW wavefront of the first particle beam emitted toward the first path 11726 transmits the sample 11724, the non-invasive measuring apparatus 1170 does not damage the sample 11724.

In addition, overall summary corresponding to FIG. 119 is shown in TABLE 30.

TABLE 30

| | (a) | (b) | (c) |
|---|---|---|---|
| Experimental setups | ~100% source open | ~50% source open | ~100% source open |
| MWE Intensity (%) of the first path 11726 | 50% | 50% | 0% |
| MWE Intensity (%) of the second path 11728 | 50% | 0% | 50% |
| MW wavefront (%) of the first path 11726 | ~50% | ~50% | ~50% |
| Sample's damage degradation (%) | ~50% | ~50% | ~0% |
| Image peaks (X) | ~4X | 1X | ~2X |
| Intensity (%) of the MWE detector 11710 | ~100% | ~50% | ~50% |
| Remarks | Sample 11724 is damaged | Sample 11724 is damaged | Sample 11724 has null or no damage |

In addition, functions of the MWE particle source 11702, the source lens 11704, the MW filter 11706, the first compensator 11708, the second compensator 11712, the object lens 11714, the third compensator 11718, the detector 11720, and the display and signal processing unit 11722 can be referred to corresponding elements of the transmission-type no-invasive diagnosis/treatment apparatus 1160, so further description thereof is omitted for simplicity.

Figure 120A:
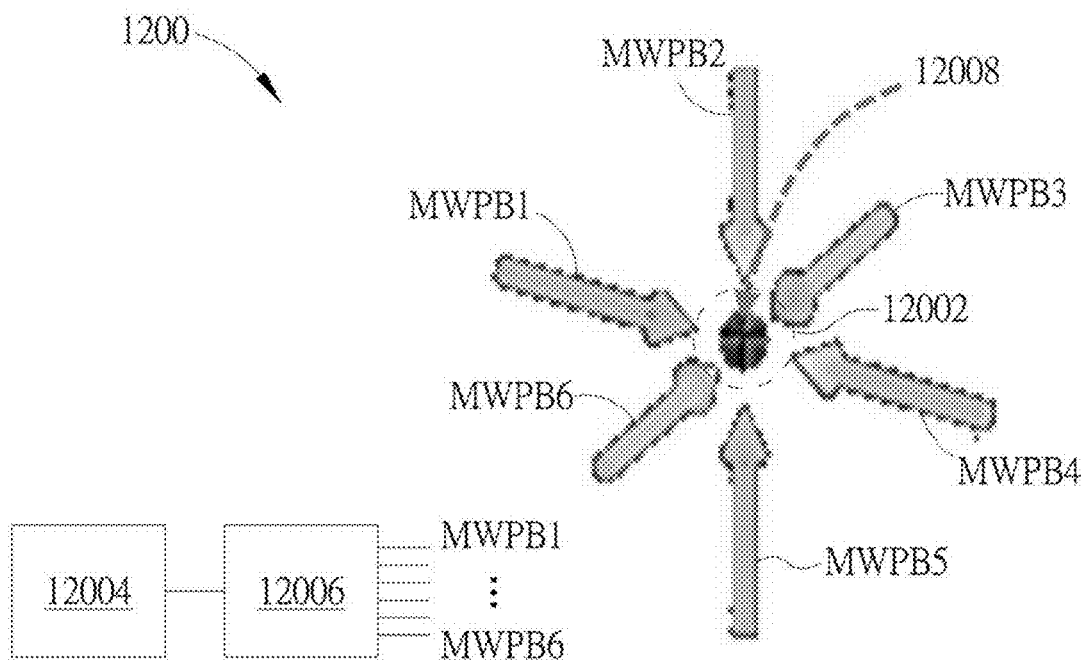
Figure 120B:
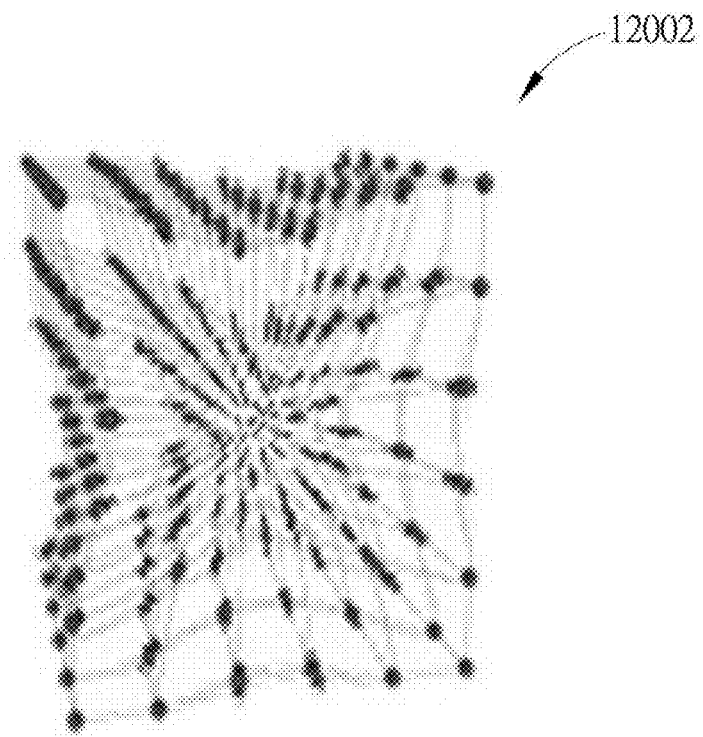

CO. Another Embodiment of the Apparatus for Generating a Virtual Space-Time Lattice by Using MW FIG. 120A is a diagram illustrating an apparatus 1200 for generating a virtual space-time lattice 12002 according to a fifth embodiment of the present invention. As shown in FIG. 120A, the apparatus 1200 includes an MWE particle source 12004 and an MW filter 12006. As shown in FIG. 120, the MW filter 12006 can receive particles emitted from the MWE particle source 12004 and generate 6 coherent matter waves of particle beams MWPB1-6 (i.e. mass-less and energy-less MW of particle beam groups) accordingly, wherein the coherent matter waves of particle beams MWPB1-6 is used for forming the virtual space-time lattice 12002 in a 3D enclosed space, and the coherent matter waves of particle beams MWPB1-6 are temporal coherent of particle beams, or spatial coherent of particle beams. However, in another embodiment of the present invention, the MW filter 12006 generates the coherent matter waves of particle beams MWPB1-3, and the other three coherent matter waves of particle beams MWPB4-6 are generated by corresponding mirrors (not shown in FIG. 120A) further included in the apparatus 1200 reflecting the coherent matter waves of particle beams MWPB1-3. In addition, FIG. 120B is a diagram illustrating magnification of the virtual space-time lattice 12002. In addition, in another embodiment of the present invention, the virtual space-time lattice 12002 can be a one-dimensional space (shown in FIG. 121A) and a two-dimensional space (shown in FIG. 121B).

In addition, MWE particle source 12004 together with the MW filter 12006 can vary coherent wavelengths of the coherent matter waves of particle beam MWPB1-6 to shrink a size of the virtual space-time lattice 12002 under thermal equilibrium environment so that a sample 12008 captured by the virtual space-time lattice 12002 can be cooled down by 1) energy evaporation or natural radiation processes along with another following step to extend the size of the virtual space-time lattice 12002 under 2) adiabatic thermal environment, wherein the sample 12008 can be comprised of nucleons, cells, atoms, molecules or the like. That is, MWE particle source 12004 together with the MW filter 12006 can modulate the coherent wave lengths of the coherent matter waves of particle beams MWPB1-6 from long to short under thermal equilibrium environment or from short to long under adiabatic thermal environment sequentially so as to further cool down the sample 12008, wherein the MWE particle source 12004 together with the MW filter 12006 can cool down the sample 12008 at about absolute zero Kevin degree state (e.g. down to below 0.001~0.000001 degree of Kelvin scale temperature) by modulating the wave lengths of the coherent matter waves of particle beams MWPB1-6 from long to short or short to long sequentially. Alternatively speaking, the MWE particle source along with the MW filter shrinks a size of the virtual space-time lattice by a plurality cycles of shortening or extending the wave lengths of the plurality of coherent matter waves of particle beams to cool down a sample captured by the virtual space-time lattice.

Because the apparatus 1200 can utilize MWE particle source 12004 together with the MW filter 12006 to cool down the sample 12008, the apparatus 1200 can control a temperature of the sample 12008 to a critical point, such that 1) when the temperature of the sample 12008 is at the critical point, chemical bonds of the sample 12008 can be either disrupted or frozen, or 2) if the sample 12008 is a tumor and the temperature of the sample 12008 is at the critical point, bio-chemical activities of the tumor can be disabled or collapsed by shrinking the virtual space-time lattice 12002 under certain thermal conditions or by varying relative locations of the virtual space-time lattice 12002 (i.e. moving around spot or locations of intersect treatment locations within the virtual space-time lattice 12002 shown in FIG. 120B).

In addition, the apparatus 1200 needs to operate in a partial vacuum and low humidity environment, and the apparatus 1200 also needs to be located within an enclosed space such that the system working environment can be sealed and protect well from being disturbed by thermal, humidity, residual chemical atoms, stray light and the like interferences.

A Magnetic MW Trap (MMT) is an apparatus that uses MW cooling with magneto-MW trapping in order to produce samples of deep cold, trapped, neutral atoms at temperatures lower than a several micro-Kelvins degree, two or three times the recoil limit of the Doppler effect (see Reference: Doppler cooling limit). By combining the small momentum of a sample 12008 with a low enough velocity and spatially dependent absorption cross section of the virtual space-time lattice 12002, atoms with initial velocities of hundreds of meters per second can be slowed toward tens of centimeters/sec or less than a mm/sec (Reference: 1) Hänsch, Theodor W., and Arthur L. Schawlow. "Cooling of gases by laser radiation." Optics Communications 13.1 (1975); 2) Metcalf, Harold J. & Straten, Peter van der (1999). Laser Cooling and Trapping. Springer-Verlag New York, Inc.).

CP. Another Embodiment of the Magnetic MW Trap (MMT)

Please refer to FIG. 122. FIG. 122 is a diagram illustrating a Magnetic MW Trap (MMT) 12202 according to a sixth embodiment of the present invention. As shown in FIG. 122, the MMT 12202 utilizes magnetic coil device 12204 to trap free atom cluster 12206 (wherein the free atom cluster 12206 is a fermion particle cluster and the like particle cluster), and utilizes MWE particle source 12004 together with coherent matter waves of particle beams MWPB1-4 generated by an MW filter (not shown in FIG. 122) to cool down the free atom cluster 12206.

In addition, a first steps of cooling down process flow (state (a)→state (b)→state (c)) of the free atom cluster 12206 can be referred to FIGS. 123A, 123B, wherein the first steps of cooling down is associated with a thermal equilibrium environment of cool temperature, such as under or below the liquid Helium temperature. As shown in FIGS. 123A, 123B, during the cooling down process flow, the MWE particle source 12004 together with MW filter can vary coherent wave lengths of the coherent matter waves of particle beams MWPB1-4 to shrink a size of the MMT 12202. For example, in the state (a) corresponding to time T0, the coherent wave lengths of the coherent matter waves of particle beams MWPB1-4 are longer, resulting in the size of the virtual lattice of MMT 12202 being large; in the state (b) corresponding to time T1, the coherent wave lengths of the coherent matter waves of particle beams MWPB1-4 are medium, resulting in the virtual lattice size of the MMT 12202 being medium; and in the state (c) corresponding to time T2, the coherent wave lengths of the coherent matter waves of particle beams MWPB1-4 are shorter, resulting in the size of the virtual lattice of MMT 12202 being small. Therefore, MWE particle source 12004 together with the MMT 12202 can vary the coherent wave lengths of the coherent matter waves of particle beams MWPB1-4 to make the free atom cluster 12206 being in absolute frozen state down to about or below 10^(−6) Kelvin degree through the first cooling down process flow (state (a)→state (b)→state (c)) under a thermal equilibrium environment, then followed by a second step cooling down process flow from state (c)→state (b)→state (a) under adiabatic thermal environment.

CQ. Another Embodiment of the Fine Atomic Clock (Reference: 1) Long-Sheng Ma, et al. "Frequency Uncertainty for Optically Referenced Femtosecond Laser Frequency Combs." IEEE Journal of Quantum Electronics 43.2 (2007); 2) Lombardi, et al. "NIST Primary Frequency Standards and the Realization of the SI Second." NCSLI Measure 2.4 (2007))

Please refer to FIG. 124. FIG. 124 is a diagram illustrating an ultra-fine precision atomic clock 1240 according to a seventh embodiment of the present invention. The principle of the atomic Clock (or oscillator) is simple: Since all atoms of a specific element are identical, they should produce the exact same frequency when they absorbenergy or release energy. The resonance or emission frequency ($f_o$) of an atomic particle oscillator is the difference between the two energy levels, a ground state with energy E1 and another excited state with energy E2, divided by Planck's constant. As shown in FIG. 124, the present invention discloses a novel ultra-fine precision atomic clock includes a low temperature cooling chamber 12402, an MWE particle source 12404 (e.g. boson, fermion or the like), an MW filter 12406, an energy injection unit 12408 comprising a least one of a micro-wave injection unit, an optical (e.g. Laser, MESAR, photon or the like) injection unit or the like, a probing unit, and an MMT unit 12412, an emission detector 12414, anatomic gun 12416, a reference cell 12418, abeam splitter 12420, a differential amplifier 12422, a frequency modulation local oscillator 12424, a phase-sensitive detector unit 12426, a voltage-controlled crystal oscillator (VCXO) 12428, a frequency synthesizer 12430, and a frequency stabilized output unit 12432. The commonly used atomic MWE particle source builds on a confined reference isotope, it is often an alkali metal, such as Cesium Cs-133 or Rubidium Rb-87 or the like, inside an MMT and RF cavity. The particles are excited to a known high energy state using optical pumping typically; when the applied RF radiation field is swept over the hyperfine spectrum of the trap free atom cluster 12206, the atom cluster 12206 will absorb the energy of the pumping light, and a photo detector provides and outputs the response of the emission radiation of the excited particles. The absorption peak steers the fly-wheel oscillator, i.e. Modulation local oscillator embedded in a VCXO feedback loop to provide a standard time signal output. The frequency errors can be made very small for an atomic Clock device, or be predictable in such a way that a high degree of accuracy, repeatability and stability can be achieved. This is why an atomic beam can be used as a primary time standard. Besides, the development of atomic clocks has led to many scientific and technological advances for human being, such as a system of precise global positioning system (GPS) and regional navigation satellite communication systems, and applications in the Internet or IoT (Internet-of-Things) areas, which depend critically on frequency and time standards. Atomic clocks are also can be used in many scientific research disciplines, such as for very long-baseline interferometry (VLBI) in radio-astronomy.

As shown in FIG. 124, the MW filter 12406 can receive particles emitted from the MWE particle source 12404 and generate 3 to 6 coherent MW of particle beams accordingly, wherein the 3 to 6 coherent MW of particle beams is used for forming a virtual space-time lattice (within the MMT unit 12412) in a confined 3D enclosed space with or without the presence of MW mirrors, and only two MW mirrors 12413 and two coherent matter waves of particle beams MWPB1-2 of the 3 to 6 or more coherent matter waves of particle beams are shown in FIG. 124. The low temperature cooling chamber 12402 is an air, humidity, electric, magnetic and thermal, etc. shielded within an enclosure space.

As shown in FIG. 124, the atomic gun 12416 is used for emitting a plurality of fermion particles (e.g. Cesium-133 (Cs) particles associated with its fine-structure emission frequency of about 9.192 GHz or other molecules having stable intrinsic fine structure emission frequencies) to the MMT unit 12412 forming a cluster of trapped (e.g. Molasses) particles, wherein the plurality of fermion particles or molecules can be trapping into the confined 3D virtual space-time lattice space forming by the plurality of 3 to 6 coherent MW of particle beams, wherein an additional pre-cooling stage or unit can be applied to the plurality of fermion particles or molecules before they can incident into the MMT unit 12412 of the cooling chamber 12402.

As shown in FIG. 124, the energy injection unit 12408 injects energy into the trapped particles or sample atom/ion to activate the trapped particles or sample atom/ion into an excitation state with higher energy.

As shown in FIG. 124, after the trapped particles are activated into the excitation state, probing beams 12410 generated by the probing unit (not shown in FIG. 124) are characterized with having MWE energy or with having MW (energy-less) and then the probing beams 12410 can activate (or induce/stimulate) emission (e.g. by fluorescence emission or by stimulated emission of radiation) of the trapped particles from the excitation state, wherein an emission frequency of the trapped particles is associated with a characteristic emission frequency of the trapped particles (e.g. the emission frequency of the trapped particles can be a fundamental frequency corresponds to the trapped particles transition in between the two energy states under certain low temperature conditions), and wherein the probing beams 12410 can have energy properties or it can have no energy or no mass properties to keep the minimal or null interference and to get the most precision and stabilized accuracy ranges (e.g. relative frequency precision up to $10^{\wedge}(-16)$ to $10^{\wedge}(-18)$ or beyond) for the emission frequency with respect to the trapped particles.

Then, the emission detector 12414 can detect and output the emission frequency or phase properties of the trapped particles by following the activation of the probing beams 12410.

In addition, a function of the MMT unit 12412 can be referred to the MMT 12202 shown in FIG. 122 and can be self-explained by the ordinary skilled person in the art accordingly. In addition, the reference cell 12418, the emission detector 12414, the differential amplifier 12422, the frequency modulation local oscillator 12424, the phase-sensitive detector unit 12426, the VCXO 12428, and the frequency synthesizer 12430 can co-work together and be characterized as a feedback loop to lock into a stable state which can deliver a frequency stabilized output signal to the frequency stabilized output unit 12432, so the frequency stabilized output unit 12432 can output a standard time clock signal, e.g. corresponding to 1 second or the like, wherein the reference cell 12418 is for providing a reference frequency or phase property and a differential amplifier unit 12422 is to sense the difference of the output property of the emission detector 12414 and the reference property providing by the reference cell. In addition, operational principles of the frequency modulation oscillator 12424, the phase-sensitive detector unit 12426, the VCXO 12428, and the frequency synthesizer 12430 are well-known to one of ordinary skill in the art corresponding to an atomic clock, so further description thereof is omitted for simplicity.

In addition, the ultra-fine precision atomic clock 1240 needs to operate in partial vacuum environment and low humidity environment within an enclosed space.

To sum up, the present invention utilizes matter wave of bosons (e.g. Photon) and/or fermions (e.g. electron, neutron) to apply to non-contact angle measuring apparatus, mission critical inspectionapparatus, non-invasive diagnosis/treatment apparatus, method for filtering matter wave from a composite particle beam, non-invasive measuring apparatus, apparatus for generating a virtual space-time lattice, and atomic clock. Because matter wave of bosons (e.g. Photon)

and/or fermions (e.g. electron, neutron) does not include energy, the present invention not only can solve disadvantages corresponding to remote angle measurement, critical dimensional (CD) and defect inspection, and atomic clock shown in description of the prior art, but can also satisfy the above mentioned future development in Nature.

Those skilled in the art will readily observe that numerous modifications and alterations of the device and method may be made while retaining the teachings of the invention. Accordingly, the above disclosure should be construed as limited only by the metes and bounds of the appended claims.

What is claimed is:

1. A non-contact angle measuring apparatus, comprising:
a matter-wave and energy (MWE) particle source for generating boson or fermion particles; and
a detector for detecting a plurality peaks or valleys of an interference pattern generated by the boson or fermion particles corresponding to a slit, a bump, or a hole of a first plane and matter waves associated with the boson or fermion particles reflected by a second plane, wherein angular locations of the plurality peaks or valleys of the interference pattern, a first distance between a joint region of the first plane and the second plane, and a second distance between the detector and the slit, the bump, or the hole are used for deciding an angle between the first plane and the second plane;
wherein the slit, the bump, or the hole has a short side length dimension with a third distance, the energy particle source is associated with one or more equivalent wavelengths, and the more equivalent wavelengths are less than $1/10$-$1/20$ of the first distance or less than $1/5$-$1/10$ of the third distance.

2. The non-contact angle measuring apparatus of claim 1, wherein the second plane is composed of transparent materials, dark materials, dielectric materials, semi-conductive materials, or conductive materials.

3. The non-contact angle measuring apparatus of claim 1, wherein the angle is defined by the joint region of the first plane and the second plane.

4. The non-contact angle measuring apparatus of claim 1, wherein the boson or fermion particles emitted by the matter-wave and energy particle source are associated with one or more equivalent MW wavelengths, wherein the one equivalent wavelength is in between 0.1 to 400 nm.

5. The non-contact angle measuring apparatus of claim 4, wherein the slit, the bump, or the hole has a short side length dimension with a third distance, and the one equivalent wave length is less than $1/10$-$1/20$ of the first distance or less than $1/5$-$1/10$ of the third distance.

6. The non-contact angle measuring apparatus of claim 1, wherein the matter-wave and energy particle source placed at a first side of the first plane, the detector placed at a second side of the first plane, and the second side of the first plane is opposite to the first side of the first plane.

7. The non-contact angle measuring apparatus of claim 1, wherein the angle is between 15 to 165 degrees, and the detector is located on a third plane or along an arc line directions.

8. The non-contact angle measuring apparatus of claim 1, wherein the non-contact angle measuring apparatus operates in a partial vacuum and low humidity environment.

9. The non-contact angle measuring apparatus of claim 1, wherein the first plane is placed along a first direction and the second plan is placed along a second direction, wherein the second direction is different from the first direction.

* * * * *